United States Patent
Sekine et al.

(10) Patent No.: US 9,929,347 B2
(45) Date of Patent: Mar. 27, 2018

(54) POLYMER COMPOUND AND LIGHT EMITTING ELEMENT USING SAME

(71) Applicants: Sumitomo Chemical Company, Limited, Tokyo (JP); Cambridge Display Technology Limited, Cambs (GB)

(72) Inventors: Chizu Sekine, Tsukuba (JP); Satoshi Mikami, Kizugawa (JP); Makoto Anryu, Tsukuba (JP); Hidenobu Kakimoto, Osaka (JP); Annette Regine Steudel, Dresden (DE); Martin John Humphries, Cambridge (GB); Kiran Timothy Kamtekar, Cambridge (GB); Elena Hojas Garcia, Suffolk (GB); Sophie Heidenhain, Altenmarkt (DE); Ruth Pegington, Cambridge (GB)

(73) Assignees: SUMITOMO CHEMICAL COMPANY, LIMTIED, Tokyo (JP); Cambridge Display Teclmology Limited, Godmanchester, Cambs (GB)

( * ) Notice: Subject to any disclaimer, the term of this patent is extended or adjusted under 35 U.S.C. 154(b) by 582 days.

(21) Appl. No.: 14/388,095

(22) PCT Filed: Mar. 26, 2013

(86) PCT No.: PCT/JP2013/058841
§ 371 (c)(1),
(2) Date: Sep. 25, 2014

(87) PCT Pub. No.: WO2013/146806
PCT Pub. Date: Oct. 3, 2013

(65) Prior Publication Data
US 2015/0115204 A1    Apr. 30, 2015

(30) Foreign Application Priority Data

Mar. 27, 2012 (JP) ................................. 2012-072305
Jun. 20, 2012 (JP) ................................. 2012-138846

(51) Int. Cl.
*C08G 73/02* (2006.01)
*H01L 51/00* (2006.01)
(Continued)

(52) U.S. Cl.
CPC .......... *H01L 51/0039* (2013.01); *C07C 25/22* (2013.01); *C07C 25/24* (2013.01);
(Continued)

(58) Field of Classification Search
None
See application file for complete search history.

(56) References Cited

U.S. PATENT DOCUMENTS 4,356,429 A    10/1982 Tang
4,539,507 A     9/1985 VanSlyke et al.
(Continued)

FOREIGN PATENT DOCUMENTS

EP    2518110 A1    10/2012
GB    2300196 A    10/1996
(Continued)

OTHER PUBLICATIONS

Office Action dated May 26, 2015 in JP Application No. P2014-507926.
(Continued)

*Primary Examiner* — Kamal Saeed
(74) *Attorney, Agent, or Firm* — Panitch Schwarze Bellsario & Nadel LLP

(57) ABSTRACT

A polymer compound is provided having constitutional units of formula (1) and formula (2), and a constitutional unit of formula (3) and/or (4'):

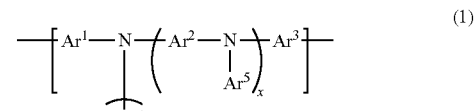

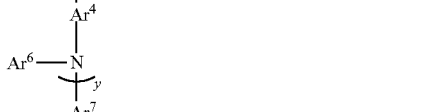

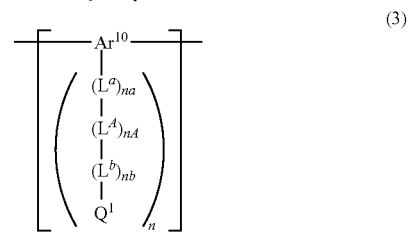

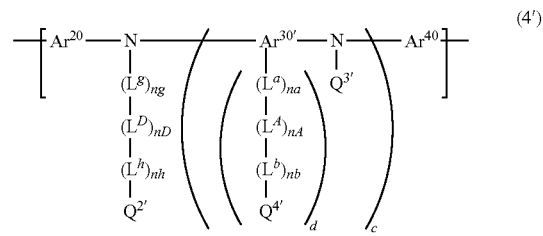

wherein $Ar^1$ to $Ar^4$, $Ar^{20}$, $Ar^{30'}$ and $Ar^{40}$ represent arylene groups or the like; $Ar^5$ to $Ar^7$ represent aryl groups or the (Continued)

like; $Ar^8$ represents (2+p)-valent aromatic hydrocarbon group or the like; $Ar^{10}$ represents (2+n)-valent aromatic hydrocarbon group or the like; $R^1$ represents alkyl group or the like; $L^a$, $L^b$, $L^g$ and $L^h$ represent alkylene groups or the like; $L^A$ and $L^D$ represent oxygen atoms or the like; $Q^1$ represents monovalent crosslinkable group; $Q^{2'}$ to $Q^{4'}$ represent monovalent crosslinkable groups or the like; x, y, c, nA and nD represent 0 or 1; p represents integer of 1 or greater; na and ng represent integer of 0 to 3; nb and nh represent integer of 0 to 12; and n represents integer of 1 to 4.

22 Claims, No Drawings

(51) Int. Cl.

| | |
|---|---|
| C07C 25/22 | (2006.01) |
| C07C 211/61 | (2006.01) |
| C07C 211/54 | (2006.01) |
| C07C 25/24 | (2006.01) |
| C07F 15/00 | (2006.01) |
| C07F 5/02 | (2006.01) |
| C07F 7/08 | (2006.01) |
| C08G 61/12 | (2006.01) |
| H01L 51/50 | (2006.01) |

(52) U.S. Cl.
CPC .......... *C07C 211/54* (2013.01); *C07C 211/61* (2013.01); *C07F 5/025* (2013.01); *C07F 7/0818* (2013.01); *C07F 15/0033* (2013.01); *C08G 61/12* (2013.01); *C08G 73/026* (2013.01); *C08G 73/0266* (2013.01); *H01L 51/0043* (2013.01); C07C 2102/06 (2013.01); C07C 2103/18 (2013.01); C08G 2261/135 (2013.01); C08G 2261/1412 (2013.01); C08G 2261/1414 (2013.01); C08G 2261/312 (2013.01); C08G 2261/3142 (2013.01); C08G 2261/3162 (2013.01); C08G 2261/411 (2013.01); C08G 2261/5242 (2013.01); C08G 2261/76 (2013.01); C08G 2261/95 (2013.01); H01L 51/0085 (2013.01); H01L 51/5012 (2013.01); H01L 51/5056 (2013.01); H01L 2251/308 (2013.01)

(56) References Cited

U.S. PATENT DOCUMENTS

| | | | |
|---|---|---|---|
| 4,990,634 A | 2/1991 | Mukai et al. | |
| 5,011,757 A | 4/1991 | Akasaki et al. | |
| 5,028,505 A | 7/1991 | Akasaki et al. | |
| 5,121,029 A | 6/1992 | Hosokawa et al. | |
| 9,331,284 B2 * | 5/2016 | Fukushima | H01L 51/0043 |
| 2004/0109955 A1 | 6/2004 | Kitano et al. | |
| 2008/0217605 A1 | 9/2008 | Wallace et al. | |
| 2008/0233429 A1 | 9/2008 | Oguma et al. | |
| 2008/0315757 A1 | 12/2008 | McKiernan et al. | |
| 2009/0315453 A1 | 12/2009 | Kobayashi et al. | |
| 2010/0201259 A1 | 8/2010 | Kobayashi | |
| 2011/0006294 A1 | 1/2011 | Tanaka et al. | |
| 2011/0108814 A1 | 5/2011 | Iida et al. | |
| 2011/0118411 A1 | 5/2011 | Anryu et al. | |
| 2011/0127516 A1 | 6/2011 | Nakatani et al. | |
| 2011/0187266 A1 | 8/2011 | Fukushima et al. | |
| 2011/0198573 A1 | 8/2011 | Iida et al. | |
| 2011/0272686 A1 | 11/2011 | Ohuchi et al. | |
| 2012/0199825 A1 | 8/2012 | Soga et al. | |
| 2012/0256537 A1 | 10/2012 | Nakatani et al. | |
| 2012/0326140 A1 | 12/2012 | Fukushima et al. | |
| 2014/0183414 A1 | 7/2014 | Umemoto et al. | |

FOREIGN PATENT DOCUMENTS

| | | |
|---|---|---|
| JP | S57-051781 A | 3/1982 |
| JP | S59-194393 A | 11/1984 |
| JP | S63-070257 A | 3/1988 |
| JP | S63-175860 A | 7/1988 |
| JP | H02-135359 A | 5/1990 |
| JP | H02-135361 A | 5/1990 |
| JP | H02-209988 A | 8/1990 |
| JP | H03-037992 A | 2/1991 |
| JP | H03-152184 A | 6/1991 |
| JP | 2004-143419 A | 5/2004 |
| JP | 2006-169265 A | 6/2006 |
| JP | 2008-106241 A | 5/2008 |
| JP | 2009-052032 A | 3/2009 |
| JP | 2009-521118 A | 5/2009 |
| JP | 2010-189630 A | 9/2010 |
| JP | 2010-215886 A | 9/2010 |
| JP | 2011-149012 A | 8/2011 |
| JP | 2011-174061 A | 9/2011 |
| JP | 2012-028726 A | 2/2012 |
| JP | 2012-036388 A | 2/2012 |
| JP | 2013-060585 A | 4/2013 |
| WO | 02/045184 A1 | 6/2002 |
| WO | 2005/049546 A1 | 6/2005 |
| WO | 2009/110642 A1 | 9/2009 |
| WO | 2009/123269 A1 | 10/2009 |
| WO | 2009/131255 A1 | 10/2009 |
| WO | 2011/049241 A1 | 4/2011 |
| WO | 2011078387 A1 | 6/2011 |
| WO | 2011/093428 A1 | 8/2011 |

OTHER PUBLICATIONS

Supplementary Search Report dated May 29, 2015 in EP Application No. 13768988.1.
Extended Search Report dated Oct. 6, 2015 in EP Application No. 13768988.1.
Office Action dated Oct. 8, 2015 in CN Application No. 201380027514.X.
Office Action dated Aug. 16, 2016 in TW Application No. 102110834.
Office Action dated May 12, 2016 in CN Application No. 201380027514.X.
Int'l Preliminary Report on Patentability dated Oct. 9, 2014 in Int'l Application No. PCT/JP2013/058841.
Int'l Search Report dated May 28, 2013 in Int'l Application No. PCT/JP2013/058841.
T. Yamamoto, "Electrically conducting and thermally stable . . . ", Prog. Polym. Sci., vol. 17, 1153-1205, 1992.
N. Miyaura et al., "Palladium-Catalyzed Cross-Coupling Reactions of Organoboron Compounds," Chem. Rev., vol. 95, 2457-2483, 1995.
T. Yamamoto et al., "A Novel Type of Poycondensation Utilizing . . . ," Bulletin of the Chemical Society of Japan, vol. 51, No. 7, 2091-2097, 1978.
X. Li et al., "Synthesis and properties of novel poly . . . ," European Polymer Journal, vol. 41, 2923-2933, 2005.
R.D. Miller et al., "Polysilane High Polymers", Che. Rev., vol. 89, 1359-1410, 1989.

* cited by examiner

POLYMER COMPOUND AND LIGHT EMITTING ELEMENT USING SAME

CROSS-REFERENCE TO RELATED APPLICATION

This application is a Section 371 of International Application No. PCT/JP2013/058841, filed Mar. 26, 2013, which was published in the Japanese language on Oct. 10, 2013, under International Publication No. WO 2013/146806 A1, and the disclosure of which is incorporated herein by reference.

TECHNICAL FIELD

The present invention relates to a polymer compound and to a composition, an organic film, an insolubilized organic film, a light emitting device, a planar light source and a display device comprising the polymer compound.

BACKGROUND ART

As polymer compounds used for production of organic electroluminescence devices (hereunder referred to as "light emitting devices") there are known, for example, polymer compounds comprising a repeating unit derived from an arylamine (Patent Literature 1), polymer compounds comprising a repeating unit derived from fluorene having a benzocyclobutane structure (Patent Literature 2), and polymer compounds comprising as a repeating unit a phenylene group with a substituent at a specific site (Patent Literature 3).

CITATION LIST

Patent Literature

[Patent Literature 1] Japanese Unexamined Patent Application Publication No. 2004-143419
[Patent Literature 2] Japanese Unexamined Patent Application Publication No. 2008-106241
[Patent Literature 3] Japanese Unexamined Patent Application Publication No. 2010-189630

SUMMARY OF INVENTION

Technical Problem

However, light emitting devices employing such polymer compounds have not always been adequate in terms of luminous efficiency.
It is therefore an object of the present invention to provide a polymer compound that is useful for production of a light emitting device with excellent luminous efficiency. It is another object of the invention to provide a composition, an organic film, an insolubilized film, a light emitting device, a planar light source and a display device comprising the polymer compound.

Solution to Problem

Specifically, the invention provides the following polymer compound, and composition, organic film, insolubilized organic film, light emitting device, planar light source and display device comprising the polymer compound.
[1] A polymer compound comprising:
a constitutional unit represented by the following formula (1),
a constitutional unit represented by the following formula (2), and
a constitutional unit represented by the following formula (3) and/or a constitutional unit represented by the following formula (4').

[Chemical Formula 1]

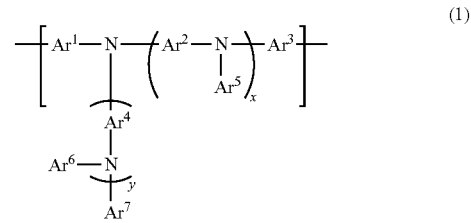

(1)

[In the formula,
$Ar^1$ and $Ar^3$ each independently represent an unsubstituted or substituted arylene group or an unsubstituted or substituted divalent heterocyclic group.
$Ar^2$ and $Ar^4$ each independently represent an unsubstituted or substituted arylene group, an unsubstituted or substituted divalent heterocyclic group, or a divalent group having two or more identical or different linked groups selected from arylene groups and divalent heterocyclic groups (the divalent group may be substituted).
$Ar^5$, $Ar^6$ and $Ar^7$ each independently represent a hydrogen atom, an unsubstituted or substituted alkyl group, an unsubstituted or substituted aryl group, or an unsubstituted or substituted monovalent heterocyclic group.
$Ar^1$, $Ar^2$, $Ar^3$, $Ar^4$, $Ar^5$, $Ar^6$ and $Ar^7$ may each be directly bonded to a group other than a group bonded to the nitrogen atom to which the group is bonded, and may be bonded via —O—, —S—, —C(=O)—, —C(=O)—O—, —N($R_a$)—, —C(=O)—N($R_a$)— or —C($R_a$)$_2$—. $R_a$ represents a hydrogen atom, an unsubstituted or substituted alkyl group, an unsubstituted or substituted alkoxy group, an unsubstituted or substituted aryl group, a halogen atom, or an unsubstituted or substituted monovalent heterocyclic group.
When two $R_a$ are present, they may be the same or different.
x and y each independently represent 0 or 1, and x+y=1.]

[Chemical Formula 2]

(2)

[In the formula,
$Ar^8$ represents a (2+p)-valent aromatic hydrocarbon group or a (2+p)-valent heterocyclic group.
$R^1$ represents an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxyl group, a nitro group or a cyano group. When a plurality of $R^1$ are present, they may be the same or different. At least one $R^1$ substitutes a hydrogen atom that is directly bonded to a carbon atom adjacent to the carbon atom forming a bond with another constitutional unit of the aromatic hydrocarbon group or heterocyclic group.
p represents an integer of 1 or greater.]

[Chemical Formula 3]

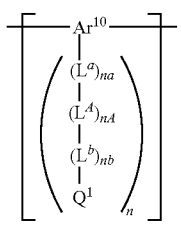
(3)

[In the formula,
na represents an integer of 0 to 3, nb represents an integer of 0 to 12, nA represents 0 or 1 and n represents an integer of 1 to 4.
$Ar^{10}$ represents an unsubstituted or substituted (2+n)-valent aromatic hydrocarbon group or an unsubstituted or substituted (2+n)-valent heterocyclic group.
$L^a$ and $L^b$ each independently represent an unsubstituted or substituted alkylene group or an unsubstituted or substituted phenylene group. When a plurality of $L^a$ are present, they may be the same or different. When a plurality of $L^b$ are present, they may be the same or different.
$L^A$ represents an oxygen atom or a sulfur atom. When a plurality of $L^A$ are present, they may be the same or different.
$Q^1$ represents a monovalent crosslinkable group. When a plurality of $Q^1$ are present, they may be the same or different.
The constitutional unit represented by formula (3) is different from the constitutional unit represented by formula (2).]

[Chemical Formula 4]

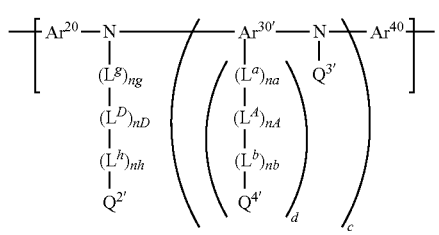
(4')

[In the formula,
c represents 0 or 1, and d represents an integer of 0 to 4,
$Ar^{20}$ and $Ar^{40}$ each independently represent an unsubstituted or substituted arylene group or an unsubstituted or substituted divalent heterocyclic group, and $Ar^{30'}$ represents an unsubstituted or substituted (2+d)-valent aromatic hydrocarbon group, an unsubstituted or substituted (2+d)-valent heterocyclic group, or a (2+d)-valent group in which two or more identical or different groups selected from among divalent aromatic hydrocarbon groups and divalent heterocyclic groups are linked (where the (2+d)-valent group may be substituted).
$Q^{2'}$, $Q^{3'}$ and $Q^{4'}$ represent a monovalent crosslinkable group, an unsubstituted or substituted alkyl group, an unsubstituted or substituted aryl group or an unsubstituted or substituted monovalent heterocyclic group, with the proviso that at least one of $Q^{2'}$, $Q^{3'}$ and $Q^{4'}$ is a monovalent crosslinkable group. When a plurality of $Q^{4'}$ are present, they may be the same or different.
na represents an integer of 0 to 3, nb represents an integer of 0 to 12, and nA represents 0 or 1.
$L^a$ and $L^b$ each independently represent an unsubstituted or substituted alkylene group or an unsubstituted or substituted phenylene group. When a plurality of $L^a$ are present, they may be the same or different. When a plurality of $L^b$ are present, they may be the same or different.
$L^A$ represents an oxygen atom or a sulfur atom. When a plurality of $L^A$ are present, they may be the same or different.
ng represents an integer of 0 to 3, nh represents an integer of 0 to 12, and nD represents 0 or 1.
$L^g$ and $L^h$ each independently represent an unsubstituted or substituted alkylene group or an unsubstituted or substituted phenylene group. When a plurality of $L^g$ are present, they may be the same or different. When a plurality of $L^h$ are present, they may be the same or different.
$L^D$ represents an oxygen atom or a sulfur atom. When a plurality of $L^D$ are present, they may be the same or different.
The constitutional unit represented by formula (4') differs from the constitutional unit represented by formula (1).]
[2] A composition comprising a polymer compound according to [1], and at least one material selected from the group consisting of hole transport materials, electron transport materials and light-emitting materials.
[3] An organic film comprising a polymer compound according to [1].
[4] An insolubilized organic film that has been insolubilized to a solvent by heating an organic film according to [3].
[5] A light emitting device having an organic film according to [3] or an insolubilized organic film according to [4].

Advantageous Effects of Invention

According to the invention it is possible to provide a polymer compound that is useful for production of a light emitting device with excellent luminous efficiency. According to the invention it is possible to provide a composition, an organic film, an insolubilized organic film, a light emitting device, a planar light source and a display device comprising the polymer compound.

DESCRIPTION OF EMBODIMENTS

The terms used throughout the present specification will now be explained, with examples where necessary.
Throughout the present specification, "Me" refers to methyl, "Et" refers to ethyl, "Ph" refers to phenyl, "t-Bu" refers to tert-butyl, "n-Bu" refers to n-butyl, "n-Hex" refers to n-hexyl and "n-Oct" refers to n-octyl.
The term "constitutional unit" refers to a unit structure of which at least one is present in the polymer compound. The "constitutional unit" is preferably present in the polymer compound as a "repeating unit" (that is, a unit structure of which two or more are present in the polymer compound).
The term "$C_x$-$C_y$" (where x and y are positive integers satisfying x<y) means that the number of carbon atoms of the partial structure corresponding to the functional group name immediately following the term is between x and y. That is, it means that when an organic group immediately following "$C_x$-$C_y$" is an organic group named with a combination of a plurality of functional group names (for example, a $C_x$-$C_y$ alkoxyphenyl group), the number of carbon atoms of the partial structure corresponding to the functional group name among the a plurality of functional group names that immediately follows "$C_x$—$C_y$," (for example, alkoxy), is between x and y. For example, "$C_1$-$C_{12}$ alkyl group" means an alkyl group with 1 to 12 carbon atoms, and "$C_1$-$C_{12}$ alkoxyphenyl group" means a phenyl group having "an alkoxy group with 1 to 12 carbon atoms".

Throughout the present specification, the term "unsubstituted or substituted" means optionally substituted with the functional group mentioned immediately after the term. For example, "unsubstituted or substituted alkyl group" means "an unsubstituted alkyl group or an alkyl group having a substituent".

Substituents include alkyl groups, alkoxy groups, alkylthio groups, aryl groups, aryloxy groups, arylthio groups, alkenyl groups, alkynyl groups, amino groups, silyl groups, halogen atoms, acyl groups, acyloxy groups, oxycarbonyl groups, monovalent heterocyclic groups, heterocyclooxy groups, heterocyclothio groups, imine residues, amide compound residues, acid imide residues, carboxyl groups, hydroxy groups, nitro groups and cyano groups. These groups may further have substituents selected from among those mentioned above.

An "alkyl group" may have a substituent, and may be a straight-chain alkyl group, a branched alkyl group or a cyclic alkyl group (cycloalkyl group). Unless otherwise specified, the number of carbon atoms of a straight-chain alkyl group is preferably 1 to 20, more preferably 1 to 15 and even more preferably 1 to 12, not counting the carbon atoms of substituents. Unless otherwise specified, the number of carbon atoms of a branched alkyl group or a cycloalkyl group is preferably 3 to 20, more preferably 3 to 15 and even more preferably 3 to 12, not counting the carbon atoms of substituents.

Examples of alkyl groups include methyl, ethyl, propyl, isopropyl, butyl, isobutyl, sec-butyl, tert-butyl, pentyl, isoamyl, hexyl, cyclohexyl, heptyl, octyl, 2-ethylhexyl, nonyl, decyl, 3,7-dimethyloctyl and dodecyl groups.

An "alkoxy group" may have a substituent, and may be a straight-chain alkoxy group, a branched alkoxy group or a cyclic alkoxy group (cycloalkoxy group). Unless otherwise specified, the number of carbon atoms of a straight-chain alkoxy group is preferably 1 to 20, more preferably 1 to 15 and even more preferably 1 to 12, not counting the carbon atoms of substituents. Unless otherwise specified, the number of carbon atoms of a branched alkoxy group or a cyclic alkoxy group is preferably 3 to 20, more preferably 3 to 15 and even more preferably 3 to 12, not counting the carbon atoms of substituents. Examples of alkoxy groups include methoxy, ethoxy, propyloxy, isopropyloxy, butoxy, isobutoxy, sec-butoxy, tert-butoxy, pentyloxy, hexyloxy, cyclohexyloxy, heptyloxy, octyloxy, 2-ethylhexyloxy, nonyloxy, decyloxy, 3,7-dimethyloctyloxy and dodecyloxy groups.

An "alkylthio group" may have a substituent, and may be a straight-chain alkylthio group, a molecular chain alkylthio group or a cyclic alkylthio group (cycloalkylthio group). Unless otherwise specified, the number of carbon atoms of a straight-chain alkylthio group is preferably 1 to 20, more preferably 1 to 15 and even more preferably 1 to 12, not counting the carbon atoms of substituents. Unless otherwise specified, the number of carbon atoms of a branched alkylthio group or a cycloalkylthio group is preferably 3 to 20, more preferably 3 to 15 and even more preferably 3 to 12, not counting the carbon atoms of substituents.

Examples of alkylthio groups include methylthio, ethylthio, propylthio, isopropylthio, butylthio, isobutylthio, sec-butylthio, tert-butylthio, pentylthio, hexylthio, cyclohexylthio, heptylthio, octylthio, 2-ethylhexylthio, nonylthio, decylthio, 3,7-dimethyloctylthio and dodecylthio groups.

An "aryl group" is an atomic group remaining after removing one hydrogen atom directly bonded to a carbon atom composing the ring of an aromatic hydrocarbon. An aryl group may have a substituent, and aryl groups include groups with benzene rings and groups with fused rings. Unless otherwise specified, the number of carbon atoms of an aryl group is preferably 6 to 60, more preferably 6 to 48 and even more preferably 6 to 30, not counting the carbon atoms of substituents.

Examples of aryl groups include phenyl, 1-naphthyl, 2-naphthyl, 1-anthracenyl, 2-anthracenyl, 9-anthracenyl and 2-fluorenyl groups.

An "aryloxy group" is a group represented by —O—$Ar^{11}$ (where $Ar^{11}$ represents the aforementioned aryl group), the aryl group of $Ar^{11}$ being optionally substituted. Unless otherwise specified, the number of carbon atoms of an aryloxy group is preferably 6 to 60, more preferably 6 to 48 and even more preferably 6 to 30, not counting the carbon atoms of substituents.

Examples of aryloxy groups include phenoxy, 1-naphthyloxy, 2-naphthyloxy, 1-anthracenyloxy, 2-anthracenyloxy, 9-anthracenyloxy and 2-fluorenyloxy groups.

An "arylthio group" is a group represented by —S—$Ar^{12}$ (where $Ar^{12}$ represents the aforementioned aryl group), the aryl group of $Ar^{12}$ being optionally substituted. Unless otherwise specified, the number of carbon atoms of a straight-chain arylthio group is preferably 6 to 60, more preferably 6 to 48 and even more preferably 6 to 30, not counting the carbon atoms of substituents.

Examples of arylthio groups include phenylthio, 1-naphthylthio, 2-naphthylthio, 1-anthracenylthio, 2-anthracenylthio, 9-anthracenylthio and 2-fluorenylthio groups.

An "alkenyl group" may have a substituent, and may be a straight-chain alkenyl group, a branched alkenyl group or a cyclic alkenyl group. Unless otherwise specified, the number of carbon atoms of a straight-chain alkenyl group is preferably 2 to 20, more preferably 2 to 15 and even more preferably 2 to 10, not counting the carbon atoms of substituents. Unless otherwise specified, the number of carbon atoms of a branched alkenyl group or a cyclic alkenyl group is preferably 3 to 20, more preferably 3 to 15 and even more preferably 3 to 10, not counting the carbon atoms of substituents.

Examples of alkenyl groups include vinyl, 1-propenyl, 2-propenyl, 1-butenyl, 2-butenyl, 1-pentenyl, 2-pentenyl, 1-hexenyl, 2-hexenyl and 1-octenyl groups.

An "alkynyl group" may have a substituent, and may be a straight-chain alkynyl group, a branched alkynyl group or a cyclic alkynyl group. Unless otherwise specified, the number of carbon atoms of a straight-chain alkynyl group is preferably 2 to 20, more preferably 2 to 15 and even more preferably 2 to 10, not counting the carbon atoms of substituents. Unless otherwise specified, the number of carbon atoms of a branched alkynyl or a cyclic alkynyl group is preferably 3 to 20, more preferably 3 to 15 and even more preferably 3 to 10, not counting the carbon atoms of substituents.

Examples of alkynyl groups include ethynyl, 1-propynyl, 2-propynyl, 1-butynyl, 2-butynyl, 1-pentynyl, 2-pentynyl, 1-hexynyl, 2-hexynyl and 1-octynyl groups.

An "amino group" may have a substituent, and it is preferably an amino group substituted with one or two substituents selected from the group consisting of alkyl, aryl, arylalkyl and monovalent heterocyclic groups (hereunder also referred to as "substituted amino group"). The substituent may be further substituted (hereunder, substituents that further substitute substituents of organic groups may be referred to as "secondary substituents"). The number of carbon atoms in a substituted amino group is preferably 1 to 60, more preferably 2 to 48 and even more preferably 2 to 40, not including the number of carbon atoms of the secondary substituents.

Substituted amino groups include methylamino, dimethylamino, ethylamino, diethylamino, propylamino, dipropylamino, isopropylamino, diisopropylamino, butylamino, isobutylamino, sec-butylamino, tert-butylamino, pentylamino, hexylamino, heptylamino, octylamino, 2-ethylhexylamino, nonylamino, decylamino, 3,7-dimethyloctylamino, dodecylamino, cyclopentylamino, dicyclopentylamino, cyclohexylamino, dicyclohexylamino, ditrifluoromethylamino, phenylamino, diphenylamino, $C_1$-$C_{12}$ alkoxyphenylamino, bis($C_1$-$C_{12}$ alkoxyphenyl)amino, $C_1$-$C_{12}$ alkylphenylamino, bis($C_1$-$C_{12}$ alkylphenyl)amino, 1-naphthylamino, 2-naphthylamino, pentafluorophenylamino, pyridylamino, pyridazinylamino, pyrimidinylamino, pyrazinylamino, triazinylamino, phenyl-$C_1$-$C_{12}$ alkylamino, $C_1$-$C_{12}$ alkoxyphenyl-$C_1$-$C_{12}$ alkylamino, di($C_1$-$C_{12}$ alkoxyphenyl-$C_1$-$C_{12}$ alkyl)amino, $C_1$-$C_{12}$ alkylphenyl-$C_1$-$C_{12}$ alkylamino, di($C_1$-$C_{12}$ alkylphenyl-$C_1$-$C_{12}$ alkyl)amino, 1-naphthyl-$C_1$-$C_{12}$ alkylamino and 2-naphthyl-$C_1$-$C_{12}$ alkylamino groups.

A "silyl group" may have a substituent, but preferably it is a silyl group substituted with 1 to 3 substituents selected from the group consisting of alkyl, aryl, arylalkyl and monovalent heterocyclic groups (hereunder referred to as "substituted silyl group"). The substituents may have secondary substituents. The number of carbon atoms in a substituted silyl group is preferably 1 to 60, more preferably 3 to 48 and even more preferably 3 to 40, not including the number of carbon atoms of secondary substituents.

Substituted silyl groups include trimethylsilyl, triethylsilyl, tripropylsilyl, tri-isopropylsilyl, dimethyl-isopropylsilyl, diethyl-isopropylsilyl, tert-butyldimethylsilyl, pentyldimethylsilyl, hexyldimethylsilyl, heptyldimethylsilyl, octyldimethylsilyl, 2-ethylhexyl-dimethylsilyl, nonyldimethylsilyl, decyldimethylsilyl, 3,7-dimethyloctyl-dimethylsilyl, dodecyldimethylsilyl, phenyl-$C_1$-$C_{12}$ alkylsilyl, $C_1$-$C_{12}$ alkoxyphenyl-$C_1$-$C_{12}$ alkylsilyl, $C_1$-$C_{12}$ alkylphenyl-$C_1$-$C_{12}$ alkylsilyl, 1-naphthyl-$C_1$-$C_{12}$ alkylsilyl, 2-naphthyl-$C_1$-$C_{12}$ alkylsilyl, phenyl-$C_1$-$C_{12}$ alkyldimethylsilyl, triphenylsilyl, tri-p-xylylsilyl, tribenzylsilyl, diphenylmethylsilyl, tert-butyldiphenylsilyl and dimethylphenylsilyl groups.

A "halogen atom" is a fluorine atom, a chlorine atom, a bromine atom or an iodine atom, and is preferably a fluorine atom.

Examples of "acyl groups" include the group —C(=O)—$R^{44}$ (where $R^{44}$ represents the aforementioned alkyl or aryl, or a monovalent heterocyclic group as described below). The alkyl, aryl and monovalent heterocyclic groups for $R^{44}$ may be substituted. Unless otherwise specified, the number of carbon atoms of an acyl group is preferably 2 to 20, more preferably 2 to 18 and even more preferably 2 to 16, not counting the carbon atoms of substituents.

Examples of acyl groups include acetyl, propionyl, butyryl, isobutyryl, pivaloyl and benzoyl groups. Also, acyl groups with substituents include acyl groups with halogen atoms as substituents (for example, trifluoroacetyl and pentafluorobenzoyl).

Examples of "acyloxy groups" include the group —O—C(=O)—$R^{45}$ (where $R^{45}$ represents the aforementioned alkyl or aryl group, or a monovalent heterocyclic group as described below). The alkyl, aryl and monovalent heterocyclic groups for $R^{45}$ may be substituted. Unless otherwise specified, the number of carbon atoms of an acyloxy group is preferably 2 to 20, more preferably 2 to 18 and even more preferably 2 to 16, not counting the carbon atoms of substituents.

Examples of acyloxy groups include acetoxy, propionyloxy, butyryloxy, isobutyryloxy, pivaloyloxy and benzoyloxy groups. Also, acyloxy groups with substituents include acyloxy groups with halogen atoms as substituents (for example, trifluoroacetyloxy and pentafluorobenzoyloxy).

Examples of "oxycarbonyl groups" include the group —C(=O)—O—$R^{46}$ (where $R^{46}$ represents the aforementioned alkyl or aryl group, or a monovalent heterocyclic group as described below). The alkyl, aryl and monovalent heterocyclic groups for $R^{46}$ may be substituted. Unless otherwise specified, the number of carbon atoms of an oxycarbonyl group is preferably 2 to 20, more preferably 2 to 18 and even more preferably 2 to 16, not counting the carbon atoms of substituents.

A "monovalent heterocyclic group" is an atomic group remaining after removing one hydrogen atom from a heterocyclic compound. The monovalent heterocyclic group may have a substituent, and monovalent heterocyclic groups include monocyclic groups and groups with fused rings. Unless otherwise specified, the number of carbon atoms in a monovalent heterocyclic group is preferably 2 to 60, more preferably 3 to 30 and even more preferably 4 to 20, not including the carbon atoms of substituents.

A heterocyclic compound is an organic compound having a cyclic structure, wherein the elements composing the ring include not only carbon atoms but also a heteroatom such as an oxygen atom, a sulfur atom, a nitrogen atom, a phosphorus atom, a boron atom, a silicon atom, a selenium atom, a tellurium atom or an arsenic atom.

Monovalent aromatic heterocyclic groups are preferred as monovalent heterocyclic groups. A "monovalent aromatic heterocyclic group" is an atomic group remaining after removing one hydrogen atom from an aromatic heterocyclic compound. Examples of aromatic heterocyclic compounds include those wherein the heterocyclic ring itself containing a heteroatom is aromatic, such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzophosphole, dibenzofuran or dibenzothiophene, and those wherein the heterocyclic ring itself containing a heteroatom is not aromatic but an aromatic ring is fused to the heterocyclic ring, such as phenoxazine, phenothiazine, dibenzoborole, dibenzosilol or benzopyran.

A "heterocyclooxy group" is —O—$Ar^{13}$ (where $Ar^{13}$ represents the aforementioned monovalent heterocyclic group), and the monovalent heterocyclic group of $Ar^{13}$ may be substituted. Unless otherwise specified, the number of carbon atoms in a heterocyclooxy group is preferably 2 to 60, more preferably 3 to 30 and even more preferably 4 to 20, not including the carbon atoms of substituents.

Examples of heterocyclooxy groups include pyridyloxy, pyridazinyloxy, pyrimidinyloxy, pyrazinyloxy and triazinyloxy groups.

A "heterocyclothio group" is —S—$Ar^{14}$ (where $Ar^{14}$ represents the aforementioned monovalent heterocyclic group), and the monovalent heterocyclic group of $Ar^{14}$ may be substituted. Unless otherwise specified, the number of carbon atoms in a heterocyclothio group is preferably 2 to 60, more preferably 3 to 30 and even more preferably 4 to 20, not including the carbon atoms of substituents.

Examples of heterocyclothio groups include pyridylthio, pyridazinylthio, pyrimidinylthio, pyrazinylthio and triazinylthio groups.

An "imine residue" is a residue remaining after removing "H" from an imine compound represented by the formula: H—N=C($R^{47}$)$_2$ or the formula: H—C($R^{48}$)=N—$R^{49}$. In the formulas, $R^{47}$, $R^{48}$ and $R^{49}$ each independently represent the aforementioned alkyl, aryl, alkenyl, alkynyl or monovalent heterocyclic groups. The alkyl, aryl, alkenyl, alkynyl and monovalent heterocyclic groups for $R^{47}$, $R^{48}$ and $R^{49}$ may be substituted. A plurality of $R^{47}$ may be the same or different, or may be linked together to form a cyclic structure.

Examples of imine residues include groups represented by the following structural formulas.

[Chemical Formula 5]

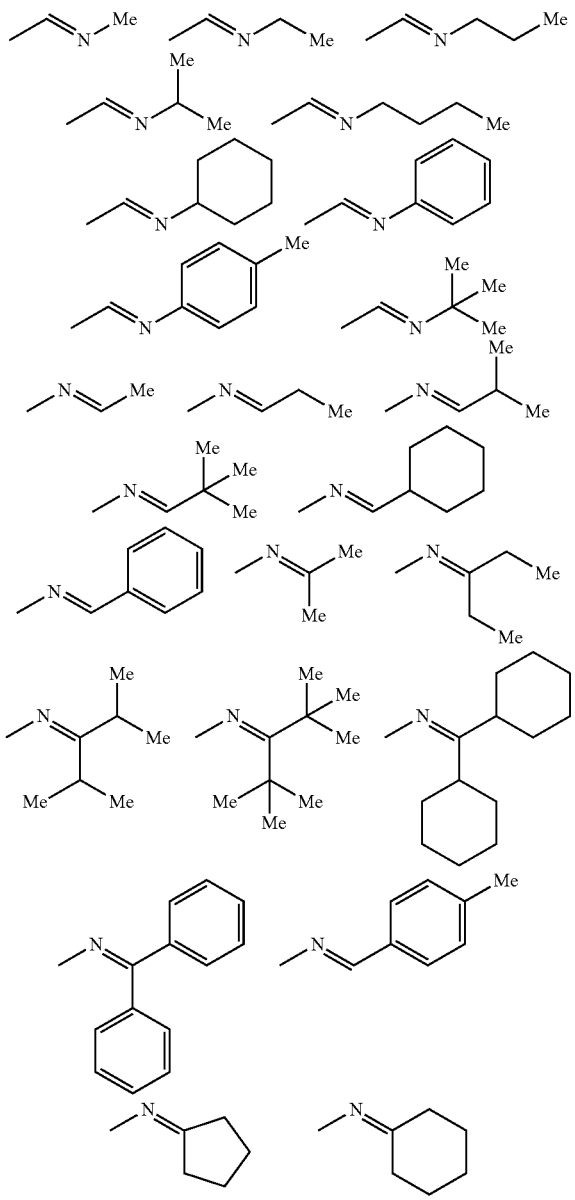

An "amide compound residue" is a residue remaining after removing "H" from an amide compound represented by the formula: H—N($R^{50}$)—C(=O)$R^{51}$ or the formula: H—C(=O)—N($R^{52}$)$_2$. In the formulas, $R^{50}$, $R^{51}$ and $R^{52}$ each independently represent a hydrogen atom or the aforementioned alkyl, aryl, alkenyl, alkynyl or monovalent heterocyclic groups. The alkyl, aryl, alkenyl, alkynyl and monovalent heterocyclic groups for $R^{50}$, $R^{51}$ and $R^{52}$ may be substituted. A plurality of $R^{52}$ may be the same or different, or may be linked together to form a cyclic structure.

Examples of amide compound residues include formamide residue, acetamide residue, propionamide residue, butyroamide residue, benzamide residue, trifluoroacetamide residue, pentafluorobenzamide residue, diformamide residue, diacetamide residue, dipropionamide residue, dibutyroamide residue, dibenzamide residue, ditrifluoroacetamide residue and dipentafluorobenzamide residue.

An acid imide residue is a residue obtained by removing one hydrogen atom directly bonded to the nitrogen atom of an acid imide. The number of carbon atoms for an acid imide residue is preferably 4 to 20, more preferably 4 to 18 and even more preferably 4 to 16.

Examples of acid imide residues include groups represented by the following structural formulas.

[Chemical Formula 6]

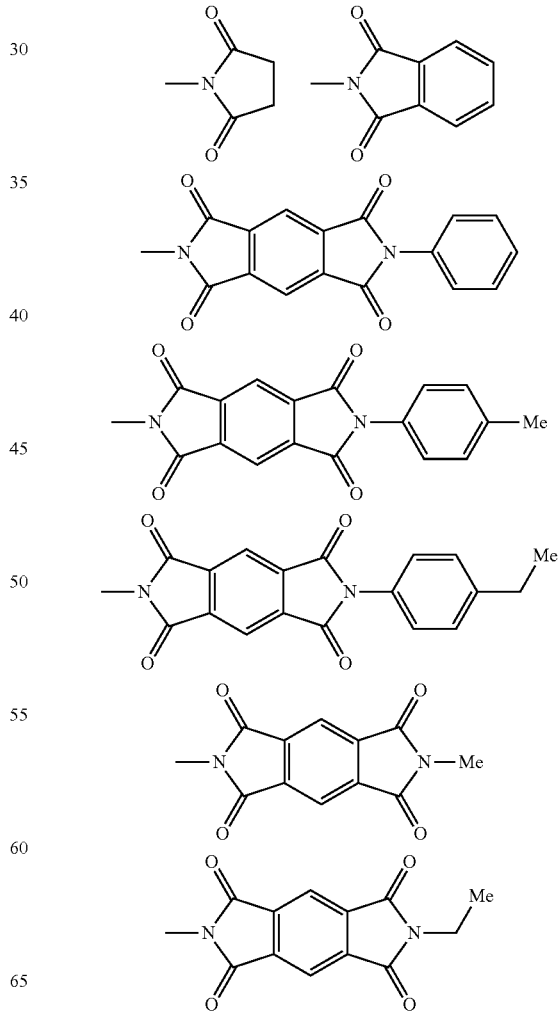

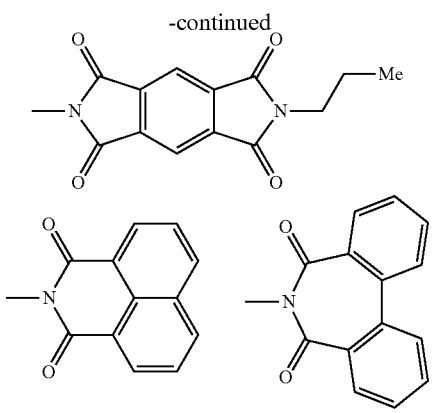

"Unsubstituted or substituted alkyl groups" include unsubstituted alkyl groups and alkyl groups with the aforementioned substituents. Unless otherwise specified, the substituents of these alkyl groups are preferably substituents selected from among alkoxy, aryl, aryloxy, monovalent heterocyclic groups, heterocyclooxy groups and halogen atoms.

"Unsubstituted or substituted aryl groups" include unsubstituted aryl groups and the aforementioned aryl groups with substituents. Unless otherwise specified, the substituents of these aryl groups are preferably substituents selected from among alkyl, alkoxy, aryl, aryloxy, monovalent heterocyclic groups, heterocyclooxy groups and halogen atoms.

"Unsubstituted or substituted monovalent heterocyclic groups" include unsubstituted monovalent heterocyclic groups and monovalent heterocyclic groups having the aforementioned substituents. Unless otherwise specified, the substituents of these monovalent heterocyclic groups are preferably substituents selected from among alkyl, alkoxy, aryl, aryloxy, monovalent heterocyclic groups, heterocyclooxy groups and halogen atoms.

"Unsubstituted or substituted arylene groups" include unsubstituted arylene groups and arylene groups with the aforementioned substituents. Unless otherwise specified, the substituents of these arylene groups are preferably substituents selected from among alkyl, alkoxy, aryl, aryloxy, monovalent heterocyclic groups, heterocyclooxy groups and halogen atoms.

An "arylene group" is an atomic group remaining after removing two hydrogen atoms directly bonded to a carbon atom composing the ring of an aromatic hydrocarbon (preferably an unsubstituted aromatic carbon ring). An arylene group may have a substituent, and arylene groups include groups with benzene rings and groups with fused rings. Unless otherwise specified, the number of carbon atoms of an arylene group is preferably 6 to 60, more preferably 6 to 48 and even more preferably 6 to 30, not counting the carbon atoms of substituents.

Examples of arylene groups include phenylene groups such as 1,4-phenylene, 1,3-phenylene and 1,2-phenylene; naphthalenediyl groups such as 1,4-naphthalenediyl, 1,5-naphthalenediyl, 2,6-naphthalenediyl and 2,7-naphthalenediyl; anthracenediyl groups such as 1,4-anthracenediyl, 1,5-anthracenediyl, 2,6-anthracenediyl and 9,10-anthracenediyl; phenanthrenediyl groups such as 2,7-phenanthrenediyl; dihydrophenanthrenediyl groups such as 9,10-dihydrophenanthrene-2,7-diyl; naphthacenediyl groups such as 1,7-naphthacenediyl, 2,8-naphthacenediyl and 5,12-naphthacenediyl; fluorenediyl groups such as 2,7-fluorenediyl and 3,6-fluorenediyl; pyrenediyl groups such as 1,6-pyrenediyl, 1,8-pyrenediyl, 2,7-pyrenediyl and 4,9-pyrenediyl; perylenediyl groups such as 3,8-perylenediyl, 3,9-perylenediyl and 3,10-perylenediyl; and spirofluorenediyl groups such as 9,9'-spirofluorene-2,7-diyl, 9,9'-spirofluorene-3,6-diyl and 9,9'-spirofluorene-2,2'-diyl.

"Unsubstituted or substituted divalent heterocyclic groups" include unsubstituted divalent heterocyclic groups and divalent heterocyclic groups having the aforementioned substituents. Unless otherwise specified, the substituents of these divalent heterocyclic groups are preferably substituents selected from among alkyl, alkoxy, aryl, aryloxy, monovalent heterocyclic groups, heterocyclooxy groups and halogen atoms.

A "divalent heterocyclic group" is an atomic group remaining after removing two hydrogen atoms from a heterocyclic compound. The divalent heterocyclic group may have a substituent, and divalent heterocyclic groups include monocyclic groups and fused ring groups. Unless otherwise specified, the number of carbon atoms in a divalent heterocyclic group is preferably 2 to 60, more preferably 3 to 30 and even more preferably 4 to 20, not including the carbon atoms of substituents.

Divalent aromatic heterocyclic groups are preferred as divalent heterocyclic groups. A "divalent aromatic heterocyclic group" is an atomic group remaining after removing two hydrogen atoms from an aromatic heterocyclic compound.

Examples of divalent heterocyclic groups include pyridinediyl groups such as 2,5-pyridinediyl and 2,6-pyridinediyl; quinolinediyl groups such as 2,6-quinolinediyl; isoquinolinediyl groups such as 1,4-isoquinolinediyl and 1,5-isoquinolinediyl; quinoxalinediyl groups such as 5,8-quinoxalinediyl; 2,1,3-benzothiadiazole groups such as 2,1,3-benzothiadiazole-4,7-diyl; benzothiazolediyl groups such as 4,7-benzothiazolediyl; dibenzosiloldiyl groups such as 2,7-dibenzosiloldiyl; dibenzofurandiyl groups such as dibenzofuran-4,7-diyl and dibenzofuran-3,8-diyl; and dibenzothiophenediyl groups such as dibenzothiophene-4,7-diyl and dibenzothiophene-3,8-diyl.

Examples of "divalent groups having two or more identical or different linked groups selected from arylene groups and divalent heterocyclic groups" include divalent groups having two groups selected from among arylene groups and divalent heterocyclic groups, linked by a single bond, as in a biphenylylene group such as 2,7-biphenylylene or 3,6-biphenylylene. Unless otherwise specified, the divalent groups may have substituents, and the substituents of the divalent groups are preferably substituents selected from among alkyl, alkoxy, aryl, aryloxy, monovalent heterocyclic groups, heterocyclooxy groups and halogen atoms.

Preferred embodiments of the polymer compound of the invention, and the composition, organic film, insolubilized organic film, light emitting device, planar light source and display device comprising the polymer compound, will now be described in detail.

(Polymer Compound)

The polymer compound of this embodiment comprises a constitutional unit represented by the following formula (1), a constitutional unit represented by the following formula (2), and a constitutional unit represented by the following formula (3) and/or a constitutional unit represented by the following formula (4'). By having such constitutional units, the polymer compound is useful for production of a light emitting device with excellent luminous efficiency.

The polymer compound of this embodiment is preferably a conjugated polymer compound. The term "conjugated polymer compound" refers to a polymer compound in which a conjugated system extends along the main chain backbone, and examples include polyarylenes with arylene groups as repeating units, such as polyfluorene and polyphenylene; polyheteroarylenes with divalent hetero aromatic groups as repeating units, such as polythiophene and polydibenzofuran; polyarylenevinylenes such as polyphenylenevinylene, and copolymers with combinations of these constitutional units. The compound need only have essentially continuous conjugation even if a heteroatom is included in the constitutional unit in the main chain, and for example, it may contain a constitutional unit derived from a triarylamine as the constitutional unit.

The constitutional units contained in the polymer compound of the invention will now be described in detail.

(First Constitutional Unit)

The first constitutional unit in the polymer compound of the invention is a constitutional unit represented by the following formula (1).

[Chemical Formula 7]

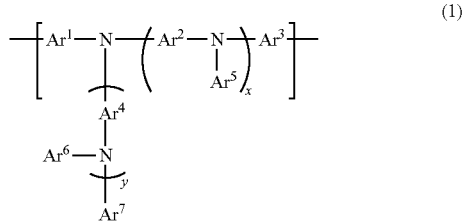

(1)

In formula (1), $Ar^1$ and $Ar^3$ each independently represent an unsubstituted or substituted arylene or an unsubstituted or substituted divalent heterocyclic group.

$Ar^2$ and $Ar^4$ each independently represent an unsubstituted or substituted arylene group, an unsubstituted or substituted divalent heterocyclic group, or a divalent group having two or more identical or different linked groups selected from arylene groups and divalent heterocyclic groups (the group may be substituted).

$Ar^5$, $Ar^6$ and $Ar^7$ each independently represent a hydrogen atom, an unsubstituted or substituted alkyl group, an unsubstituted or substituted aryl group or an unsubstituted or substituted monovalent heterocyclic group.

$Ar^1$, $Ar^2$, $Ar^3$, $Ar^4$, $Ar^5$, $Ar^6$ and $Ar^7$ may each be directly bonded to a group other than a group bonded to the nitrogen atom to which the group is bonded, and may be bonded via —O—, —S—, —C(=O)—, —C(=O)—O—, —N($R_a$)—, —C(=O)—N($R_a$)— or —C($R_a$)$_2$—. $R_a$ represents a hydrogen atom, an unsubstituted or substituted alkyl group, an unsubstituted or substituted alkoxy group, an unsubstituted or substituted aryl group, a halogen atom, or an unsubstituted or substituted monovalent heterocyclic group. When two $R_a$ are present, they may be the same or different.

x and y each independently represent 0 or 1, and preferably x+y=1.

$Ar^5$, $Ar^6$ and $Ar^7$ are preferably unsubstituted or substituted aryl groups, and more preferably formula (1) is the following formula (1A).

[Chemical Formula 8]

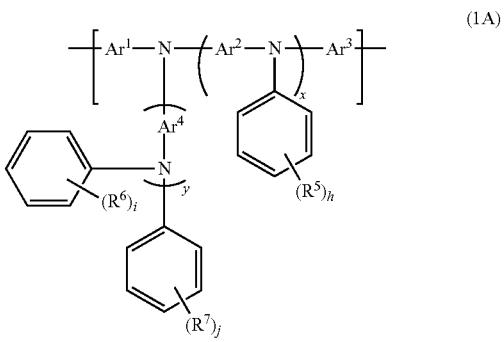

(1A)

In formula (1A), $R^5$, $R^6$ and $R^7$ each independently represent an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxy group, a nitro group or a cyano group. When a plurality of $R^5$ are present, they may be the same or different, when a plurality of $R^6$ are present, they may be the same or different, and when a plurality of $R^7$ are present, they may be the same or different. These groups may also have the aforementioned substituents. $R^5$, $R^6$ and $R^7$ are preferably alkyl, alkoxy or aryl groups, and more preferably alkyl groups.

h, i and j each independently represent an integer of 0 to 5. h, i and j are preferably integers of 0 to 3, and more preferably integers of 1 to 3.

The number of carbon atoms of an arylene group represented by $Ar^1$, $Ar^2$, $Ar^3$ or $Ar^4$ will usually be 6 to 60, preferably 6 to 48, more preferably 6 to 20 and even more preferably 6 to 14, not counting the carbon atoms of substituents.

Examples of arylene groups include phenylene groups (for example, 1,2-phenylene, 1,3-phenylene and 1,4-phenylene), naphthalenediyl groups (for example, 1,4-naphthalenediyl, 2,6-naphthalenediyl and 2,7-naphthalenediyl), anthracenediyl groups (for example, 2,6-anthracenediyl and 9,10-anthracenediyl), phenanthrenediyl groups (for example, 2,7-phenanthrenediyl), dihydrophenanthrenediyl groups (for example, 9,10-dihydrophenanthrene-2,7-diyl), naphthacenediyl groups (for example, 5,12-naphthacenediyl), fluorenediyl groups (for example, 2,7-fluorenediyl and 3,6-fluorenediyl), spirofluorenediyl groups (for example, 9,9'-spirofluorene-2,7-diyl, 9,9'-spirofluorene-3,6-diyl and 9,9'-spirofluorene-2,2'-diyl) and perylenediyl groups (for example, 3,8-perylenediyl), which groups may be substituted.

Examples of divalent heterocyclic groups represented by $Ar^1$, $Ar^2$, $Ar^3$ and $Ar^4$ include 2,5-pyrrolediyl, 2,1,3-benzothiadiazole-4,7-diyl, dibenzofurandiyl, dibenzothiophenediyl and dibenzosiloldiyl, which groups may be substituted.

Examples of divalent groups having two or more identical or different linked groups selected from among arylene groups and divalent heterocyclic groups, represented by $Ar^2$ and $Ar^4$, include groups represented by the following formula (B-1), formula (B-2), formula (B-3), formula (B-4), formula (B-5), formula (B-6) and formula (B-7), with groups represented by formula (B-1) being preferred. These groups may also have the aforementioned substituents. Groups represented by formula (B-1), formula (B-2) and formula (B-3) are sometimes referred to as biphenylylene groups.

[Chemical Formula 9]

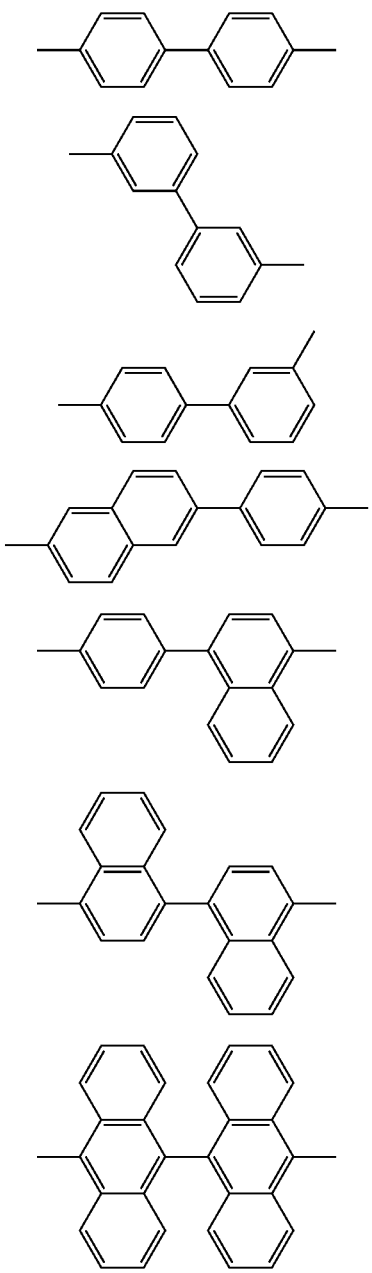

When a group represented by Ar$^1$, Ar$^2$, Ar$^3$ or Ar$^4$ has a substituent, the substituent may be any of the aforementioned substituents, and is preferably alkyl, alkoxy or aryl and more preferably alkyl.

Ar$^1$ and Ar$^3$ are preferably unsubstituted or substituted arylene groups, more preferably unsubstituted or substituted phenylene groups, and even more preferably unsubstituted or substituted 1,4-phenylene groups.

Ar$^2$ or Ar$^4$ is preferably an unsubstituted or substituted arylene or a divalent group having two or more identical or different linked groups selected from among arylene groups and divalent heterocyclic groups (which groups may be substituted), more preferably an unsubstituted or substituted phenylene group, an unsubstituted or substituted biphenylylene group, an unsubstituted or substituted spirofluorenediyl group, an unsubstituted or substituted phenanthrenediyl group, an unsubstituted or substituted dihydrophenanthrenediyl group or an unsubstituted or substituted fluorenediyl group, even more preferably an unsubstituted or substituted fluorenediyl group, and most preferably an unsubstituted or substituted 2,7-fluorenediyl group, for excellent lifespan characteristics of the light emitting device to be produced using the polymer compound of this embodiment.

The groups represented by Ar$^1$ and Ar$^3$ are preferably unsubstituted or substituted phenylene groups and more preferably unsubstituted or substituted 1,4-phenylene groups, for excellent luminous efficiency of the light emitting device to be produced using the polymer compound of this embodiment.

For excellent luminous efficiency of the light emitting device to be produced using the polymer compound of this embodiment, the groups represented by Ar$^2$ and Ar$^4$ are preferably unsubstituted or substituted phenylene, unsubstituted or substituted biphenylylene, unsubstituted or substituted spirofluorenediyl, unsubstituted or substituted phenanthrenediyl, unsubstituted or substituted dihydrophenanthrenediyl or unsubstituted or substituted fluorenediyl groups, and for excellent lifespan characteristics of the light emitting device to be produced using the polymer compound of this embodiment, they are more preferably unsubstituted or substituted fluorenediyl groups and even more preferably unsubstituted or substituted 2,7-fluorenediyl groups.

The group represented by R$_a$ is preferably a hydrogen atom, an unsubstituted alkyl group, an unsubstituted alkoxy group, an unsubstituted aryl group, a halogen atom or an unsubstituted monovalent heterocyclic group.

The definitions and examples of unsubstituted or substituted alkyl groups, unsubstituted or substituted alkoxy groups, unsubstituted or substituted aryl groups, halogen atoms and unsubstituted or substituted monovalent heterocyclic groups represented by R$_a$ are the same definitions and examples of alkyl groups, alkoxy groups, aryl groups, halogen atoms and monovalent heterocyclic groups mentioned above as substituents.

As mentioned above, x and y represent 0 or 1. Specifically, x=0 and y=0, x=0 and y=1, x=1 and y=0, or x=1 and y=1. For example, when Ar$^8$ is a fluorenediyl group, x=0 and y=0, x=0 and y=1, x=1 and y=0, or x=1 and y=1.

As mentioned above, x and y represent 0 or 1, and preferably x+y=1. Specifically, x=0 and y=1, or x=1 and y=0.

More preferably, x and y are x=1 and y=0, for excellent characteristics (for example, luminance life) of the light emitting device to be produced using the polymer compound of this embodiment.

For excellent characteristics (such as luminance life) of the light emitting device to be produced using the polymer compound of this embodiment, the constitutional unit represented by formula (1) is preferably a constitutional unit represented by the following formula (9a), formula (9b), formula (9c), formula (9d), formula (9e) or formula (9f), more preferably a constitutional unit represented by formula (9c), formula (9d) or formula (9e), and even more preferably a constitutional unit represented by formula (9c) or formula (9e).

[Chemical Formula 10]

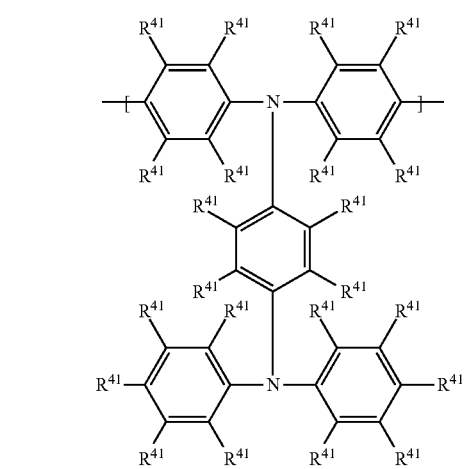
(9a)

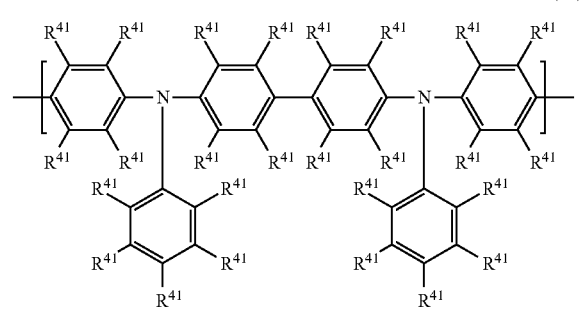
(9b)

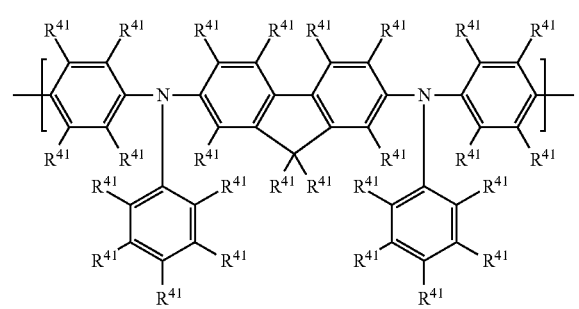
(9c)

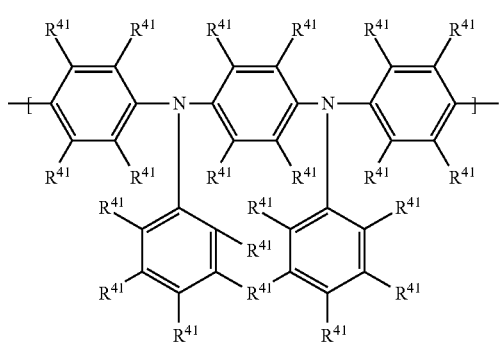
(9d)

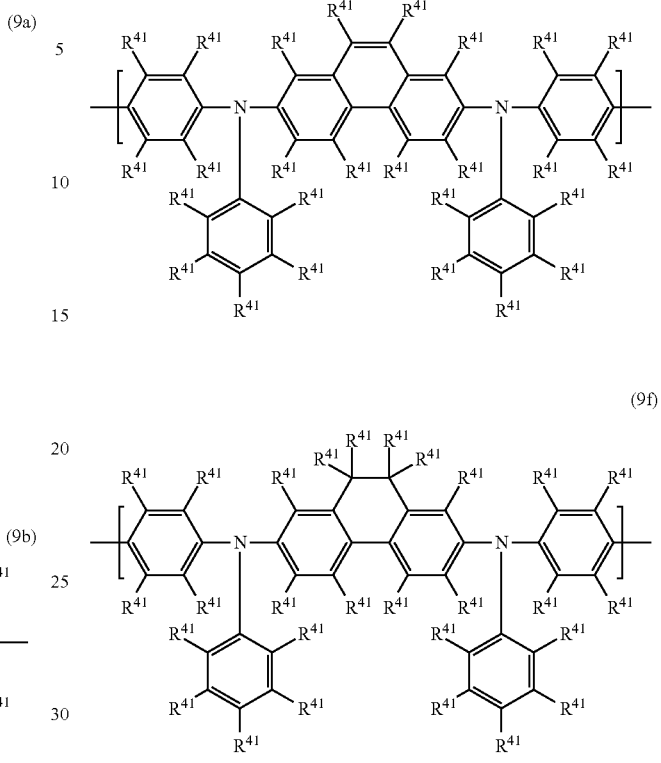
(9e)
(9f)

In formulas (9a) to (9f), $R^{41}$ represents a hydrogen atom, an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxy group, a nitro group or a cyano group, preferably a hydrogen atom, an alkyl group, an alkoxy group, an aryl group, an aryloxy group, an arylalkyl group, an arylalkoxy group, a substituted amino group, an acyl group or a cyano group, and more preferably a hydrogen atom, an alkyl group, an alkoxy group or an aryl group. A plurality of $R^{41}$ may be the same or different, or may be bonded together to form a cyclic structure together with the respective carbon atoms to which they are bonded.

Formulas (9a) to (9f) will usually be constitutional units represented by the following formulas (9-001) to (9-086), preferably constitutional units represented by formulas (9-001) to (9-005), formulas (9-012) to (9-059) or formulas (9-070) to (9-086) and more preferably constitutional units represented by formulas (9-012) to (9-059) or formulas (9-071) to (9-078), and for excellent characteristics (for example, luminance life) of the light emitting device to be produced using the polymer compound of this embodiment, they are even more preferably constitutional units represented by formulas (9-020) to (9-059) or formulas (9-071) to (9-078) and most preferably constitutional units represented by formulas (9-036) to (9-059) or formulas (9-071) to (9-074).

[Chemical Formula 11]
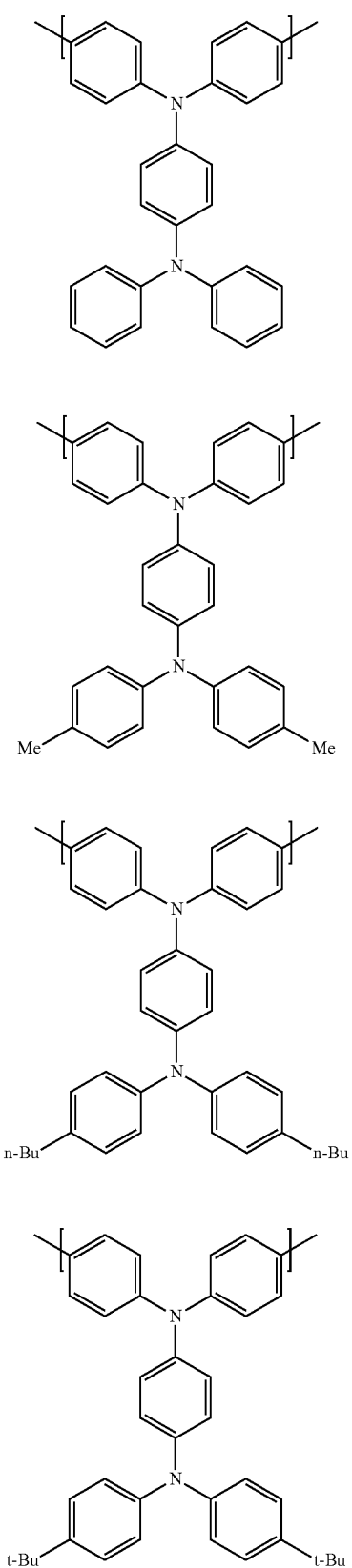
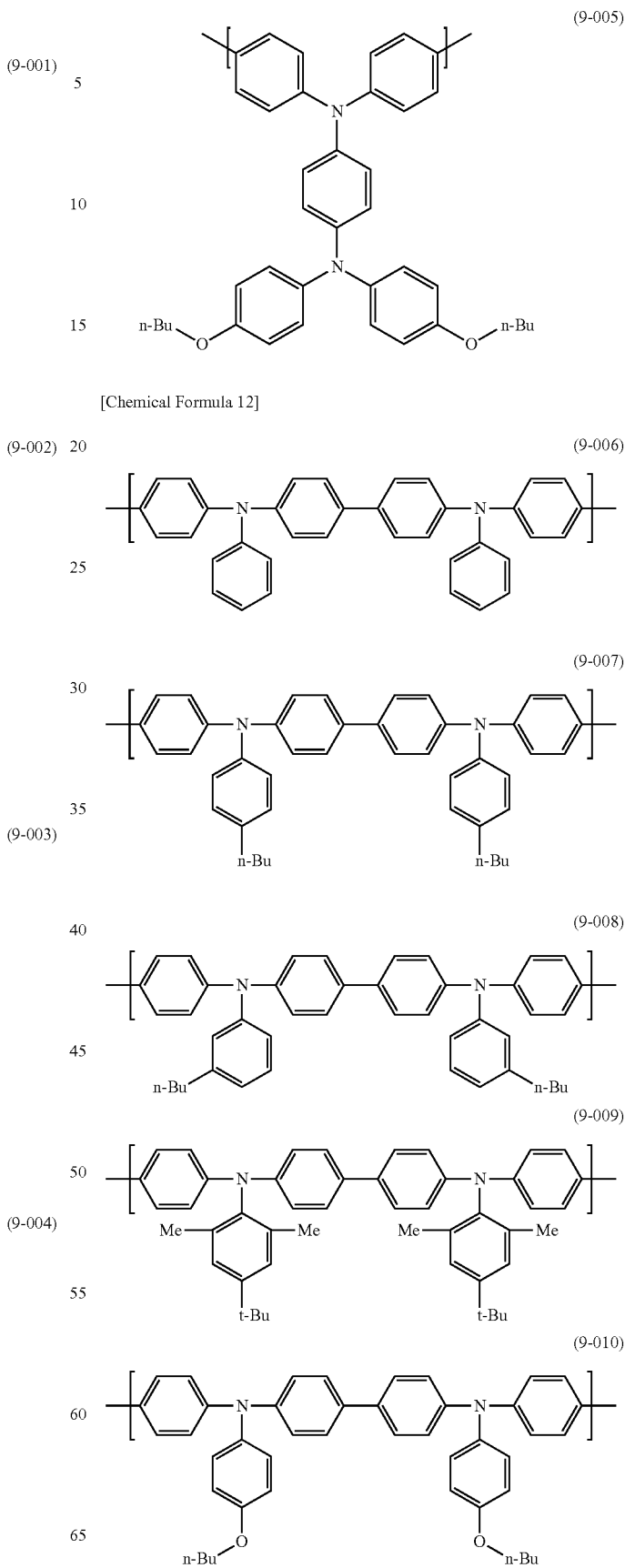

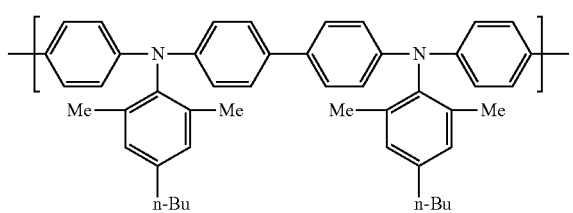
(9-011)
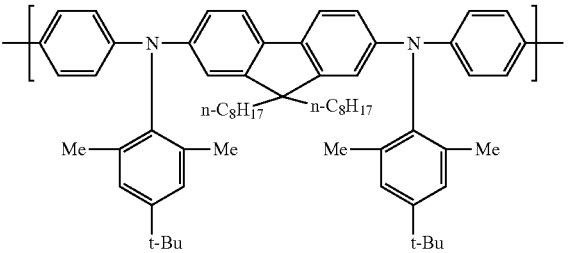
(9-017)
[Chemical Formula 13]
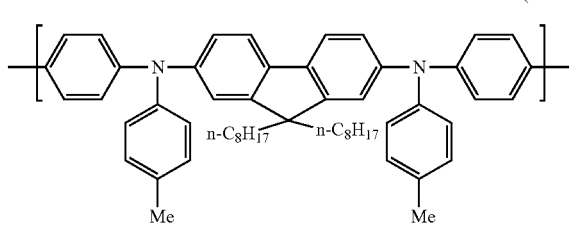
(9-012)
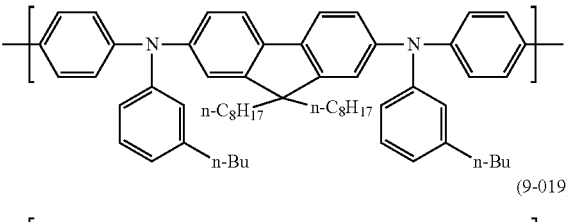
(9-018)
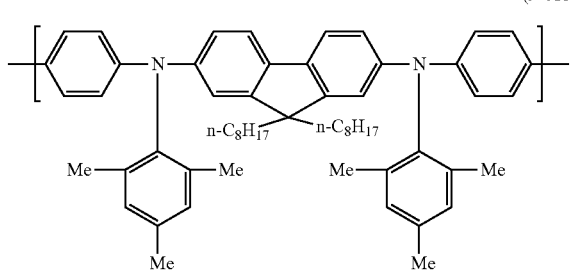
(9-013)
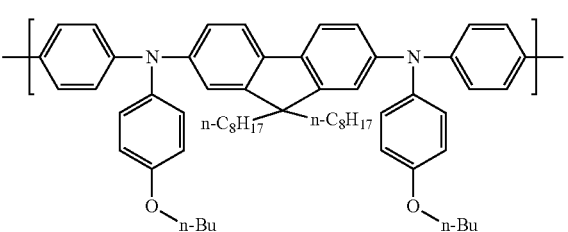
(9-019)
[Chemical Formula 14]
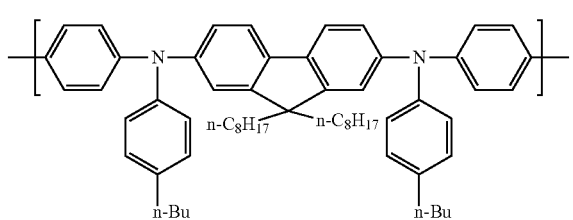
(9-014)
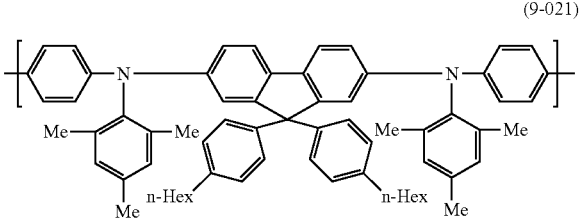
(9-020)
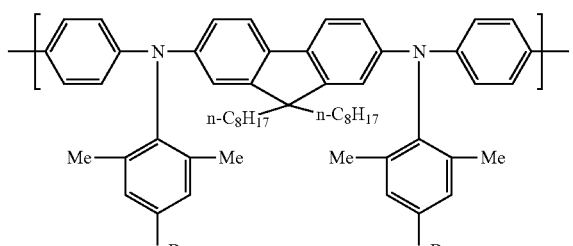
(9-015)
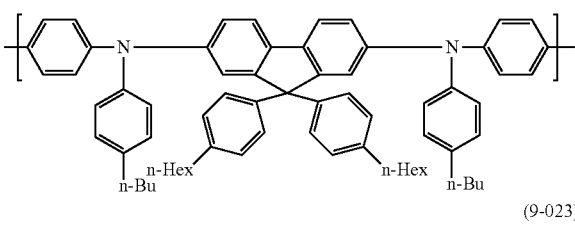
(9-021)
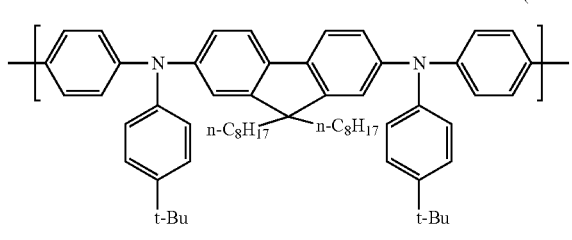
(9-016)
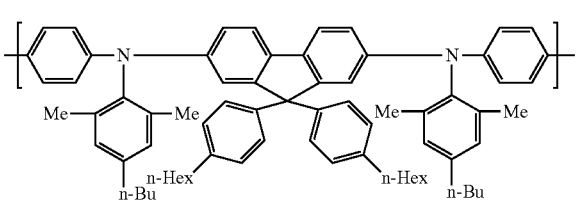
(9-022)
(9-023)

(9-024)
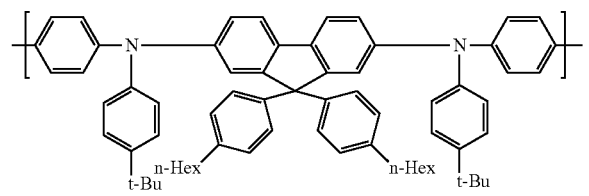
(9-025)
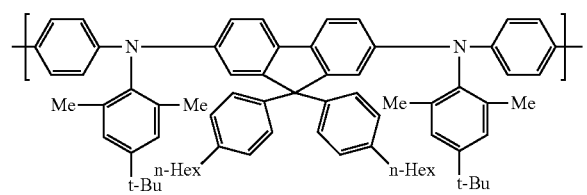
(9-026)
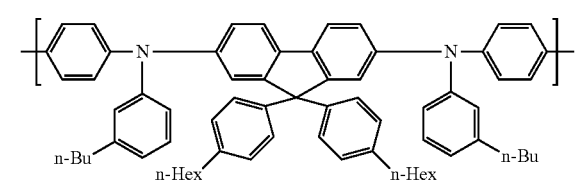
(9-027)
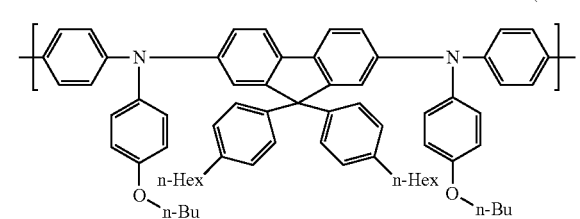
[Chemical Formula 15]
(9-028)
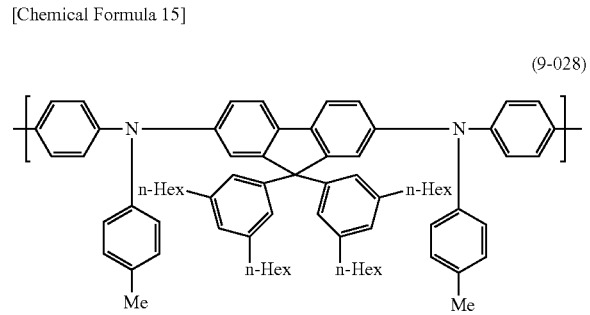
(9-029)
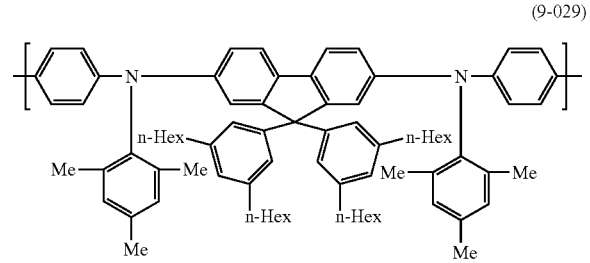
(9-030)
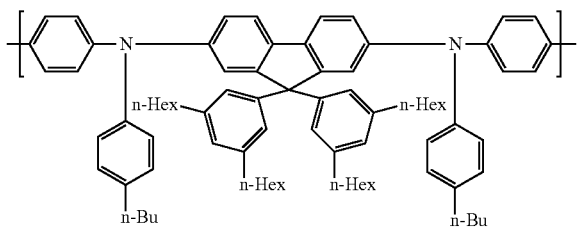
(9-031)
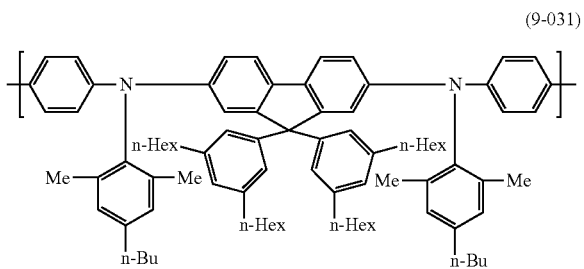
(9-032)
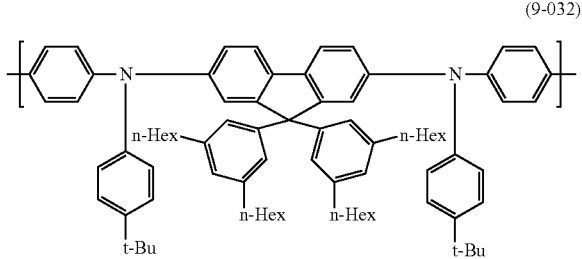
(9-033)
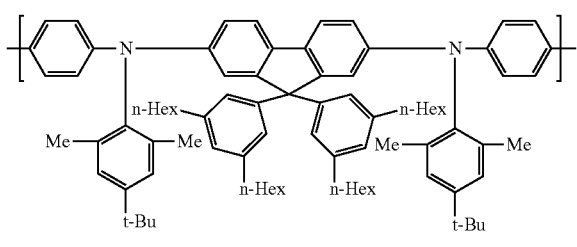
(9-034)
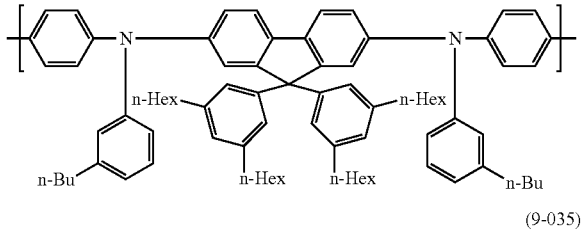
(9-035)
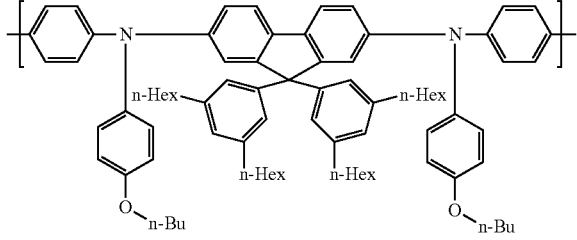

[Chemical Formula 16]
(9-036)
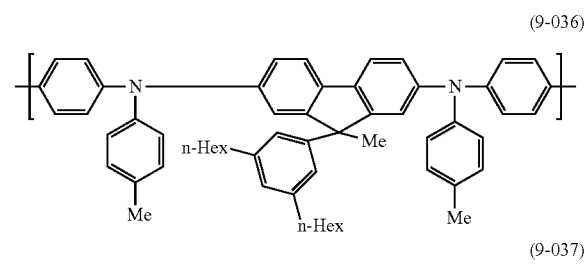
(9-037)
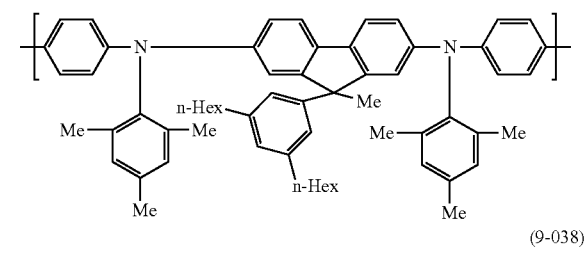
(9-038)
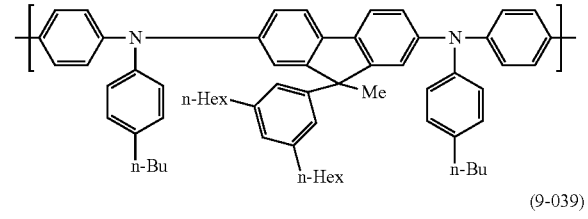
(9-039)
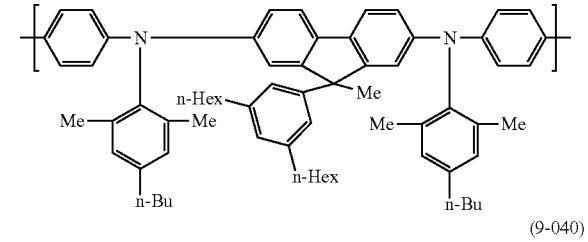
(9-040)
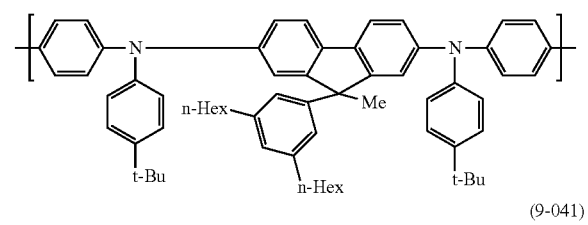
(9-041)
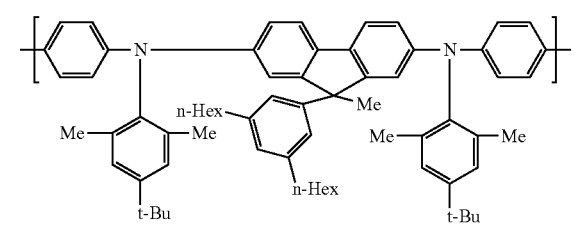
(9-042)
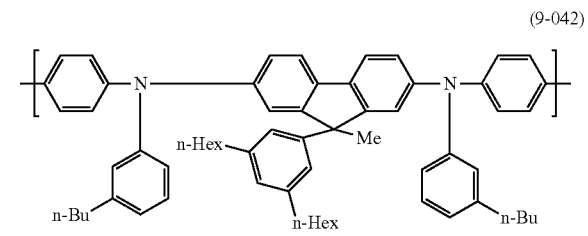
(9-043)
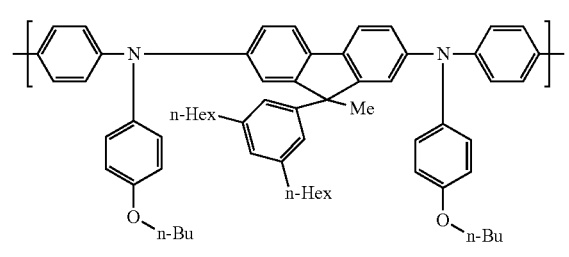
[Chemical Formula 17]
(9-044)
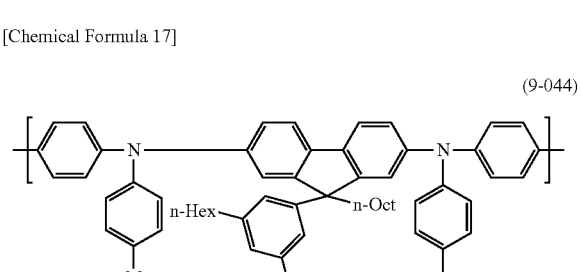
(9-045)
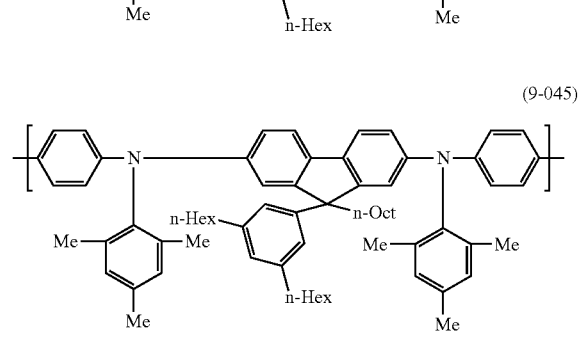
(9-046)
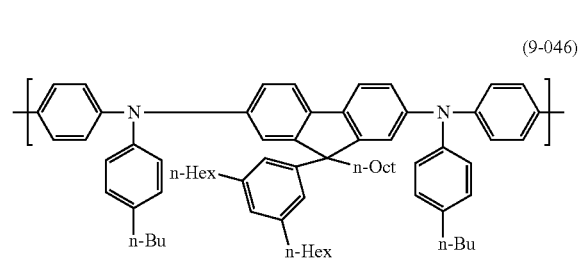
(9-047)
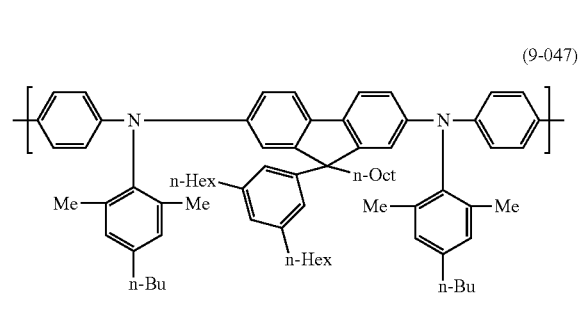
(9-048)
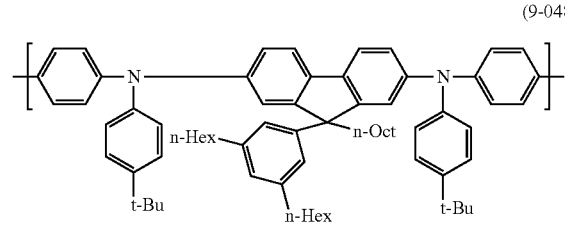

(9-049)
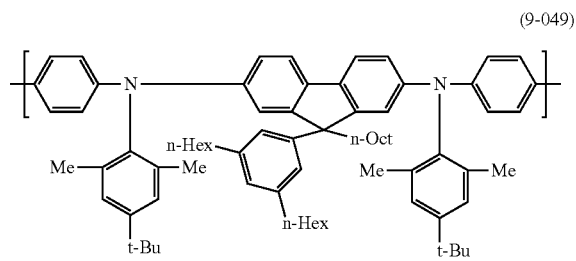
(9-050)
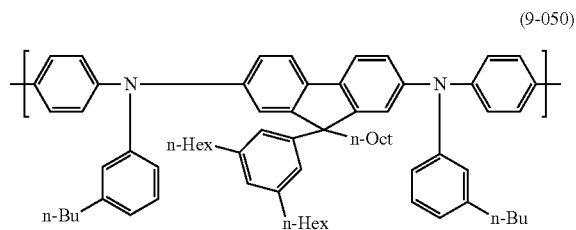
(9-051)
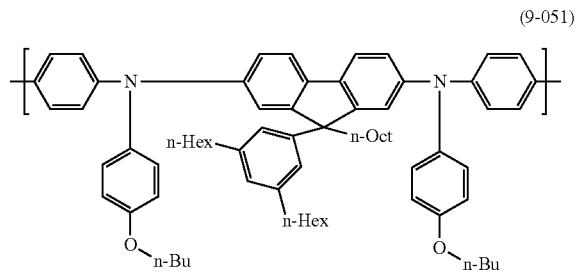
[Chemical Formula 18]
(9-052)
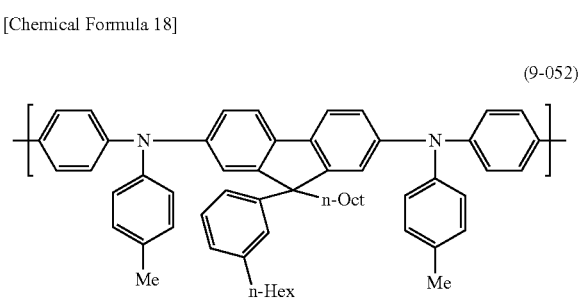
(9-053)
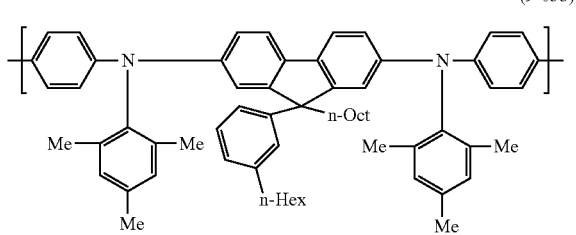
(9-054)
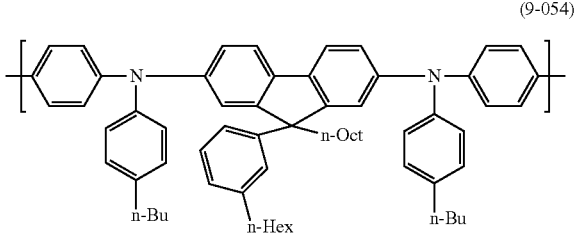
(9-055)
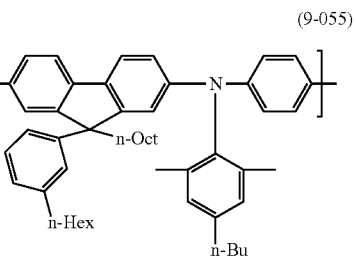
(9-056)
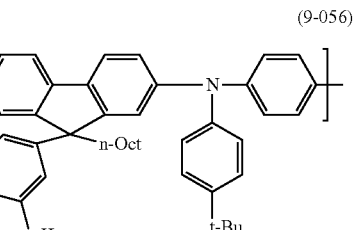
(9-057)
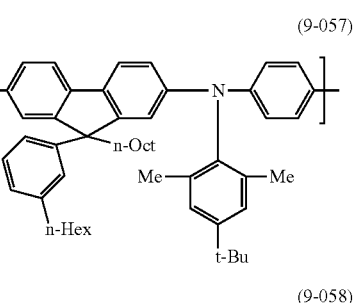
(9-058)
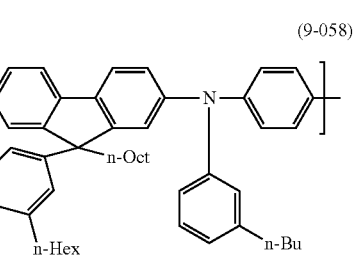
(9-059)
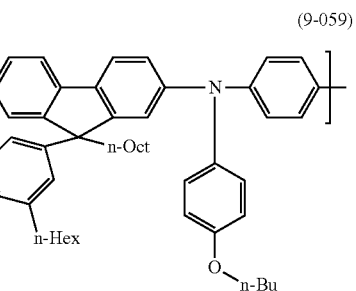
[Chemical Formula 19]
(9-060)

-continued
(9-061)
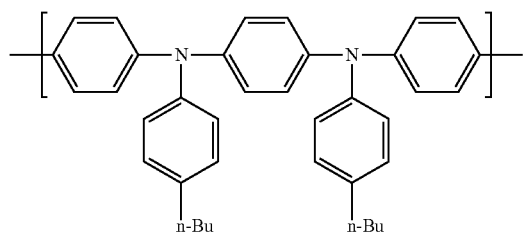
(9-067)
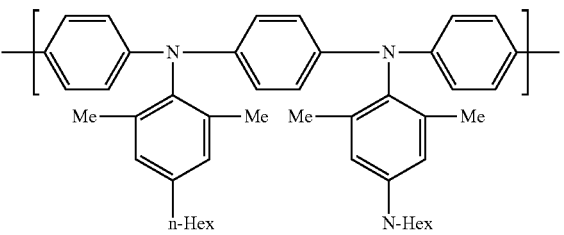
(9-062)
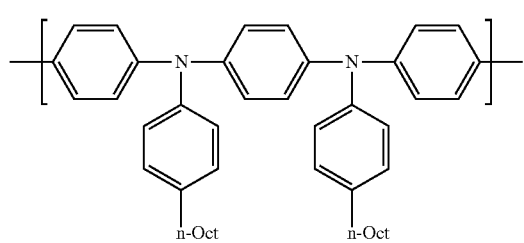
(9-068)
(9-063)
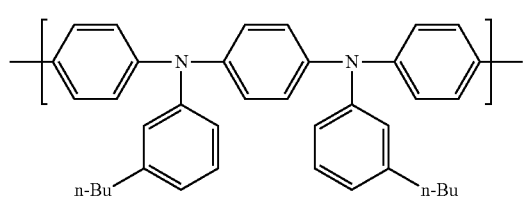
(9-064)
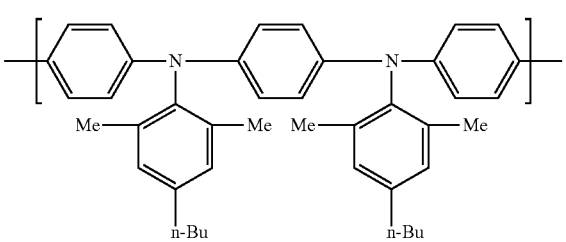
(9--069)
(9-065)
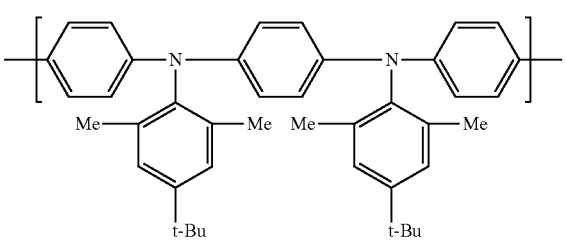
[Chemical Formula 20]
(9-066)
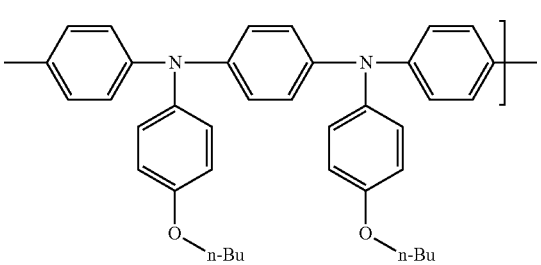
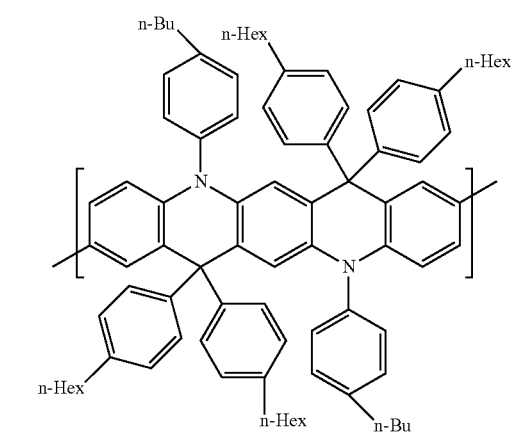

[Chemical Formula 21]
(9-071)
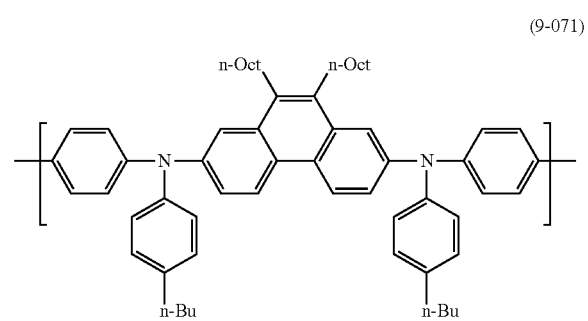
(9-072)
(9-073)
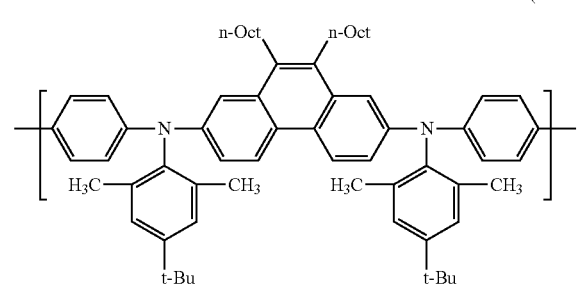
(9-074)
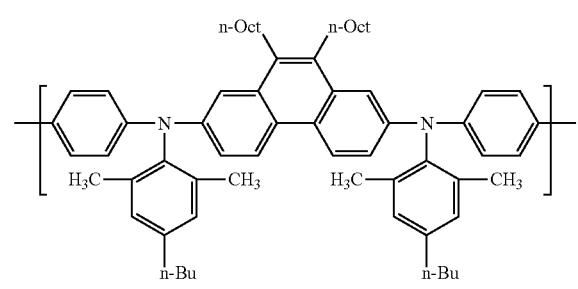
[Chemical Formula 22]
(9-075)
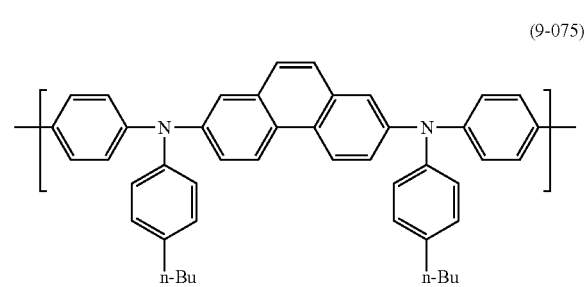
(9-076)
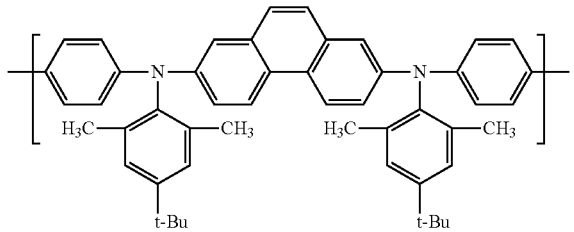
(9-077)
(9-078)
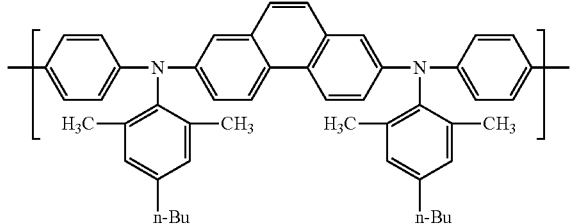
[Chemical Formula 23]
(9-079)
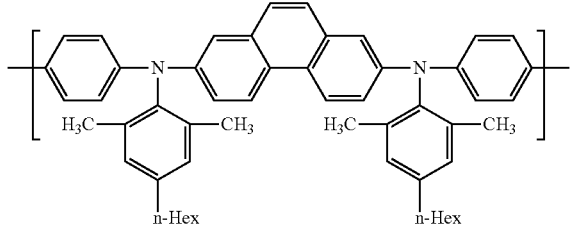
(9-080)
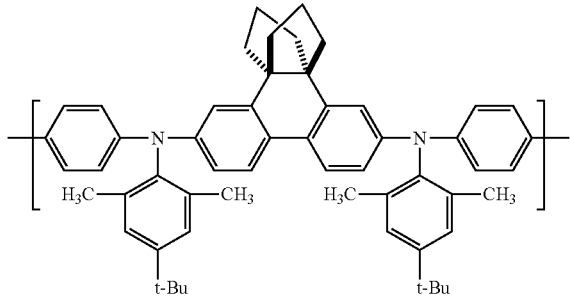

-continued (9-081)

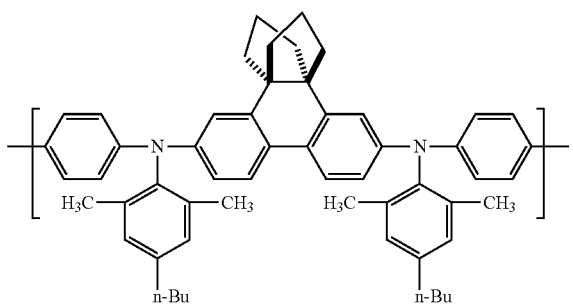

[Chemical Formula 24]

(9-082)

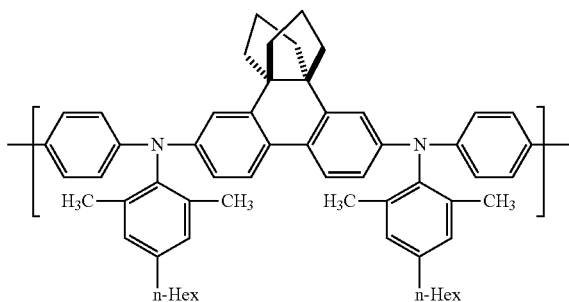

(9-083)

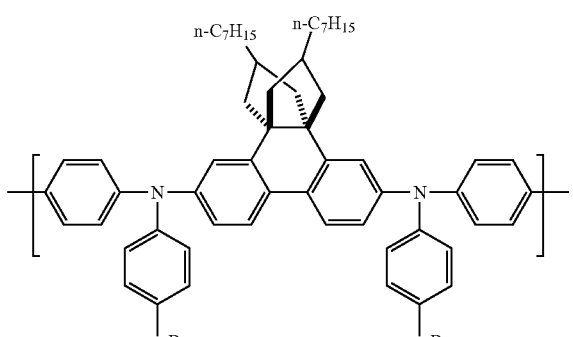

(9-084)

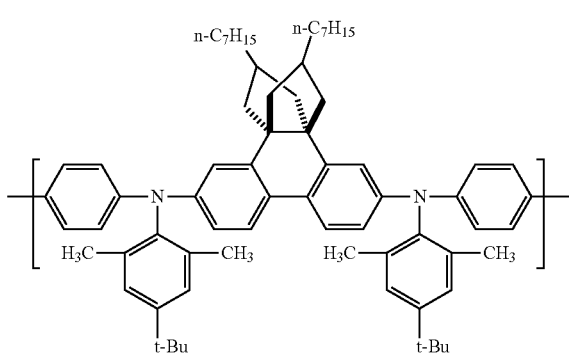

-continued (9-085)

(9-086)

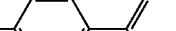

The polymer compound of this embodiment may have one of the aforementioned constitutional units as the first constitutional unit, or it may have a plurality of different constitutional units among the aforementioned constitutional units.

(Second Constitutional Unit)

The second constitutional unit in the polymer compound of the invention is a constitutional unit represented by the following formula (2).

[Chemical Formula 25]

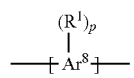

(2)

In formula (2), $Ar^8$ represents a (2+p)-valent aromatic hydrocarbon group or a (2+p)-valent heterocyclic group.

$R^1$ represents an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxyl group, a nitro group or a cyano group. When a plurality of $R^1$ are present, they may be the same or different. At least one $R^1$ substitutes a hydrogen atom that is directly bonded to a carbon atom adjacent to the carbon atom forming a bond with another constitutional unit of the aromatic hydrocarbon group or heterocyclic group.

p represents an integer of 1 or greater.

The (2+p)-valent aromatic hydrocarbon group or (2+p)-valent heterocyclic group represented by $Ar^8$ is the same arylene group or divalent heterocyclic group as represented by $Ar^1$, $Ar^2$, $Ar^3$ and $Ar^4$. Also, the group represented by $Ar^8$ may have any of the aforementioned substituents in addition to $R^1$. The "other constitutional unit" mentioned above may be a constitutional unit represented by formula (2) (that is, a constitutional unit represented by formula (2) may be bonded in a continuing manner).

The number of carbon atoms of the (2+p)-valent aromatic hydrocarbon group represented by $Ar^8$ will usually be 6 to 60, and is preferably 6 to 48, more preferably 6 to 20 and even more preferably 6 to 14. As (2+p)-valent aromatic hydrocarbon groups there are preferred trivalent, tetravalent or pentavalent aromatic hydrocarbon groups, and for easier synthesis of the monomer starting materials, trivalent or tetravalent aromatic hydrocarbon groups are more preferred and tetravalent groups are especially preferred. Here, a "(2+p)-valent aromatic hydrocarbon group" is an atomic group remaining after removing (2+p) hydrogen atoms directly bonded to a carbon atom composing the ring of an aromatic hydrocarbon (preferably an unsubstituted aromatic carbon ring), and it includes groups with benzene rings and groups with fused rings.

The group represented by $Ar^8$ is preferably a (2+p)-valent aromatic hydrocarbon group.

The group represented by $Ar^8$ is preferably a phenylene, naphthalenediyl, phenanthrenediyl, dihydrophenanthrenediyl or fluorenediyl group, more preferably a phenylene or fluorenediyl group and even more preferably a 1,4-phenylene or 2,7-fluorenediyl group, for more excellent luminous efficiency of the light emitting device to be produced using the polymer compound of this embodiment.

The group represented by $R^1$ is preferably an alkyl, alkoxy, aryl, aryloxy, arylalkyl, arylalkoxy, substituted amino, acyl or cyano group, and more preferably it is an alkyl, alkoxy or aryl group.

p represents an integer of 1 or greater as mentioned above, but it is preferably an integer of 1 to 4, and for easier synthesis of the monomer starting materials it is more preferably 1 or 2 and even more preferably 2.

Of the groups represented by formula (2), preferred as those wherein $Ar^8$ is a (2+p)-valent aromatic hydrocarbon group are groups represented by the following formulas (10a) to (10k), and for excellent characteristics (such as luminance life) of the light emitting device to be produced using the polymer compound of this embodiment, there are preferred groups represented by formula (10a), formula (10b), formula (10h), formula (10i), formula (10j) or formula (10k), and there are more preferred groups represented by formula (10a), formula (10h), formula (10j) or formula (10k).

[Chemical Formula 26]

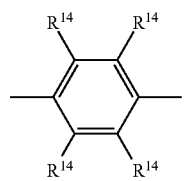
(10a)

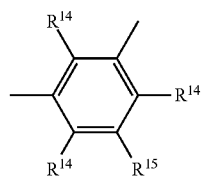
(10b)

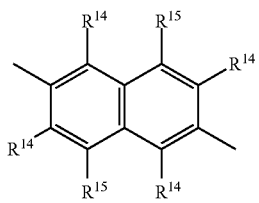
(10c)

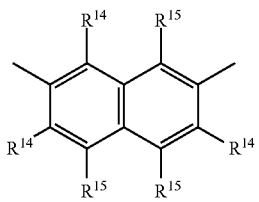
(10d)

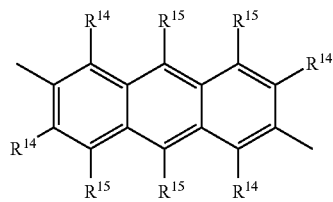
(10e)

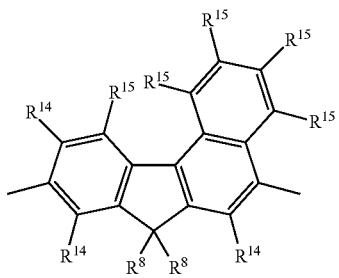
(10f)

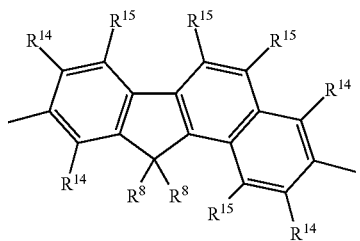
(10g)

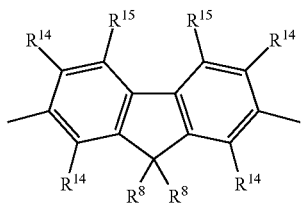
(10h)

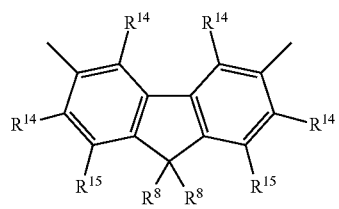
(10i)

-continued

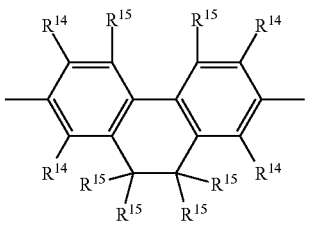
(10j)

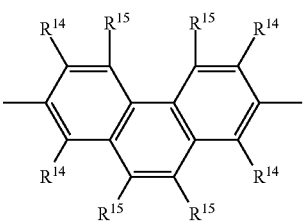
(10k)

Of the groups represented by formula (2), preferred as those wherein $Ar^8$ is a (2+p)-valent heterocyclic group are groups represented by the following formulas (10l) to (10p).

[Chemical Formula 27]

(10l)

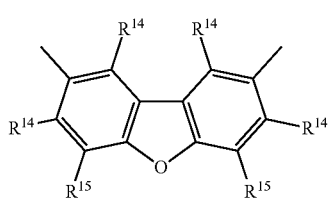
(10m)

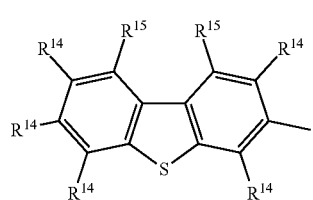
(10n)

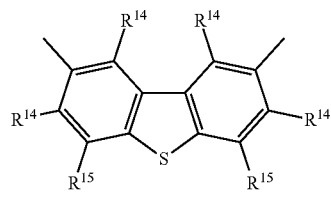
(10o)

-continued

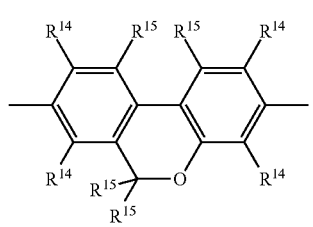
(10p)

In formulas (10a) to (10p), $R^{14}$ and $R^{15}$ represent a hydrogen atom, an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxy group, a nitro group or a cyano group, preferably a hydrogen atom, a alkyl group, an alkoxy group, an aryl group, an aryloxy group, an arylalkyl group, an arylalkoxy group, a substituted amino group, an acyl group or a cyano group, and more preferably a hydrogen atom, an alkyl group, an alkoxy group or an aryl group. A plurality of $R^{14}$ may be the same or different. A plurality of $R^{15}$ may be the same or different. Also, adjacent $R^{14}$ may be bonded together to form a cyclic structure with the respective carbon atoms to which they are bonded, adjacent $R^{15}$ may be bonded together to form a cyclic structure with the respective carbon atoms to which they are bonded, or adjacent $R^{14}$ and $R^{15}$ may be bonded together to form a cyclic structure with the respective carbon atoms to which they are bonded.

In formulas (10a) to (10p), at least one $R^{14}$ group represents a group other than a hydrogen atom (that is, $R^1$).

In formulas (10f) to (10i), $R^8$ represents a hydrogen atom, an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxy group, a nitro group or a cyano group, and preferably it is a hydrogen atom, an alkyl group, an alkoxy group or an aryl group. A plurality of $R^8$ may be the same or different, or may be bonded together to form a cyclic structure together with the respective carbon atoms to which they are bonded.

The constitutional unit represented by formula (2) will usually be a constitutional unit represented by the following formulas (10-1) to (10-173), and is preferably a constitutional unit represented by formulas (10-1) to (10-18) or formulas (10-41) to (10-173) and more preferably a constitutional unit represented by formulas (10-1) to (10-18), formulas (10-41) to (10-76), formulas (10-85) to (10-128) or formulas (10-154) to (10-173), while for excellent characteristics (such as luminance life) of the light emitting device to be produced using the polymer compound of this embodiment, it is even more preferably a constitutional unit represented by formulas (10-1) to (10-18), formulas (10-59) to (10-68), formulas (10-85) to (10-128) or formulas (10-154) to (10-168) and most preferably a constitutional unit represented by formulas (10-1) to (10-18), formulas (10-59) to (10-63), formulas (10-85) to (10-92), formulas (10-101) to (10-104), formulas (10-113) to (10-116), formulas (10-125) to (10-128) or formulas (10-164) to (10-168).
[Chemical Formula 28]
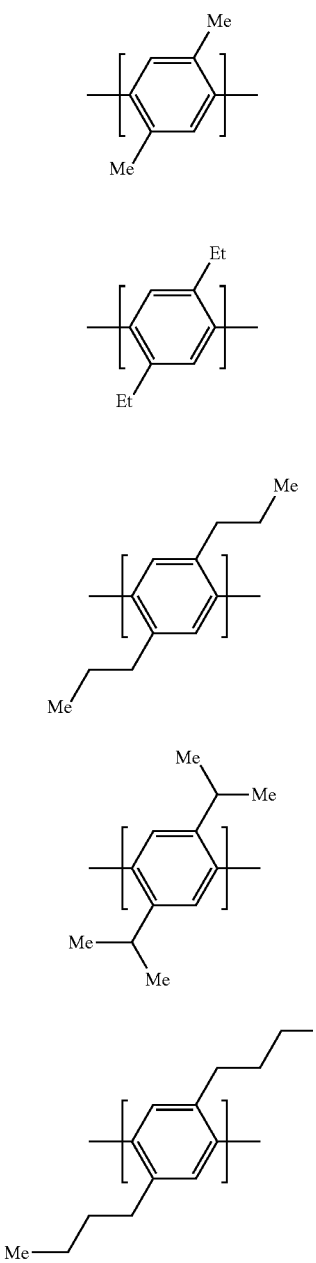
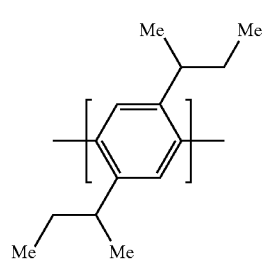
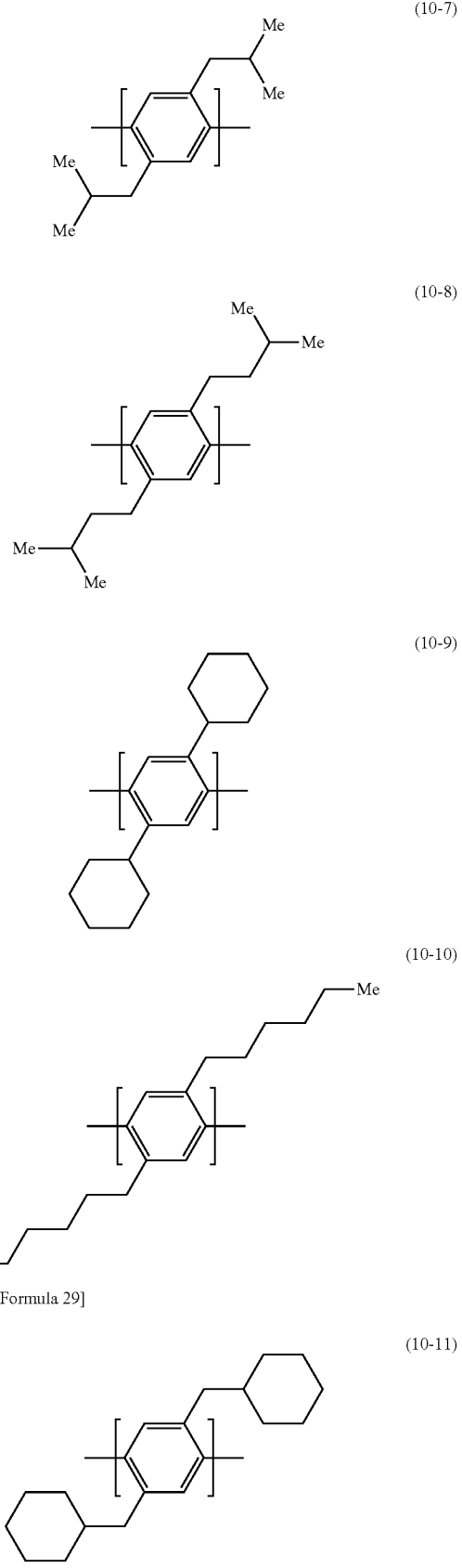
[Chemical Formula 29]

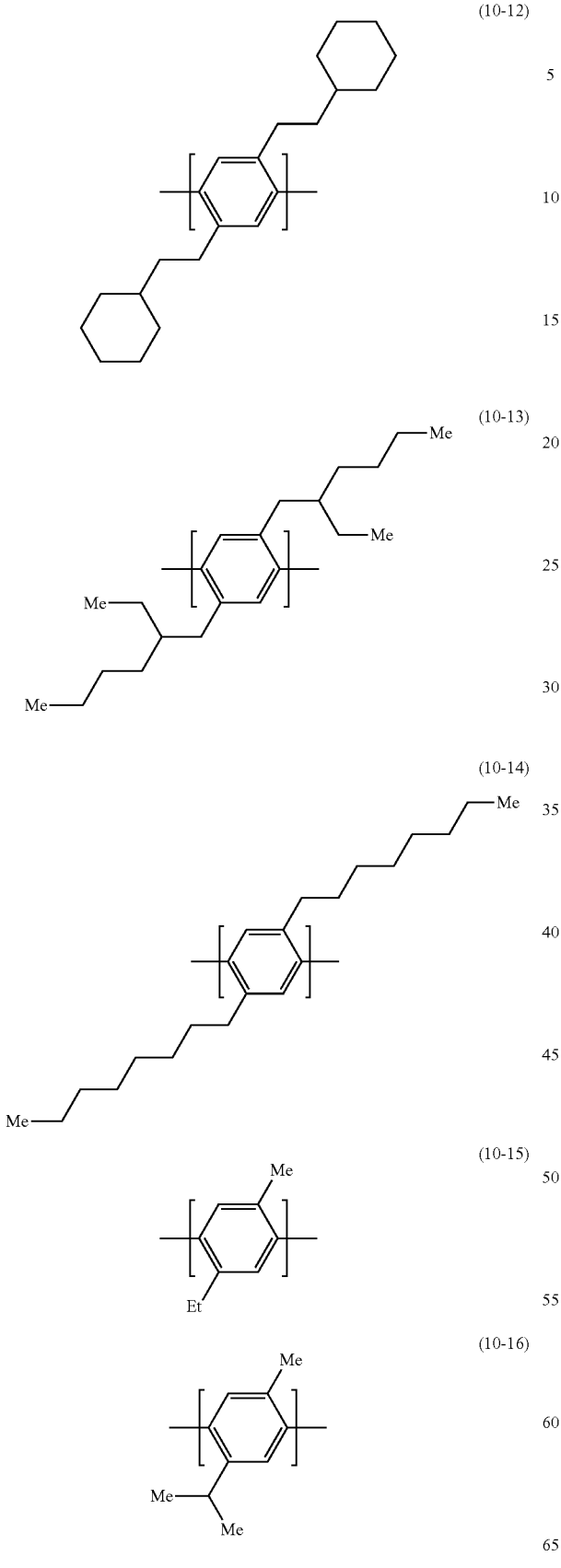
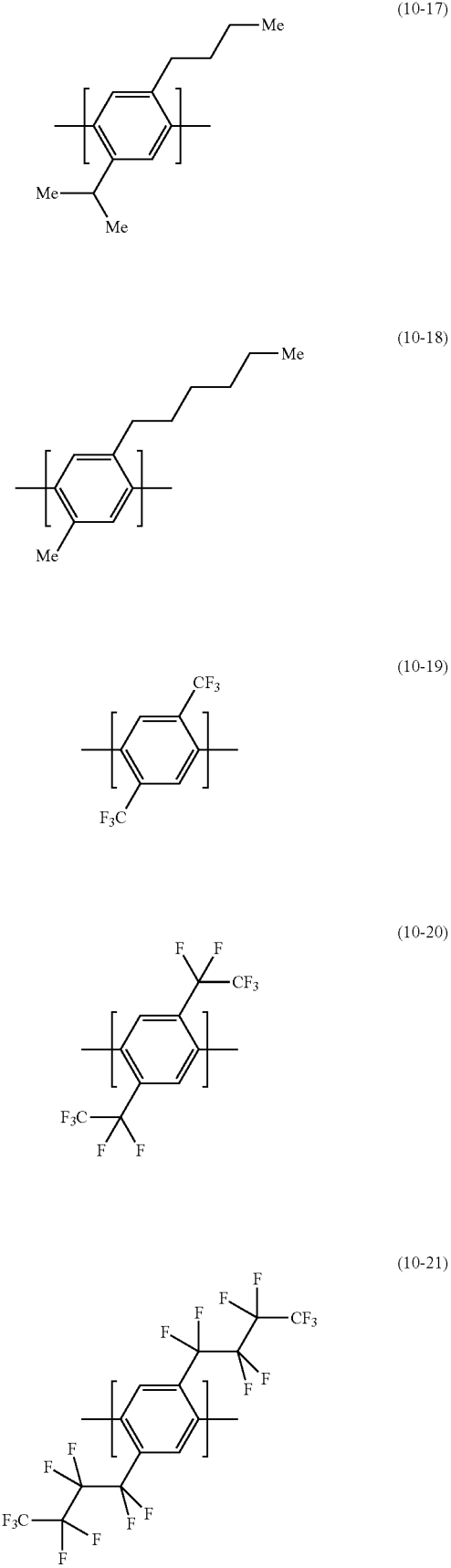

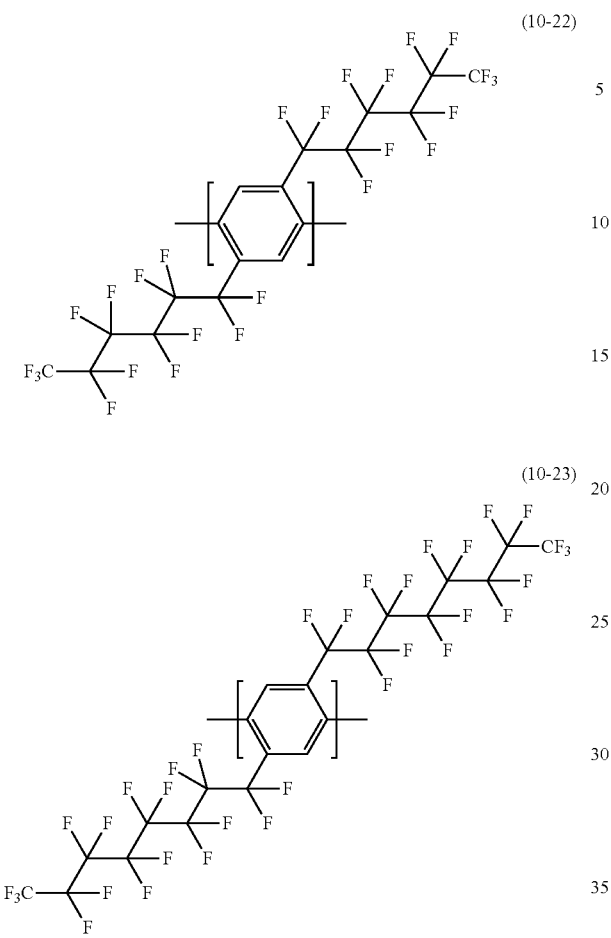
(10-22)
(10-23)
[Chemical Formula 30]
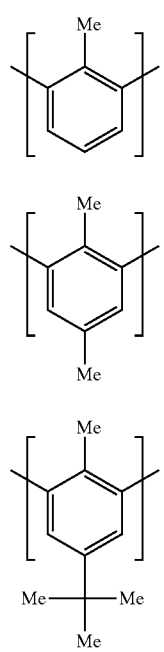
(10-24)
(10-25)
(10-26)
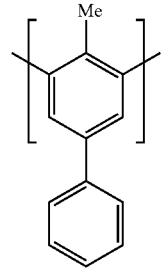
(10-27)
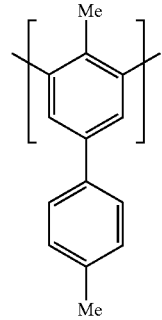
(10-28)
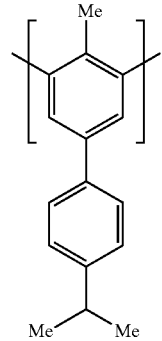
(10-29)
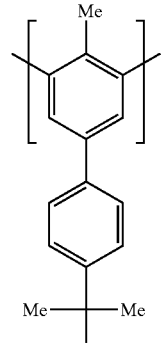
(10-30)
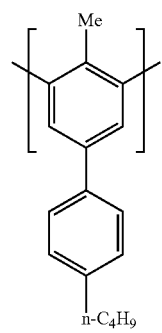
(10-31)

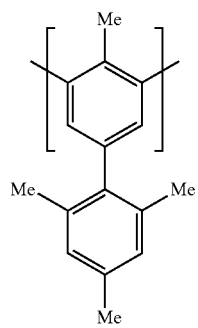 (10-32)
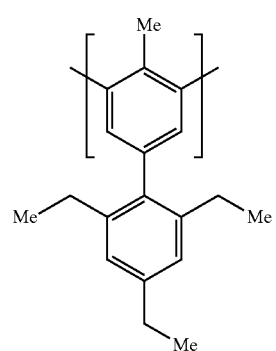 (10-33)
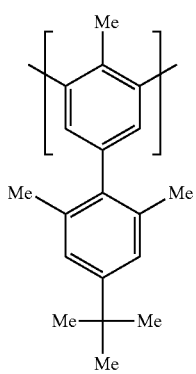 (10-34)
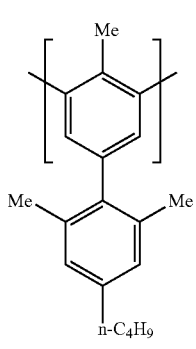 (10-35)
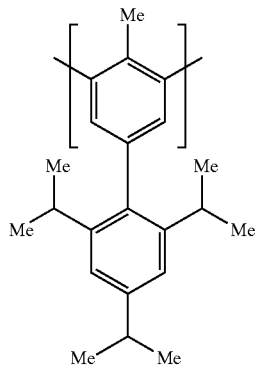 (10-36)
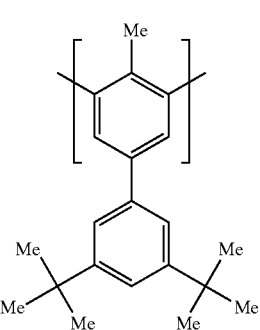 (10-37)
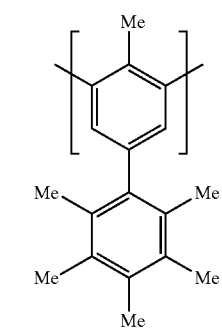 (10-38)
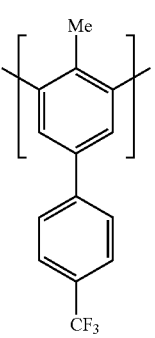 (10-39)

(10-40)
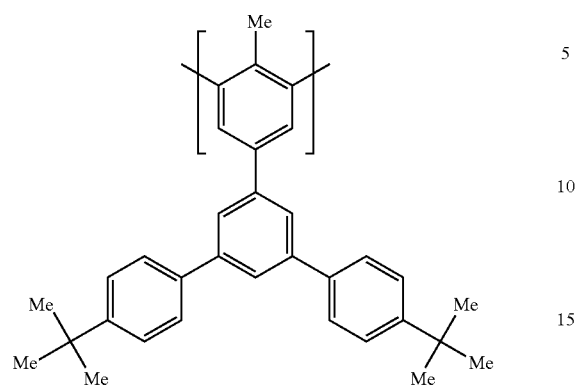
[Chemical Formula 32]
(10-41)
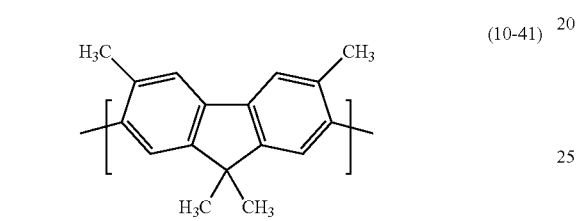
(10-42)
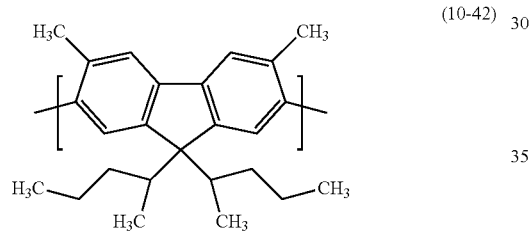
(10-43)
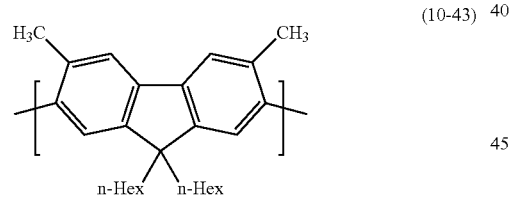
(10-44)
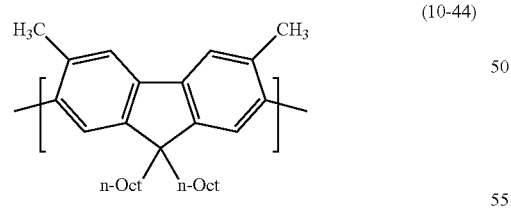
(10-45)
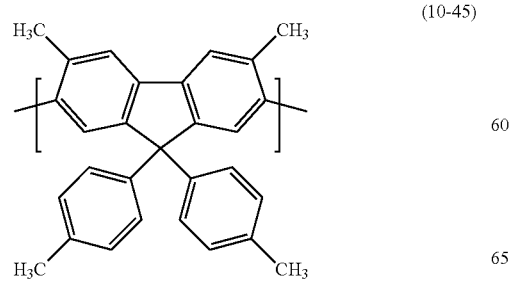
(10-46)
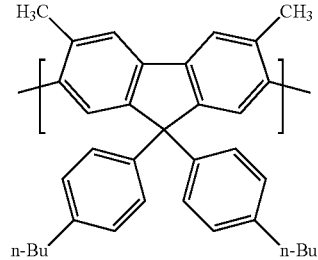
(10-47)
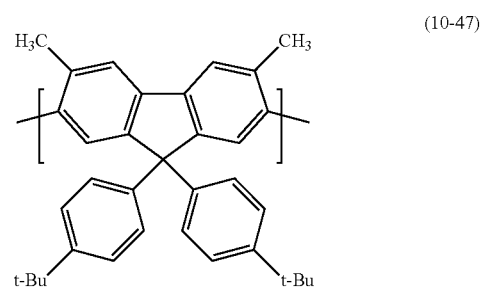
(10-48)
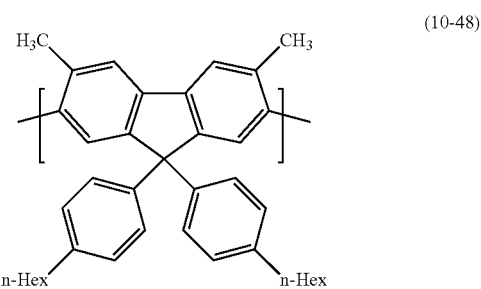
[Chemical Formula 33]
(10-49)
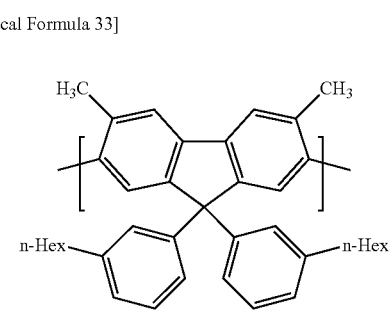
(10-50)
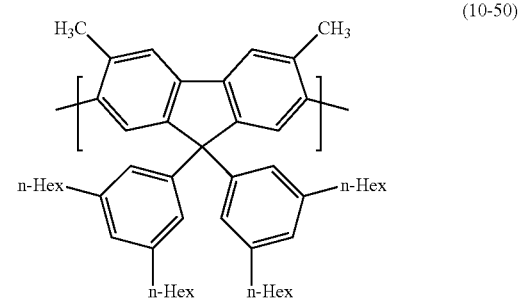

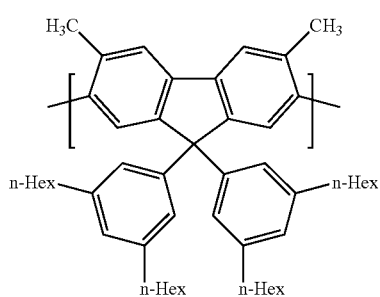
(10-51)
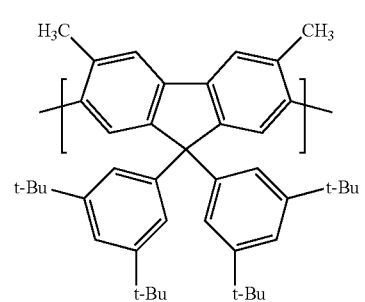
(10-52)
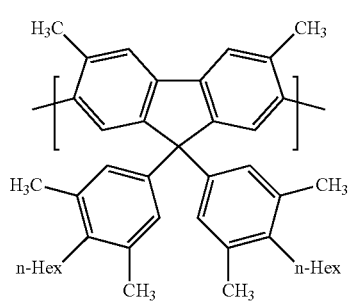
(10-53)
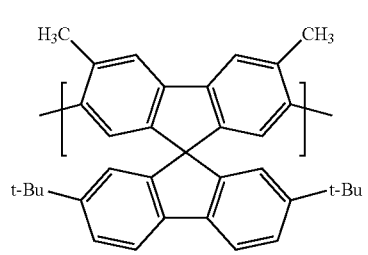
(10-54)
[Chemical Formula 34]
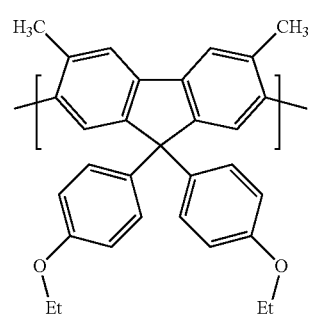
(10-55)
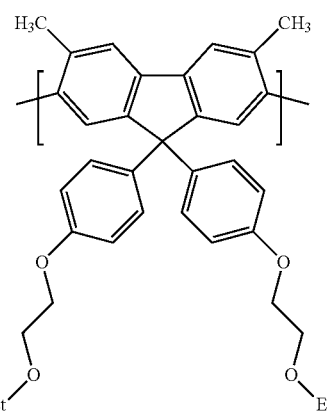
(10-56)
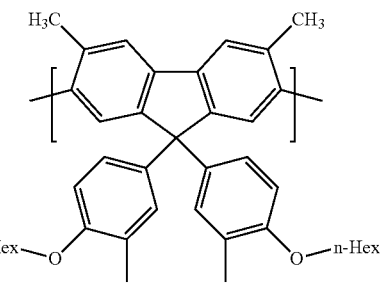
(10-57)
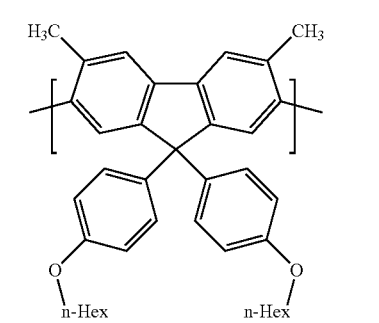
(10-58)
[Chemical Formula 35]
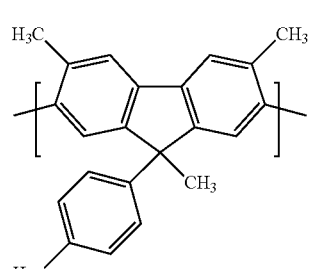
(10-59)
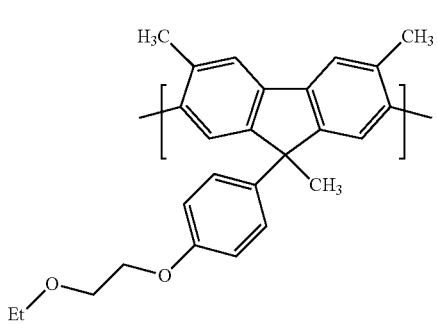
(10-60)

(10-61) 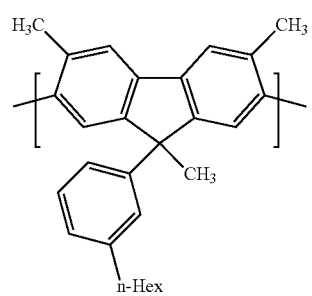
(10-62) 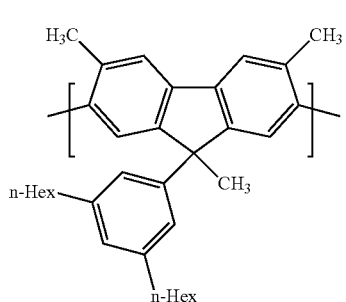
(10-63) 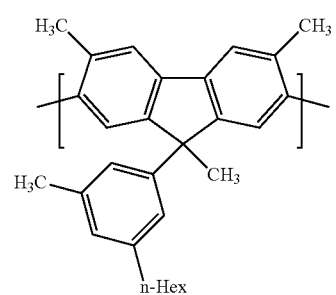
[Chemical Formula 36]
(10-64) 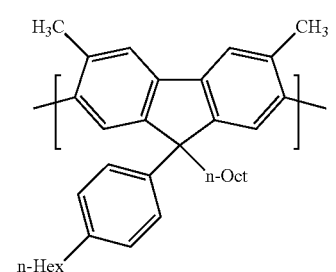
(10-65) 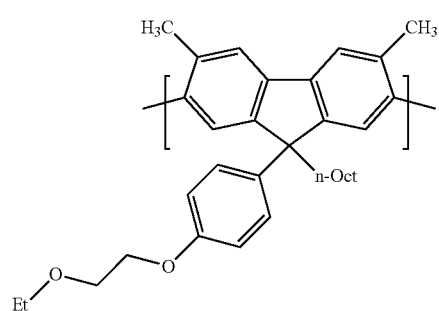
(10-66) 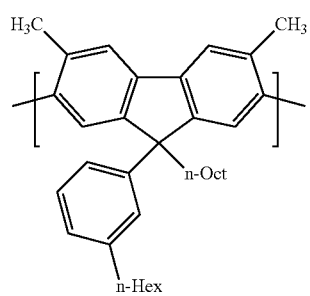
(10-67) 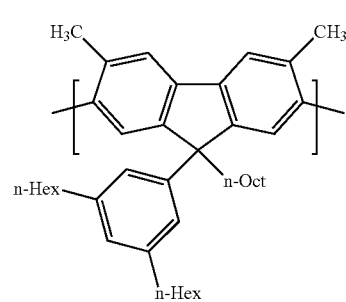
(10-68) 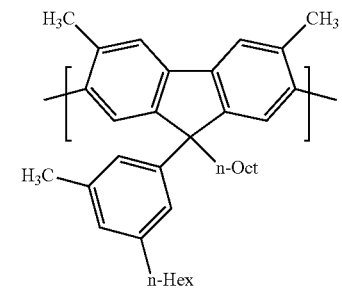
[Chemical Formula 37]
(10-69) 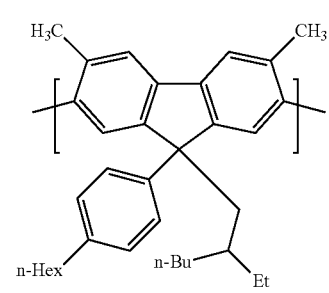
(10-70) 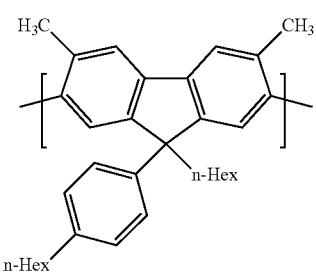

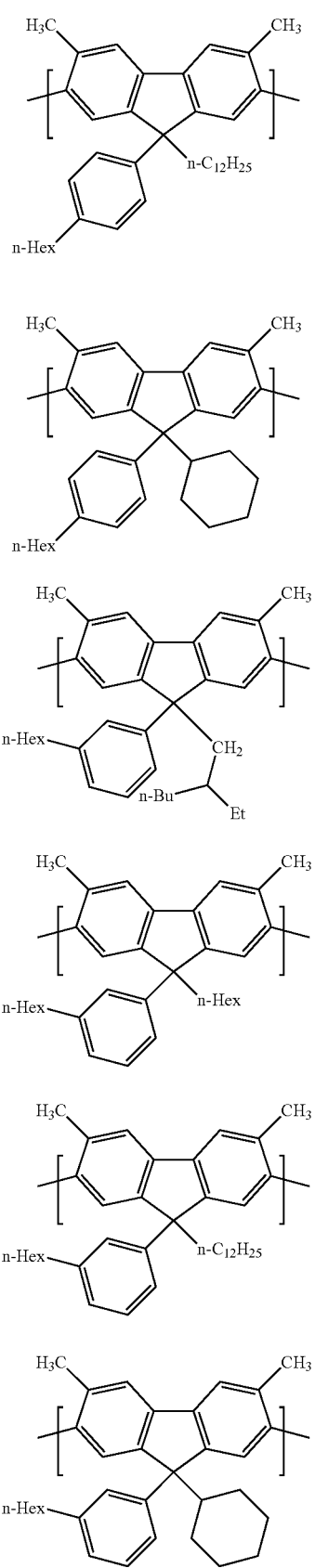
(10-71)
(10-72)
(10-73)
(10-74)
(10-75)
(10-76)
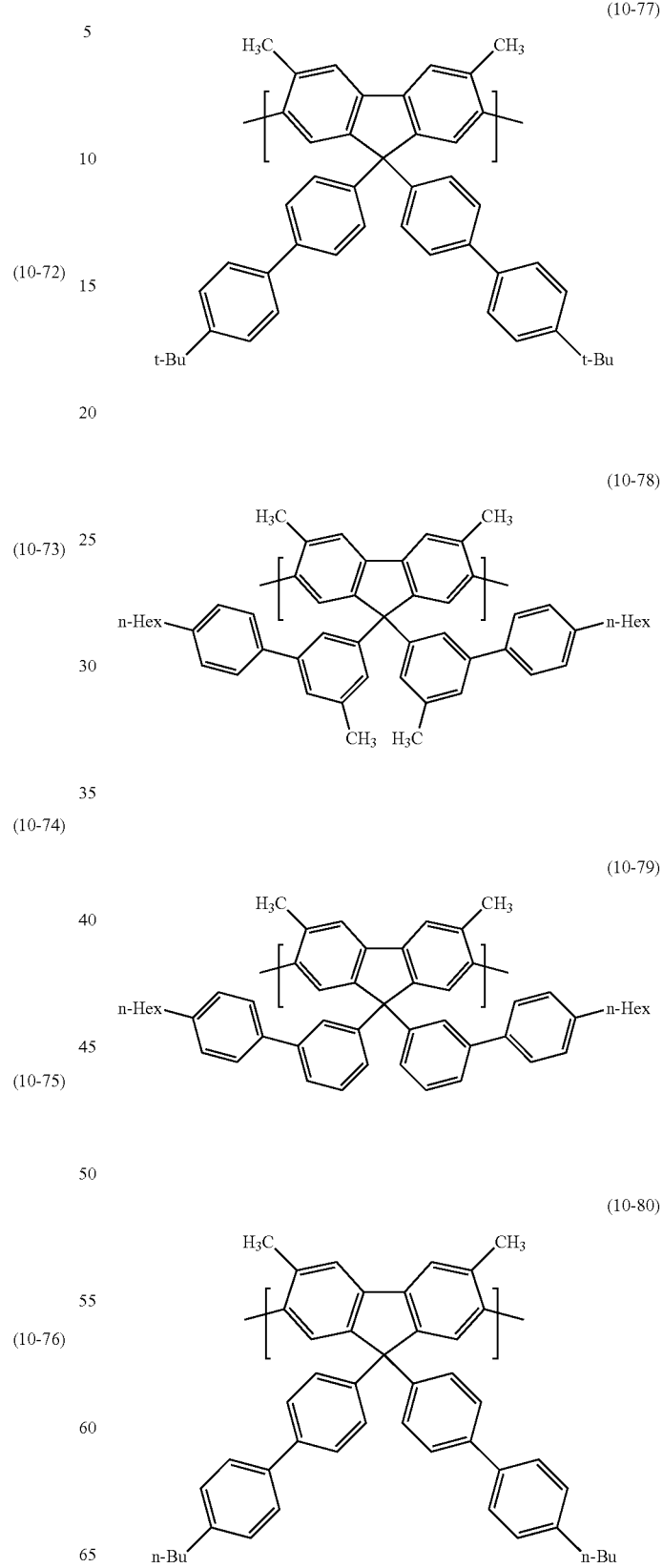
[Chemical Formula 38]
(10-77)
(10-78)
(10-79)
(10-80)

[Chemical Formula 39]
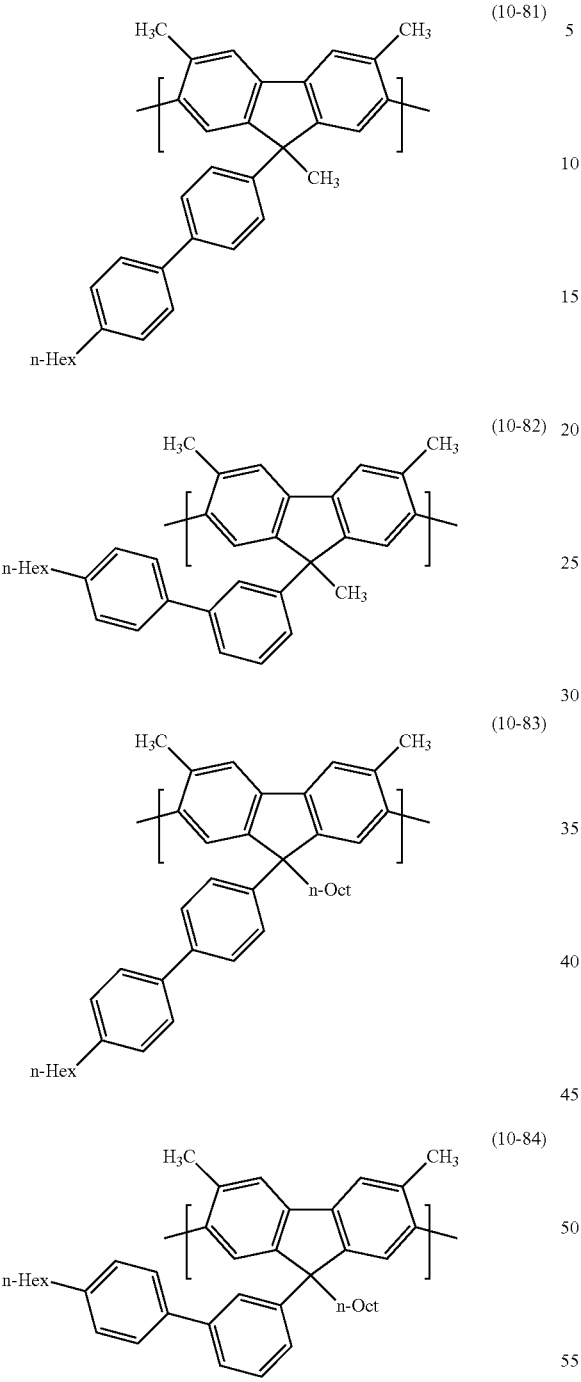
[Chemical Formula 40]
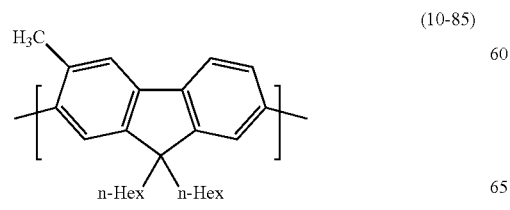
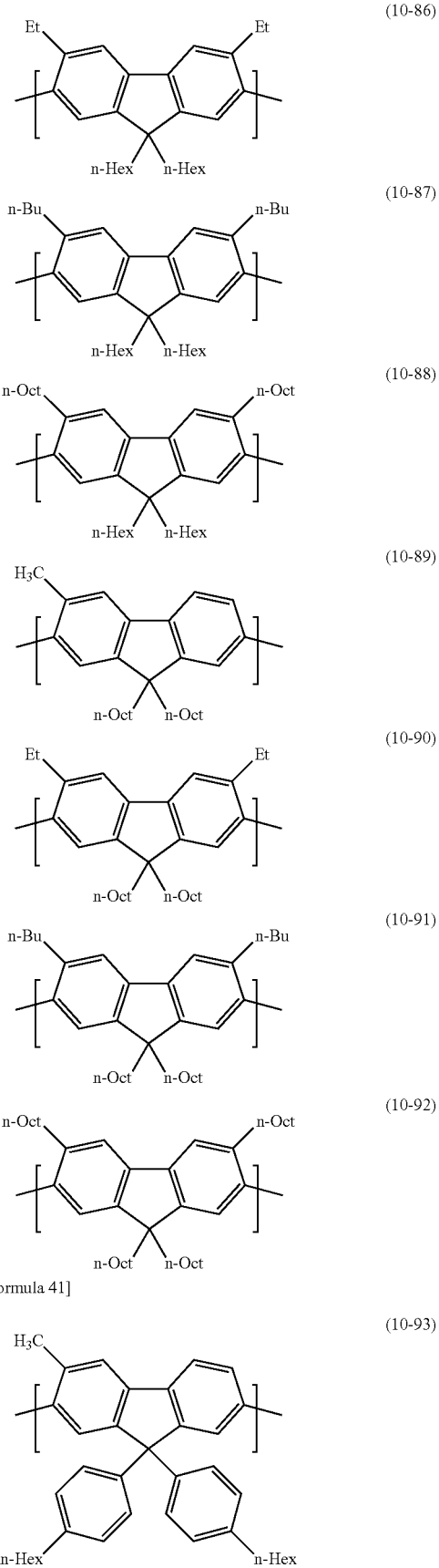
[Chemical Formula 41]

(10-94) 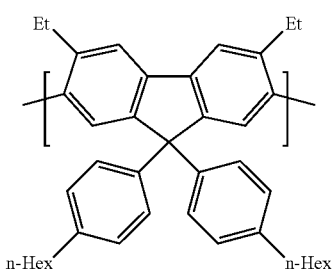
(10-95) 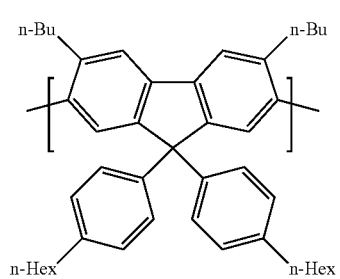
(10-96) 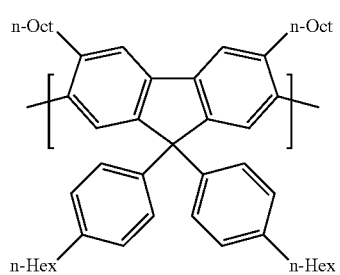
(10-97) 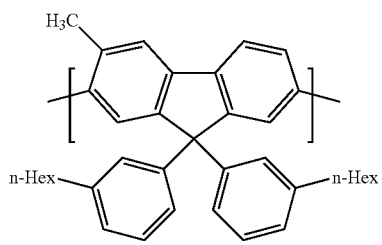
(10-98) 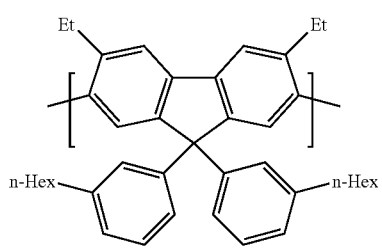
(10-99) 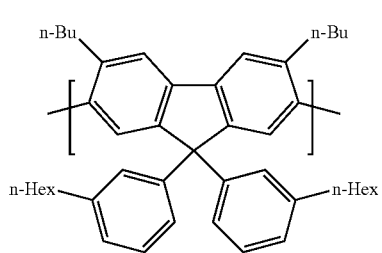
(10-100) 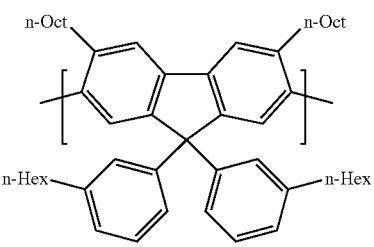
[Chemical Formula 42]
(10-101) 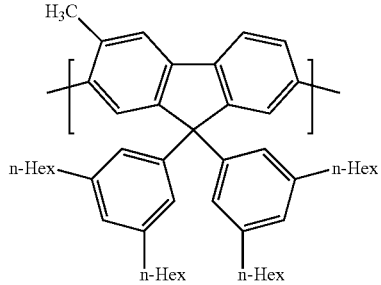
(10-102) 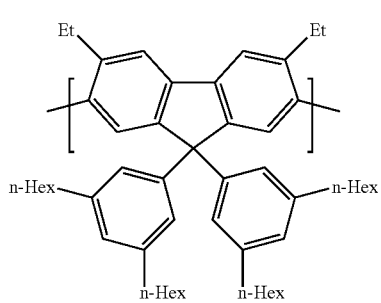
(10-103) 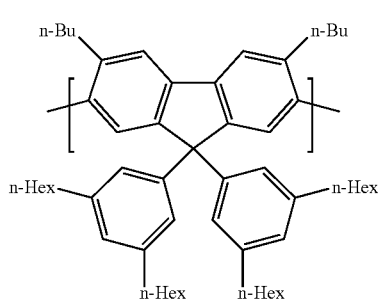
(10-104) 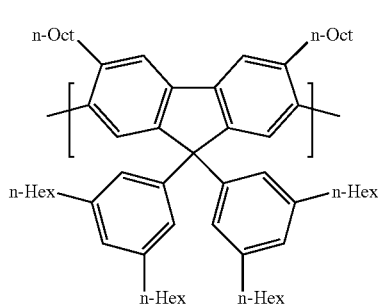

[Chemical Formula 43]
(10-105)
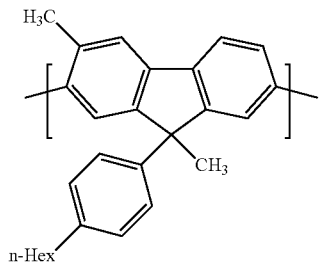
(10-106)
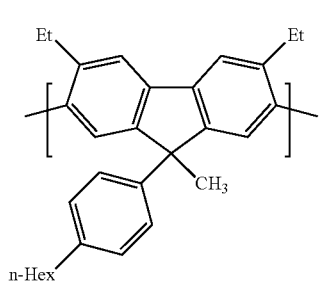
(10-107)
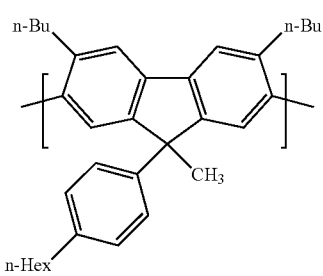
(10-108)
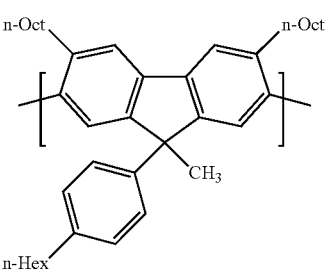
(10-109)
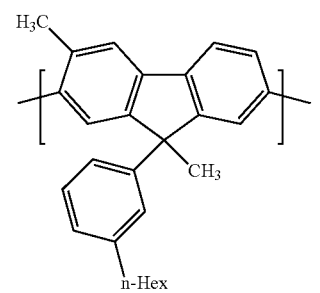
(10-110)
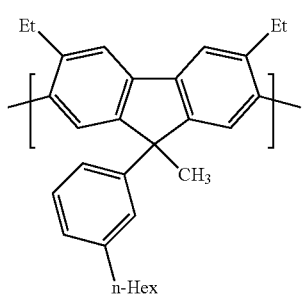
(10-111)
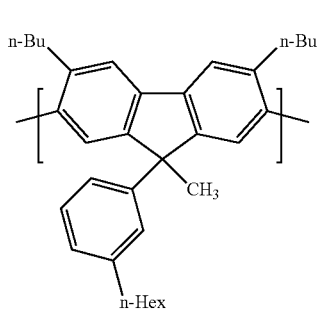
(10-112)
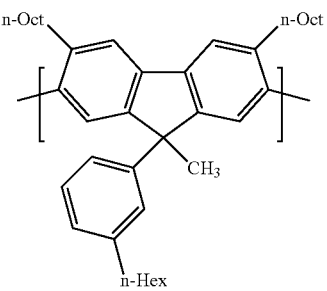
[Chemical Formula 44]
(10-113)
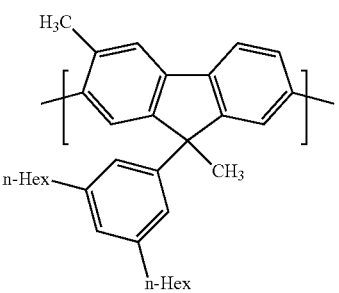
(10-114)
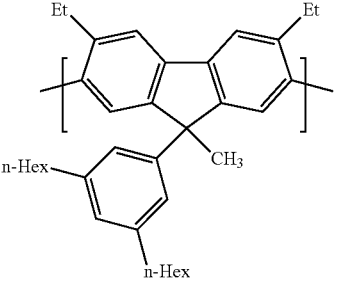

-continued
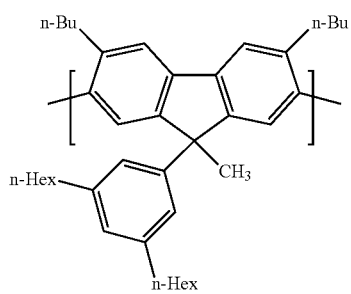
(10-115)
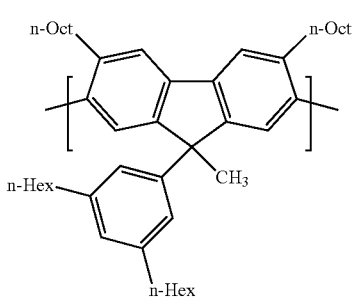
(10-116)
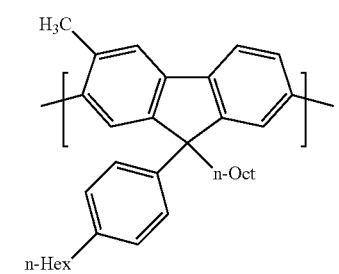
(10-117)
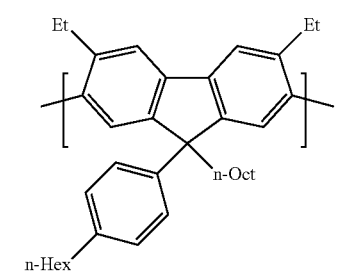
(10-118)
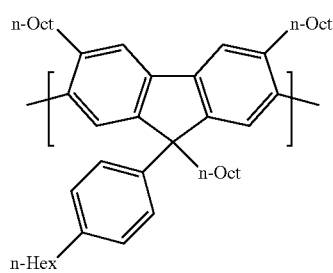
(10-119)
-continued
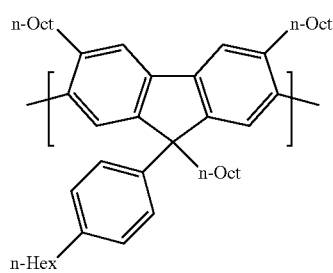
(10-120)
[Chemical Formula 45]
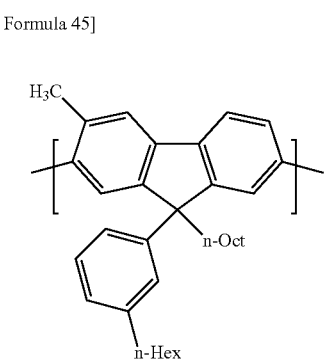
(10-121)
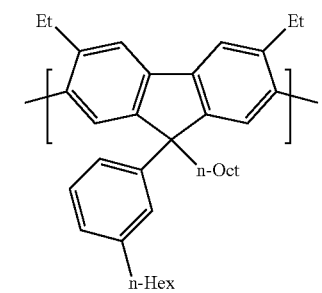
(10-122)
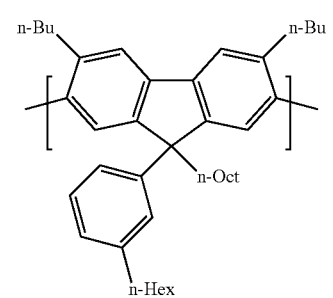
(10-123)
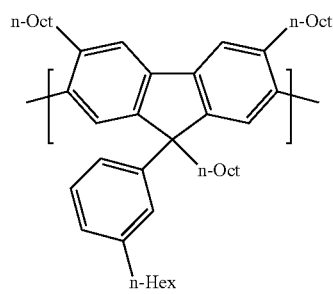
(10-124)

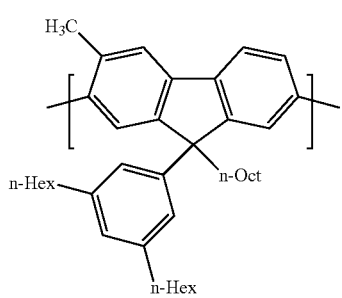 (10-125)
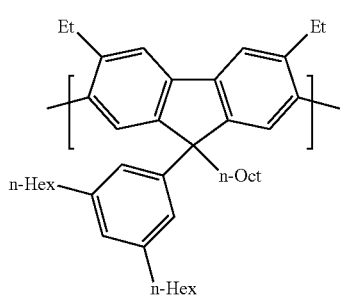 (10-126)
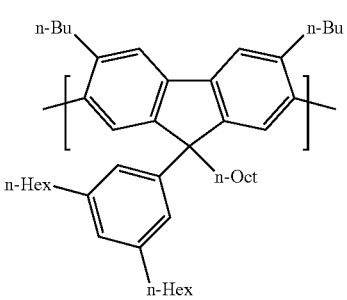 (10-127)
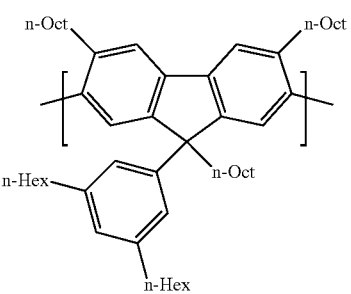 (10-128)
[Chemical Formula 46]
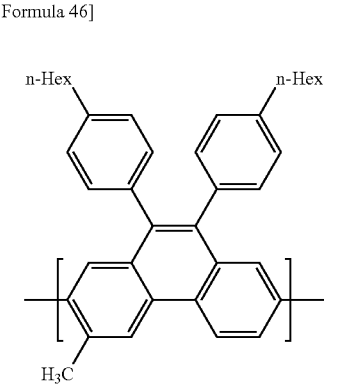 (10-129)
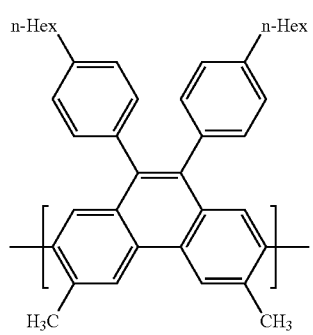 (10-130)
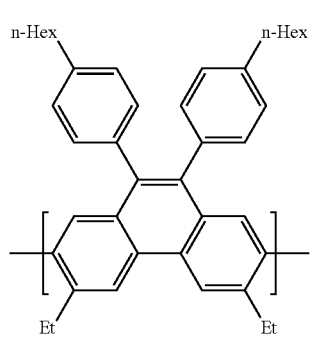 (10-131)
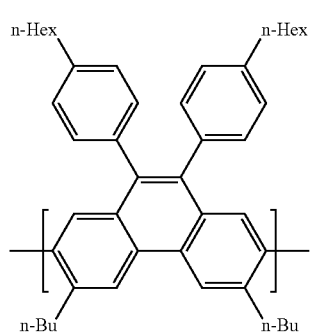 (10-132)
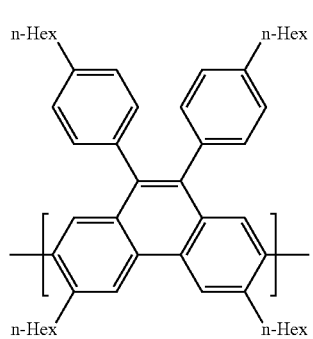 (10-133)

[Chemical Formula 47]
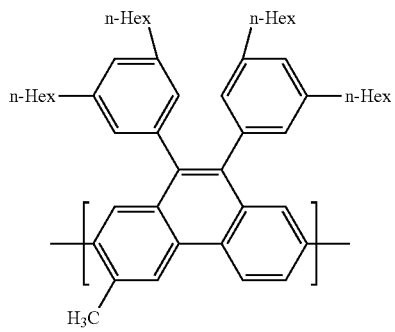
(10-134)
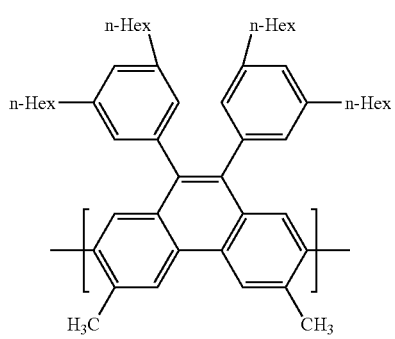
(10-135)
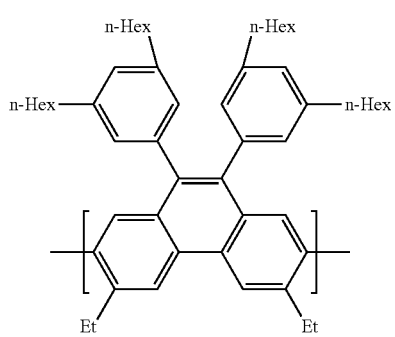
(10-136)
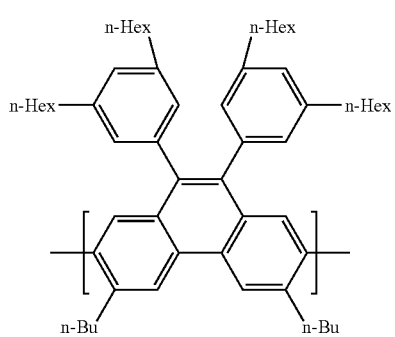
(10-137)
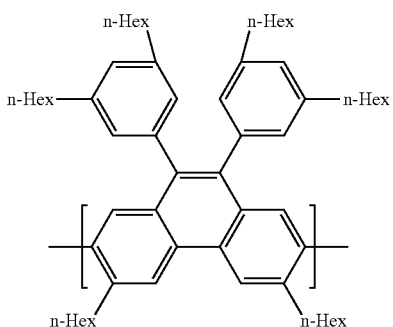
(10-138)
[Chemical Formula 48]
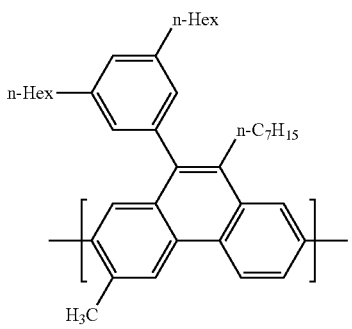
(10-139)
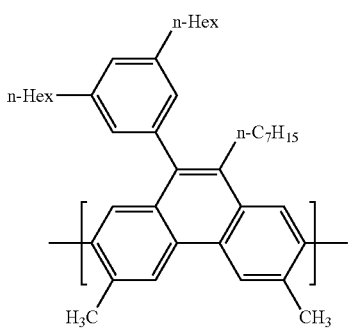
(10-140)
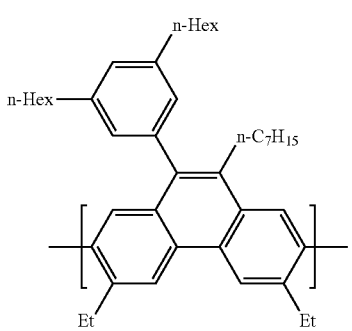
(10-141)

[Chemical Formula 49]
(10-142) 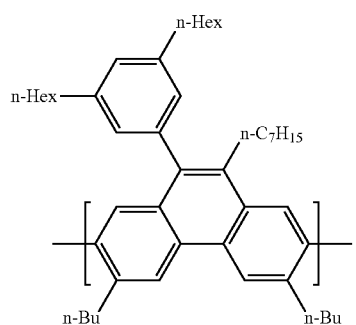
(10-143) 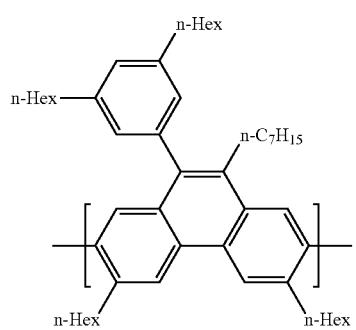
(10-144) 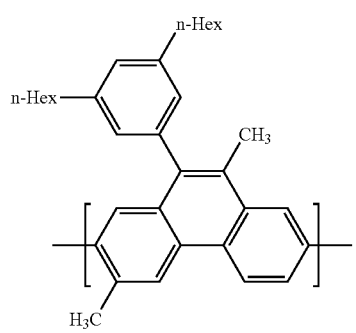
(10-145) 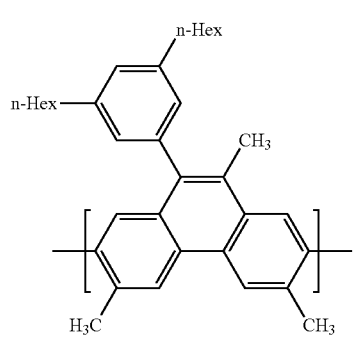
(10-146) 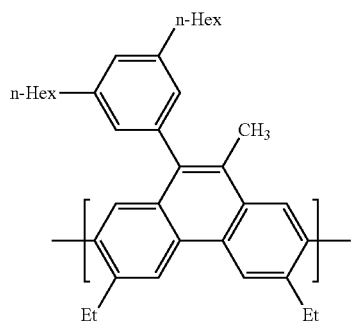
(10-147) 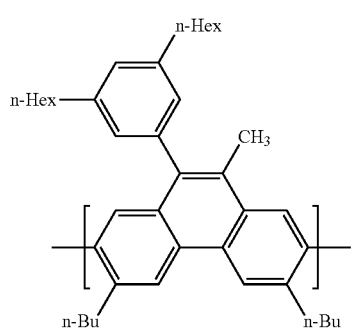
(10-148) 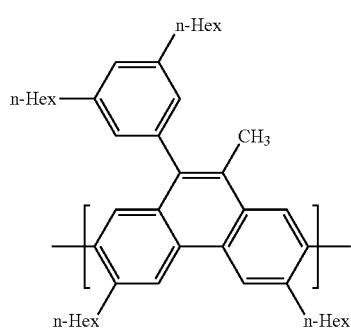
[Chemical Formula 50]
(10-149) 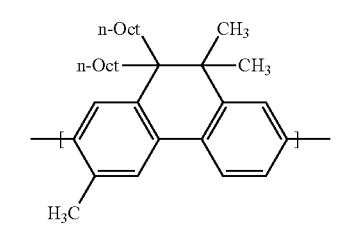
(10-150) 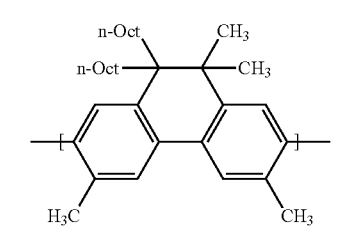

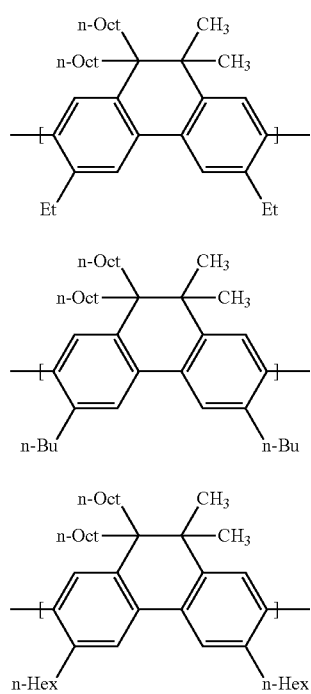
(10-151)
(10-152)
(10-153)
[Chemical Formula 51]
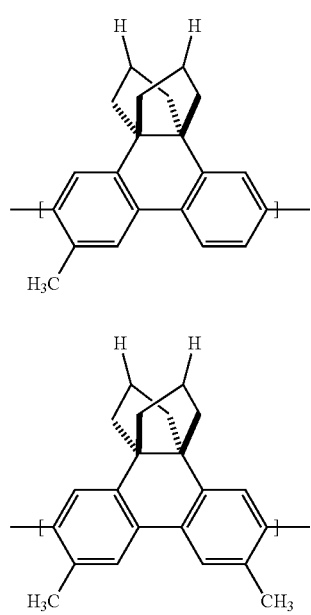
(10-154)
(10-155)
(10-156)
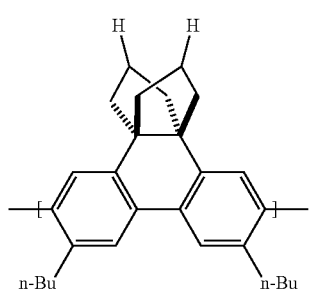
(10-157)
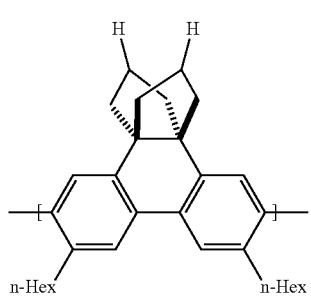
(10-158)
[Chemical Formula 52]
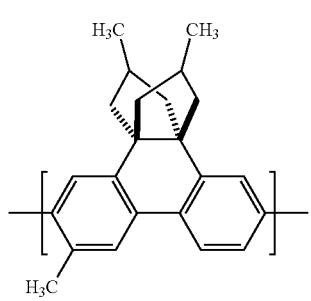
(10-159)
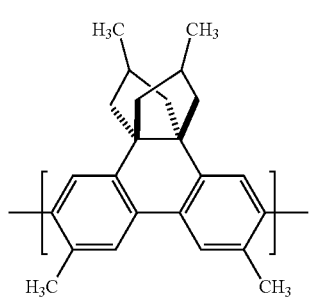
(10-160)
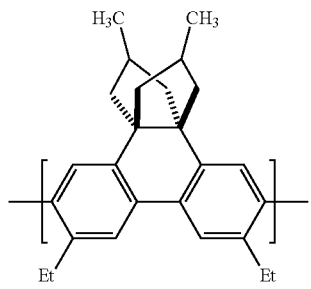
(10-161)

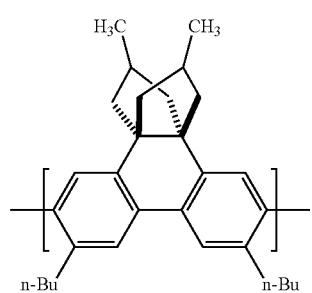 (10-162)
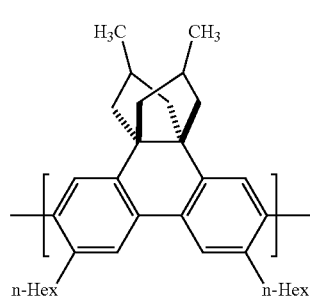 (10-163)
[Chemical Formula 53]
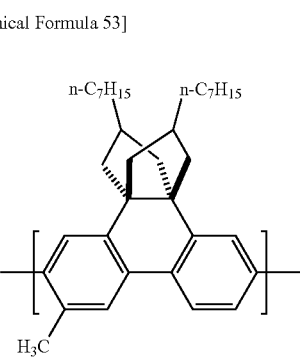 (10-164)
(10-165)
(10-166)
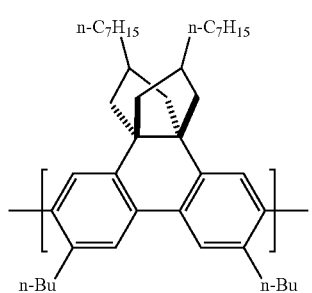 (10-167)
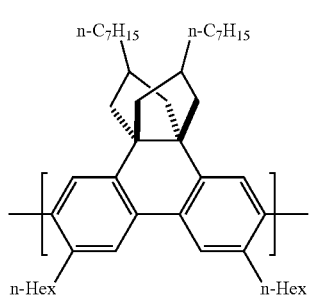 (10-168)
[Chemical Formula 54]
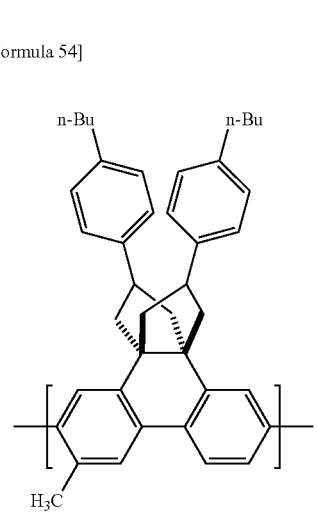 (10-169)
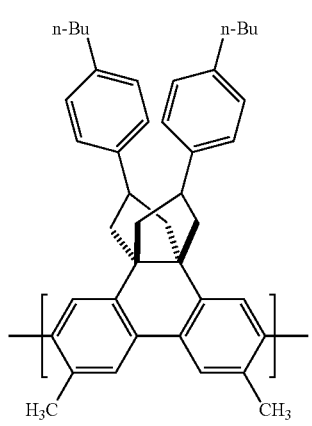 (10-170)

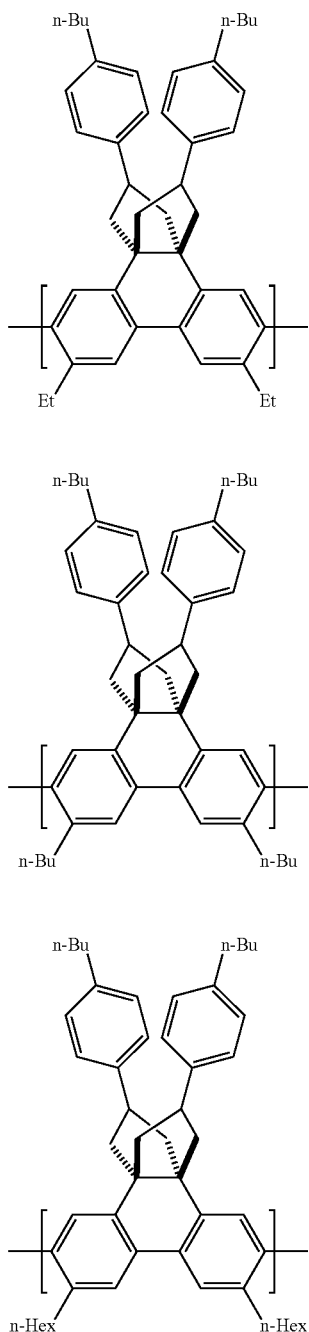

(10-171)

(10-172)

(10-173)

The polymer compound of this embodiment may have one of the aforementioned constitutional units as the second constitutional unit, or it may have a plurality of different constitutional units among the aforementioned constitutional units.

(Third Constitutional Unit)

The third constitutional unit in the polymer compound of the invention is a constitutional unit selected from among constitutional units represented by the following formula (3) and constitutional units represented by the following formula (4').

[Chemical Formula 55]

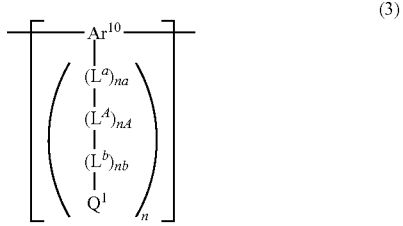

(3)

In formula (3), na represents an integer of 0 to 3, nb represents an integer of 0 to 12, nA represents 0 or 1 and n represents an integer of 1 to 4.

$Ar^{10}$ represents an unsubstituted or substituted (2+n)-valent aromatic hydrocarbon group or an unsubstituted or substituted (2+n)-valent heterocyclic group.

$L^a$ and $L^b$ each independently represent an unsubstituted or substituted alkylene group or an unsubstituted or substituted phenylene group. When a plurality of $L^a$ are present, they may be the same or different. When a plurality of $L^b$ are present, they may be the same or different.

$L^A$ represents an oxygen atom or a sulfur atom.

$Q^1$ represents a monovalent crosslinkable group. When a plurality of $Q^1$ are present, they may be the same or different.

The constitutional unit represented by formula (3) is different from the constitutional unit represented by formula (2).

In formula (3), na represents an integer of 0 to 3, and for easier synthesis of the monomer starting materials, it is preferably 0 to 2, more preferably 0 or 1 and even more preferably 0.

In formula (3), nb represents an integer of 0 to 12, and for easier synthesis of the monomer starting materials, it is preferably 0 to 10 and more preferably 0 to 8.

In formula (3), nA represents 0 or 1, and for excellent hole transport properties and durability of the light emitting device to be produced using the polymer compound of this embodiment, it is preferably 0. Here, "durability" includes luminance life, for example.

In formula (3), n is an integer of 1 to 4, and for excellent hole transport properties and durability of the light emitting device to be produced using the polymer compound of this embodiment, it is preferably an integer of 1 to 3 and more preferably 2.

In formula (3), the number of carbon atoms of the unsubstituted or substituted (2+n)-valent aromatic hydrocarbon group represented by $Ar^{10}$ is usually 6 to 60, preferably 6 to 48, more preferably 6 to 20 and even more preferably 6 to 14. As (2+n)-valent aromatic hydrocarbon groups there are preferred divalent, trivalent, tetravalent or pentavalent aromatic hydrocarbon groups, with trivalent and tetravalent aromatic hydrocarbon groups being more preferred. Here, a "(2+n)-valent aromatic hydrocarbon group" is an atomic group remaining after removing (2+n) hydrogen atoms bonded to a carbon atom composing the ring of an aromatic hydrocarbon (preferably an unsubstituted aromatic carbon ring), and it includes groups with benzene rings and groups with fused rings. The number of carbon atoms of the substituents is not included in this number of carbon atoms.

Aromatic hydrocarbons include benzene, naphthalene, anthracene, 1-tetracene, pyrene, perylene, fluorene, benzofluorene, phenanthrene, dihydrophenanthrene, chrysene and coronene, and for more excellent stability of the polymer compound of this embodiment and excellent hole transport properties of the light emitting device to be produced using the polymer compound, benzene, naphthalene, anthracene, pyrene, fluorene, benzofluorene, phenanthrene and dihydrophenanthrene are preferred, and benzene, naphthalene and fluorene are more preferred.

In formula (3), the number of carbon atoms of the unsubstituted or substituted (2+n)-valent heterocyclic group represented by $Ar^{10}$ is usually 3 to 60 and preferably 3 to 20. The (2+n)-valent heterocyclic group is preferably a divalent, trivalent, tetravalent or pentavalent heterocyclic group, and more preferably it is a divalent, trivalent or tetravalent heterocyclic group. The (2+n)-valent heterocyclic group is preferably a (2+n)-valent aromatic heterocyclic group. Here, "(2+n)-valent heterocyclic group" means an atomic group remaining after removing (2+n) hydrogen atoms bonded to a carbon atom composing the ring of a heterocyclic compound, and it includes monocyclic groups and groups with fused rings. The number of carbon atoms of the substituents is not included in this number of carbon atoms.

Examples of heterocyclic compounds include pyridine, pyrimidine, triazine, quinoline, isoquinoline, quinoxaline, dibenzofuran, dibenzothiophene, carbazole, phenoxazine, phenothiazine, benzothiadiazole and dibenzosilol.

When the group represented by $Ar^{10}$ in formula (3) has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group or a cyano group, more preferably an alkyl group, an alkoxy group, an aryl group, an aryloxy group, an arylalkyl group, an arylalkoxy group, a substituted amino group, an acyl group or a cyano group, and even more preferably an alkyl group, an alkoxy group or an aryl group.

In formula (3), $Ar^{10}$ is preferably an unsubstituted or substituted (2+n)-valent aromatic hydrocarbon group, for excellent hole transport properties and durability of the light emitting device to be produced using the polymer compound of this embodiment.

In formula (3), alkylene groups represented by $L^a$ and $L^b$ may be straight-chain, branched or cyclic, and may be substituted. For easier synthesis of the monomer starting materials, straight-chain alkylene groups are preferred. The number of carbon atoms for straight-chain alkylene and branched alkylene groups will usually be 1 to 20 and is preferably 1 to 10 and more preferably 1 to 6. The number of carbon atoms for a cycloalkylene group will usually be 3 to 20 and is preferably 3 to 10 and more preferably 3 to 6.

Alkylene groups include methylene, 1,2-ethylene, 1,3-propylene, 1,3-butylene, 1,3-pentylene, 1,4-pentylene, 1,5-pentylene, 1,4-hexylene, 1,6-hexylene, 1,7-heptylene, 1,6-octylene and 1,8-octylene groups.

In formula (3), phenylene groups represented by $L^a$ and $L^b$ may be substituted. Phenylene groups include o-phenylene, m-phenylene and p-phenylene groups. Suitable substituents for phenylene groups include alkyl groups, alkoxy groups, halogen atoms and cyano groups.

In formula (3), $L^a$ is preferably a phenylene group for easier synthesis of the monomer starting materials.

In formula (3), $L^b$ is preferably an alkylene group for easier synthesis of the monomer starting materials.

In formula (3), $L^A$ represents an oxygen atom or a sulfur atom and is preferably an oxygen atom for easier synthesis of the monomer starting materials.

In formula (3), $Q^1$ represents a monovalent crosslinkable group. Examples for $Q^1$ include an unsubstituted or substituted aziridinyl group, an unsubstituted or substituted azetidinyl group, an azide group, an unsubstituted or substituted epoxy group, an unsubstituted or substituted oxetanyl group, an unsubstituted or substituted alkenyl group, an unsubstituted or substituted alkynyl group, and a group with a cyclobutene structure, and for easier synthesis of the monomer starting materials, it is preferably an unsubstituted or substituted aziridinyl group, azide group, an unsubstituted or substituted epoxy group, an unsubstituted or substituted oxetanyl group, an unsubstituted or substituted alkenyl group, an unsubstituted or substituted alkynyl group, an unsubstituted or substituted aryl group with a cyclobutene structure or an unsubstituted or substituted monovalent heterocyclic group with a cyclobutene structure, more preferably an unsubstituted or substituted alkenyl group, an unsubstituted or substituted aryl group with a cyclobutene structure, or an unsubstituted or substituted monovalent heterocyclic group with a cyclobutene structure, and even more preferably an unsubstituted or substituted alkenyl group or an unsubstituted or substituted aryl group with a cyclobutene structure.

Examples for $Q^1$ in formula (3) include groups represented by the following formulas (Q-1), (Q-2) and (Q-01) to (Q-19), and for easier synthesis of the monomer starting materials it is preferably a group represented by formulas (Q-1), (Q-2), (Q-01), (Q-03), (Q-04) or (Q-06) to (Q-18), more preferably a group represented by formulas (Q-1), (Q-2) or (Q-09) to (Q-18), and even more preferably a group represented by formula (Q-1) or (Q-2).

[Chemical Formula 56]

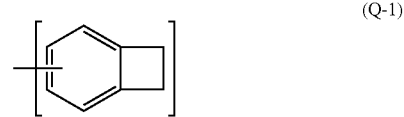

(Q-1)

The benzocyclobutene ring in formula (Q-1) may be substituted. Examples of substituents for formula (Q-1) include an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted amino group, an unsubstituted or substituted silyl group, a halogen atom, an acyl group, an acyloxy group, an imine residue, a carbamoyl group, an acid imide group, an unsubstituted or substituted monovalent heterocyclic group, an unsubstituted or substituted carboxyl group, a cyano group or a nitro group.

[Chemical Formula 57]

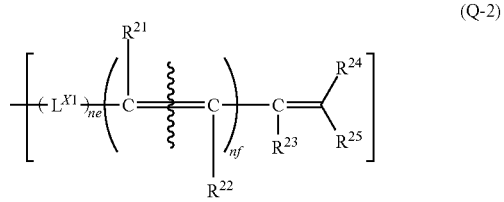

(Q-2)

In formula (Q-2), ne and nf each independently represent 0 or 1. $L^{X1}$ is an oxygen atom, a sulfur atom or a carbonyl group or a group represented by —O—CO—.

$R^{21}$, $R^{22}$, $R^{23}$, $R^{24}$ and $R^{25}$ each independently represent a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted monovalent heterocyclic group, an unsubstituted or substituted amino group, an unsubstituted or substituted silyl group, an unsubstituted or substituted acyl group, an unsubstituted or substituted acyloxy group, a halogen atom, a cyano group or a nitro group.

In formula (Q-2), the compound having a double bond indicated with a wave line means that it may be the E-form or Z-form, or a mixture of the E-form and Z-form.

[Chemical Formula 58]

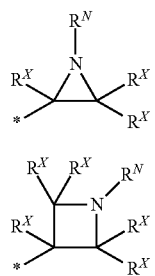
(Q-01)

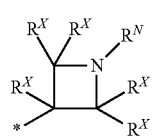
(Q-02)

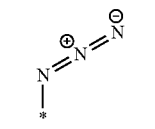
(Q-03)

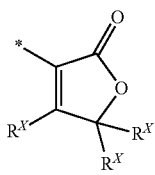
(Q-04)

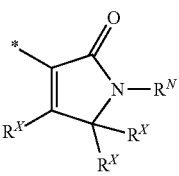
(Q-05)

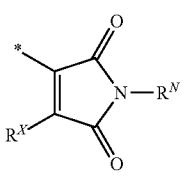
(Q-06)

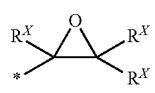
(Q-07)

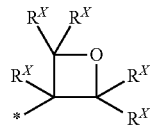
(Q-08)

[Chemical Formula 59]

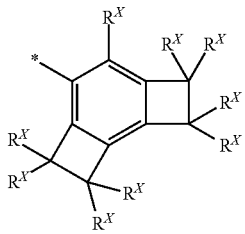
(Q-09)

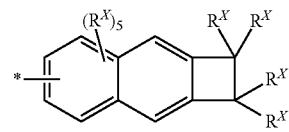
(Q-10)

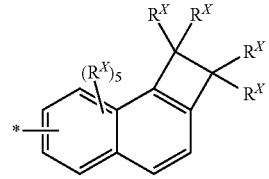
(Q-11)

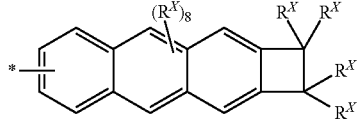
(Q-12)

[Chemical Formula 60]

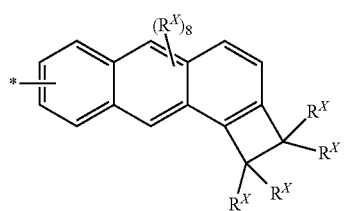
(Q-13)

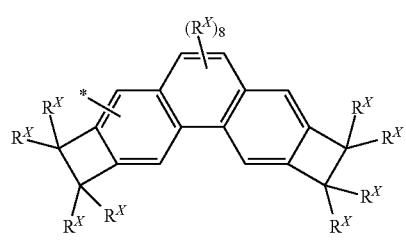
(Q-14)

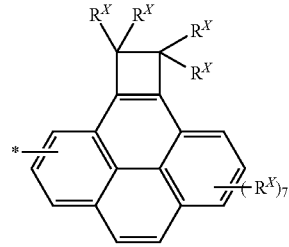
(Q-15)

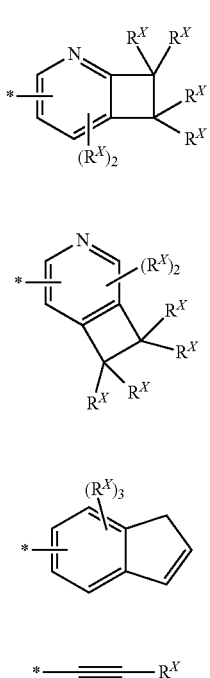

(Q-16)

(Q-17)

(Q-18)

(Q-19)

In formulas (Q-01) to (Q-19):

$R^X$ represents a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted amino group, an unsubstituted or substituted silyl group, a halogen atom, an acyl group, an acyloxy group, an imine residue, a carbamoyl group, an acid imide group, an unsubstituted or substituted monovalent heterocyclic group, an unsubstituted or substituted carboxyl group, a cyano group or a nitro group. A plurality of $R^X$ may be the same or different.

$R^N$ represents a hydrogen atom or an unsubstituted or substituted alkyl group, an unsubstituted or substituted acyl group, an unsubstituted or substituted aryl group or an unsubstituted or substituted monovalent heterocyclic group.

For easier synthesis of the monomer starting materials, $R^X$ is preferably a hydrogen atom, an unsubstituted or substituted alkyl group, an unsubstituted or substituted alkoxy group, an unsubstituted or substituted aryl group, an unsubstituted or substituted aryloxy group or an unsubstituted or substituted monovalent heterocyclic group, and more preferably a hydrogen atom, an unsubstituted or substituted alkyl group, an unsubstituted or substituted alkoxy group or an unsubstituted or substituted aryl group.

For easier synthesis of the monomer starting materials, $R^N$ is preferably an aryl-substituted alkyl group, an unsubstituted or substituted acyl group, or an unsubstituted or substituted monovalent heterocyclic group. In formulas (Q-01) to (Q-19), "*" indicates a bonding site.

Formula (Q-1) may be the following formula (Q-1-1) or (Q-1-2), and for easier synthesis of the monomer starting materials it is preferably formula (Q-1-1).

[Chemical Formula 61]

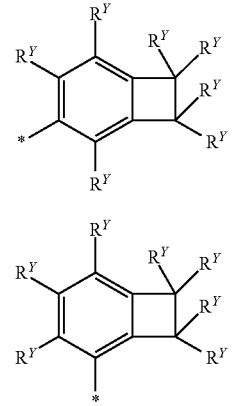

(Q-1-1)

(Q-1-2)

In formulas (Q-1-1) and (Q-1-2):

$R^Y$ represents a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted amino group, an unsubstituted or substituted silyl group, a halogen atom, an acyl group, an acyloxy group, an imine residue, a carbamoyl group, an acid imide group, an unsubstituted or substituted monovalent heterocyclic group, an unsubstituted or substituted carboxyl group, a cyano group or nitro group. When a plurality of $R^Y$ are present, they may be the same or different.

For easier synthesis of the monomer starting materials, $R^Y$ is preferably a hydrogen atom, an unsubstituted or substituted alkyl group, an unsubstituted or substituted alkoxy group, an unsubstituted or substituted aryl group, an unsubstituted or substituted aryloxy group or an unsubstituted or substituted monovalent heterocyclic group, more preferably a hydrogen atom, an unsubstituted or substituted alkyl group, an unsubstituted or substituted alkoxy group or an unsubstituted or substituted aryl group, and even more preferably a hydrogen atom or an unsubstituted or substituted alkyl group. In formulas (Q-1-1) to (Q-1-2), "*" indicates a bonding site.

In formula (Q-2), ne represents 0 or 1, and for excellent hole transport properties and durability of the light emitting device to be produced using the polymer compound of this embodiment, it is preferably 0.

In formula (Q-2), of represents an integer of 0 or 1, and for easier synthesis of the monomer starting materials, it is preferably 0.

For formula (Q-2), $L^{X1}$ represents an oxygen atom, a sulfur atom, a carbonyl group or the group —O—CO—, and for easier synthesis of the monomer starting materials it is preferably a carbonyl group or the group —O—CO—.

In formula (Q-2), $R^{21}$, $R^{22}$, $R^{23}$, $R^{24}$ and $R^{25}$ are preferably a hydrogen atom, an alkyl group, an alkoxy group, an aryl group, an aryloxy group, a heterocyclic group, a halogen atom or cyano group, more preferably a hydrogen atom, an alkyl group or a fluorine atom and even more preferably a hydrogen atom, for excellent hole transport properties and durability of the light emitting device to be produced using the polymer compound of this embodiment.

For excellent hole transport properties and durability of the light emitting device to be produced using the polymer compound of this embodiment, the constitutional unit represented by formula (3) is preferably a constitutional unit represented by the following formula (3-1).

[Chemical Formula 62]

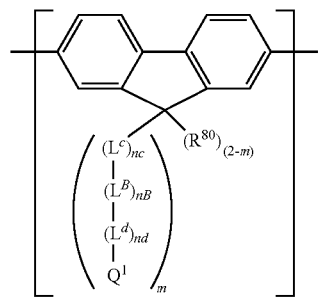

(3-1)

Here, nc represents an integer of 0 to 3, nd represents an integer of 0 to 12, nB represents 0 or 1 and m represents 1 or 2.

$L^c$ and $L^d$ each independently represent an unsubstituted or substituted alkylene group or an unsubstituted or substituted phenylene group. When a plurality of $L^c$ are present, they may be the same or different. When a plurality of $L^d$ are present, they may be the same or different.

$L^B$ represents an oxygen atom or a sulfur atom. When a plurality of $L^B$ are present, they may be the same or different. $Q^1$ has the same meaning as explained above. When a plurality of $Q^1$ are present, they may be the same or different. $R^{80}$ represents a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group or an unsubstituted or substituted heterocyclooxy group.

In formula (3-1), m represents 1 or 2, and from the viewpoint of hole transport properties and durability of the light emitting device to be produced using the polymer compound of this embodiment, and from the viewpoint of conversion of the organic film copolymer comprising the polymer compound to an insolubilized organic film, it is preferably 2.

$L^c$ has the same meaning as $L^a$ above, with the same examples and preferred ranges as $L^a$.

$L^d$ has the same meaning as $L^b$ above, with the same examples and preferred ranges as $L^b$.

$L^B$ has the same meaning as $L^A$ above, with the same examples and preferred ranges as $L^A$.

$Q^1$ has the same meaning as $Q^1$ of formula (3), with the same examples and preferred ranges as formula (3).

For excellent hole transport properties and durability of the light emitting device employing the polymer compound of this embodiment, $R^{80}$ in formula (3-1) is preferably an unsubstituted or substituted alkyl group or an unsubstituted or substituted aryl group, more preferably a substituted aryl group and even more preferably an alkyl-substituted aryl group.

In formula (3-1), the fluorene ring may have a substituent, and the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group or a cyano group, more preferably an alkyl group, an alkoxy group, an aryl group, an aryloxy group, an arylalkyl group, an arylalkoxy group, a substituted amino group, an acyl group or a cyano group and even more preferably an alkyl group, an alkoxy group or an aryl group.

For excellent hole transport properties and durability of the light emitting device to be produced using the polymer compound of this embodiment, the constitutional unit represented by formula (3) is preferably a constitutional unit represented by the following formula (3-2).

[Chemical Formula 63]

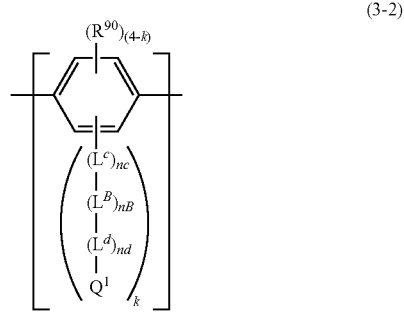

(3-2)

In formula (3-2), nc represents an integer of 0 to 3, nd represents an integer of 0 to 12, nB represents 0 or 1 and k represents an integer of 1 to 4.

$L^c$ and $L^d$ each independently represent an unsubstituted or substituted alkylene group or an unsubstituted or substituted phenylene group. When a plurality of $L^c$ are present, they may be the same or different. When a plurality of $L^d$ are present, they may be the same or different.

$L^B$ represents an oxygen atom or a sulfur atom. When a plurality of $L^B$ are present, they may be the same or different. $Q^1$ has the same meaning as explained above. When a plurality of $Q^1$ are present, they may be the same or different. $R^{90}$ represents a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group or an unsubstituted or substituted heterocyclooxy group. When a plurality of $R^{90}$ are present, they may be the same or different.

In formula (3-2), k represents an integer of 1 to 4, and from the viewpoint of excellent hole transport properties and durability of the light emitting device to be produced using the polymer compound of this embodiment, and conversion of the organic film comprising the polymer compound of this embodiment to an insolubilized organic film, it is preferably 1 or 2 and more preferably 2.

For excellent hole transport properties and durability of the light emitting device employing the polymer compound of this embodiment, $R^{90}$ in formula (3-2) is preferably a hydrogen atom, an unsubstituted or substituted alkyl group or an unsubstituted or substituted aryl group, and for easier synthesis of the monomer starting materials it is more preferably a hydrogen atom.

The constitutional unit represented by formula (3) may be, for example, a constitutional unit represented by the following formulas (3-101) to (3-155), preferably a constitutional unit represented by formulas (3-101) to (3-107), (3-111), (3-114), (3-116) to (3-119), (3-125), (3-132) to (3-143), (3-147) to (3-149) or (3-155), more preferably a constitutional unit represented by formulas (3-101) to (3-105), (3-107), (3-111), (3-114), (3-117) to (3-119), (3-132), (3-134), (3-136), (3-137), (3-140) to (3-143) or (3-147) to (3-149), even more preferably a constitutional unit represented by formulas (3-103), (3-105), (3-132), (3-137) or (3-140), and most preferably a constitutional unit represented by formula (3-132) or (3-140).
[Chemical Formula 64]
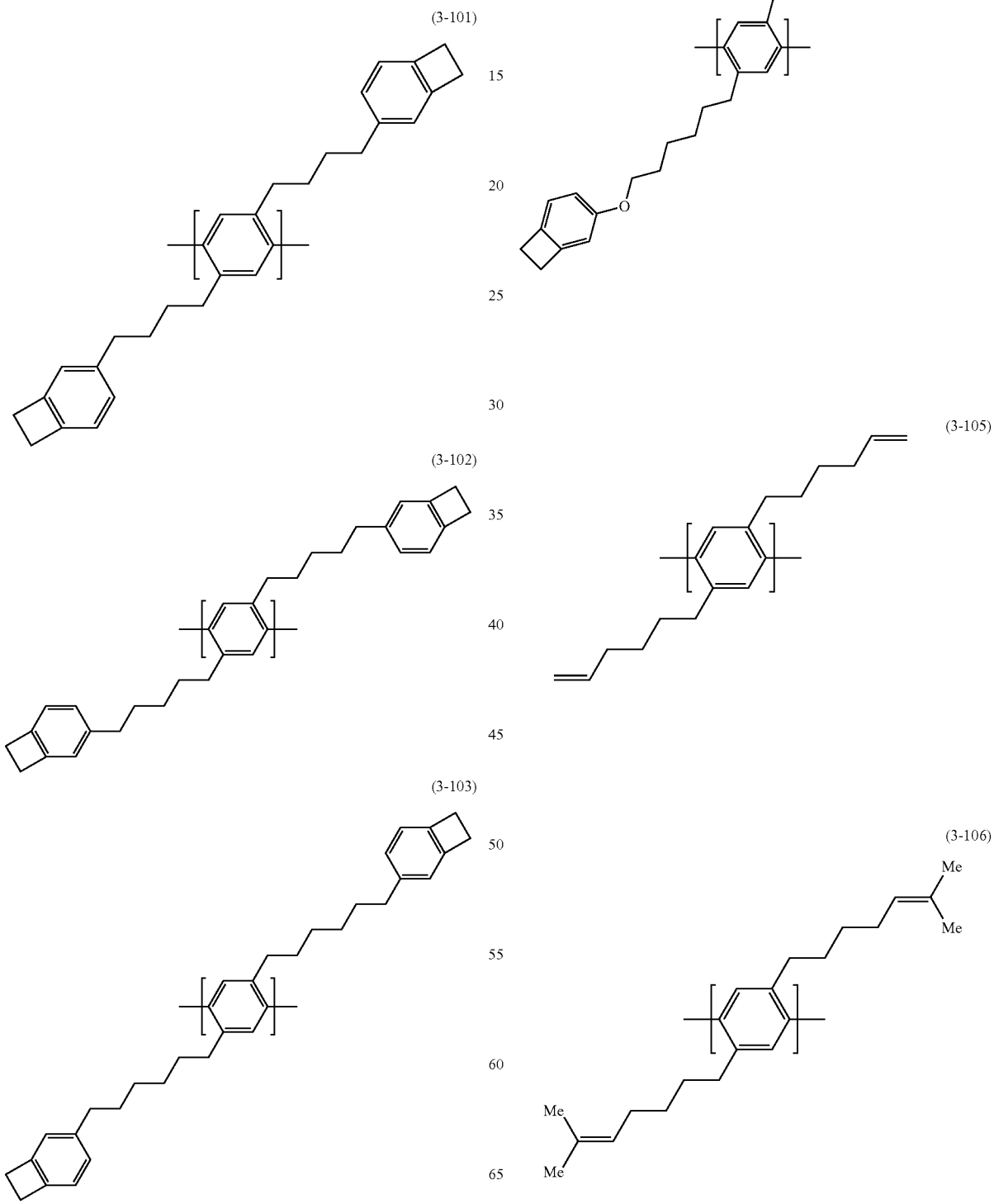

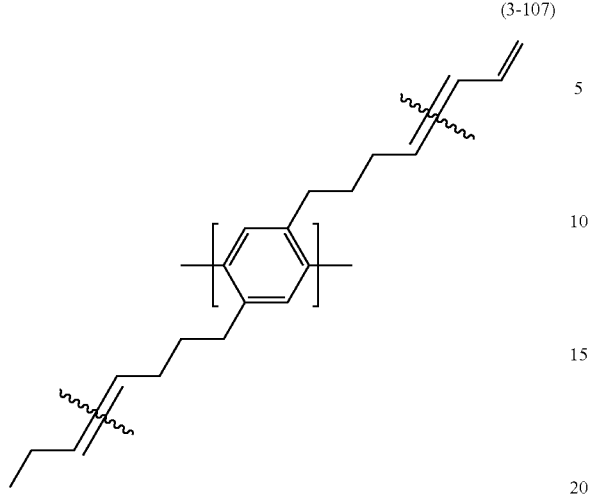
(3-107)
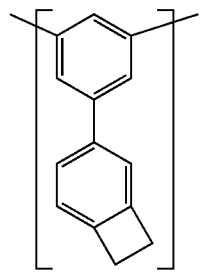
(3-111)
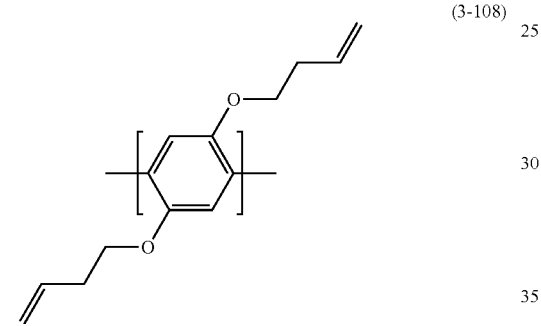
(3-108)
[Chemical Formula 65]
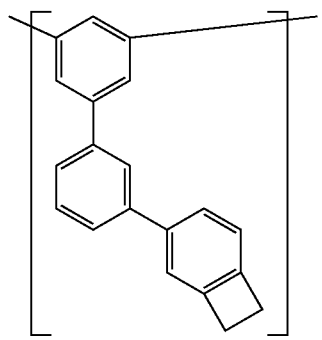
(3-112)
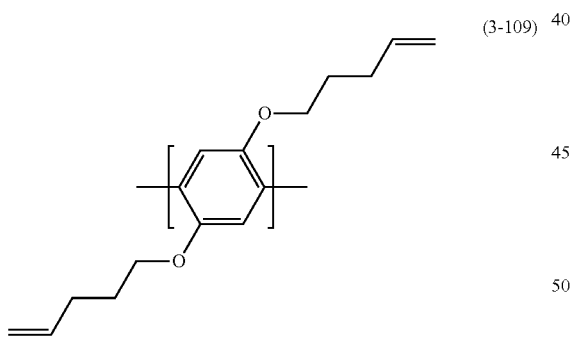
(3-109)
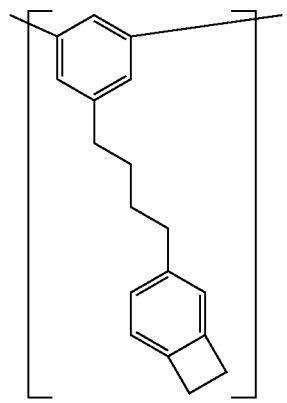
(3-113)
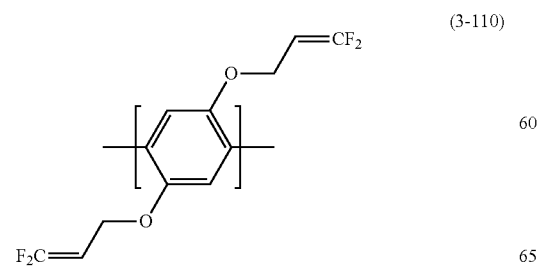
(3-110)
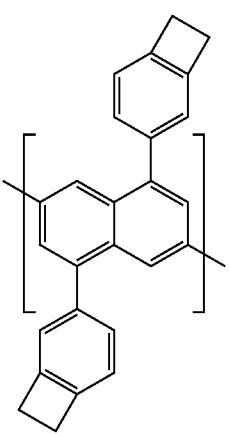
(3-114)

(3-115)
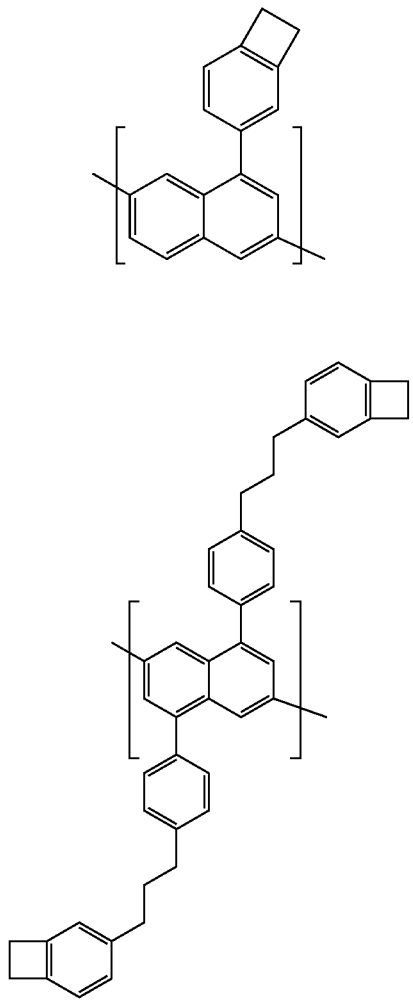
(3-116)
(3-117)
(3-118)
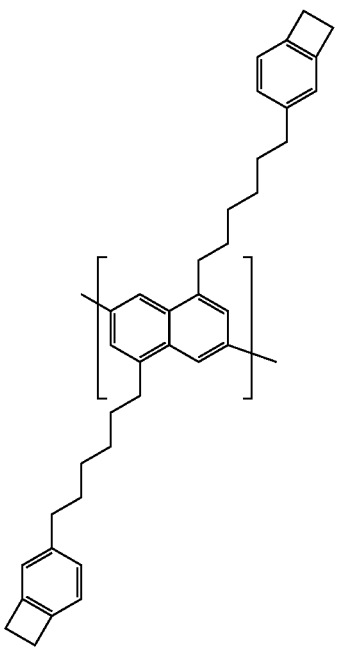
[Chemical Formula 66]
(3-119)
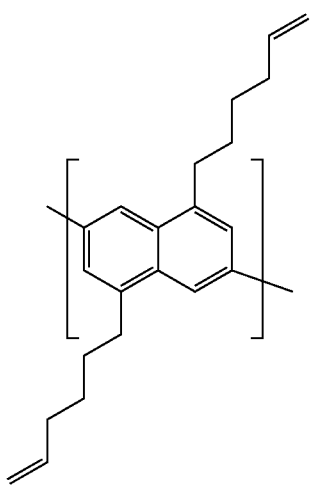

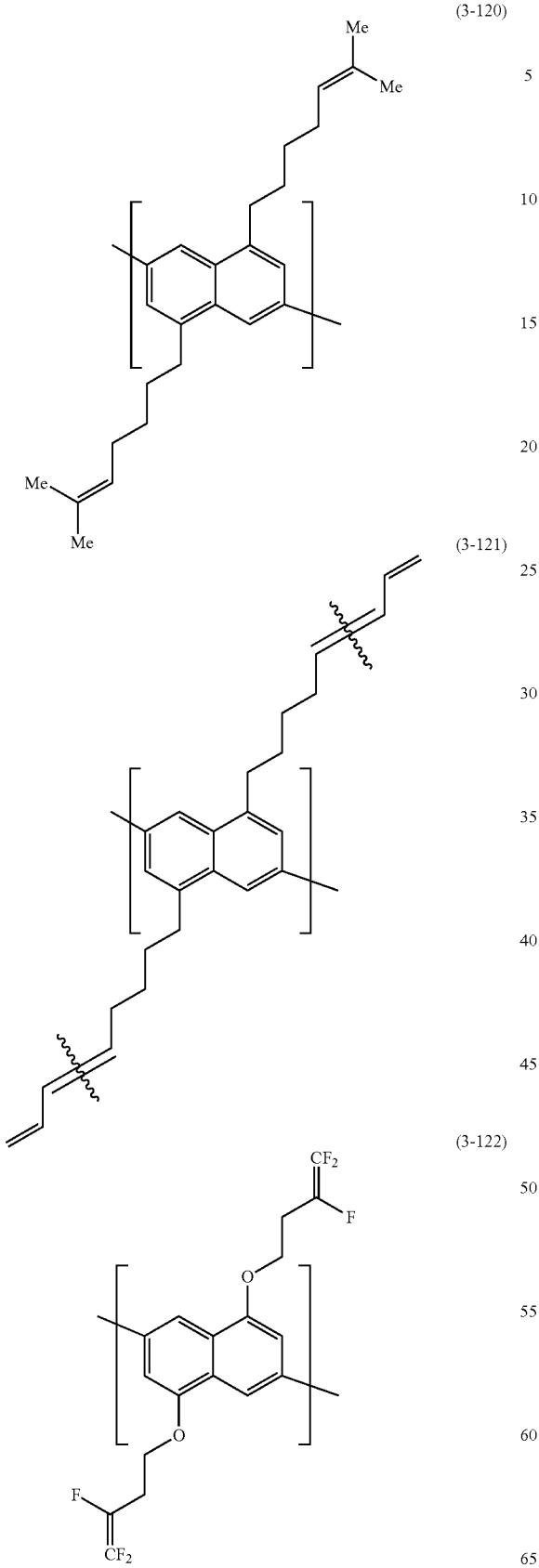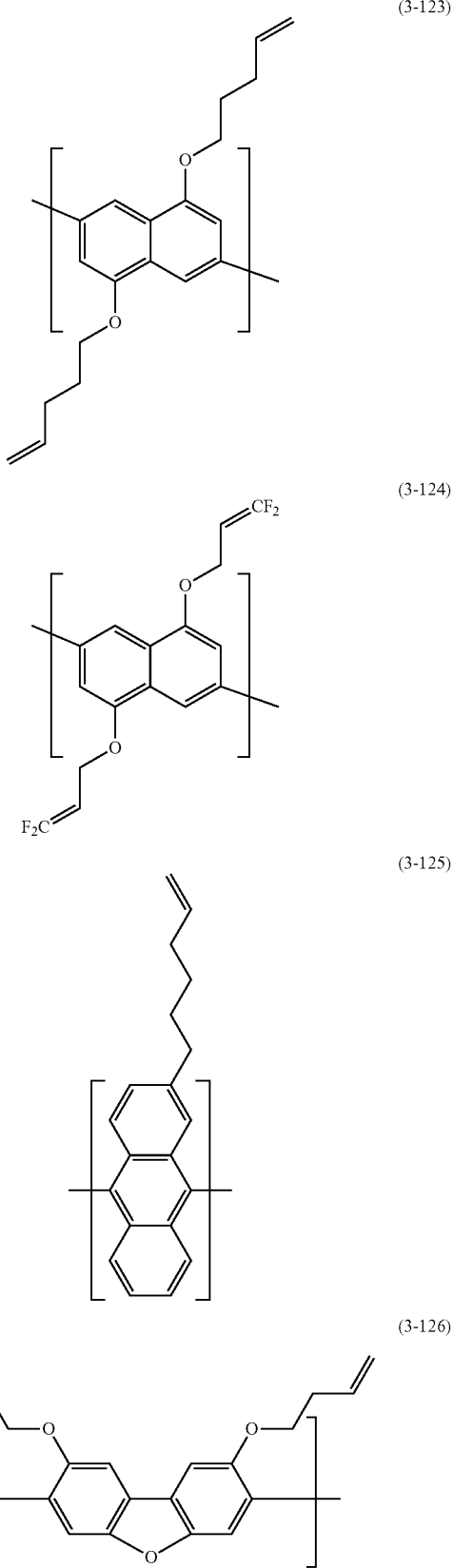

[Chemical Formula 67]
(3-127)
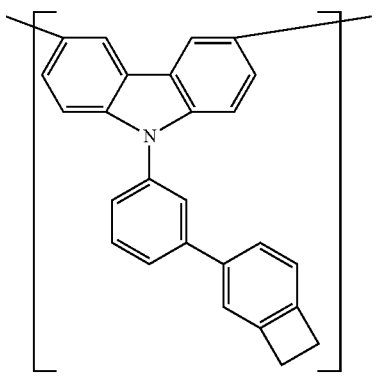
(3-128)
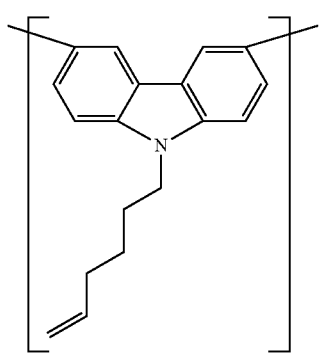
(3-129)
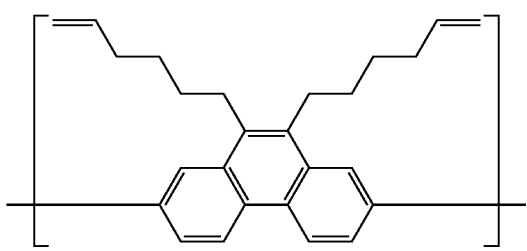
(3-130)
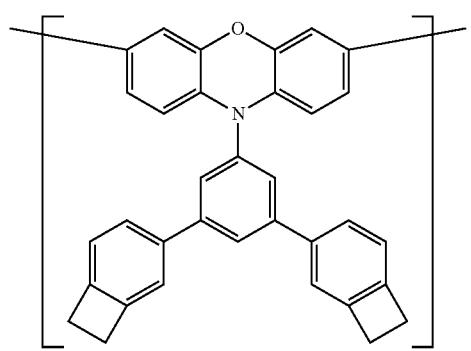
(3-131)
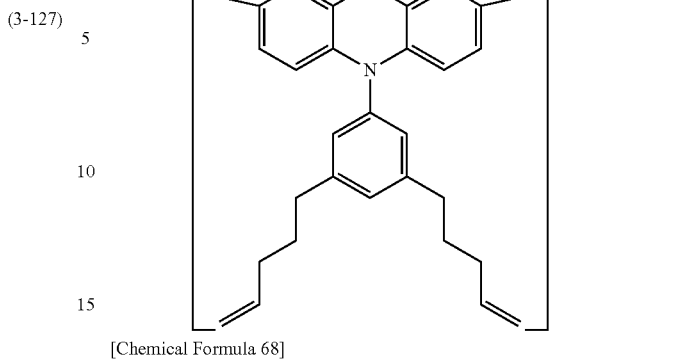
[Chemical Formula 68]
(3-132)
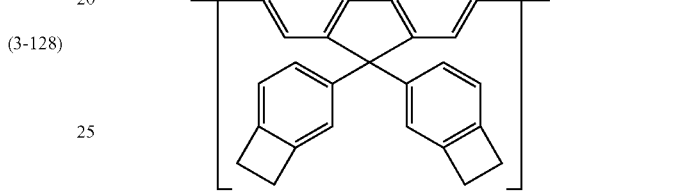
(3-133)
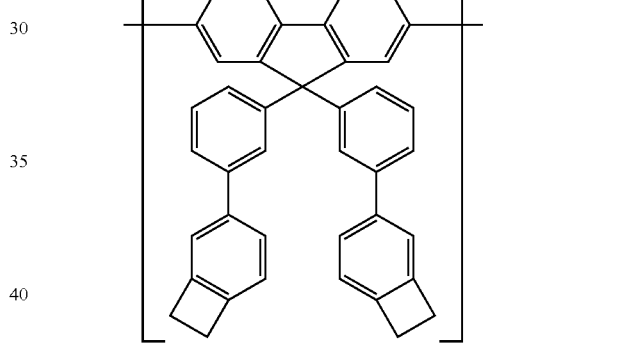
(3-134)
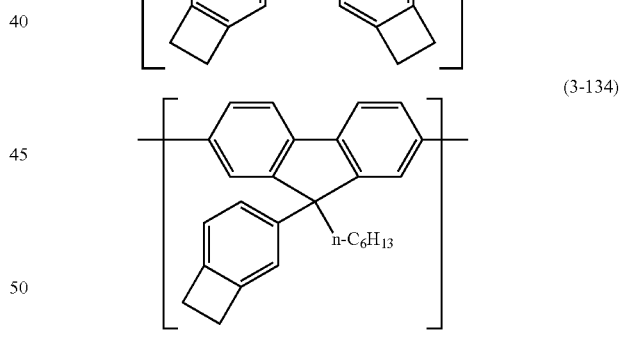
(3-135)
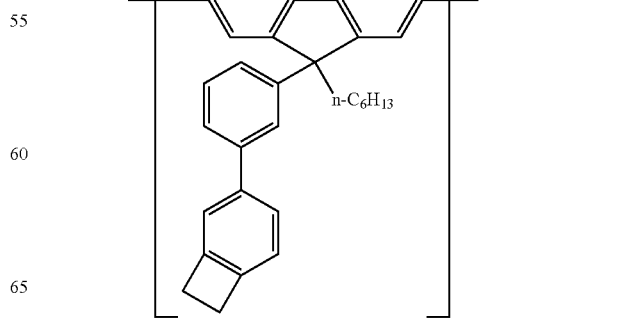

(3-136)
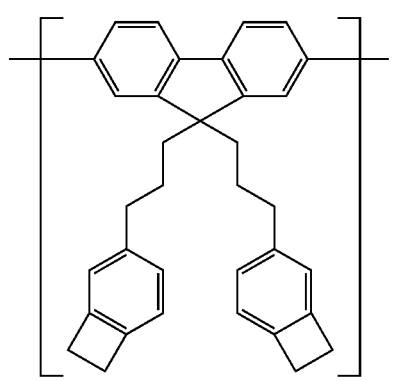
(3-139)
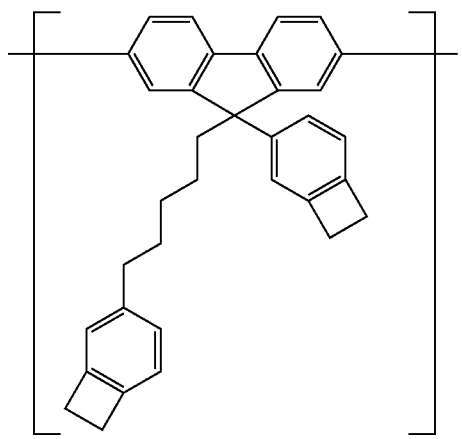
(3-137)
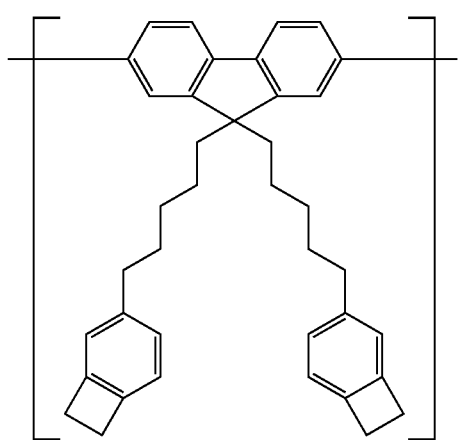
(3-140)
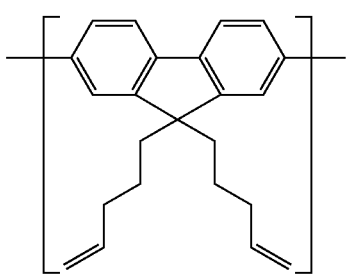
[Chemical Formula 69]
(3-141)
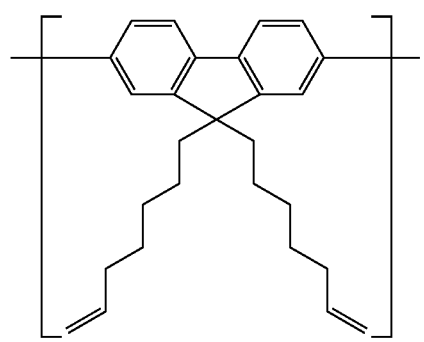
(3-138)
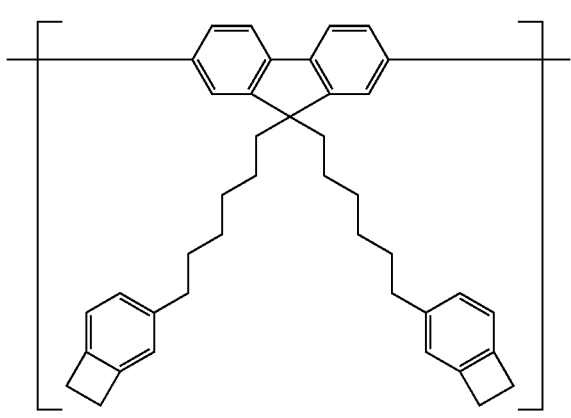
(3-142)
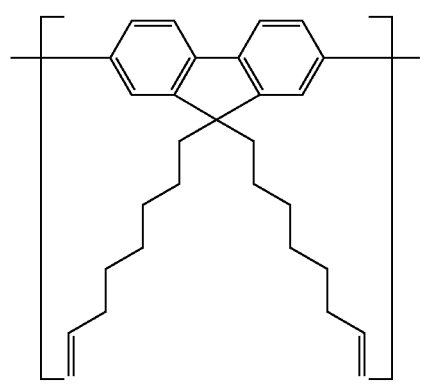

(3-143)
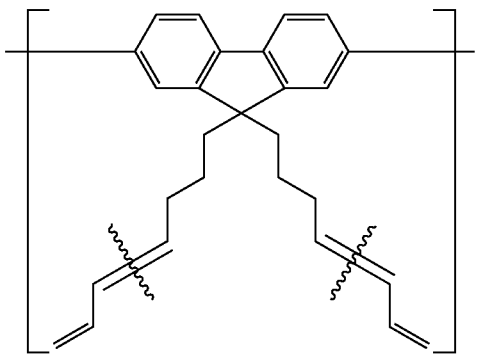
[Chemical Formula 70]
(3-144)
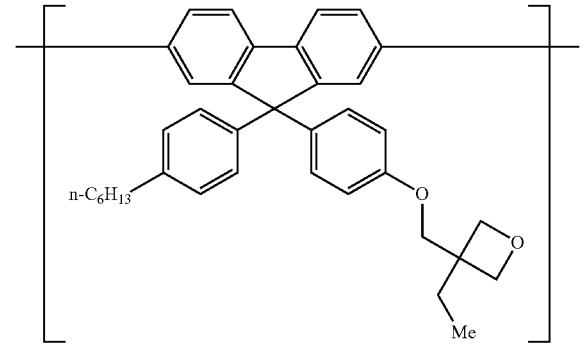
(3-145)
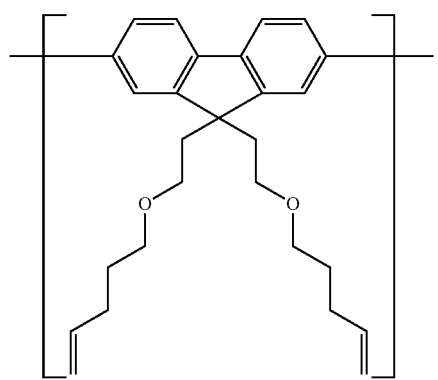
(3-146)
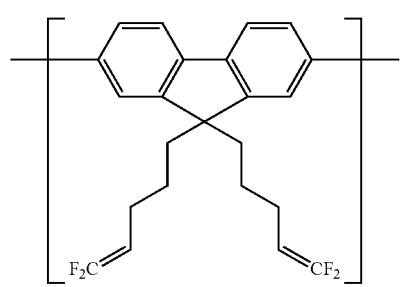
[Chemical Formula 71]
(3-147)
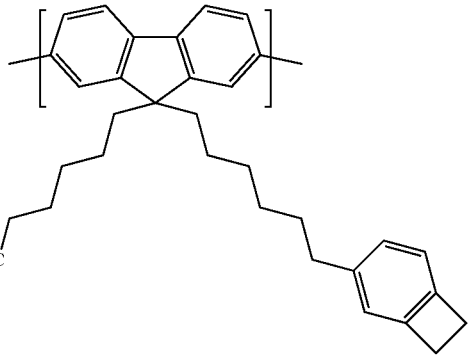
(3-148)
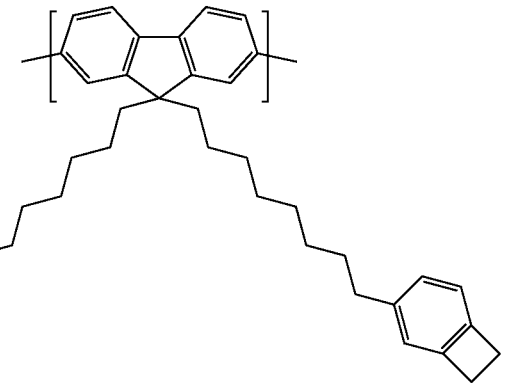
(3-149)
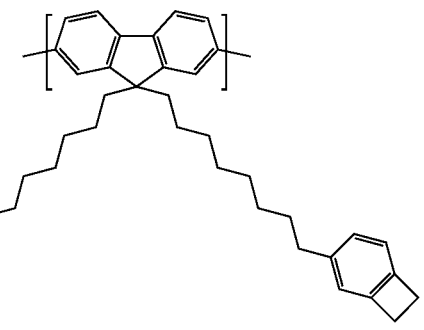
(3-150)
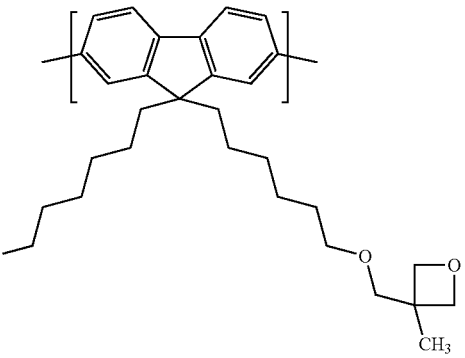

[Chemical Formula 72]

(3-151)
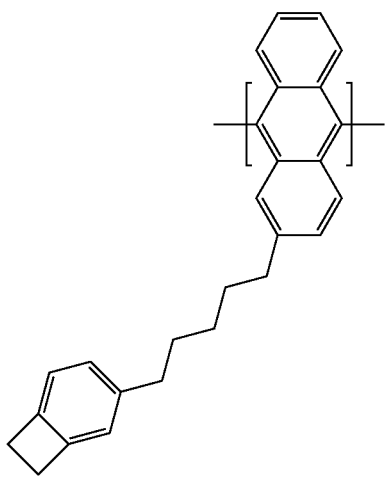

(3-152)
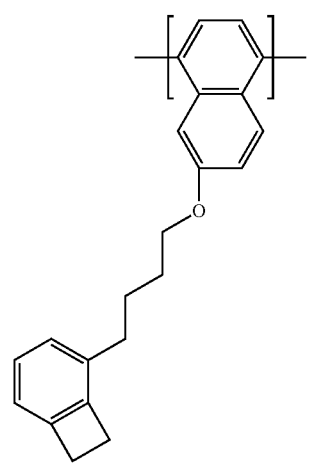

(3-153)
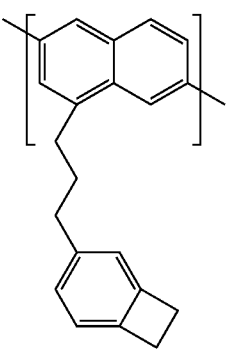

[Chemical Formula 73]

(3-154)
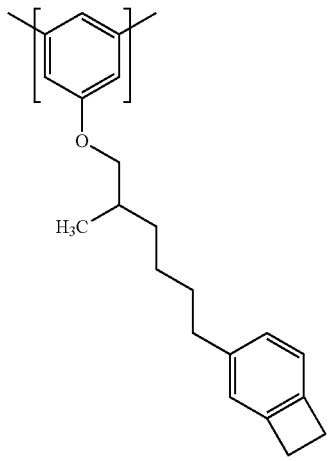

(3-155)
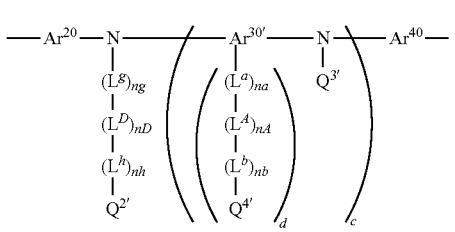

The polymer compound of this embodiment may have a single type of constitutional unit represented by formula (3) as the third constitutional unit or it may have a plurality of different constitutional units among the constitutional units represented by formula (3), but from the viewpoint of conversion of the organic film to an insolubilized organic film, preferably it contains at least one type of monovalent crosslinkable group represented by formula (Q-1), contains at least one type of monovalent crosslinkable group represented by formula (Q-2) or contains at least one type each of a monovalent crosslinkable group represented by formula (Q-1) and formula (Q-2), and more preferably it contains one or more types each of a monovalent crosslinkable group represented by formula (Q-1) and formula (Q-2).

[Chemical Formula 74]

(4')
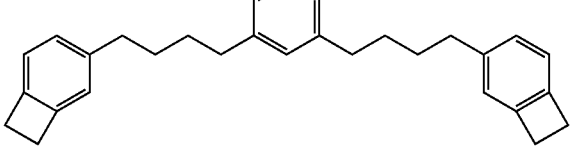

In formula (4'), c represents 0 or 1, and d represents an integer of 0 to 4.

$Ar^{20}$ and $Ar^{40}$ each independently represent an unsubstituted or substituted arylene group or an unsubstituted or substituted divalent heterocyclic group, and $Ar^{30'}$ represents an unsubstituted or substituted (2+d)-valent aromatic hydrocarbon group, an unsubstituted or substituted (2+d)-valent heterocyclic group, or a (2+d)-valent group having a structure in which two or more identical or different rings selected from among aromatic rings and heterocyclic rings are linked (where the (2+d)-valent group may be substituted).

$Q^{2'}$, $Q^{3'}$ and $Q^{4'}$ each independently represent a monovalent crosslinkable group, an unsubstituted or substituted alkyl group, an unsubstituted or substituted aryl group or an unsubstituted or substituted monovalent heterocyclic group, with the proviso that at least one of $Q^{2'}$, $Q^{3'}$ and $Q^{4'}$ is a monovalent crosslinkable group. When a plurality of $Q^{4'}$ are present, they may be the same or different.

na represents an integer of 0 to 3, nb represents an integer of 0 to 12, and nA represents 0 or 1.

$L^a$ and $L^b$ each independently represent an unsubstituted or substituted alkylene group or an unsubstituted or substituted phenylene group. When a plurality of $L^a$ are present they may be the same or different. When a plurality of $L^b$ are present they may be the same or different.

$L^A$ represents an oxygen atom or a sulfur atom. When a plurality of $L^A$ are present, they may be the same or different.

ng represents an integer of 0 to 3, nh represents an integer of 0 to 12, and nD represents 0 or 1.

$L^g$ and $L^h$ each independently represent an unsubstituted or substituted alkylene group or an unsubstituted or substituted phenylene group. When a plurality of $L^g$ are present, they may be the same or different. When a plurality of $L^h$ are present, they may be the same or different.

$L^D$ represents an oxygen atom or a sulfur atom. When a plurality of $L^D$ are present, they may be the same or different.

The constitutional unit represented by formula (4') differs from the constitutional unit represented by formula (1).

In formula (4'), na and ng each independently represent an integer of 0 to 3, and for easier synthesis of the monomer starting materials, preferably an integer of 0 to 2, more preferably 0 or 1 and even more preferably 0.

In formula (4'), nb and nh each independently represent an integer of 0 to 12, and for easier synthesis of the monomer starting materials, preferably an integer of 0 to 10 and more preferably an integer of 0 to 8.

In formula (4'), nA and nD each independently represent 0 or 1 and, for excellent hole transport properties and durability (especially luminance life) of the light emitting device to be produced using the polymer compound of this embodiment, they are preferably 0.

In formula (4'), d is an integer of 0 to 4, but for excellent hole transport properties and durability of the light emitting device to be produced using the polymer compound of this embodiment, it is preferably an integer of 0 to 3 and more preferably an integer of 0 to 2. In formula (4'), the arylene groups of $Ar^{20}$ and $Ar^{40}$ may be, for example, 1,2-phenylene, 1,3-phenylene, 1,4-phenylene, 1,4-naphthalenediyl, 2,6-naphthalenediyl, 2,7-naphthalenediyl, 2,6-anthracenediyl, 9,10-anthracenediyl, 2,7-phenanthrenediyl, 5,12-naphthacenediyl, 2,7-fluorenediyl, 3,6-fluorenediyl, 1,6-pyrenediyl, 2,7-pyrenediyl or 3,8-perylenediyl, and are preferably 1,4-phenylene, 2,7-fluorenediyl, 2,6-anthracenediyl, 9,10-anthracenediyl, 2,7-phenanthrenediyl or 1,6-pyrenediyl groups and more preferably 1,4-phenylene group. These groups may also have the aforementioned substituents.

In formula (4'), the divalent heterocyclic groups of $Ar^{20}$ and $Ar^{40}$ may be, for example, 2,5-pyrrolediyl, dibenzofurandiyl, dibenzothiophenediyl or 2,1,3-benzothiadiazole-4,7-diyl groups. These groups may also have the aforementioned substituents.

In formula (4'), $Ar^{20}$ and $Ar^{40}$ are preferably unsubstituted or substituted arylene groups, for excellent hole transport properties and durability of the light emitting device to be produced using the polymer compound of this embodiment.

In formula (4'), the number of carbon atoms of the unsubstituted or substituted (2+d)-valent aromatic hydrocarbon group represented by $Ar^{30'}$ will usually be 6 to 60, preferably 6 to 48, more preferably 6 to 20 and even more preferably 6 to 14, not counting the carbon atoms of substituents. As (2+d)-valent aromatic hydrocarbon groups there are preferred divalent, trivalent, tetravalent or pentavalent aromatic hydrocarbon groups, with trivalent and tetravalent aromatic hydrocarbon groups being more preferred. Here, a "(2+d)-valent aromatic hydrocarbon group" is an atomic group remaining after removing (2+d) hydrogen atoms directly bonded to a carbon atom composing the ring of an aromatic hydrocarbon (preferably an unsubstituted aromatic carbon ring), and it includes groups with benzene rings and groups with fused rings.

Aromatic hydrocarbons include, for example, benzene, naphthalene, anthracene, 1-tetracene, pyrene, perylene, fluorene, benzofluorene, phenanthrene, dihydrophenanthrene, chrysene and coronene, and for excellent stability of the polymer compound of this embodiment and excellent hole transport properties of the light emitting device to be produced using the polymer compound of this embodiment, benzene, naphthalene, anthracene, pyrene, fluorene, benzofluorene, phenanthrene and dihydrophenanthrene are preferred, and benzene, naphthalene and fluorene are more preferred.

In formula (4'), the number of carbon atoms of the unsubstituted or substituted (2+d)-valent heterocyclic group represented by $Ar^{30'}$ is usually 3 to 60 and preferably 3 to 20, not counting the carbon atoms of substituents. The (2+d)-valent heterocyclic group is preferably a divalent, trivalent, tetravalent or pentavalent heterocyclic group, and more preferably it is a divalent, trivalent or tetravalent heterocyclic group. The (2+d)-valent heterocyclic group is preferably a (2+d)-valent aromatic heterocyclic group. Here, "(2+d)-valent heterocyclic group" means an atomic group remaining after removing (2+d) hydrogen atoms directly bonded to a carbon atom composing the ring of a heterocyclic compound, and it includes monocyclic groups and groups with fused rings.

Examples of heterocyclic compounds include pyridine, pyrimidine, triazine, quinoline, isoquinoline, quinoxaline, dibenzofuran, dibenzothiophene, carbazole, phenoxazine, phenothiazine, benzothiadiazole and dibenzosilol.

In formula (4'), the (2+d)-valent group represented by $Ar^{30'}$, having a structure in which two or more identical or different rings selected from among aromatic rings and heterocyclic rings are linked, is preferably a group represented by formula (B-1), formula (B-2), formula (B-3), formula (B-4), formula (B-5), formula (B-6) or formula (B-7), and more preferably a group represented by formula (B-1). These groups may also have the aforementioned substituents.

When the groups represented by $Ar^{20}$, $Ar^{40}$ and $Ar^{30'}$ in formula (4') have substituents, the substituents are preferably a alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group or a cyano group, more preferably an alkyl group, an alkoxy group, an aryl group, an aryloxy group, an arylalkyl group, an arylalkoxy group, a substituted amino group, an acyl group or a cyano group, and even more preferably an alkyl group, an alkoxy group or an aryl group.

In formula (4'), $Ar^{30'}$ is preferably an unsubstituted or substituted (2+d)-valent aromatic hydrocarbon group, for excellent hole transport properties and durability of the light emitting device to be produced using the polymer compound of this embodiment.

In formula (4'), the alkylene groups represented by $L^a$, $L^b$, $L^g$ and $L^h$ may be straight-chain, branched or cyclic, and may be substituted. For easier synthesis of the monomer starting materials, straight-chain alkylene groups are preferred. The number of carbon atoms for straight-chain alkylene and branched alkylene groups will usually be 1 to 20 and is preferably 1 to 10 and more preferably 1 to 6. The number of carbon atoms for a cycloalkylene group will usually be 3 to 20 and is preferably 3 to 10 and more preferably 3 to 6.

Alkylene groups include methylene, 1,2-ethylene, 1,3-propylene, 1,3-butylene, 1,3-pentylene, 1,4-pentylene, 1,5-pentylene, 1,4-hexylene, 1,6-hexylene, 1,7-heptylene, 1,6-octylene and 1,8-octylene groups.

In formula (4'), the phenylene groups represented by $L^a$, $L^b$, $L^g$ and $L^h$ may be substituted. Phenylene groups include o-phenylene, m-phenylene and p-phenylene groups. Suitable substituents for phenylene groups include an alkyl group, an alkoxy group, a halogen atom and a cyano group.

In formula (4'), $L^a$ and $L^g$ are preferably phenylene groups for easier synthesis of the monomer starting materials.

In formula (4'), $L^b$ and $L^h$ are preferably alkylene groups for easier synthesis of the monomer starting materials.

In formula (4'), each of $L^A$ and $L^D$ represents an oxygen atom or a sulfur atom and is preferably an oxygen atom for easier synthesis of the monomer starting materials.

In formula (4'), $Q^{2'}$, $Q^{3'}$ and $Q^{4'}$ each independently represent a monovalent crosslinkable group, an unsubstituted or substituted alkyl group, an unsubstituted or substituted aryl group or an unsubstituted or substituted monovalent heterocyclic group, with the proviso that at least one of $Q^{2'}$, $Q^{3'}$ and $Q^{4'}$ is a monovalent crosslinkable group.

Examples for the monovalent crosslinkable groups represented by $Q^{2'}$, $Q^{3'}$ and $Q^{4'}$ in formula (4') include an unsubstituted or substituted aziridinyl group, an unsubstituted or substituted azetidinyl group, an azide group, an unsubstituted or substituted epoxy group, an unsubstituted or substituted oxetanyl group, an unsubstituted or substituted alkenyl group, an unsubstituted or substituted alkynyl group, and group with a cyclobutene structure, and for easier synthesis of the monomer starting materials, they are preferably an unsubstituted or substituted aziridinyl group, an azide group, an unsubstituted or substituted epoxy group, an unsubstituted or substituted oxetanyl group, an unsubstituted or substituted alkenyl group, an unsubstituted or substituted alkynyl group, an unsubstituted or substituted aryl group with a cyclobutene structure or an unsubstituted or substituted monovalent heterocyclic group with a cyclobutene structure, more preferably an unsubstituted or substituted alkenyl group, an unsubstituted or substituted aryl group with a cyclobutene structure or an unsubstituted or substituted monovalent heterocyclic group with a cyclobutene structure, and even more preferably an unsubstituted or substituted alkenyl group or an unsubstituted or substituted aryl group with a cyclobutene structure.

Examples of monovalent crosslinkable groups represented by $Q^{2'}$, $Q^{3'}$ and $Q^{4'}$ in formula (4') include monovalent crosslinkable groups represented by formulas (Q-1), (Q-2), (Q-01) to (Q-19), (Q-1-1) and (Q-1-2), and for easier synthesis of the monomer starting materials, they are preferably monovalent crosslinkable groups represented by formulas (Q-1), (Q-2), (Q-01), (Q-03), (Q-04), (Q-06) to (Q-18), (Q-1-1) and (Q-1-2), more preferably monovalent crosslinkable groups represented by formulas (Q-1), (Q-2), (Q-09) to (Q-19), (Q-1-1) and (Q-1-2), and even more preferably monovalent crosslinkable groups represented by formulas (Q-1), (Q-1-1), (Q-1-2) and (Q-2).

When $Q^{2'}$, $Q^{3'}$ or $Q^{4'}$ is a group other than a monovalent crosslinkable group, $Q^{2'}$, $Q^{3'}$ or $Q^{4'}$ is preferably an unsubstituted or substituted aryl group and more preferably an unsubstituted or substituted phenyl group. Such a structure will result in excellent hole transport properties and durability of the light emitting device to be produced using the polymer compound of this embodiment.

Unsubstituted or substituted alkyl groups represented by $Q^{2'}$, $Q^{3'}$ and $Q^{4'}$ in formula (4') are the same as the "alkyl groups" mentioned above as substituents, but they are preferably $C_1$-$C_{20}$ alkyl groups.

Unsubstituted or substituted aryl groups represented by $Q^{2'}$, $Q^{3'}$ and $Q^{4'}$ in formula (4') are the same as the "aryl groups" mentioned above as substituents, but they are preferably phenyl, 1-naphthyl, 2-naphthyl, 1-anthracenyl, 2-anthracenyl, 9-anthracenyl or 2-fluorenyl groups.

Unsubstituted or substituted monovalent heterocyclic groups represented by $Q^{2'}$, $Q^{3'}$ and $Q^{4'}$ in formula (4') are the same as the "monovalent heterocyclic groups" mentioned above as substituents, but they are preferably pyridyl, pyrimidyl, triazyl or quinolyl groups.

The constitutional unit represented by formula (4') is preferably a constitutional unit represented by the following formula (4'-1), for easier synthesis of the monomer starting materials.

[Chemical Formula 75]

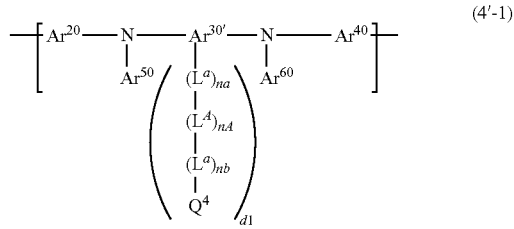

(4'-1)

$Ar^{20}$, $Ar^{30'}$, $Ar^{40}$, $L^a$, $L^b$, $L^A$, na, nb and nA have the same meanings as for formula (4').

d1 represents an integer of 1 to 4.

$Ar^{50}$ and $Ar^{60}$ each independently represent an unsubstituted or substituted aryl group or an unsubstituted or substituted monovalent heterocyclic group.

$Q^4$ represents a monovalent crosslinkable group.

In formula (4'-1), d1 is an integer of 1 to 4, but for excellent hole transport properties and durability of the light emitting device to be produced using the polymer compound of this embodiment, it is preferably an integer of 1 to 3 and more preferably 2.

In formula (4'-1), $Ar^{50}$ and $Ar^{60}$ each independently represent an unsubstituted or substituted aryl or unsubstituted or substituted monovalent heterocyclic group, but for excellent hole transport properties and durability of the light emitting device to be produced using the polymer compound of this embodiment, they are preferably unsubstituted or substituted aryl groups.

Unsubstituted or substituted aryl groups represented by $Ar^{50}$ and $Ar^{60}$ in formula (4'-1) are the same as the "aryl groups" mentioned above as substituents, but they are preferably phenyl, 1-naphthyl, 2-naphthyl, 1-anthracenyl, 2-anthracenyl, 9-anthracenyl or 2-fluorenyl groups.

Unsubstituted or substituted monovalent heterocyclic groups represented by $Ar^{50}$ and $Ar^{60}$ in formula (4'-1) are the same as the "monovalent heterocyclic groups" mentioned above as substituents, but they are preferably pyridyl, pyrimidyl, triazyl or quinolyl groups.

Examples for monovalent crosslinkable groups represented by $Q^4$ in formula (4'-1) include an unsubstituted or substituted aziridinyl group, an unsubstituted or substituted azetidinyl group, an azide group, an unsubstituted or substituted epoxy group, an unsubstituted or substituted oxetanyl group, an unsubstituted or substituted alkenyl group, an unsubstituted or substituted alkynyl group, and group with a cyclobutene structure, and for easier synthesis of the monomer starting materials, it is preferably an unsubstituted or substituted aziridinyl group, an azide group, an unsubstituted or substituted epoxy group, an unsubstituted or substituted oxetanyl group, an unsubstituted or substituted alkenyl group, an unsubstituted or substituted alkynyl group, an unsubstituted or substituted aryl group with a cyclobutene structure or an unsubstituted or substituted monovalent heterocyclic group with a cyclobutene structure, more preferably an unsubstituted or substituted alkenyl group, an unsubstituted or substituted aryl group with a cyclobutene structure, or an unsubstituted or substituted monovalent heterocyclic group with a cyclobutene structure, and even more preferably an unsubstituted or substituted alkenyl or an unsubstituted or substituted aryl with a cyclobutene structure.

Examples of monovalent crosslinkable groups represented by $Q^4$ in formula (4'-1) include monovalent crosslinkable groups represented by formulas (Q-1), (Q-2), (Q-01) to (Q-19), (Q-1-1) and (Q-1-2), and for easier synthesis of the monomer starting materials, it is preferably a monovalent crosslinkable group represented by any of formulas (Q-1), (Q-2), (Q-01), (Q-03), (Q-04), (Q-06) to (Q-18), (Q-1-1) and (Q-1-2), more preferably a monovalent crosslinkable group represented by any of formulas (Q-1), (Q-2), (Q-09) to (Q-19), (Q-1-1) and (Q-1-2), and even more preferably a monovalent crosslinkable group represented by any of formulas (Q-1), (Q-1-1), (Q-1-2) and (Q-2).

[Chemical Formula 76]

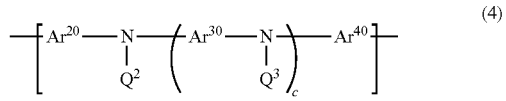

(4)

Formula (4') is preferably formula (4) above, for easier synthesis of the monomer starting materials.

In formula (4), c, $Ar^{20}$ and $Ar^{40}$ have the same meanings explained above.

$Ar^{30}$ represents an unsubstituted or substituted arylene group, an unsubstituted or substituted divalent heterocyclic group, or a divalent group having two or more identical or different linked groups selected from arylene groups and divalent heterocyclic groups (the group may be substituted).

$Q^2$ represents a monovalent crosslinkable group, and $Q^3$ represents a monovalent crosslinkable group, an unsubstituted or substituted alkyl group, an unsubstituted or substituted aryl group or an unsubstituted or substituted monovalent heterocyclic group.

In formula (4), c is preferably 0 for easier synthesis of the monomer starting materials and for excellent hole transport properties and durability of the light emitting device to be produced using the polymer compound of this embodiment.

In formula (4), the groups represented by $Ar^{20}$, $Ar^{30}$ and $Ar^{40}$ are preferably unsubstituted or substituted arylene groups for excellent hole transport properties and durability of the light emitting device to be produced using the polymer compound of this embodiment.

In formula (4), the arylene groups of $Ar^{20}$, $Ar^{30}$ and $Ar^{40}$ may be, for example, 1,2-phenylene, 1,3-phenylene, 1,4-phenylene, 1,4-naphthalenediyl, 2,6-naphthalenediyl, 2,7-naphthalenediyl, 2,6-anthracenediyl, 9,10-anthracenediyl, 2,7-phenanthrenediyl, 5,12-naphthacenediyl, 2,7-fluorenediyl, 3,6-fluorenediyl, 1,6-pyrenediyl, 2,7-pyrenediyl or 3,8-perylenediyl, and are preferably 1,4-phenylene, 2,7-fluorenediyl, 2,6-anthracenediyl, 9,10-anthracenediyl, 2,7-phenanthrenediyl or 1,6-pyrenediyl groups and more preferably 1,4-phenylene groups. These groups may also have the aforementioned substituents.

In formula (4), the divalent heterocyclic groups of $Ar^{20}$, $Ar^{30}$ and $Ar^{40}$ may be, for example, 2,5-pyrrolediyl, dibenzofurandiyl, dibenzothiophenediyl or 2,1,3-benzothiadiazole-4,7-diyl groups, and these groups may have the aforementioned substituents.

The divalent group having two or more identical or different linked groups selected from among arylene groups and divalent heterocyclic groups for $Ar^{30}$ in formula (4) is preferably a group represented by formula (B-1), (B-2), (B-3), (B-4), (B-5), (B-6) or (B-7), and more preferably a group represented by formula (B-1). These groups may also have the aforementioned substituents.

When the groups represented by $Ar^{20}$, $Ar^{30}$, and $Ar^{40}$ in formula (4) have substituents, the substituents may be an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group or a cyano group, preferably an alkyl group, an alkoxy group, an aryl group, an aryloxy group, an arylalkyl group, an arylalkoxy group, a substituted amino group, an acyl group or a cyano group, and more preferably an alkyl group, an alkoxy group or an aryl group.

The monovalent crosslinkable group represented by $Q^2$ in formula (4) may be, for example, a group represented by formula (Q-1), (Q-2) or (Q-01) to (Q-19), and for excellent hole transport properties and durability of the light emitting device to be produced using the polymer compound of this embodiment, it is preferably a group represented by formula (Q-1), (Q-2), (Q-01), (Q-03), (Q-04) or (Q-06) to (Q-18), more preferably a group represented by formula (Q-1), (Q-2) or (Q-07) to (Q-18), and even more preferably a group represented by formula (Q-1).

The monovalent crosslinkable group represented by $Q^3$ in formula (4) may be, for example, a group represented by formula (Q-1), (Q-2) or (Q-01) to (Q-19), and for excellent hole transport properties and durability of the light emitting device to be produced using the polymer compound of this embodiment, it is preferably a group represented by formula (Q-1), (Q-2), (Q-01), (Q-03), (Q-04) or (Q-06) to (Q-18), more preferably a group represented by formula (Q-1), (Q-2)

or (Q-07) to (Q-18), and even more preferably a group represented by formula (Q-1).

Unsubstituted or substituted alkyl groups represented by $Q^3$ in formula (4) may be the same as the "alkyl groups" mentioned above as substituents, but they are preferably $C_1$-$C_{20}$ alkyl groups.

Unsubstituted or substituted aryl groups represented by $Q^3$ in formula (4) are the same as the "aryl groups" mentioned above as substituents, but they are preferably phenyl, 1-naphthyl, 2-naphthyl, 1-anthracenyl, 2-anthracenyl, 9-anthracenyl or 2-fluorenyl groups.

Unsubstituted or substituted monovalent heterocyclic groups represented by $Q^3$ in formula (4) are the same as the "monovalent heterocyclic groups" mentioned above as substituents, but they are preferably pyridyl, pyrimidyl, triazyl or quinolyl groups.

In formula (4), $Q^3$ is preferably the same monovalent crosslinkable group as $Q^1$, for easier synthesis of the monomer starting materials.

When the group represented by $Q^3$ in formula (4) has a substituent, the substituent is preferably an alkyl group, an alkoxy group, an aryl group, an aryloxy group, an arylalkyl group, an arylalkoxy group, an arylalkenyl group, an arylalkynyl group, an amino group, a substituted amino group, a halogen atom, an acyl group, an acyloxy group, a monovalent heterocyclic group, a carboxyl group, a nitro group or a cyano group, more preferably an alkyl group, an alkoxy group, an aryl group, an aryloxy group, an arylalkyl group, an arylalkoxy group, a substituted amino group, an acyl group or a cyano group, and even more preferably an alkyl group, an alkoxy group or an aryl group.

Constitutional units represented by formula (4') include, for example, constitutional units represented by formulas (4-101) to (4-127), and they are preferably constitutional units represented by formulas (4-101) to (4-110) or formulas (4-115) to (4-127), more preferably constitutional units represented by formula (4-101), formulas (4-105) to (4-108), formula (4-115) or formulas (4-117) to (4-124), even more preferably constitutional units represented by formula (4-101), formula (4-105), formula (4-107), formula (4-115), formula (4-118), formula (4-120) or formula (4-124), and most preferably constitutional units represented by formula (4-101), formula (4-115), formula (4-118) or formula (4-120).

[Chemical Formula 77]

(4-101)

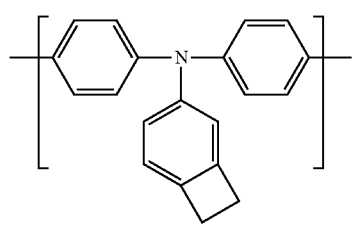

(4-102)

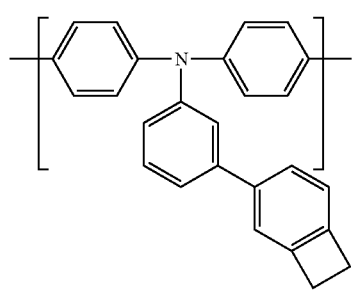

(4-103)

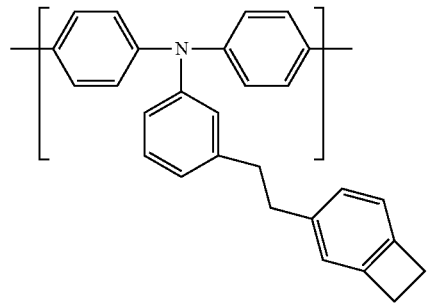

(4-104)

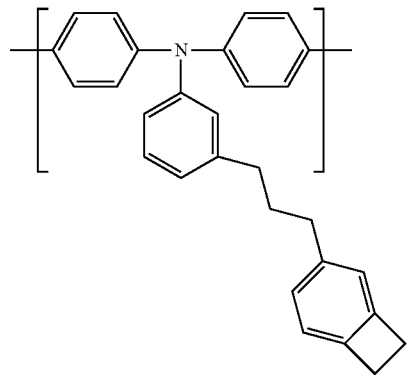

(4-105)

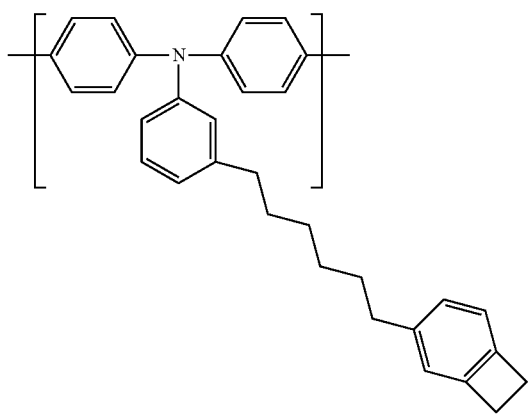

(4-106)

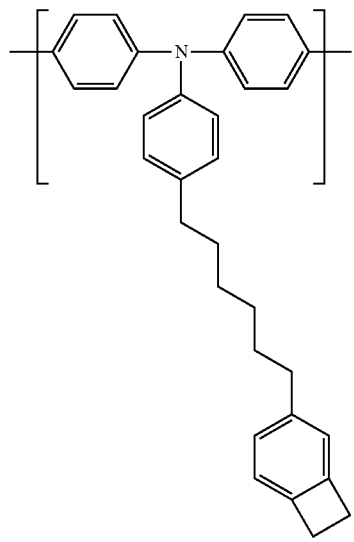
(4-107)
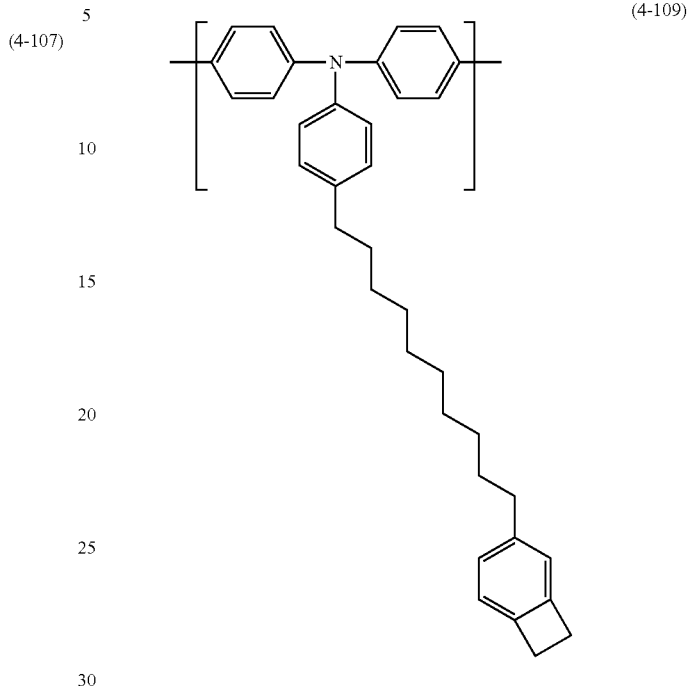
(4-109)
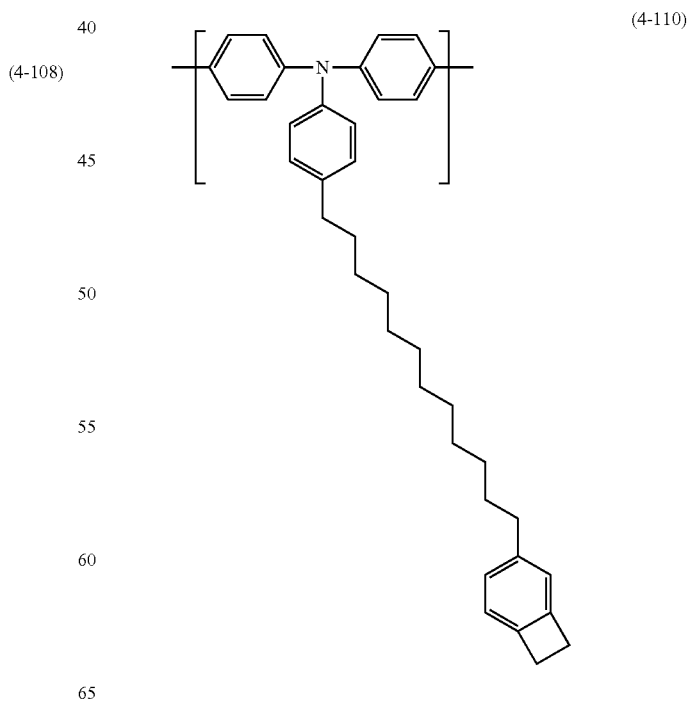
(4-110)
(4-108)

(4-111)
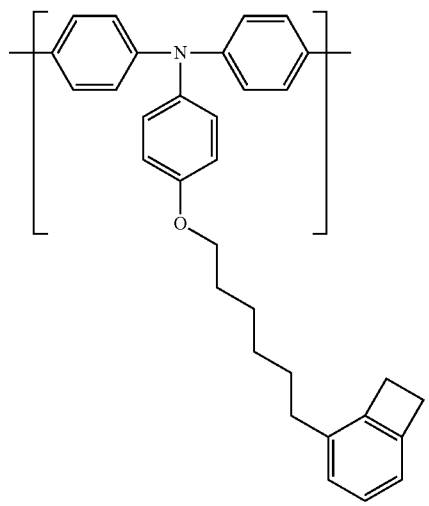
(4-112)
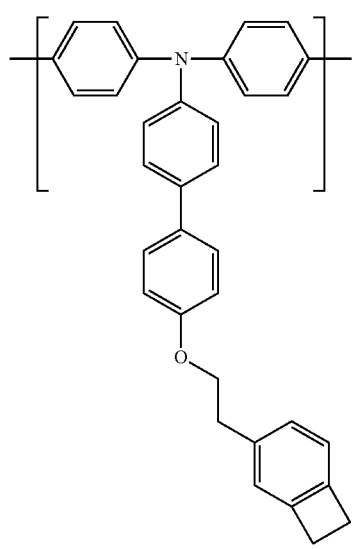
(4-113)
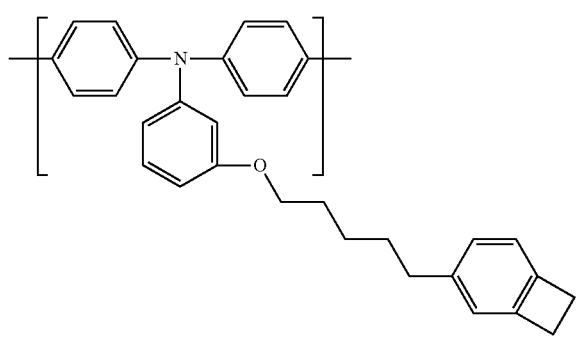
(4-114)
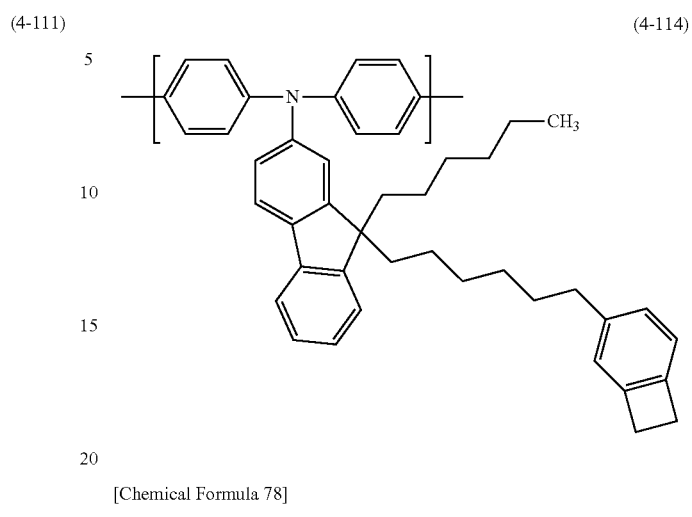
[Chemical Formula 78]
(4-115)
(4-116)
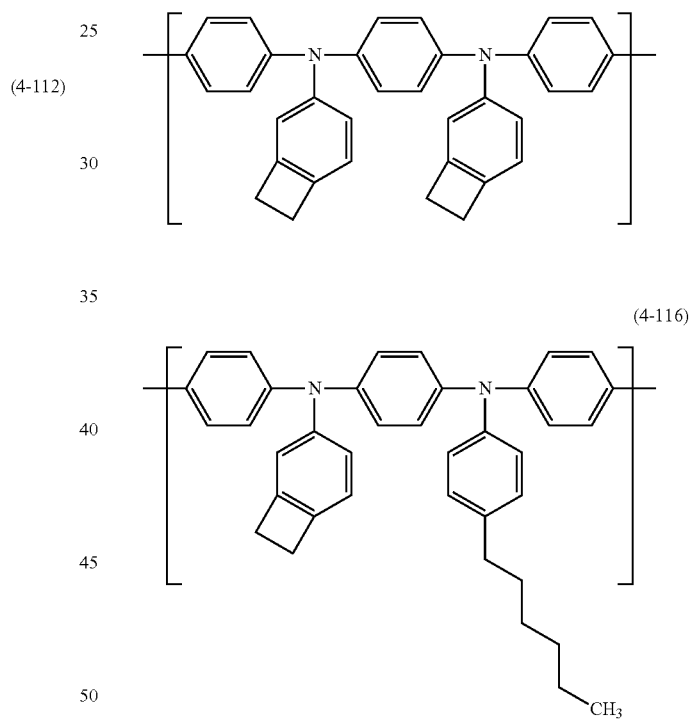
(4-117)
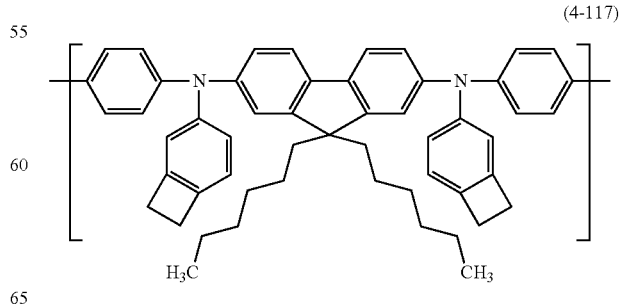

-continued
(4-118)
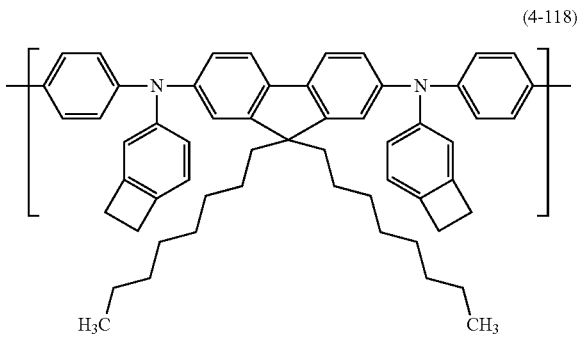
(4-119)
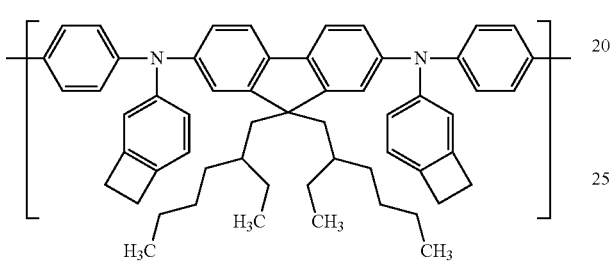
[Chemical Formula 79]
(4-120)
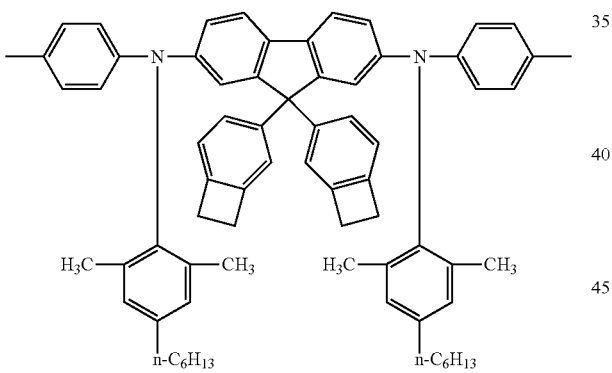
(4-121)
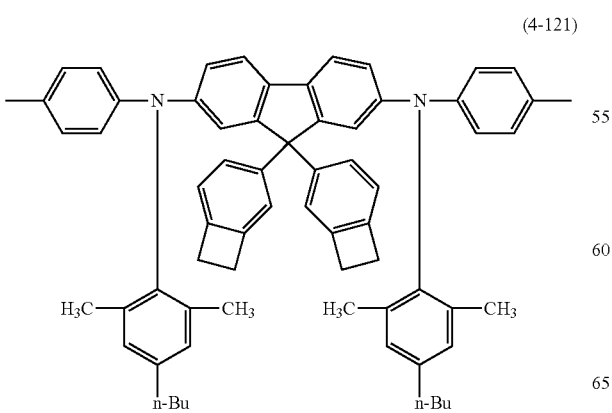
-continued
(4-122)
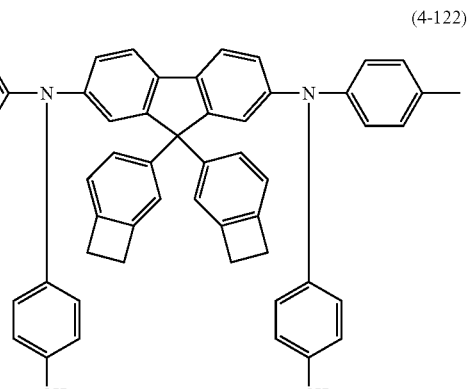
(4-123)
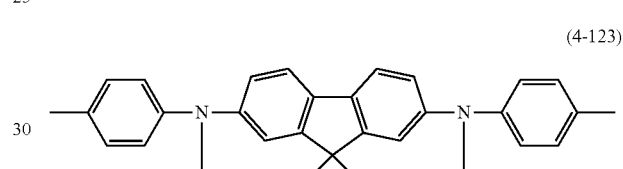
(4-124)
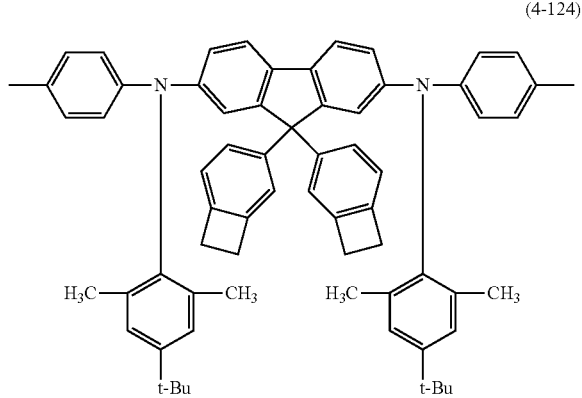

(4-125)

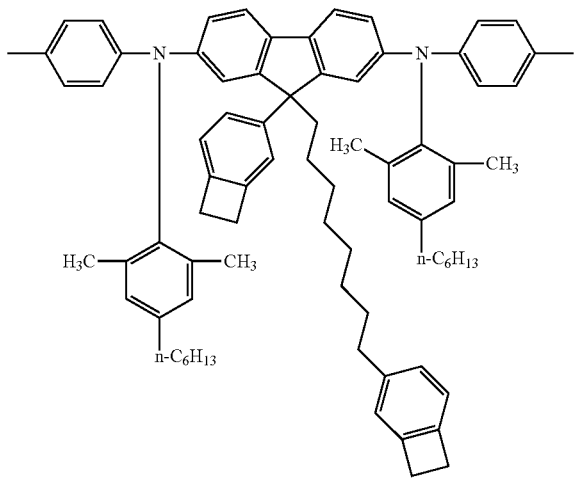

(4-126)

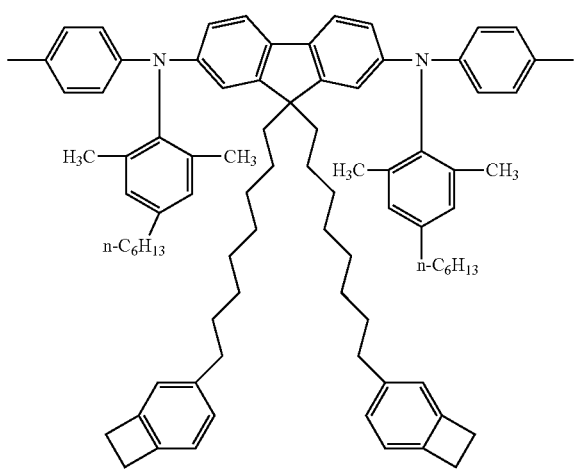

(4-127)

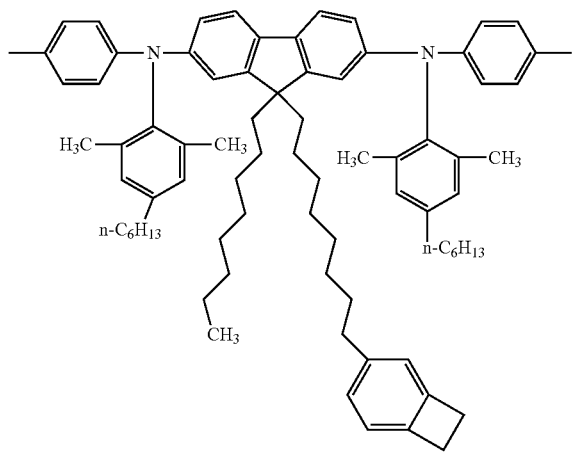

The polymer compound of the invention is a polymer compound comprising a constitutional unit represented by formula (1), a constitutional unit represented by formula (2), and a constitutional unit represented by formula (3) and/or a constitutional unit represented by formula (4') below, but it is preferably a polymer compound comprising a constitutional unit represented by formula (1), a constitutional unit represented by formula (2) and at least two constitutional units selected from the group consisting of constitutional units represented by formula (3) and constitutional units represented by formula (4'), it is more preferably a polymer compound comprising a constitutional unit represented by formula (1), a constitutional unit represented by formula (2) and at least two constitutional units represented by formula (3), for excellent durability of the light emitting device to be produced using the polymer compound of this embodiment, it is even more preferably a polymer compound comprising a constitutional unit represented by formula (1), a constitutional unit represented by formula (2) and two constitutional units represented by formula (3), it is especially preferably a polymer compound comprising a constitutional unit represented by formula (1), a constitutional unit represented by formula (2) and two constitutional units selected from among constitutional units represented by formula (3-103), constitutional units represented by formula (3-105), constitutional units represented by formula (3-132), constitutional units represented by formula (3-137) and constitutional units represented by formula (3-140), and it is most preferably a polymer compound comprising a constitutional unit represented by formula (1), a constitutional unit represented by formula (2), a constitutional unit represented by formula (3-132) and a constitutional unit represented by formula (3-140).

(Other Constitutional Units)

The polymer compound of the invention may also comprise constitutional units other than the first constitutional unit, second constitutional unit and third constitutional unit.

The first constitutional unit, second constitutional unit and third constitutional unit of the polymer compound of the invention may be linked with nonconjugated structures (that is, other constitutional units). Examples of nonconjugated structures include the following structures, as well as combinations of two or more of the structures.

[Chemical Formula 80]

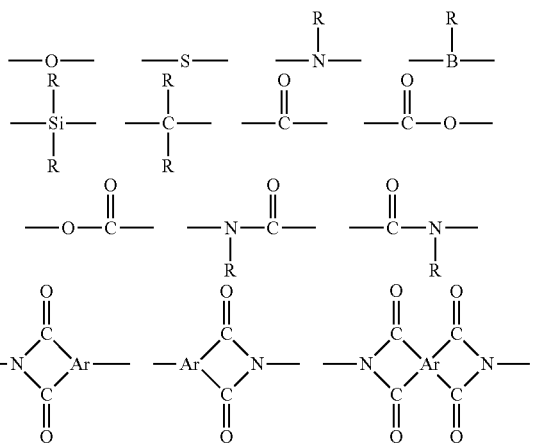

[In the formula,

R represents a hydrogen atom or an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxyl group, a nitro group or a cyano group.

Ar represents a $C_{6-60}$ aromatic hydrocarbon group optionally containing a heteroatom.]

The heteroatom in the formula may be an oxygen atom, a sulfur atom, a nitrogen atom, a silicon atom, a boron atom, a phosphorus atom, a selenium atom or the like.

The content (total content) of the first constitutional unit is preferably 0.1 to 99.9 mol %, more preferably 1 to 99 mol %, even more preferably 5 to 70 mol % and most preferably 10 to 50 mol % with respect to the total constitutional units in the polymer compound, for excellent luminous efficiency of the light emitting device to be produced using the polymer compound of this embodiment.

The content (total content) of the second constitutional unit is preferably 0.1 to 99.9 mol %, more preferably 1 to 99.9 mol %, even more preferably 10 to 99 mol % and most preferably 30 to 70 mol % with respect to the total constitutional units in the polymer compound, for excellent luminous efficiency of the light emitting device to be produced using the polymer compound of this embodiment.

The content (total content) of the third constitutional unit is preferably 0.1 to 99.9 mol %, more preferably 1 to 99 mol %, even more preferably 2 to 50 mol % and most preferably 3 to 30 mol % with respect to the total constitutional units in the polymer compound, for excellent thermal crosslinkability during fabrication of a light emitting device using the polymer compound of this embodiment.

For excellent luminous efficiency of the produced light emitting device, the polymer compound of this embodiment preferably has an energy gap of 2.9 eV or greater, calculated from the absorption edge obtained by absorption spectrometry.

When polymerizable groups described below remain on the end groups in the polymer compound of this embodiment, the luminescence property and usable life of the light emitting device may potentially be reduced when the polymer compound is used. The end groups are therefore preferably stable groups (for example, aryl or monovalent aromatic heterocyclic groups).

The polymer compound of this embodiment may be any copolymer such as a block copolymer, random copolymer, alternating copolymer or graft copolymer.

The polymer compound of this embodiment is useful as a light-emitting material, charge transport material or charge injection material, and when used it may be used in combination with other compounds as the composition described below.

The polymer compound of this embodiment has a polystyrene-equivalent number-average molecular weight of preferably $1 \times 10^3$ to $1 \times 10^7$ and more preferably $1 \times 10^4$ to $5 \times 10^6$, as measured by gel permeation chromatography (hereunder, "GPC"). The polymer compound of this embodiment also has a polystyrene-equivalent weight-average molecular weight of preferably $1 \times 10^4$ to $5 \times 10^7$ and more preferably $5 \times 10^4$ to $1 \times 10^7$.

For excellent durability in various processes for production of light emitting devices and heat resistance of the produced light emitting device, the glass transition temperature of the polymer compound of this embodiment is preferably 70° C. or higher.

A light emitting device to be produced using a polymer compound of this embodiment is a high-performance light emitting device capable of driving with excellent luminous efficiency. Consequently, the light emitting device is useful for liquid crystal display backlights, curved or flat light sources for illumination, segment display devices, dot matrix flat panel displays and the like. In addition, the polymer compound of this embodiment can be used as a laser pigment, an organic solar cell material, an organic semiconductor for an organic transistor, a material for a conductive film such as an electric conductive film or organic semiconductor film, or a luminescent film material that emits fluorescence or phosphorescence.

Examples of combinations of constitutional units for the polymer compound of this embodiment are shown in Table 1 and Table 2 below.

TABLE 1

| Polymer compound (example) | Chemical Structural formula | | | |
| --- | --- | --- | --- | --- |
| | First structural unit Formula (1) | Second structural unit Formula (2) | Third structural unit Formula (3) | Formula (4) |
| P-1 | Formula (9-047) | Formula (10-168) | Formula (3-132) Formula (3-140) | |
| P-2 | Formula (9-047) | Formula (10-168) | Formula (3-132) | |
| P-3 | Formula (9-047) | Formula (10-168) | Formula (3-140) Formula (3-137) | |
| P-4 | Formula (9-047) | Formula (10-168) | Formula (3-101) Formula (3-105) | |
| P-5 | Formula (9-047) | Formula (10-168) | | Formula (4-101) |
| P-6 | Formula (9-047) | Formula (10-168) | Formula (3-140) | Formula (4-120) |
| P-7 | Formula (9-073) | Formula (10-168) | Formula (3-132) Formula (3-140) | |
| P-8 | Formula (9-047) | Formula (10-168) | Formula (3-132) Formula (3-140) | |
| P-9 | Formula (9-067) | Formula (10-168) | Formula (3-140) | Formula (4-120) |
| P-10 | Formula (9-011) | Formula (10-168) | Formula (3-101) Formula (3-105) | |
| P-11 | Formula (9-012) | Formula (10-168) | | Formula (4-101) |
| P-12 | Formula (9-073) | Formula (10-140) | Formula (3-132) Formula (3-140) | |
| P-13 | Formula (9-047) | Formula (10-140) | Formula (3-132) Formula (3-140) | |
| P-14 | Formula (9-067) | Formula (10-140) | Formula (3-132) | |
| P-15 | Formula (9-011) | Formula (10-140) | | Formula (4-101) |
| P-16 | Formula (9-012) | Formula (10-140) | Formula (3-140) | Formula (4-120) |
| P-17 | Formula (9-073) | Formula (10-87) | Formula (3-132) Formula (3-140) | |
| P-18 | Formula (9-047) | Formula (10-87) | Formula (3-132) Formula (3-140) | |
| P-19 | Formula (9-067) | Formula (10-87) | Formula (3-101) Formula (3-105) | |
| P-20 | Formula (9-011) | Formula (10-87) | Formula (3-132) | |
| P-21 | Formula (9-012) | Formula (10-87) | Formula (3-140) Formula (3-137) | |
| P-22 | Formula (9-047) | Formula (10-62) | Formula (3-132) Formula (3-140) | |
| P-23 | Formula (9-047) | Formula (10-62) | Formula (3-132) Formula (3-140) | |

TABLE 1-continued

| Polymer compound (example) | Chemical Structural formula | | | |
|---|---|---|---|---|
| | First structural unit Formula (1) | Second structural unit Formula (2) | Third structural unit Formula (3) | Formula (4) |
| P-24 | Formula (9-047) | Formula (10-62) | Formula (3-132) Formula (3-140) | |
| P-25 | Formula (9-047) | Formula (10-62) | Formula (3-132) | |
| P-26 | Formula (9-047) | Formula (10-62) | Formula (3-140) Formula (3-137) | |
| P-27 | Formula (9-047) | Formula (10-62) | Formula (3-101) Formula (3-105) | |
| P-28 | Formula (9-047) | Formula (10-62) | | Formula (4-101) |
| P-29 | Formula (9-047) | Formula (10-62) | Formula (3-140) | Formula (4-120) |
| P-30 | Formula (9-073) | Formula (10-62) | Formula (3-132) Formula (3-140) | |
| P-31 | Formula (9-012) | Formula (10-62) | Formula (3-132) Formula (3-140) | |
| P-32 | Formula (9-070) | Formula (10-62) | Formula (3-132) | |
| P-33 | Formula (9-011) | Formula (10-62) | Formula (3-140) Formula (3-137) | |
| P-34 | Formula (9-067) | Formula (10-62) | Formula (3-101) Formula (3-105) | |
| P-35 | Formula (9-003) | Formula (10-62) | | Formula (4-101) |
| P-36 | Formula (9-080) | Formula (10-62) | Formula (3-140) | Formula (4-120) |
| P-37 | Formula (9-067) | Formula (10-62) | Formula (3-140) Formula (3-137) | |
| P-38 | Formula (9-011) | Formula (10-62) | Formula (3-140) | Formula (4-120) |
| P-39 | Formula (9-073) | Formula (10-114) | Formula (3-132) Formula (3-140) | |
| P-40 | Formula (9-047) | Formula (10-114) | Formula (3-132) Formula (3-140) | |

TABLE 2

| Polymer compound (example) | Chemical Structural formula | | | |
|---|---|---|---|---|
| | First structural unit Formula (1) | Second structural unit Formula (2) | Third structural unit Formula (3) | Formula (4) |
| P-41 | Formula (9-067) | Formula (10-114) | | Formula (4-101) |
| P-42 | Formula (9-011) | Formula (10-114) | Formula (3-140) Formula (3-137) | |
| P-43 | Formula (9-012) | Formula (10-114) | Formula (3-101) Formula (3-105) | |
| P-44 | Formula (9-047) | Formula (10-10) | Formula (3-132) Formula (3-140) | |
| P-45 | Formula (9-047) | Formula (10-10) | Formula (3-132) | |
| P-46 | Formula (9-047) | Formula (10-10) | Formula (3-140) Formula (3-137) | |
| P-47 | Formula (9-047) | Formula (10-10) | Formula (3-101) Formula (3-105) | |
| P-48 | Formula (9-047) | Formula (10-10) | | Formula (4-101) |
| P-49 | Formula (9-047) | Formula (10-10) | Formula (3-140) | Formula (4-120) |
| P-50 | Formula (9-012) | Formula (10-10) | Formula (3-132) Formula (3-140) | |
| P-51 | Formula (9-012) | Formula (10-10) | Formula (3-132) | |
| P-52 | Formula (9-012) | Formula (10-10) | Formula (3-140) Formula (3-137) | |
| P-53 | Formula (9-012) | Formula (10-10) | Formula (3-101) Formula (3-105) | |
| P-54 | Formula (9-012) | Formula (10-10) | | Formula (4-101) |
| P-55 | Formula (9-012) | Formula (10-10) | Formula (3-140) | Formula (4-120) |
| P-56 | Formula (9-073) | Formula (10-10) | Formula (3-132) Formula (3-140) | |
| P-57 | Formula (9-012) | Formula (10-10) | Formula (3-132) Formula (3-140) | |
| P-58 | Formula (9-070) | Formula (10-10) | | Formula (4-101) |
| P-59 | Formula (9-011) | Formula (10-10) | Formula (3-132) Formula (3-140) | |
| P-60 | Formula (9-067) | Formula (10-10) | Formula (3-132) Formula (3-140) | |
| P-61 | Formula (9-003) | Formula (10-10) | Formula (3-140) Formula (3-137) | |
| P-62 | Formula (9-080) | Formula (10-10) | Formula (3-140) Formula (3-137) | |
| P-63 | Formula (9-067) | Formula (10-10) | Formula (3-132) | |
| P-64 | Formula (9-011) | Formula (10-10) | | Formula (4-101) |
| P-65 | Formula (9-073) | Formula (10-24) | Formula (3-140) | Formula (4-120) |
| P-66 | Formula (9-047) | Formula (10-24) | Formula (3-140) Formula (3-137) | |
| P-67 | Formula (9-067) | Formula (10-24) | Formula (3-101) Formula (3-105) | |
| P-68 | Formula (9-011) | Formula (10-24) | Formula (3-132) | |
| P-69 | Formula (9-012) | Formula (10-24) | Formula (3-140) | Formula (4-120) |
| P-70 | Formula (9-073) | Formula (10-18) | Formula (3-101) Formula (3-105) | |
| P-71 | Formula (9-047) | Formula (10-18) | Formula (3-132) | |
| P-72 | Formula (9-067) | Formula (10-18) | Formula (3-140) Formula (3-137) | |
| P-73 | Formula (9-011) | Formula (10-18) | Formula (3-140) | Formula (4-120) |
| P-74 | Formula (9-012) | Formula (10-18) | Formula (3-101) Formula (3-105) | |

(Method for Producing Polymer Compound)

The polymer compound of this embodiment can be produced, for example, by condensation polymerization of a compound represented by the following formula (1M) (hereunder also referred to as "compound 1M"), a compound represented by the following formula (2M) (hereunder also referred to as "compound 2M"), and a compound represented by the following formula (3M) (hereunder also referred to as "compound 3M") and/or a compound represented by the following formula (4'M) (hereunder also referred to as "compound 4'M"). Throughout the present specification, compound 1M, compound 2M, compound 3M and compound 4'M will also be collectively referred to as "monomer".

[Chemical Formula 81]

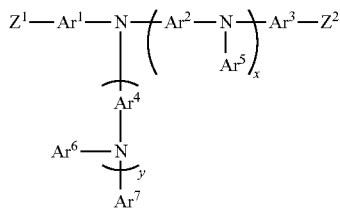

(1M)

In formula (1M), $Ar^1$, $Ar^2$, $Ar^3$, $Ar^4$, $Ar^5$, $Ar^6$, $Ar^7$, x and y have the same definitions as above, and $Z^1$ and $Z^2$ each independently represent a group selected from among substituent group A or substituent group B below.

[Chemical Formula 82]

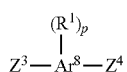

(2M)

In formula (2M), $Ar^8$, $R^1$ and p have the same definitions as above, and $Z^3$ and $Z^4$ each independently represent a group selected from among substituent group A or substituent group B below.

[Chemical Formula 83]

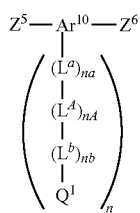

(3M)

In formula (3M), $Ar^{10}$, $L^a$, $L^b$, $L^A$, na, nb, nA, n and $Q^1$ have the same definitions as above, and $Z^5$ and $Z^6$ each independently represent a group selected from among substituent group A or substituent group B below.

[Chemical Formula 84]

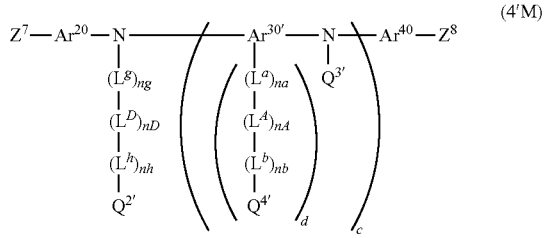

(4'M)

In formula (4'M), $Ar^{20}$, $Ar^{30'}$, $Ar^{40}$, c, d, $Q^{2'}$, $Q^{3'}$, $Q^{4'}$, $L^a$, $L^b$, $L^A$, $L^g$, $L^h$, $L^D$, na, nb, nA, ng, nh and nD have the same definitions as above, and $Z^7$ and $Z^8$ each independently represent a group selected from among substituent group A or substituent group B below.

<Substituent Group A>

A chlorine atom, a bromine atom, an iodine atom and groups represented by —O—S(=O)$_2$R$^{31}$ (where R$^{31}$ represents an alkyl group, or an aryl group optionally substituted with an alkyl group, an alkoxy group, a nitro group, a fluorine atom or a cyano group).

<Substituent Group B>

Groups represented by —B(OR$^{32}$)$_2$ (where R$^{32}$ represents a hydrogen atom or an alkyl group, and a plurality of R$^{32}$ may be the same or different, and may be bonded together to form a cyclic structure together with the oxygen atom to which they are bonded), groups represented by —BF$_3$Q$^{10}$ (where y represents a monovalent cation selected from the group consisting of Li$^+$, Na$^+$, K$^+$, Rb$^+$ and Cs$^+$), groups represented by —MgY$^1$ (where Y$^1$ represents a chlorine atom, a bromine atom or an iodine atom), groups represented by —ZnY$^2$ (where Y$^2$ represents a chlorine atom, a bromine atom or an iodine atom), and groups represented by —Sn(R$^{33}$)$_3$ (where R$^{33}$ represents a hydrogen atom or an alkyl group, and a plurality of R$^{33}$ may be the same or different, and may be bonded together to form a cyclic structure together with the tin atom to which they are bonded).

Compounds having groups selected from among substituent group A and compounds having groups selected from among substituent group B are known to undergo condensation polymerization by commonly known coupling reaction, so that the carbon atoms bonded to those groups become bonded together. Thus, if a compound A having two groups selected from among substituent group A and a compound B having two groups selected from among substituent group B are supplied to a commonly known coupling reaction, it is possible to obtain a condensation polymer of compound A and compound B by condensation polymerization.

Also, a compound having a group selected only from among substituent group A can be used to obtain a condensation polymer by a method of polymerization with a Ni(0) catalyst, for example (Yamamoto polymerization) (Progress in Polymer Science), Vol. 17, p. 1153-1205, 1992).

In such condensation polymerization, the first constitutional unit is derived from compound 1M and the second constitutional unit is derived from compound 2M. The third constitutional unit is derived from at least one type of compound selected from the group consisting of compound 3M and compound 4'M.

The condensation polymerization method includes, for example, a method of polymerization by Suzuki coupling reaction (Chem. Rev. Vol. 95, p. 2457-2483 (1995)), a method of polymerization by Grignard reaction (Bull. Chem. Soc. Jpn., Vol. 51, p. 2091 (1978)), a method of polymerization with a Ni(0) catalyst (Progress in Polymer Science, Vol. 17, p. 1153-1205, 1992), or a method of polymerization by Stille coupling reaction (European Polymer Journal Vol. 41, p. 2923-2933 (2005)). Of these methods, polymerization by Suzuki coupling reaction and polymerization with a Ni(0) catalyst are preferred from the viewpoint of ease of starting material synthesis and convenience of the polymerization reaction procedure, while from the viewpoint of easier control of the polymer compound structure, methods of polymerization by aryl-aryl cross-coupling reaction such as Suzuki coupling reaction, Grignard reaction or Stille coupling reaction are preferred, and polymerization reaction by Suzuki coupling reaction is especially preferred.

The condensation polymerization method includes a method of reacting the aforementioned compounds together with a suitable catalyst or base as necessary. When a method of polymerization by Suzuki coupling reaction is selected, the ratio of the total number of moles of the group selected from among substituent group A and the total number of moles of the group selected from among substituent group B in each compound is preferably adjusted to obtain a polymer compound with the desired molecular weight. For most purposes, the ratio of the number of moles of the latter with respect to the number of moles of the former is preferably 0.95 to 1.05, more preferably 0.98 to 1.02 and even more preferably 0.99 to 1.01.

The monomers may be synthesized and isolated beforehand, or they may be synthesized in the reaction system and used directly. When the obtained polymer compound is to be used for production of a light emitting device, its purity will affect the performance of the light emitting device. Therefore, these monomers are preferably purified by methods such as distillation, chromatography, sublimation purification and recrystallization, or combinations thereof.

In the method for producing a polymer compound of this embodiment, the monomers are preferably polymerized in the presence of a catalyst. The catalyst used for polymerization by Suzuki coupling reaction may be a transition metal complex, for example, a palladium complex such as palladium[tetrakis(triphenylphosphine)], [tris(dibenzylideneacetone)]dipalladium, palladium acetate, dichlorobistriphenylphosphinepalladium, dichlorobis[tris(2-methoxyphenyl)phosphine]palladium or dichlorobis[tri-t-butylphosphine]palladium, or a complex of these transition metal complexes coordinated with a ligand such as triphenylphosphine, tri-tert-butylphosphine or tricyclohexylphosphine For polymerization with a Ni(0) catalyst, the Ni(0) catalyst may be a transition metal complex, for example a nickel complex such as nickel[tetrakis(triphenylphosphine)], [1,3-bis(diphenylphosphino)propane]dichloronickel or [bis(1,4-cyclooctadiene)]nickel, or a complex of these transition metal complexes coordinated with a ligand such as triphenylphosphine, tri-tert-butylphosphine, tricyclohexylphosphine, diphenylphosphinopropane, substituted or unsubstituted bipyridyl or substituted or unsubstituted phenanthroline.

The catalyst may be synthesized beforehand or prepared in the reaction system and used directly. These catalysts may be used alone or in combinations of two or more.

The amount of catalyst used may be an amount that is effective as a catalyst, and for example, it will usually be 0.0001 to 300 mol %, preferably 0.001 to 50 mol % and more preferably 0.01 to 20 mol %, in terms of the number of moles of the transition metal with respect to 100 mol % as the total of all of the monomers in the polymerization reaction.

For a method of polymerization by Suzuki coupling reaction it is preferred to use a base, with bases including inorganic bases such as sodium carbonate, potassium carbonate, cesium carbonate, potassium fluoride, cesium fluoride and tripotassium phosphate, and organic bases such as tetramethylammonium hydroxide, tetraethylammonium hydroxide, tetrapropylammonium hydroxide and tetrabutylammonium hydroxide.

The amount of base used will usually be 50 to 2000 mol % and preferably 100 to 1000 mol % with respect to 100 mol % as the total of all of the monomers in the polymerization reaction.

The polymerization reaction may be carried out in the absence of a solvent or in the presence of a solvent, but it will usually be carried out in the presence of an organic solvent. The organic solvent may be toluene, xylene, mesitylene, tetrahydrofuran, 1,4-dioxane, dimethoxyethane, N,N-dimethylacetamide, N,N-dimethylformamide or the like. In order to minimize secondary reactions, the solvent is generally preferred to be one that has been subjected to deoxidizing treatment. Such organic solvents may be used alone or in combinations of two or more.

The amount of organic solvent used is preferably an amount for a total concentration of 0.1 to 90 wt %, more preferably 1 to 50 wt % and even more preferably 2 to 30 wt % for the total monomers in the polymerization reaction.

The reaction temperature for the polymerization reaction is preferably between −100° C. and 200° C., more preferably between −80° C. and 150° C. and even more preferably between 0° C. and 120° C. The reaction time will usually be at least 1 hour, and is preferably 2 to 500 hours.

In order to prevent polymerizable groups (such as $Z^1$ and $Z^2$) from remaining at the ends of the polymer compound of this embodiment in the polymerization reaction, a compound represented by the following formula (1T) may be used as a chain terminator. This will allow a polymer compound to be obtained in which the ends are aryl or monovalent aromatic heterocyclic groups.

$$Z^T—Ar^T \tag{1T}$$

In formula (1T), $Ar^T$ represents optionally substituted aryl or an optionally substituted monovalent aromatic heterocyclic group, and $Z^T$ represents a chemical group selected from the group consisting of substituent group A and substituent group B. The aryl and monovalent aromatic heterocyclic groups for $Ar^T$ may be any of the same as the aryl and monovalent aromatic heterocyclic groups mentioned for $R^1$ above.

Post-treatment following polymerization reaction may be carried out by a known method, and for example, a method of removing water-soluble impurities by liquid separation, or a method of adding the polymerized reaction solution to a lower alcohol such as methanol and filtering and drying the deposited precipitate, can be carried out either alone or in combination.

When the purity of the polymer compound of this embodiment is low, it may be purified by a common method such as recrystallization, reprecipitation, continuous extraction with a Soxhlet extractor or column chromatography, but when the polymer compound of this embodiment is to be used to produce a light emitting device, the purity will affect the performance of the light emitting device, including its luminescence properties, and therefore the condensation polymerization is preferably followed by purification treatment, such as reprecipitation purification or fractionation by chromatography.

(Compound)

The compound of this embodiment is a compound represented by the following formula (4-1), which is useful for production of the polymer compound described above.

[Chemical Formula 85]

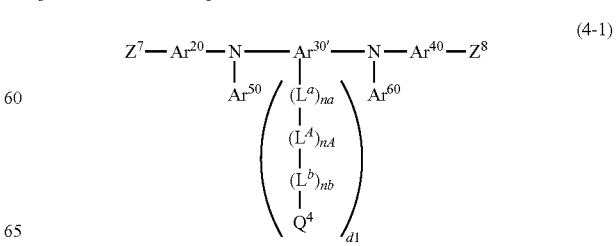

(4-1)

In formula (4-1), $Z^7$, $Z^8$, $Ar^{20}$, $Ar^{30'}$, $Ar^{40}$, d1, $Q^4$, $L^a$, $L^b$, $L^A$, na, nb and nA are as defined above.

Preferred forms of the compounds represented by formula (4-1) are compounds represented by the following formula (4-2).

[Chemical Formula 86]

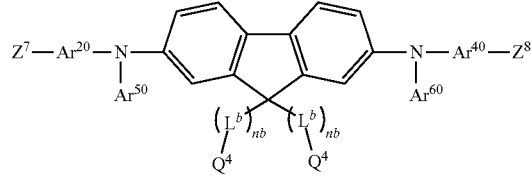

(4-2)

In formula (4-2), $Z^7$, $Z^8$, $Ar^{20}$, $Ar^{40}$, $Ar^{50}$, $Ar^{60}$, $Q^4$, nb and $L^b$ have the same meanings explained above.

Preferred forms of the compounds represented by formula (4-2) are compounds represented by the following formula (4-3).

[Chemical Formula 87]

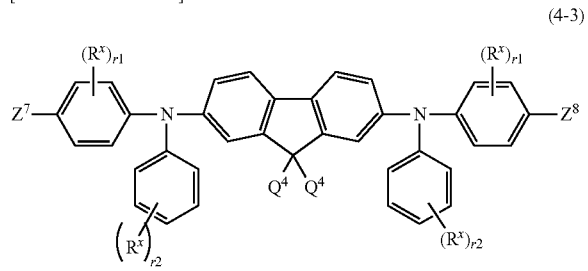

(4-3)

In formula (4-3), $Z^7$, $Z^8$ and $Q^4$ have the same meanings explained above. $R^x$ represents a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted amino group, an unsubstituted or substituted silyl group, a halogen atom, an acyl group, an acyloxy group, an imine residue, a carbamoyl group, an acid imide group, an unsubstituted or substituted monovalent heterocyclic group, an unsubstituted or substituted carboxyl group, a cyano group or a nitro group. A plurality of $R^x$ may be the same or different. r1 represents an integer of 0 to 4, and r2 represents an integer of 0 to 5.

The compounds represented by formula (4-3) may be synthesized, for example, by the following scheme A.

Scheme A

[Chemical Formula 88]

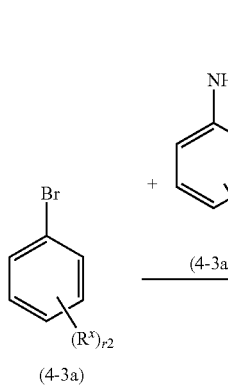

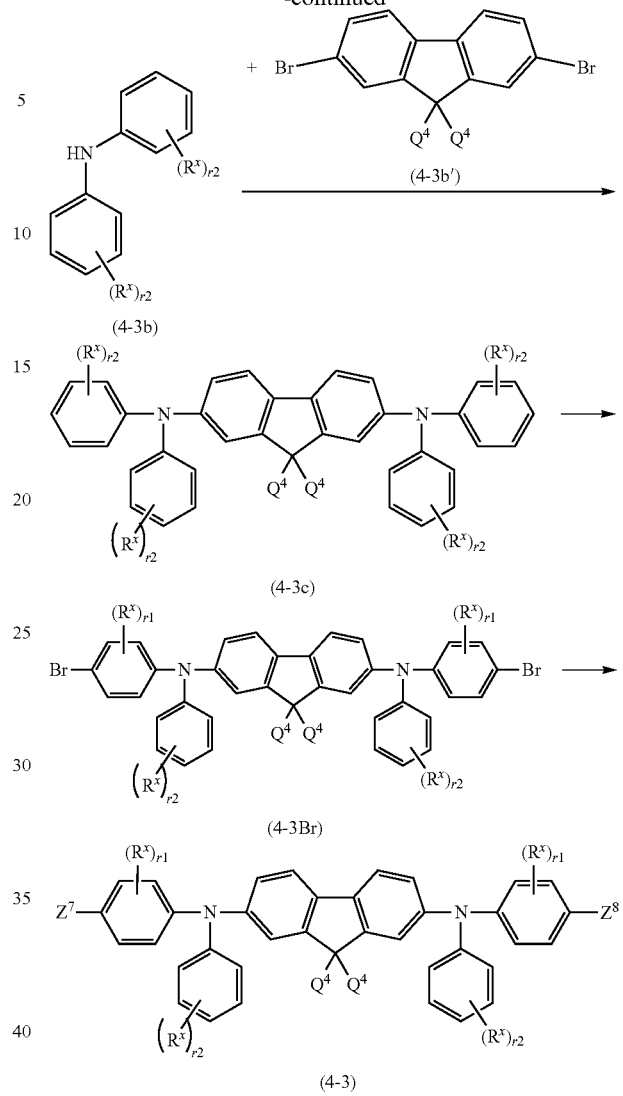

In scheme A, a compound represented by formula (4-3a), for example, can be derived to a compound represented by formula (4-3b) by Buchwald reaction with a base such as sodium tert-butoxide, a palladium compound such as [tris(dibenzylideneacetone)]dipalladium, and a compound represented by formula (4-3a'), in an organic solvent.

A compound represented by formula (4-3b) can be derived to a compound represented by formula (4-3c) by Buchwald reaction with a base such as sodium tert-butoxide, a palladium compound such as [tris(dibenzylideneacetone)]dipalladium, and a compound represented by formula (4-3b'), in an organic solvent.

A compound represented by formula (4-3c) can be derived to a compound represented by formula (4-3Br) by reaction with a brominating agent such as N-bromosuccinimide in an organic solvent.

A compound represented by formula (4-3Br) can be derived to a compound represented by formula (4-3) having the groups represented by Z7 and Z8 converted to groups selected from among substituent group A except for bromine atom, or substituent group B, by a known method. Also, a compound represented by formula (4-3Br) can be used directly as a compound represented by formula (4-3).

Preferred forms of the compounds represented by formula (4-3) are compounds represented by the following formula (4-4).

[Chemical Formula 89]

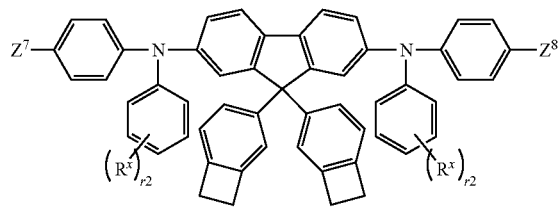

(4-4)

In formula (4-4), $Z^7$ and $Z^8$ have the same meanings as above. $R^x$ represents a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted amino group, an unsubstituted or substituted silyl group, a halogen atom, an acyl group, an acyloxy group, an imine residue, a carbamoyl group, an acid imide group, an unsubstituted or substituted monovalent heterocyclic group, an unsubstituted or substituted carboxyl group, a cyano group or a nitro group. A plurality of $R^x$ may be the same or different. r2 has the same meaning as above.

The compound of this embodiment is a compound represented by the following formula (3-3), which is useful for production of the polymer compound described above.

[Chemical Formula 90]

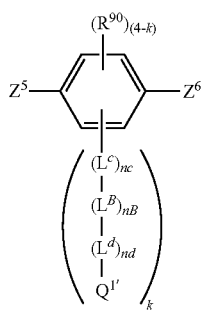

(3-3)

In formula (3-3), $Z^5$ and $Z^6$ have the same definitions as $Z^7$ and $Z^8$ above.
nc represents an integer of 0 to 3, nd represents an integer of 0 to 12, nB represents 0 or 1 and k represents an integer of 1 to 4.
$L^c$ and $L^d$ each independently represent an unsubstituted or substituted alkylene group or an unsubstituted or substituted phenylene group. When a plurality of $L^c$ are present, they may be the same or different. When a plurality of $L^d$ are present, they may be the same or different.
$L^B$ represents an oxygen atom or a sulfur atom. When a plurality of $L^B$ are present, they may be the same or different.
$Q^{1'}$ represents an unsubstituted or substituted aryl group having a cyclobutene structure or an unsubstituted or substituted monovalent heterocyclic group having a cyclobutene structure. When a plurality of $Q^1$ are present, they may be the same or different.
$R^{90}$ represents a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group or an unsubstituted or substituted heterocyclooxy group. When a plurality of $R^{90}$ are present, they may be the same or different.

Preferred forms of the compounds represented by formula (3-3) are compounds represented by the following formula (3-4).

[Chemical Formula 91]

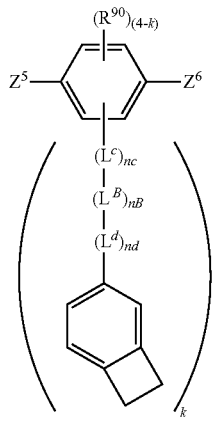

(3-4)

In formula (3-4), nc, nd, nB, k, $L^c$, $L^d$, $L^B$, $R^{90}$, $Z^5$ and $Z^6$ have the same meanings as above, and nd is preferably an integer of 1 to 12.

Preferred forms of the compounds represented by formula (3-4) are compounds represented by the following formula (3-5).

[Chemical Formula 92]

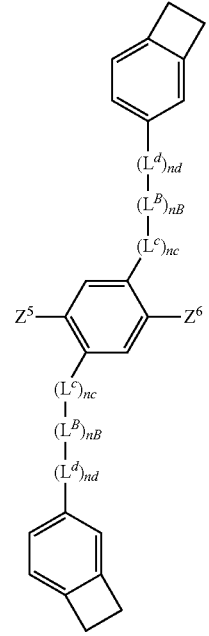

(3-5)

In formula (3-5), nc, nd, nB, $L^c$, $L^d$, $L^B$, $Z^5$ and $Z^6$ have the same meanings as above.

Preferred forms of the compounds represented by formula (3-5) are compounds represented by the following formula (3-6).

[Chemical Formula 93]

(3-6)

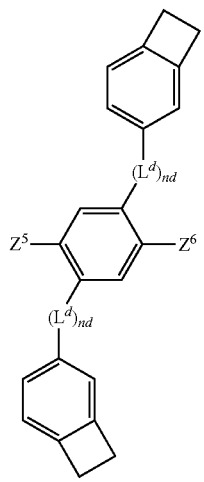

In formula (3-6), nd, $L^d$, $Z^5$ and $Z^6$ have the same meanings as above.

The compounds represented by formula (3-6) may be synthesized, for example, by the following scheme B.

Scheme B

[Chemical Formula 94]

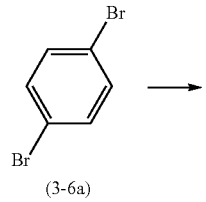

(3-6a)

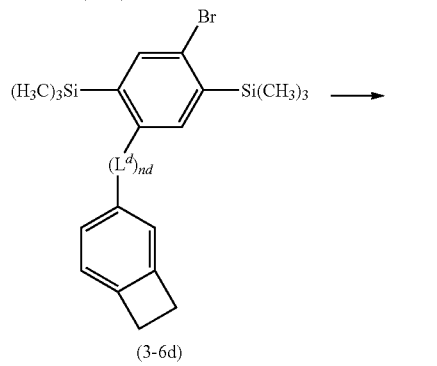

-continued

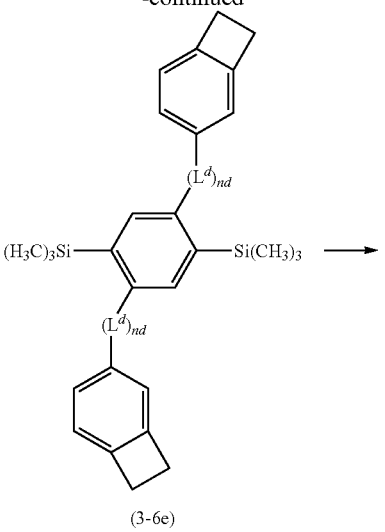

(3-6e)

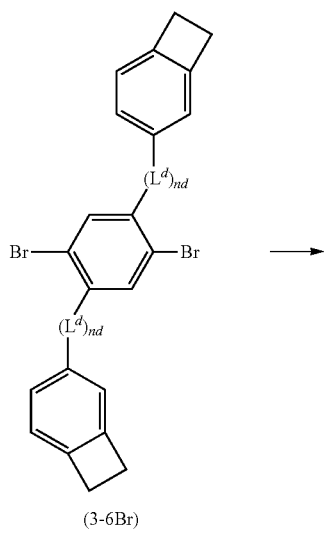

(3-6Br)

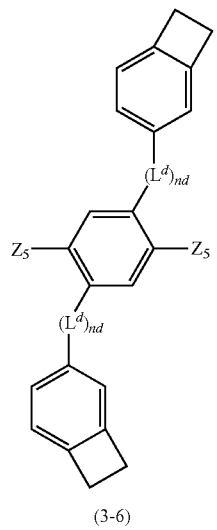

(3-6)

In scheme B, for example, an aryl anion may be generated by reaction between a compound represented by formula (3-6a) and a base which may be a lithium amide such as lithium diisopropylamide, in an organic solvent, and trimethylsilyl chloride added to derive a compound represented by formula (3-6b).

A compound represented by formula (3-6b) can be derived to a compound represented by formula (3-6d), for example, by reacting a lithiating agent, for example, an alkyllithium such as butyllithium, in an organic solvent to generate a lithiated compound by halogen-metal exchange reaction, and then adding a compound represented by formula (3-6c).

A compound represented by formula (3-6d) can be derived to a compound represented by formula (3-6e), for example, by reacting a lithiating agent, for example, an alkyllithium such as butyllithium, in an organic solvent to generate a lithiated compound by halogen-metal exchange reaction, and then adding a compound represented by formula (3-6c).

A compound represented by formula (3-6e) can be derived to a compound represented by formula (3-6Br) by, for example, reaction with a brominating agent such as N-bromosuccinimide or bromine in an organic solvent.

A compound represented by formula (3-6Br) can be derived to a compound represented by formula (3-6) having the groups represented by Z5 and Z6 converted to groups selected from among substituent group A except for bromine atom, or substituent group B, by a known method. Also, a compound represented by formula (3-6Br) may be used directly as a compound represented by formula (3-6).

(Composition)

The composition of the invention comprises a polymer compound of the invention and at least one material selected from the group consisting of hole transport materials, electron transport materials and light-emitting materials. The composition can be suitably used for manufacture of a light emitting device.

Hole transport materials include polyvinylcarbazole and its derivatives, polysilane and its derivatives, polysiloxane derivatives having aromatic amines on side chains or the main chain, pyrazoline derivatives, arylamine derivatives, stilbene derivatives, polyaniline and its derivatives, polythiophene and its derivatives, polypyrrole and its derivatives, poly(p-phenylenevinylene) and its derivatives and poly(2,5-thienylenevinylene) and its derivatives. Additional hole transport materials include those mentioned in Japanese Unexamined Patent Application Publication SHO No. 63-70257, Japanese Unexamined Patent Application Publication SHO No. 63-175860, Japanese Unexamined Patent Application Publication HEI No. 2-135359, Japanese Unexamined Patent Application Publication HEI No. 2-135361, Japanese Unexamined Patent Application Publication HEI No. 2-209988, Japanese Unexamined Patent Application Publication HEI No. 3-37992 and Japanese Unexamined Patent Application Publication HEI No. 3-152184.

The content of a hole transport material is preferably 1 to 500 parts by weight and more preferably 5 to 200 parts by weight with respect to 100 parts by weight of the polymer compound of the invention in the composition.

Electron transport materials include oxadiazole derivatives, quinodimethane and its derivatives, benzoquinone and its derivatives, naphthoquinone and its derivatives, anthraquinone and its derivatives, tetracyanoquinodimethane and its derivatives, fluorenone derivatives, diphenyldicyanoethylene and its derivatives, diphenoquinone derivatives, metal complexes of 8-hydroxyquinoline and its derivatives, polyquinoline and its derivatives, polyquinoxaline and its derivatives, polyfluorene and its derivatives, anthracene and its derivatives, and anthracene and fluorene copolymer. Additional electron transport materials include those mentioned in Japanese Unexamined Patent Application Publication SHO No. 63-70257, Japanese Unexamined Patent Application Publication SHO No. 63-175860, Japanese Unexamined Patent Application Publication HEI No. 2-135359, Japanese Unexamined Patent Application Publication HEI No. 2-135361, Japanese Unexamined Patent Application Publication HEI No. 2-209988, Japanese Unexamined Patent Application Publication HEI No. 3-37992 and Japanese Unexamined Patent Application Publication HEI No. 3-152184.

The content of an electron transport material is preferably 1 to 500 parts by weight and more preferably 5 to 200 parts by weight with respect to 100 parts by weight of the polymer compound of the invention in the composition.

The light-emitting material may be a low molecular fluorescent material or phospholuminescent material, with phospholuminescent materials being preferred. Examples of light-emitting materials include naphthalene derivatives, anthracene and its derivatives, anthracene and fluorene copolymers, perylene and its derivatives, pigments such as polymethine-based pigments, xanthene-based pigments, coumarin-based pigments and cyanine-based pigments, metal complexes with 8-hydroxyquinoline as a ligand, metal complexes with 8-hydroxyquinoline derivatives as ligands, other fluorescent metal complexes, aromatic amines, tetraphenylcyclopentadiene and its derivatives, tetraphenylbutadiene and its derivatives, low molecular compound fluorescent materials such as stilbene-based, silicon-containing aromatic, oxazole-based, furoxan-based, thiazole-based, tetraarylmethane-based, thiadiazole-based, pyrazole-based, metacyclophane-based and acetylene-based compounds, metal complexes such as iridium complexes and platinum complexes, triplet emitting complexes, and the like. They also include the light-emitting materials mentioned in Japanese Unexamined Patent Application Publication SHO No. 57-51781 and Japanese Unexamined Patent Application Publication SHO No. 59-194393.

Examples of phospholuminescent materials include those listed below, among which compounds represented by Ir-2a to Ir-6a, Ir-10a to Ir-13a, Ir-17a to Ir-24a, Ir-2b to Ir-6b, Ir-10b to Ir-13b, Ir-18b to Ir-29b, Ir-1c to Ir-14c and Ir-1d to Ir-19d are preferred, and compounds represented by Ir-10a to Ir-13a, Ir-17a to Ir-24a, Ir-10b to Ir-13b, Ir-18b to Ir-29b, Ir-1c, Ir-5c, Ir-8c, Ir-10c to Ir-14c, Ir-1d to Ir-2d, Ir-6d to Ir-12d and Ir-15d to Ir-19d are more preferred, from the viewpoint of luminance life. In the following examples, the Rp shown as a substituent on the dendron site is preferably an alkyl or alkoxy group and more preferably an alkyl group, while from the viewpoint of ease of synthesis and ease of dissolution of the phospholuminescent compound to be obtained in an organic solvent when it is to be used for fabrication of a light emitting device, it is even more preferably a tert-butyl, hexyl or ethylhexyl group substituent.

[Chemical Formula 95]
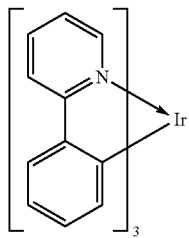 Ir-1a
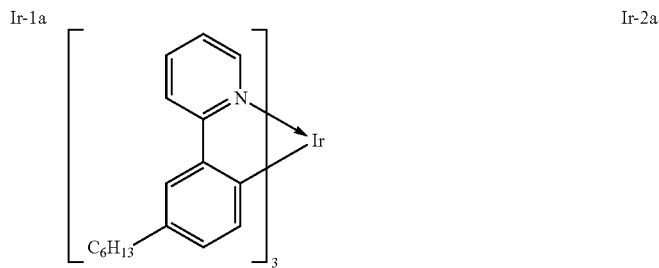 Ir-2a
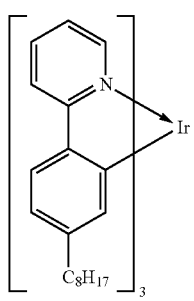 Ir-3a
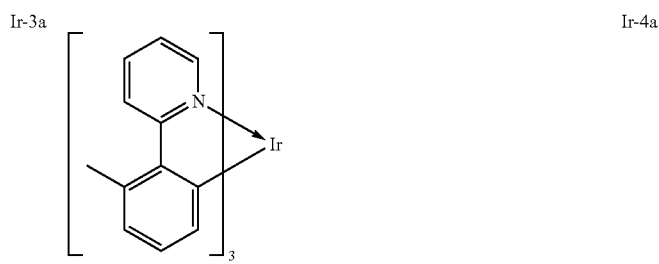 Ir-4a
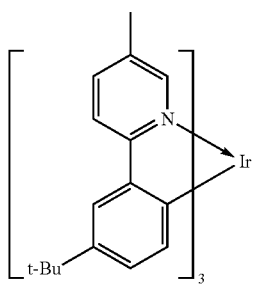 Ir-5a
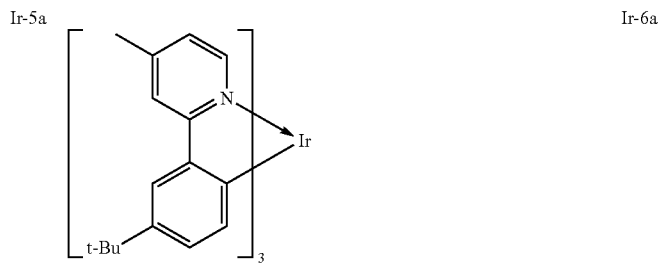 Ir-6a
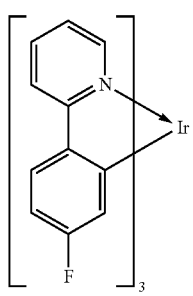 Ir-7a
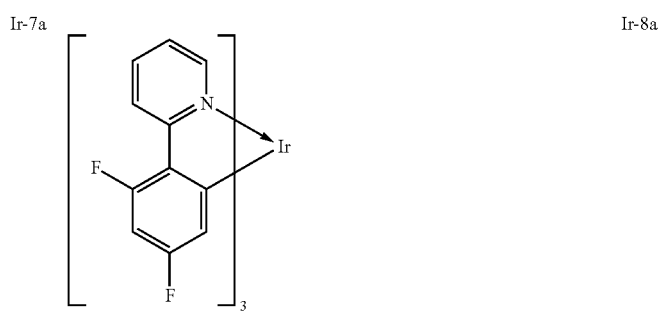 Ir-8a
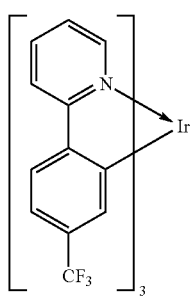 Ir-9a
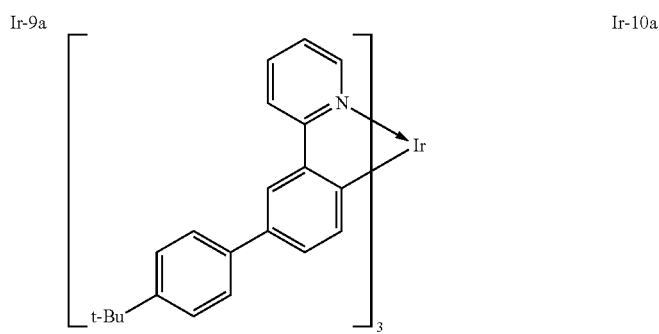 Ir-10a Ir-11a
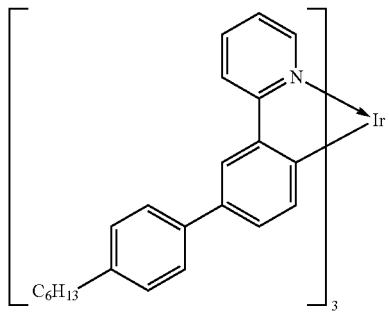
[Chemical Formula 96]
Ir-12a
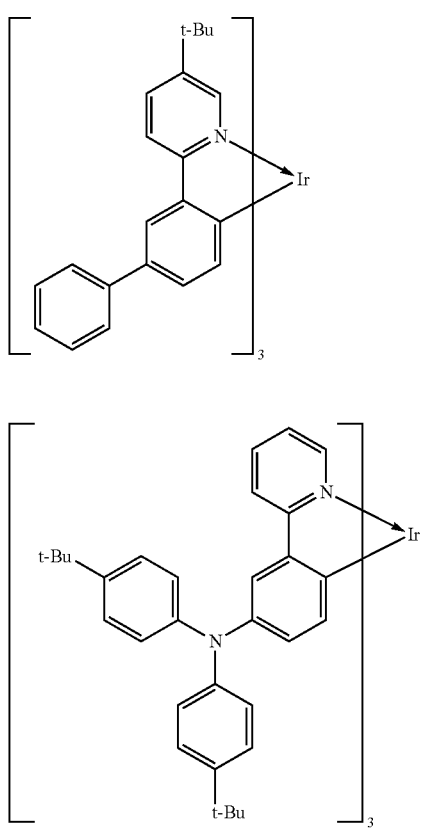
Ir-14a
Ir-16a
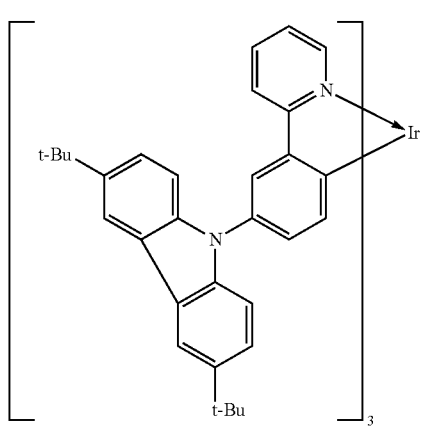
Ir-13a
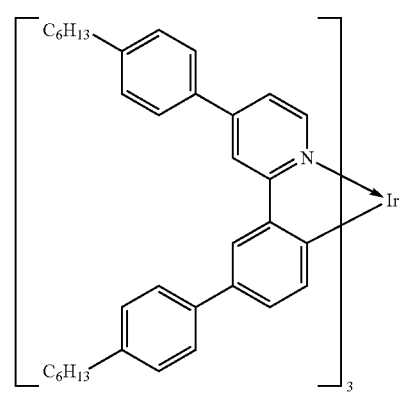
Ir-15a
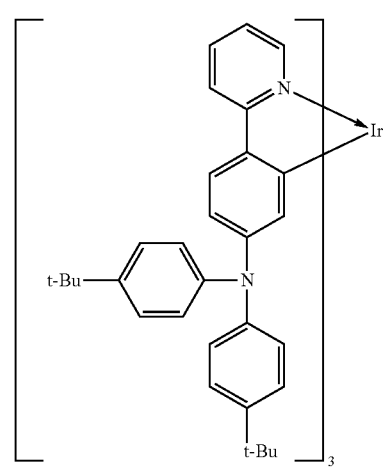

-continued
[Chemical Formula 97]
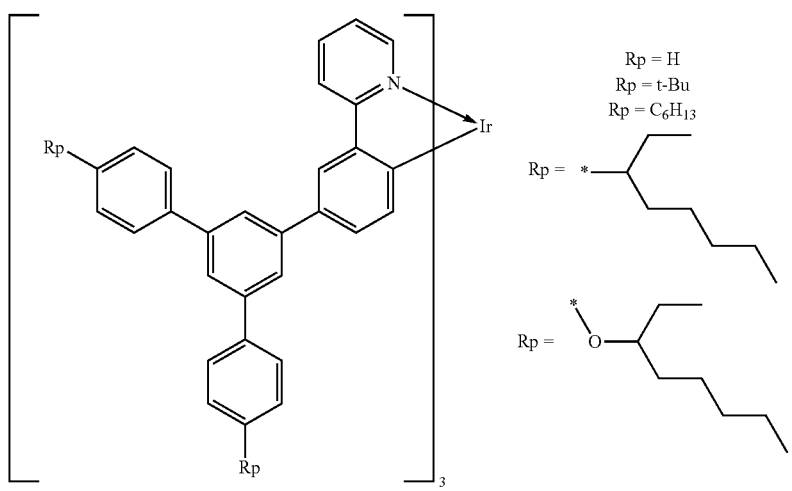
Ir-17a
[Chemical Formula 98]
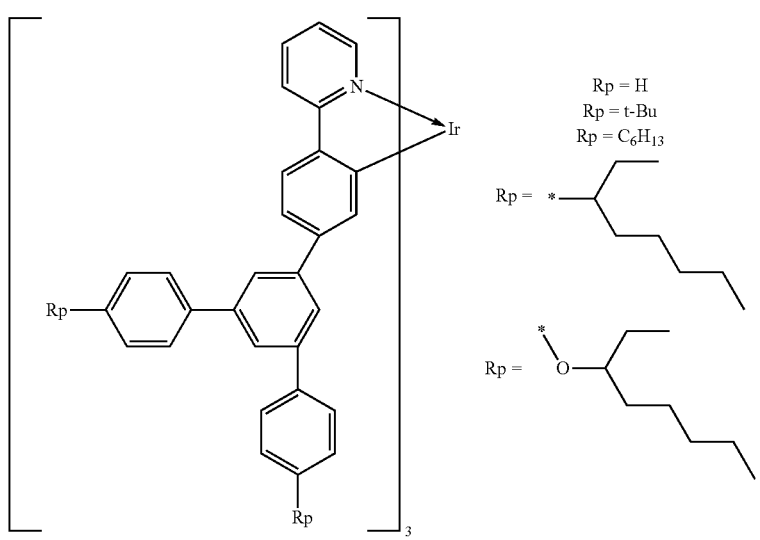
Ir-18a
[Chemical Formula 99]
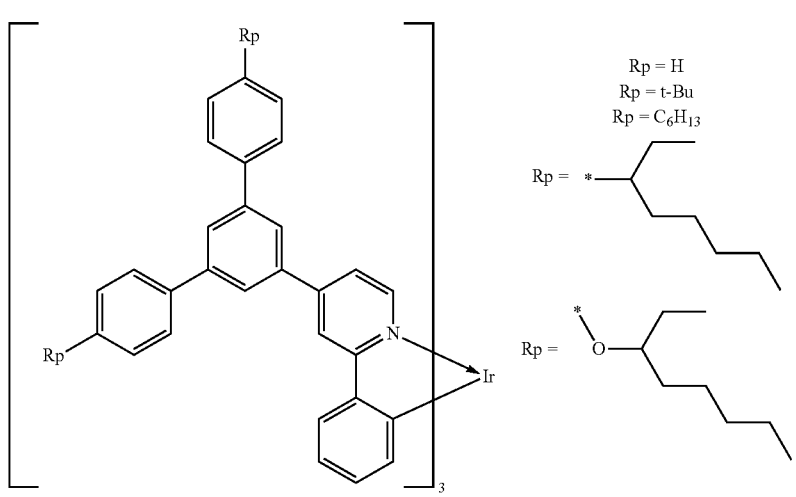
Ir-19a -continued
[Chemical Formula 100]
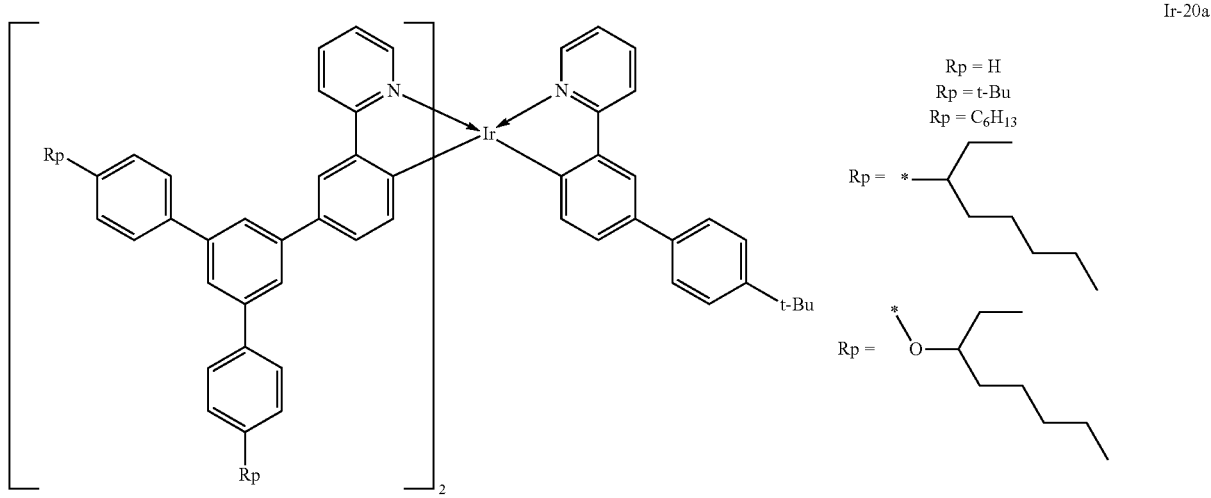
Ir-20a
[Chemical Formula 101]
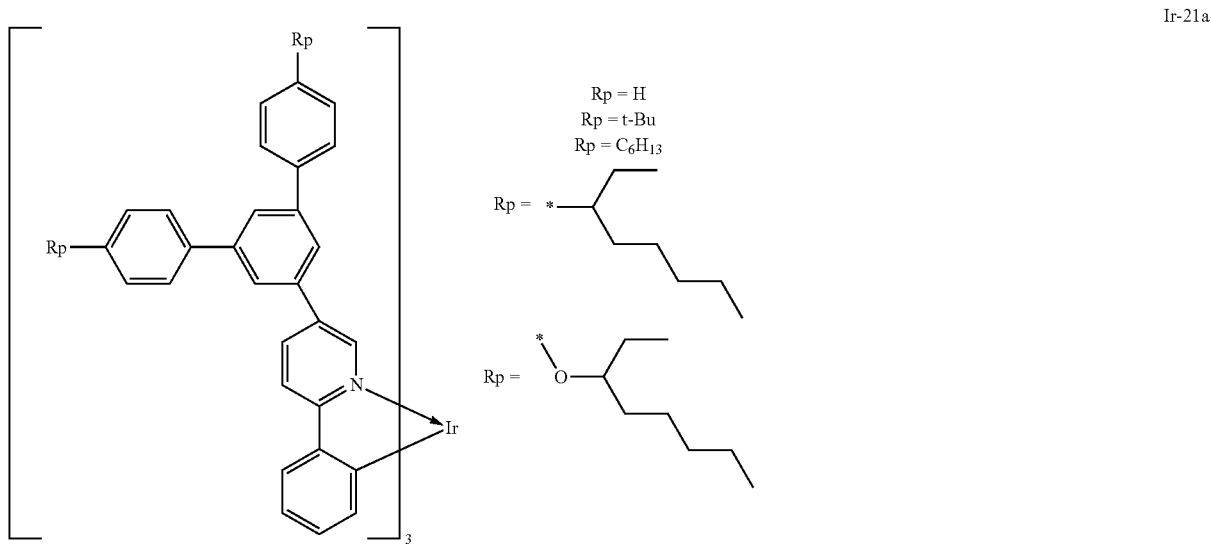
Ir-21a
[Chemical Formula 102]
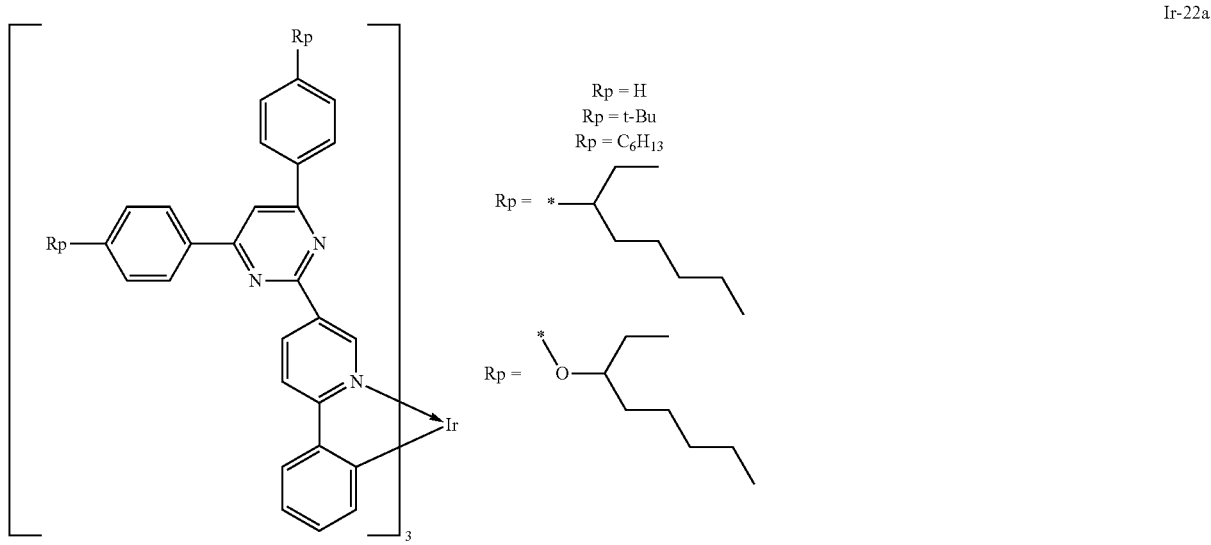
Ir-22a

[Chemical Formula 103]
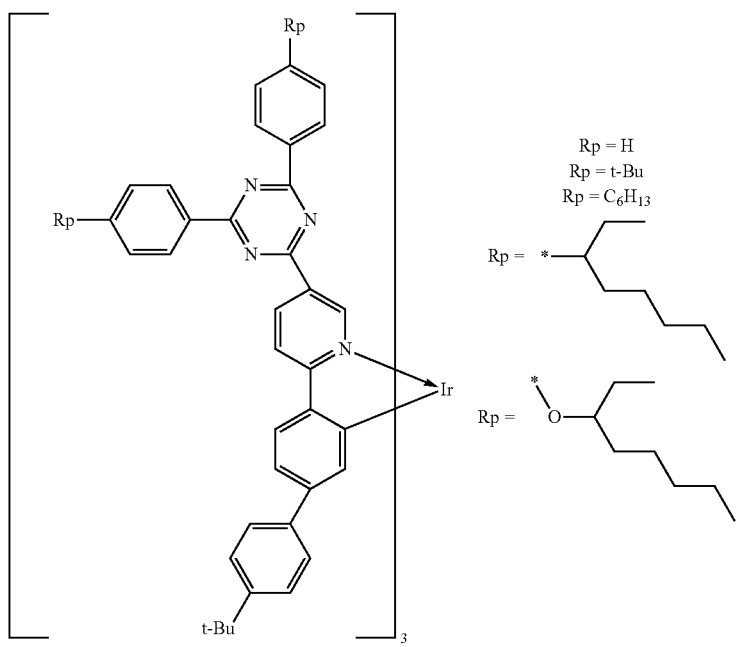
Ir-23a
Rp = H
Rp = t-Bu
Rp = C₆H₁₃
[Chemical Formula 104]
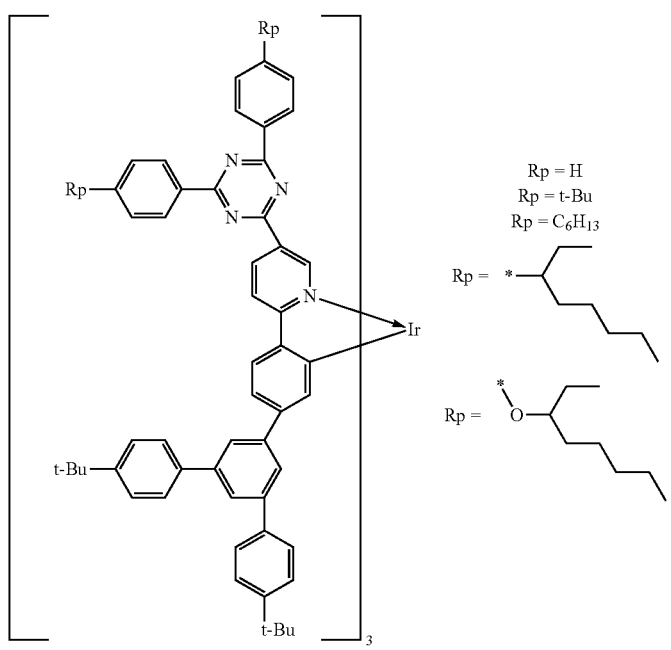
Ir-24a
Rp = H
Rp = t-Bu
Rp = C₆H₁₃
[Chemical Formula 105]
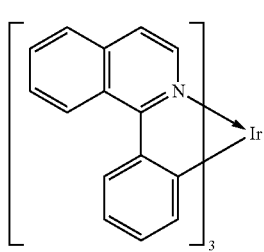
Ir-1b
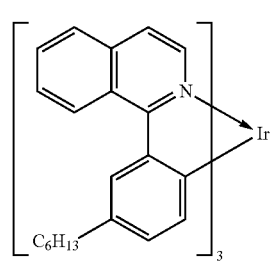
Ir-2b

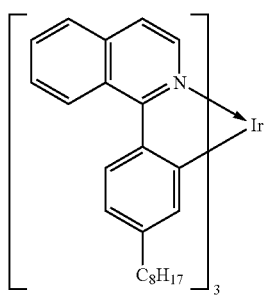 Ir-3b
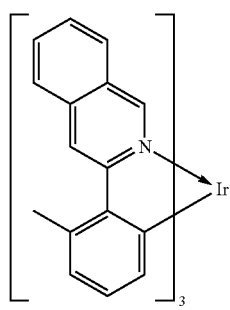 Ir-4b
[Chemical Formula 106]
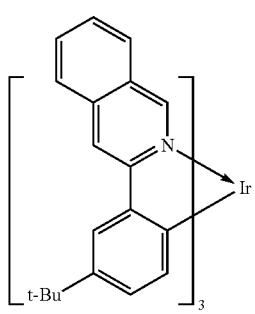 Ir-5b
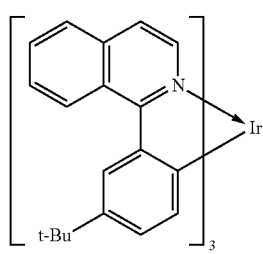 Ir-6b
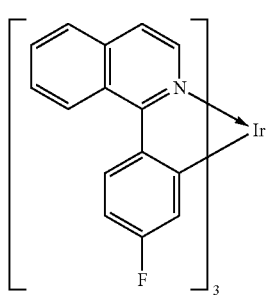 Ir-7b
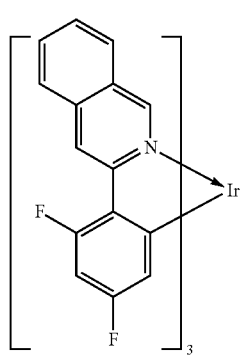 Ir-8b
[Chemical Formula 107]
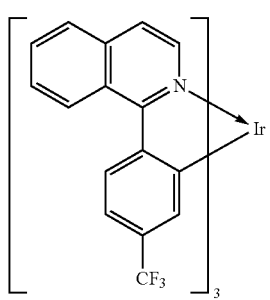 Ir-9b
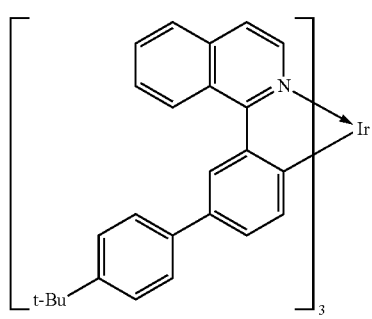 Ir-10b

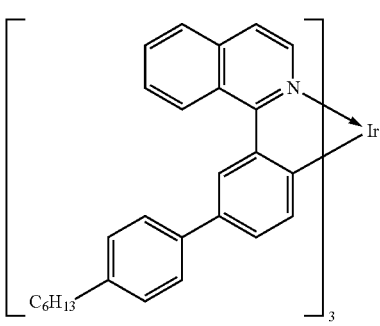
Ir-11b
[Chemical Formula 108]
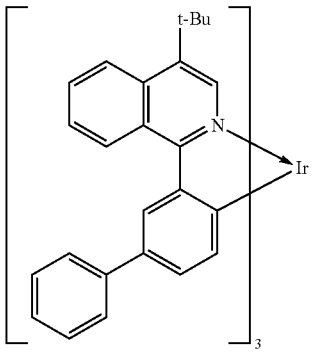
Ir-12b
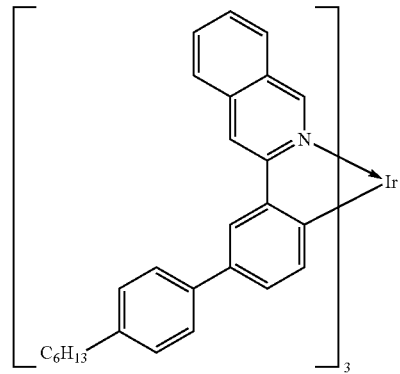
Ir-13b
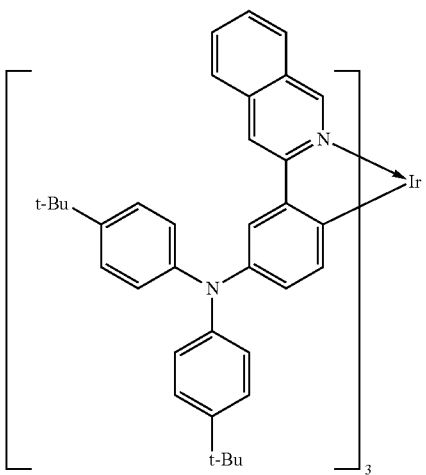
Ir-14b

[Chemical Formula 109]
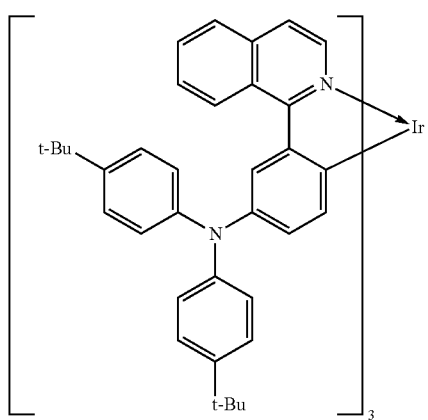
Ir-15b
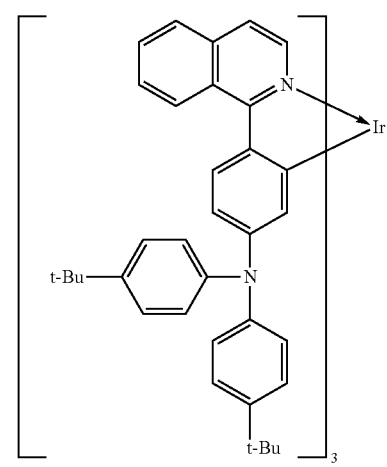
Ir-16b
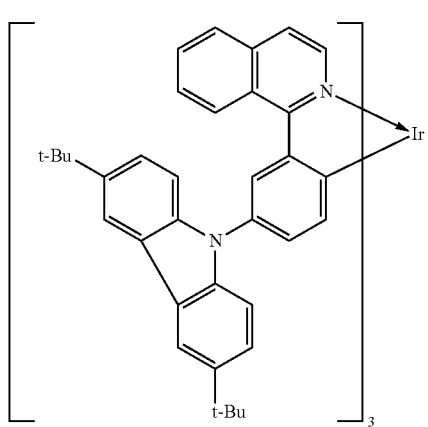
Ir-17b
[Chemical Formula 110]
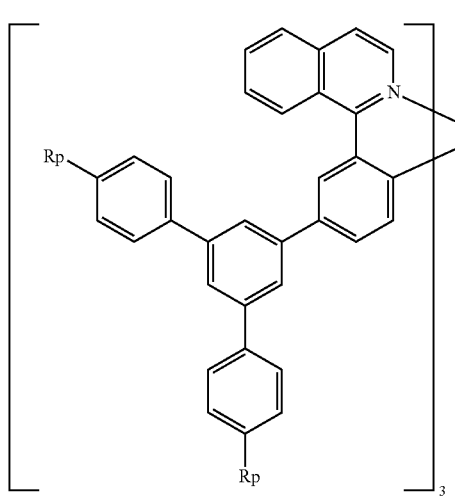
Ir-18b
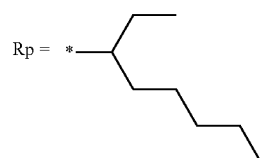
Rp = H
Rp = t-Bu
Rp = $C_6H_{13}$
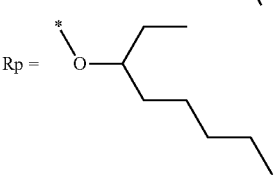

[Chemical Formula 111]
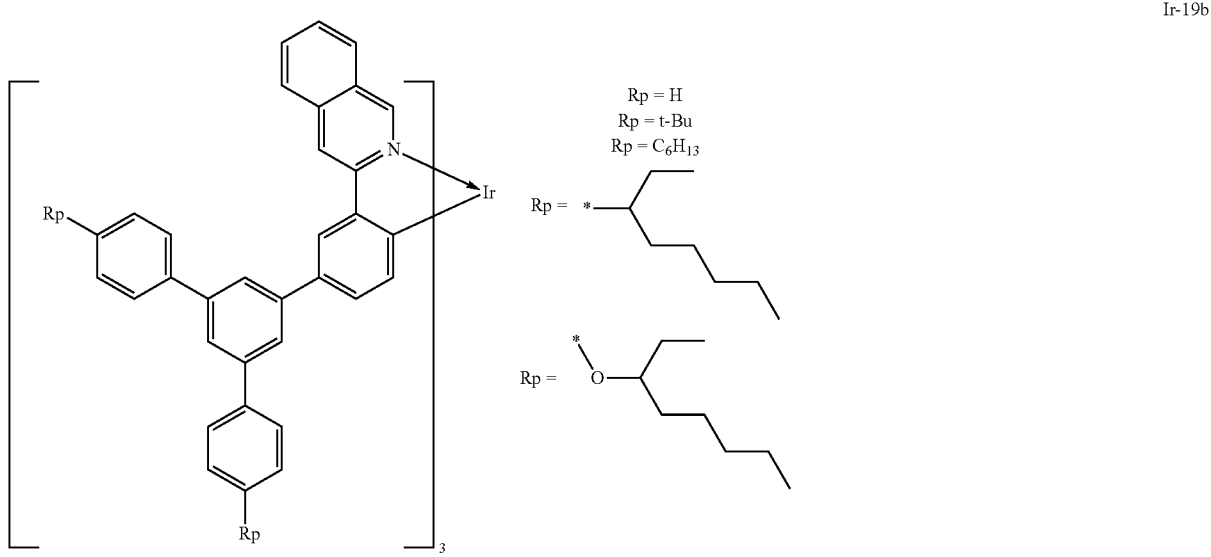
Ir-19b
[Chemical Formula 112]
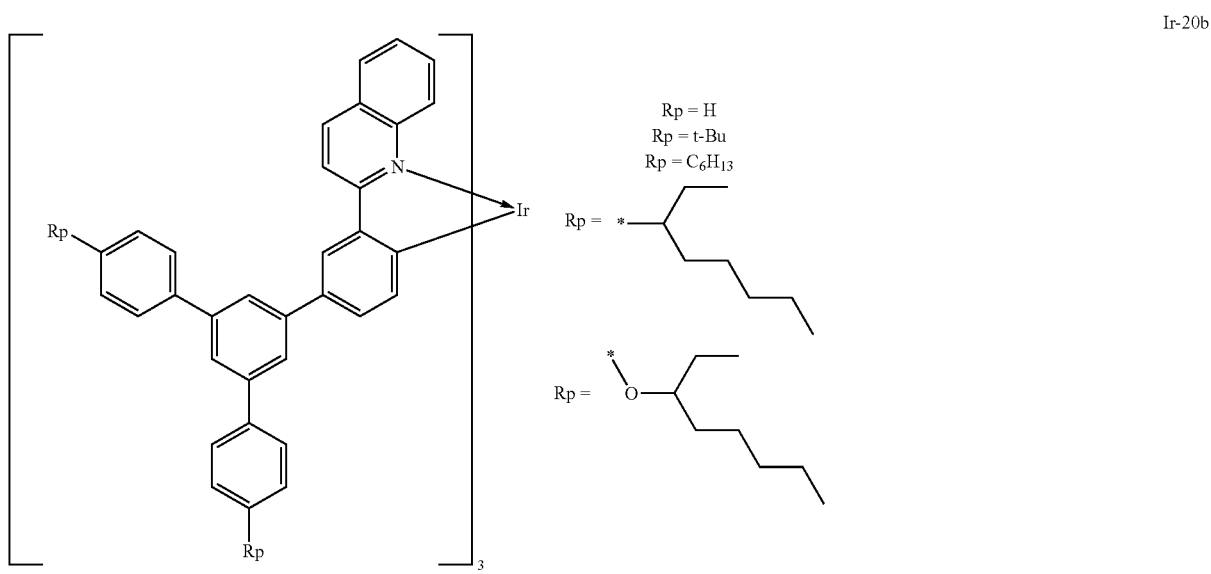
Ir-20b

[Chemical Formula 113]
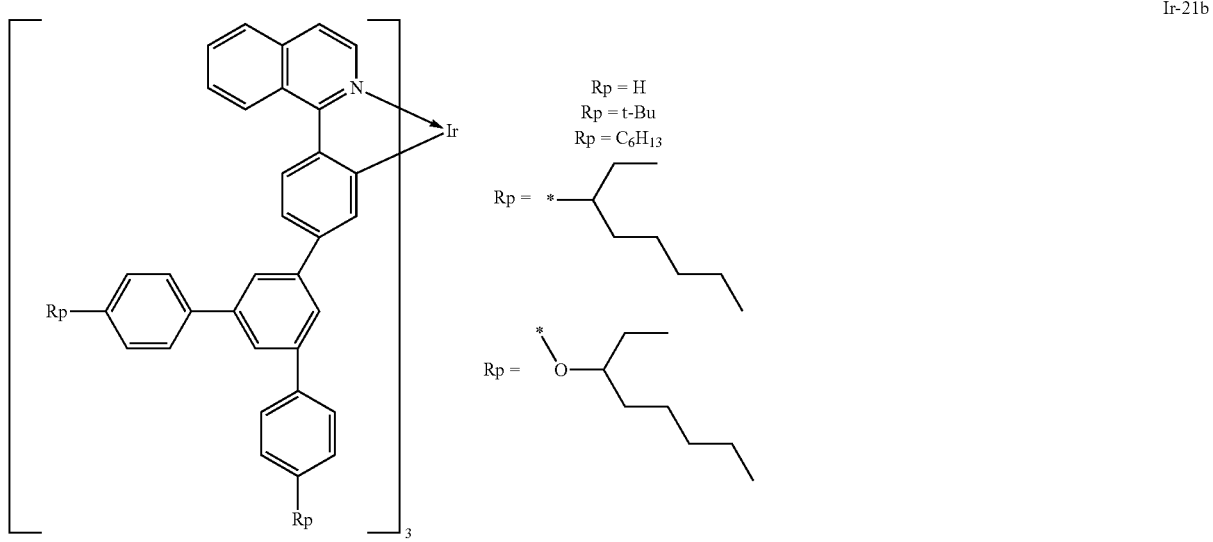
Ir-21b
[Chemical Formula 114]
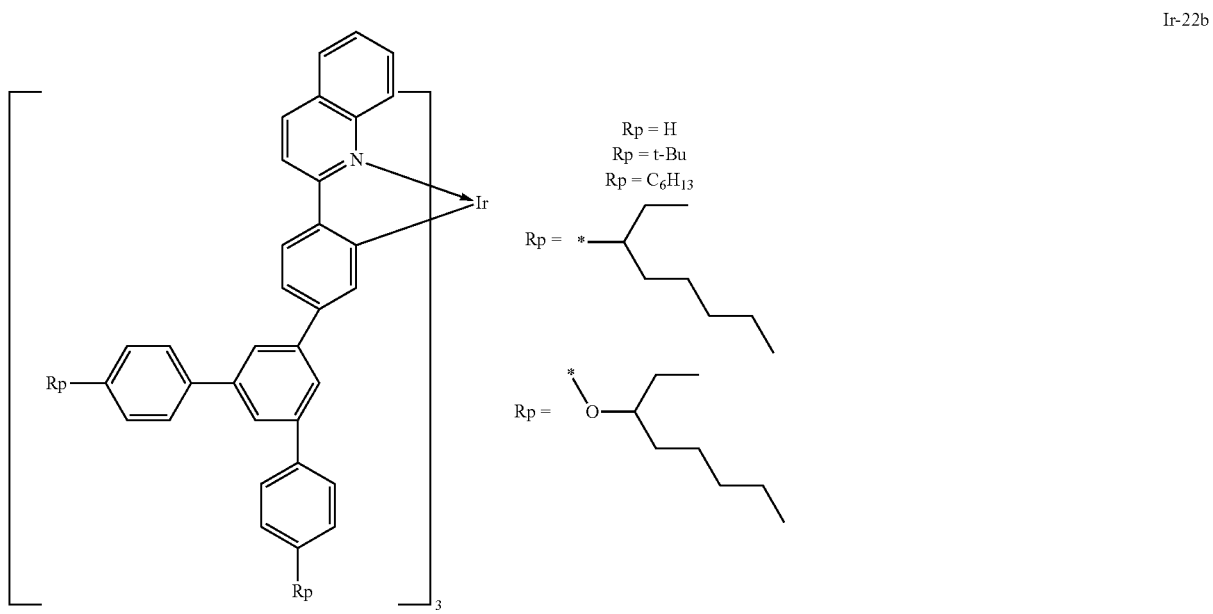
Ir-22b

[Chemical Formula 115]
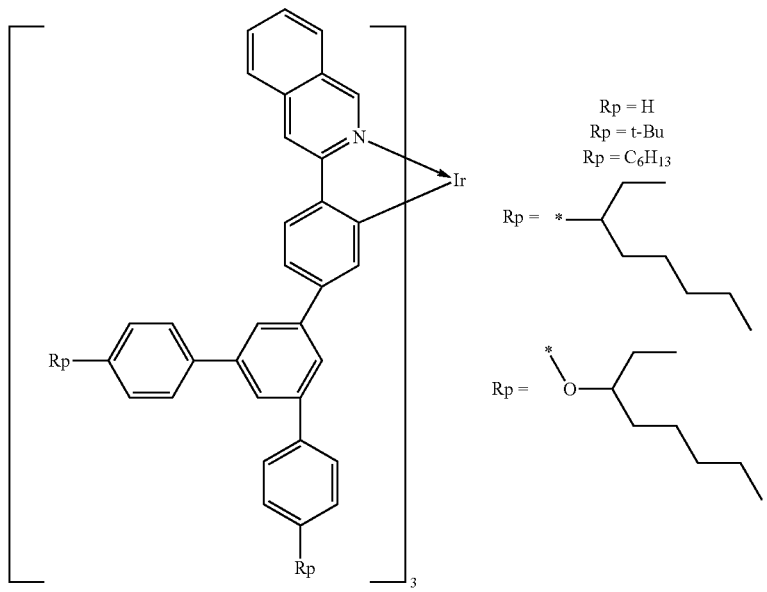
Ir-23b
[Chemical Formula 116]
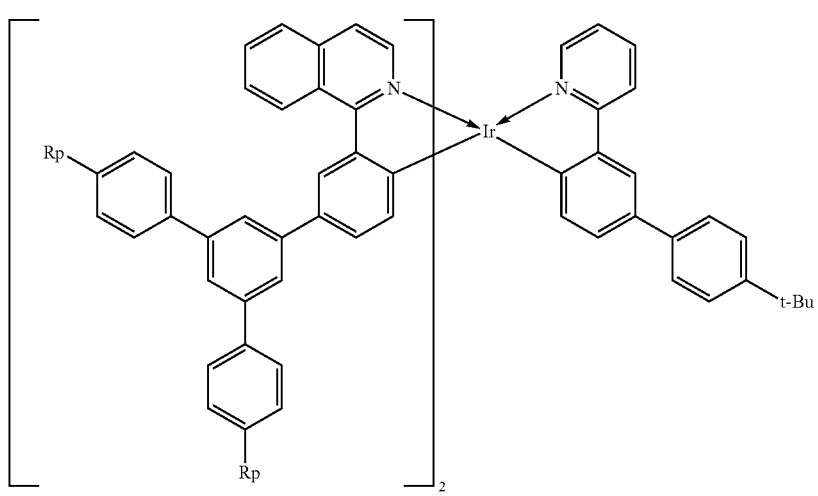
Ir-24b
[Chemical Formula 117]
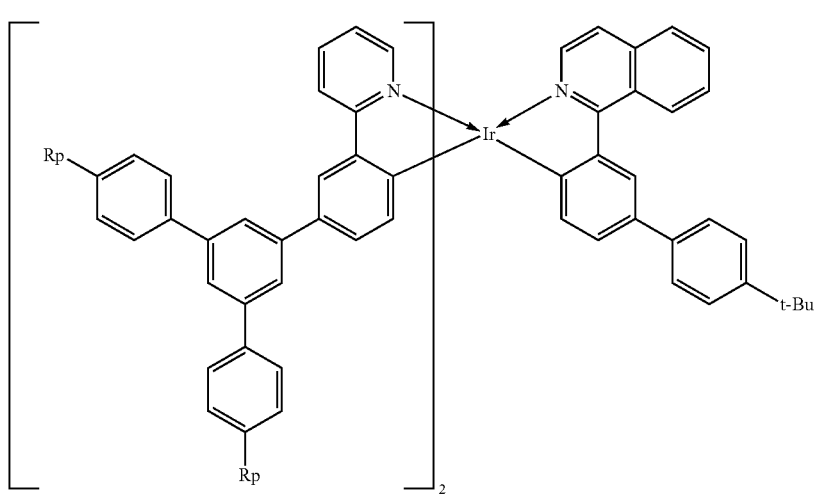
Ir-25b

[Chemical Formula 118]
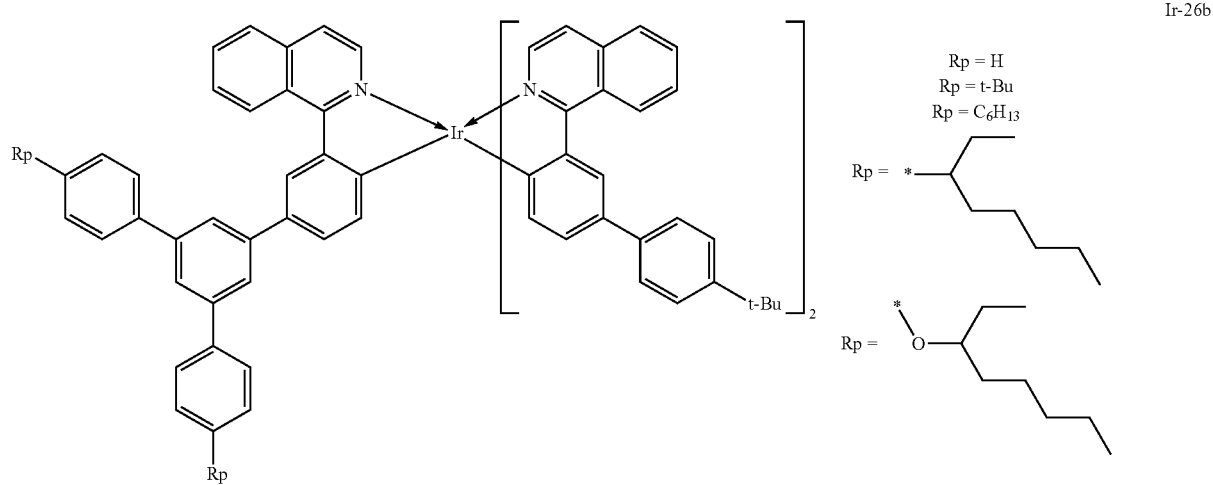
Ir-26b
[Chemical Formula 119]
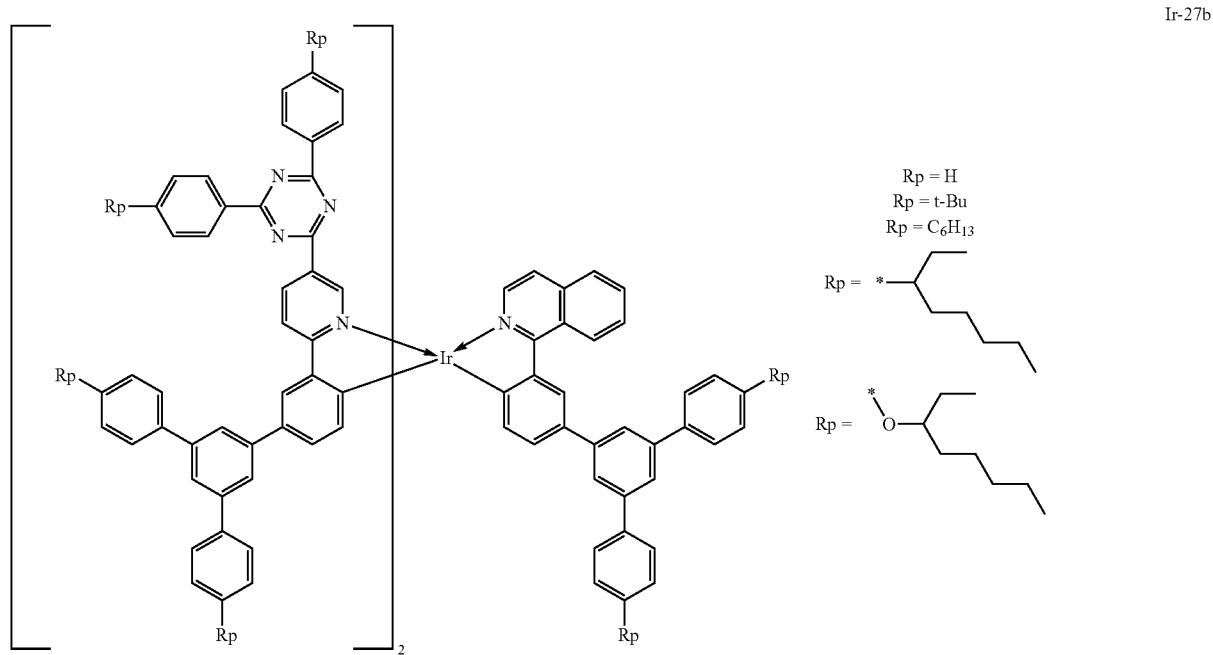
Ir-27b

[Chemical Formula 120]
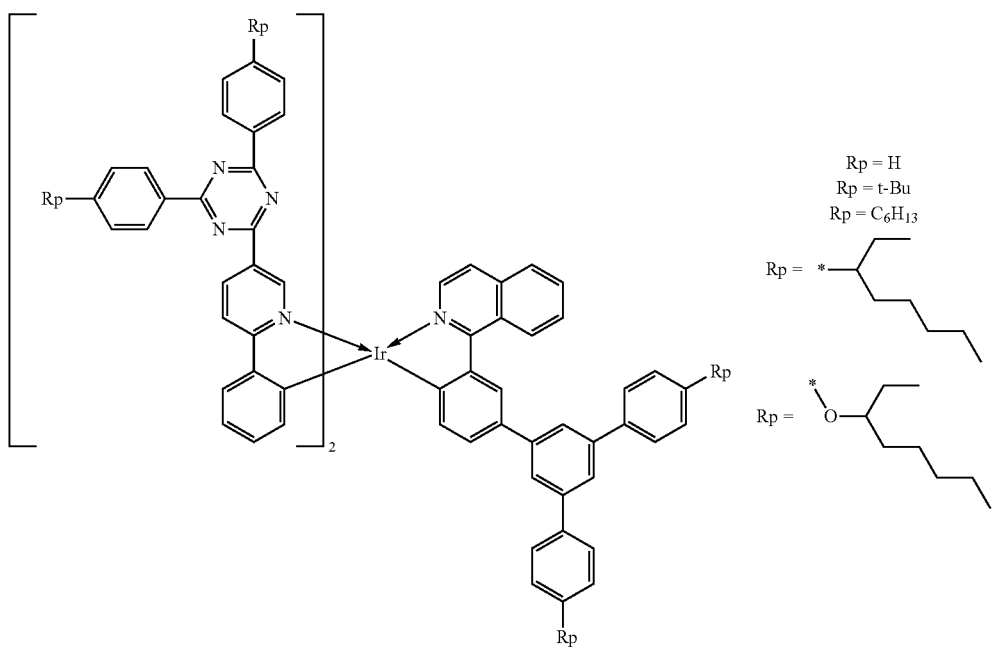
Ir-28b
Rp = H
Rp = t-Bu
Rp = C$_6$H$_{13}$
Rp = *
Rp = *
[Chemical Formula 121]
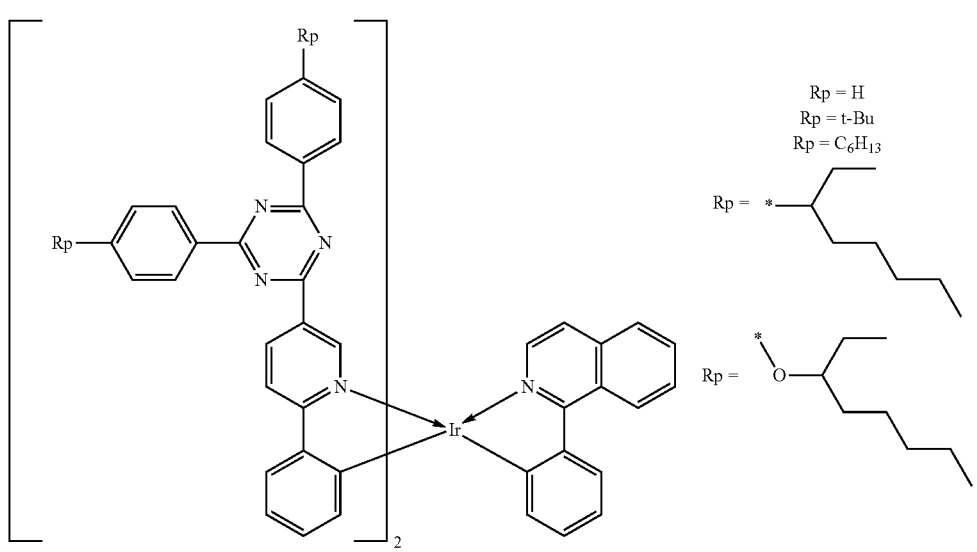
Ir-29b
Rp = H
Rp = t-Bu
Rp = C$_6$H$_{13}$
Rp = *
Rp = *
[Chemical Formula 122]
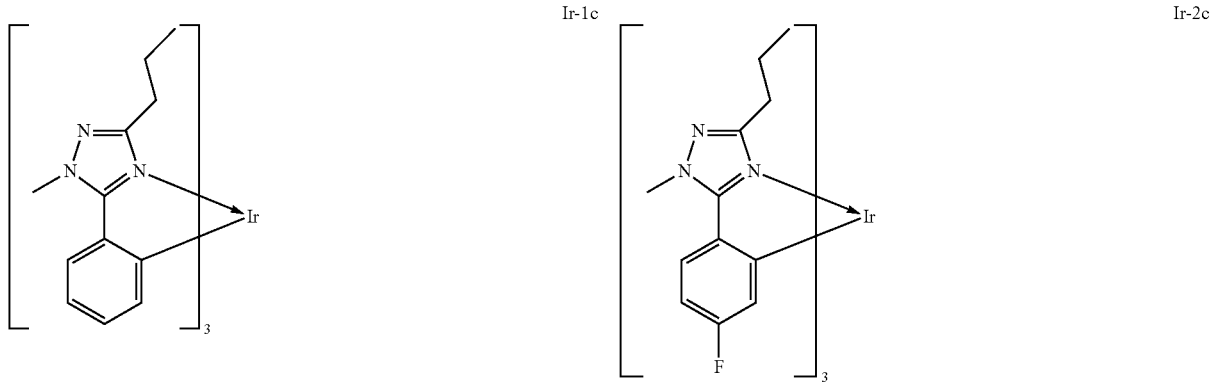
Ir-1c          Ir-2c

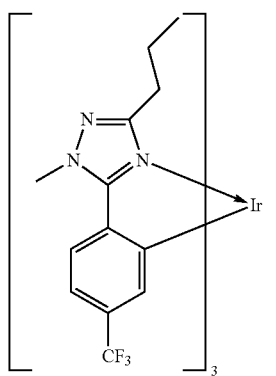
Ir-3c
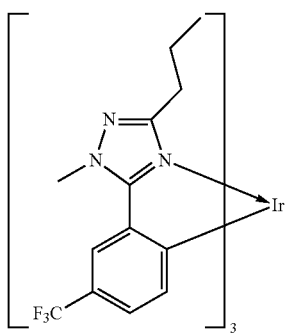
Ir-4c
[Chemical Formula 123]
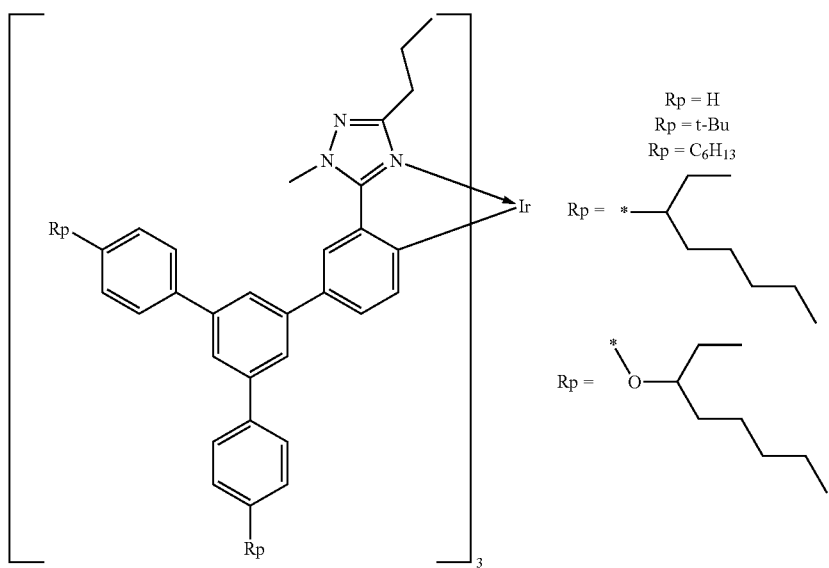
Ir-5c
Rp = H
Rp = t-Bu
Rp = C$_6$H$_{13}$
Rp = 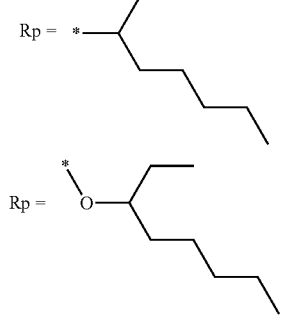
[Chemical Formula 124]
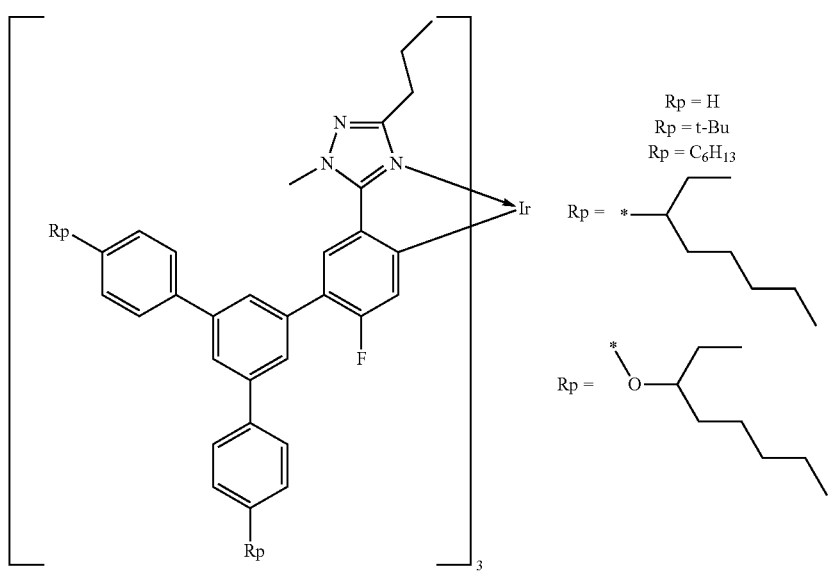
Ir-6c
Rp = H
Rp = t-Bu
Rp = C$_6$H$_{13}$
Rp = 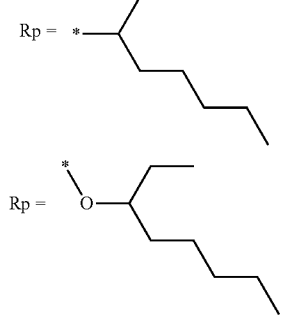

[Chemical Formula 125]
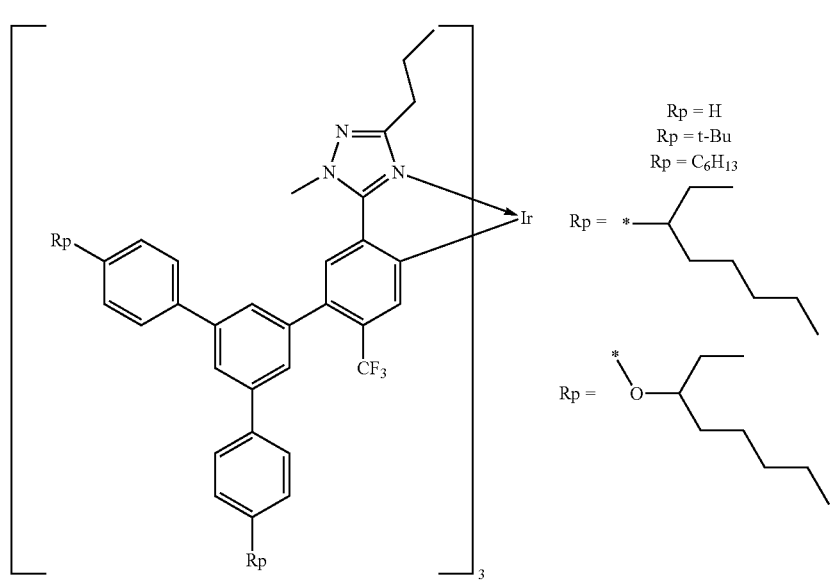
Ir-7c
[Chemical Formula 126]
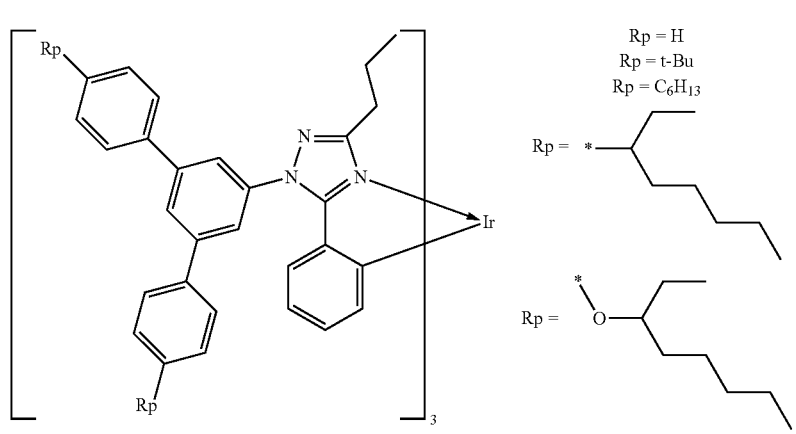
Ir-8c
[Chemical Formula 127]
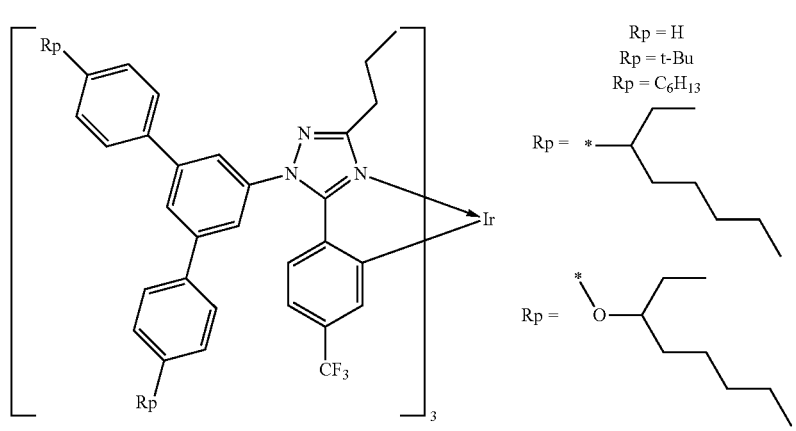
Ir-9c

[Chemical Formula 128]
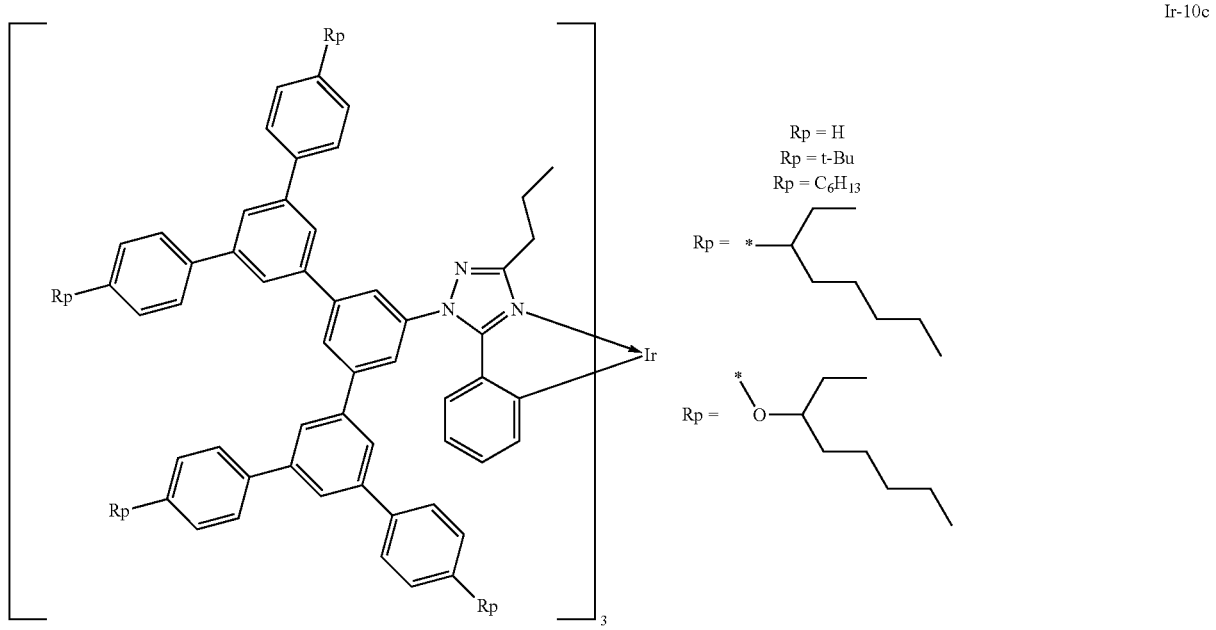
Ir-10c
[Chemical Formula 129]
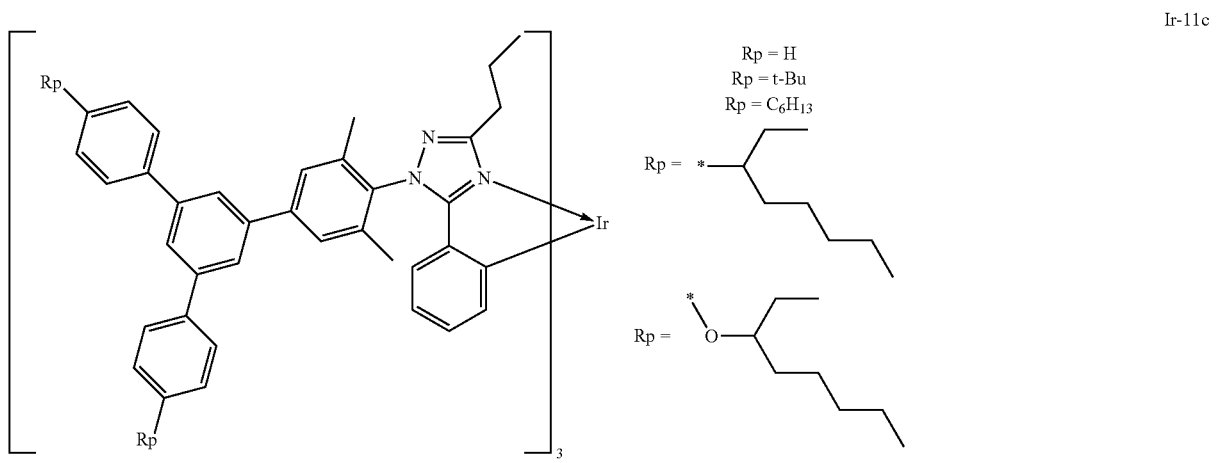
Ir-11c -continued
[Chemical Formula 130]
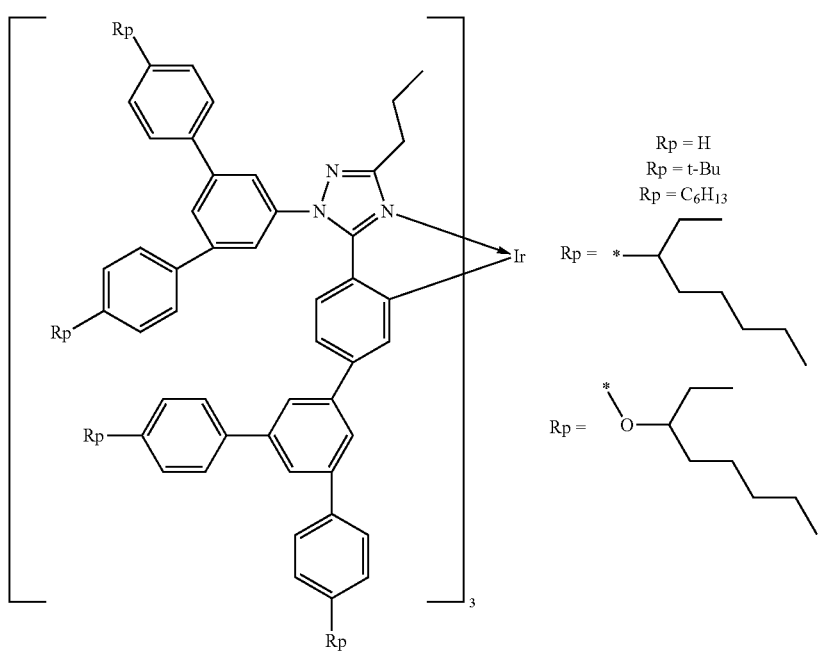
Ir-12c
[Chemical Formula 131]
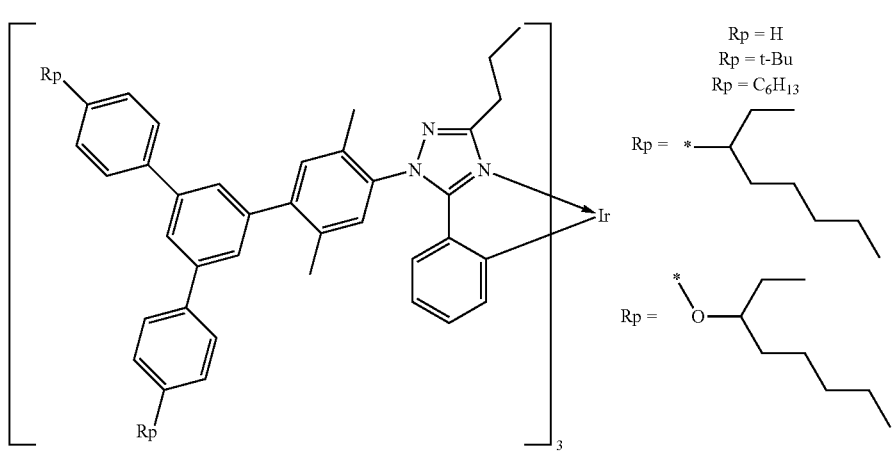
Ir-13c
[Chemical Formula 132]
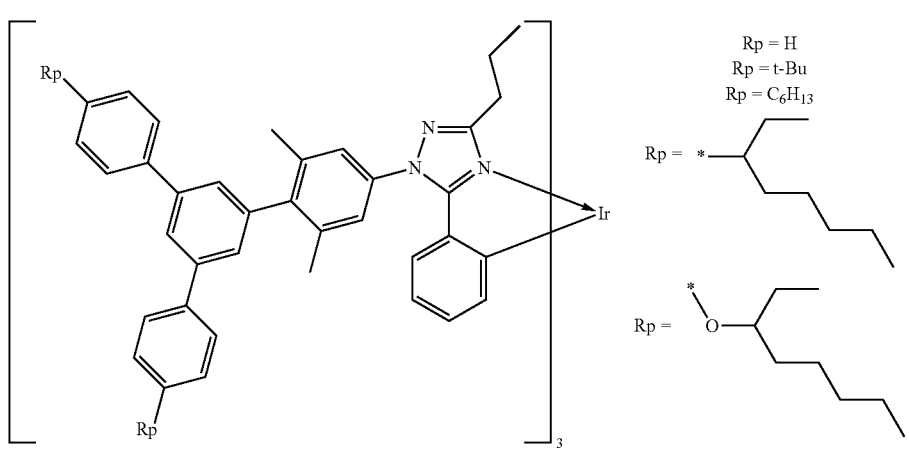
Ir-14c -continued
[Chemical Formula 133]
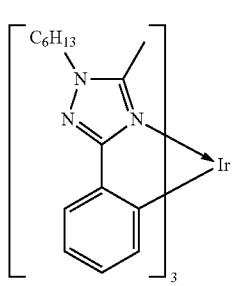 Ir-1d
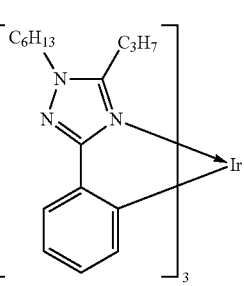 Ir-2d
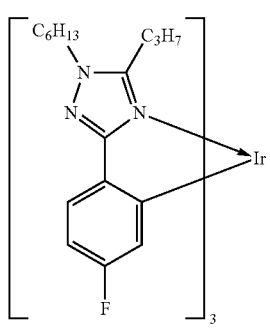 Ir-3d
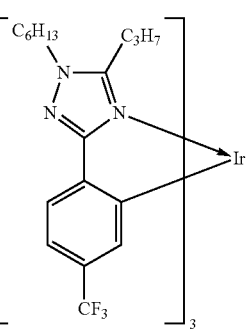 Ir-4d
[Chemical Formula 134]
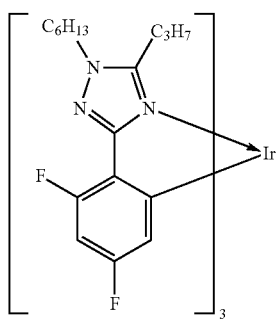 Ir-5d
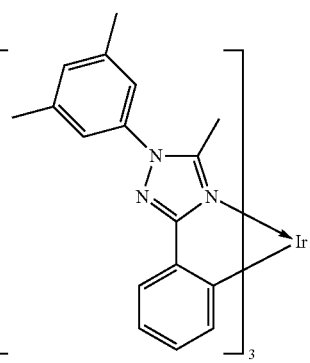 Ir-6d
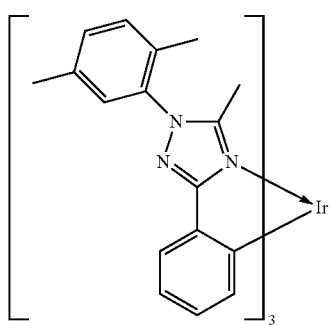 Ir-7d

[Chemical Formula 135]
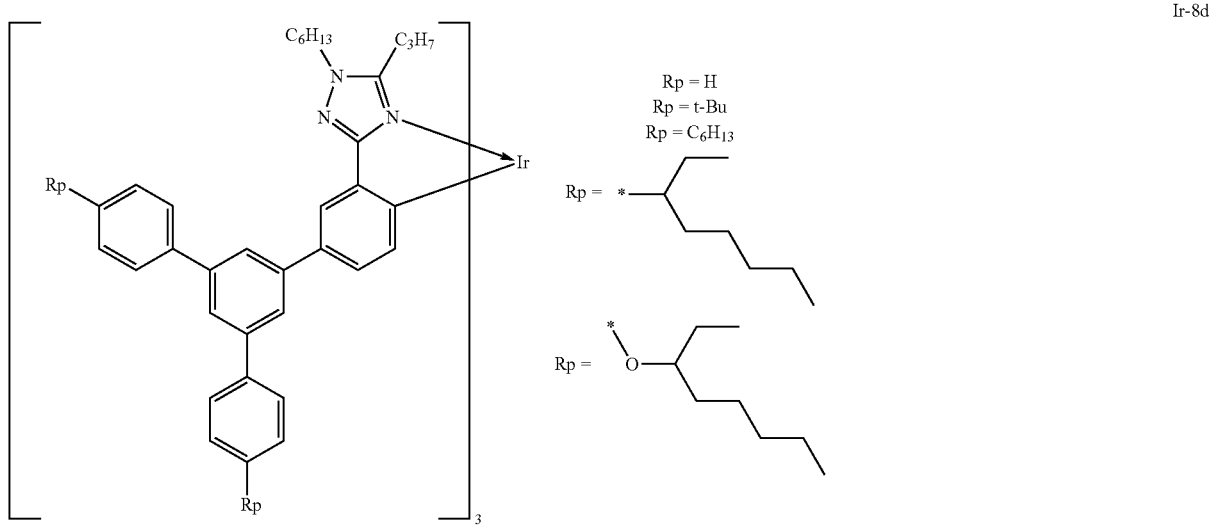
Ir-8d
[Chemical Formula 136]
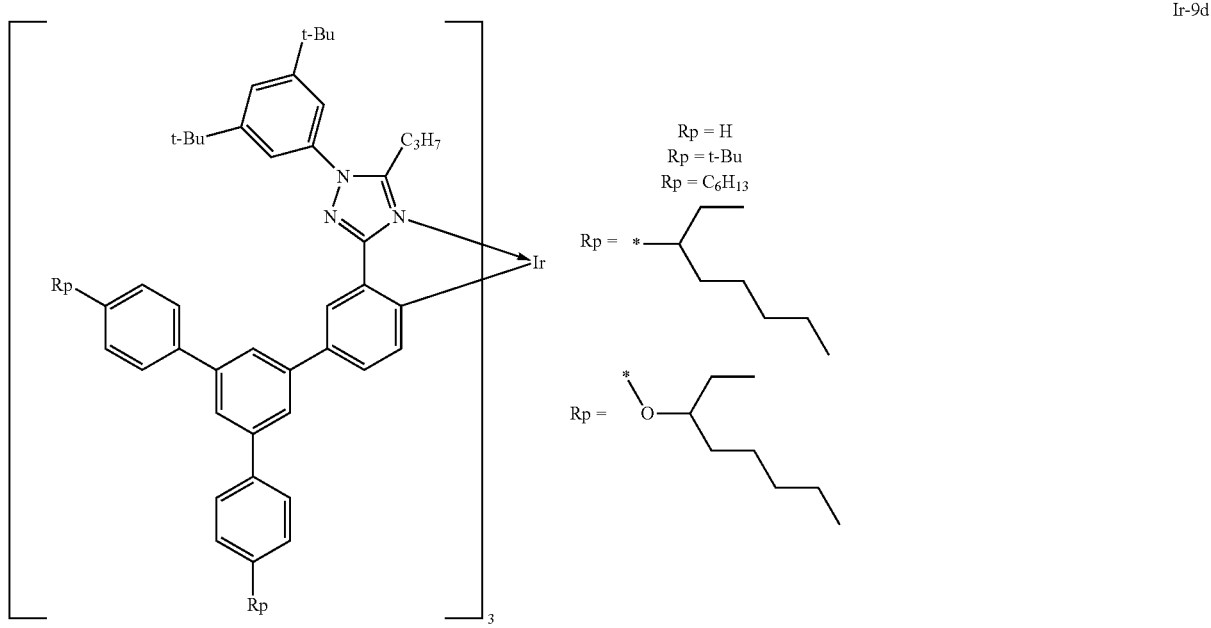
Ir-9d

[Chemical Formula 137]
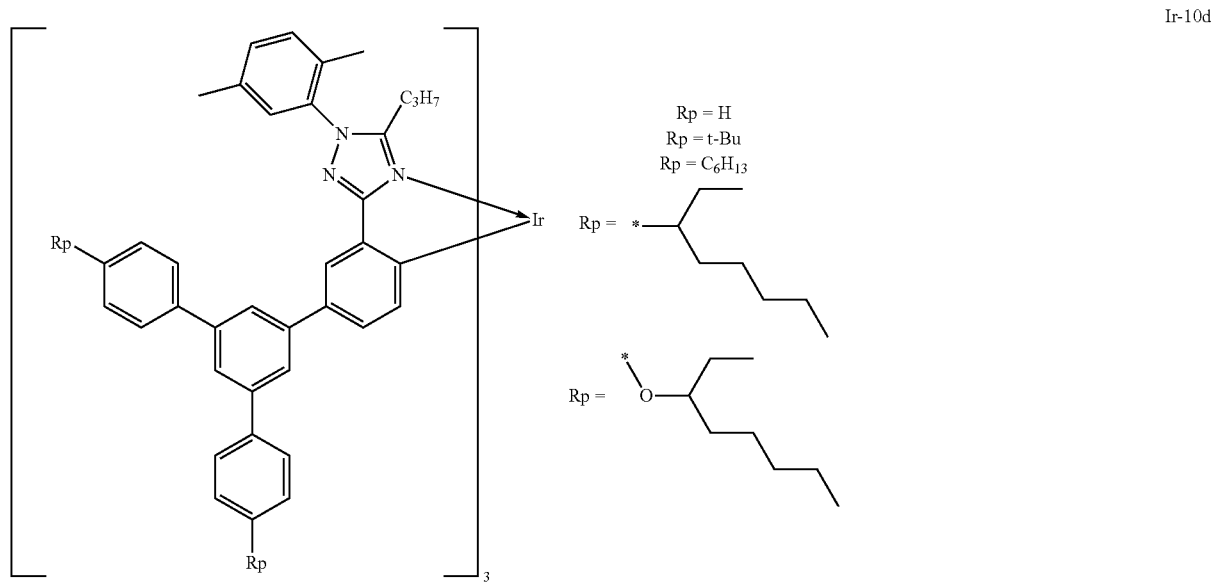
Ir-10d
[Chemical Formula 138]
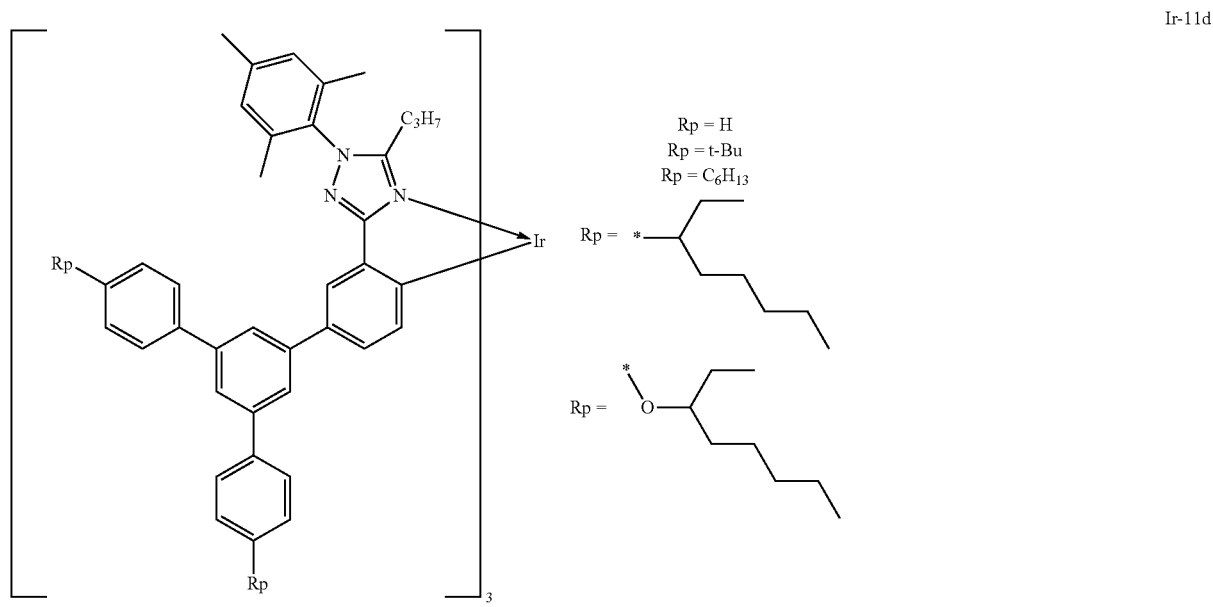
Ir-11d -continued
[Chemical Formula 139]
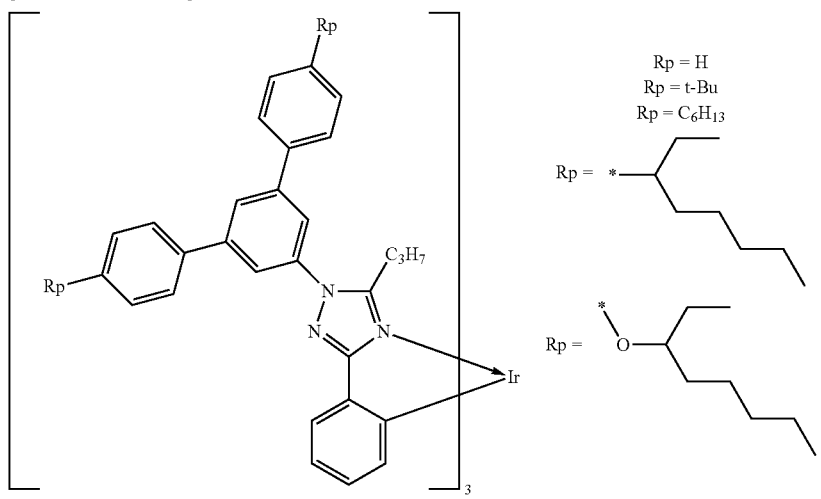
Ir-12d
[Chemical Formula 140]
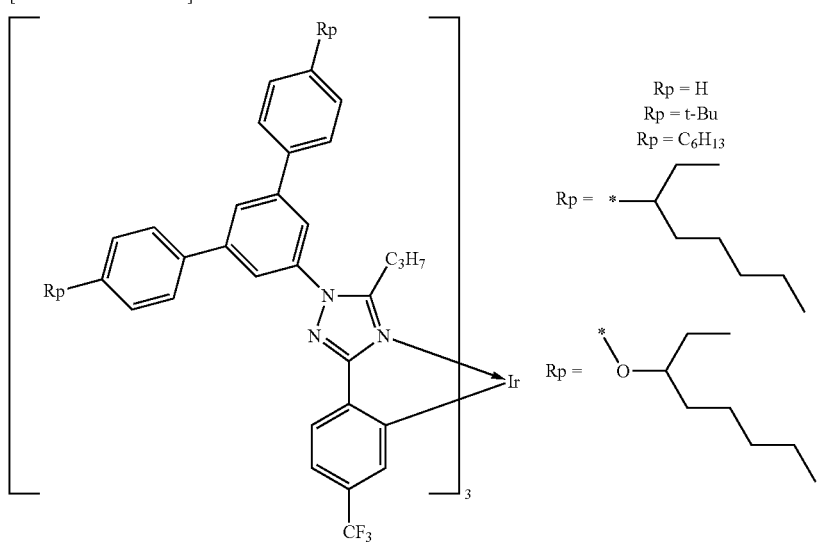
Ir-13d
[Chemical Formula 141]
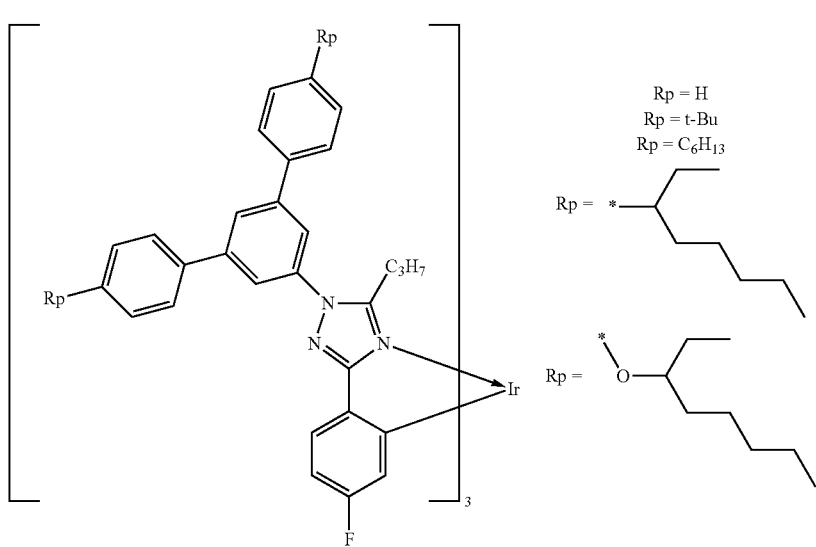
Ir-14d

[Chemical Formula 142]
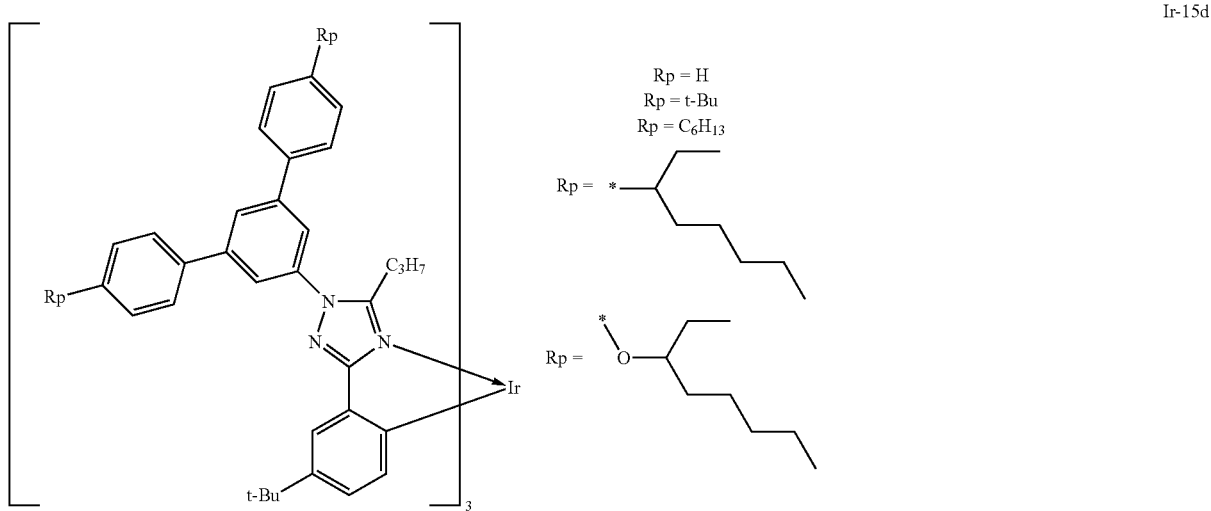
Ir-15d
[Chemical Formula 143]
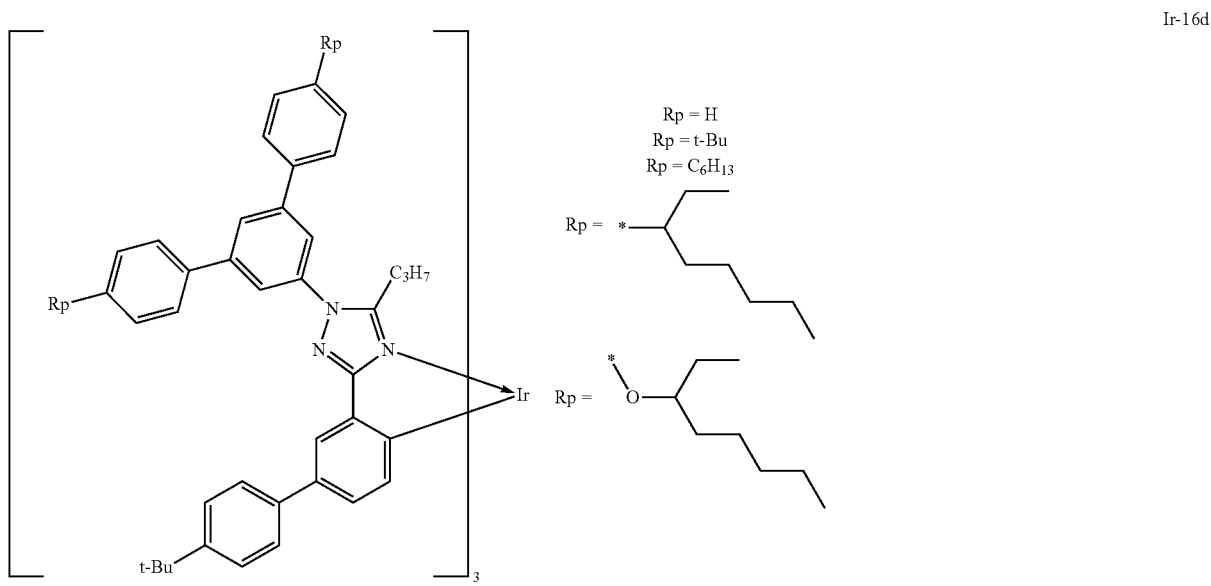
Ir-16d

[Chemical Formula 144]
Ir-17d
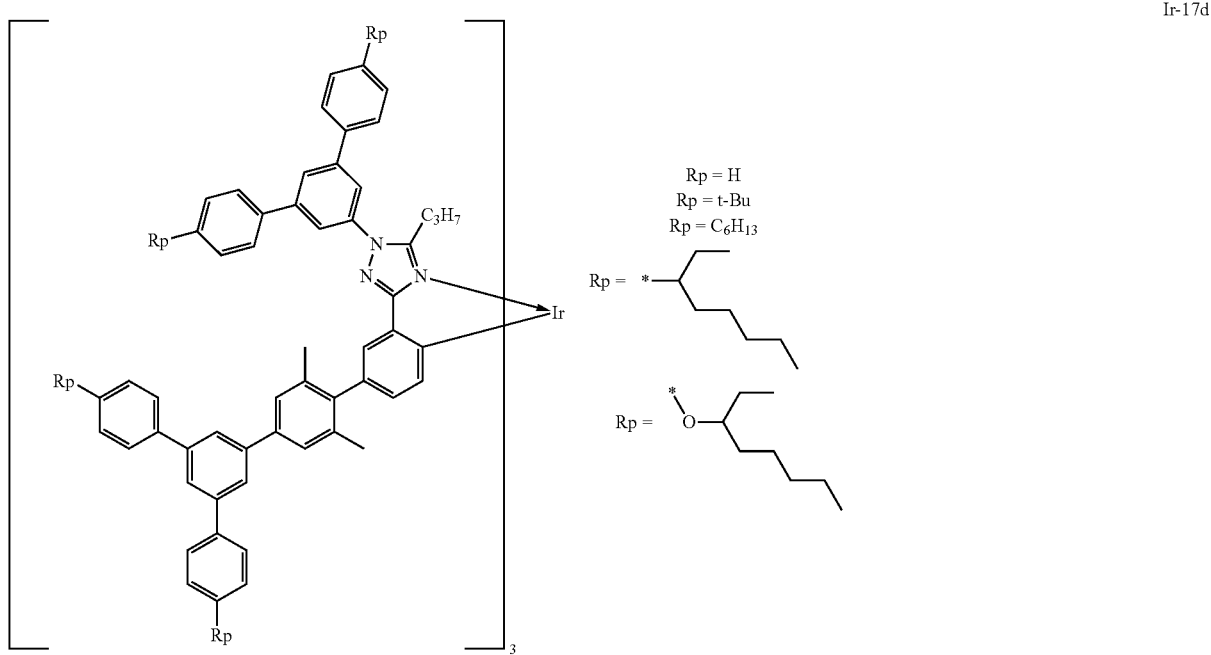
[Chemical Formula 145]
Ir-18d
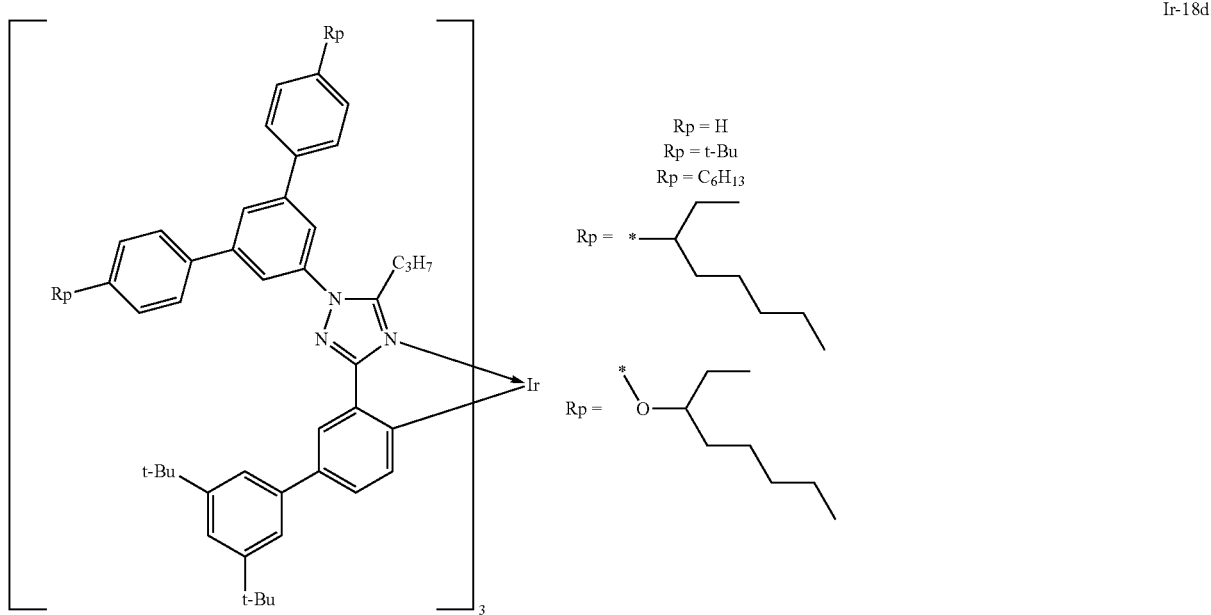

[Chemical Formula 146]
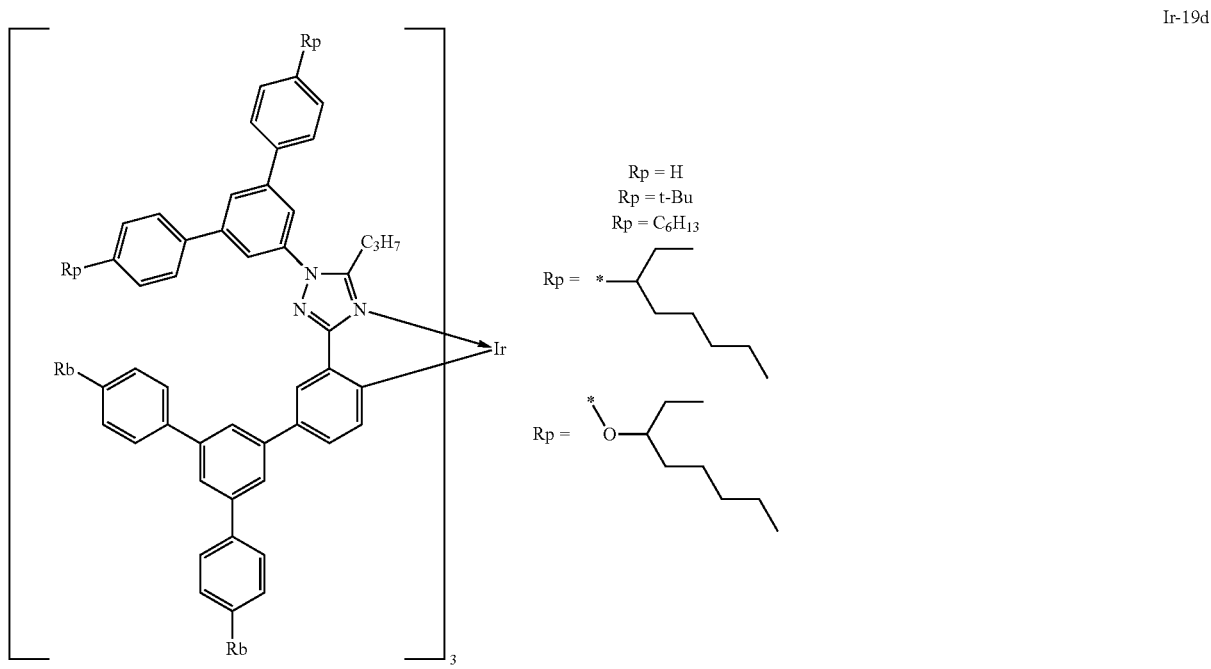
Ir-19d
Rp = H
Rp = t-Bu
Rp = C₆H₁₃
[Chemical Formula 147]
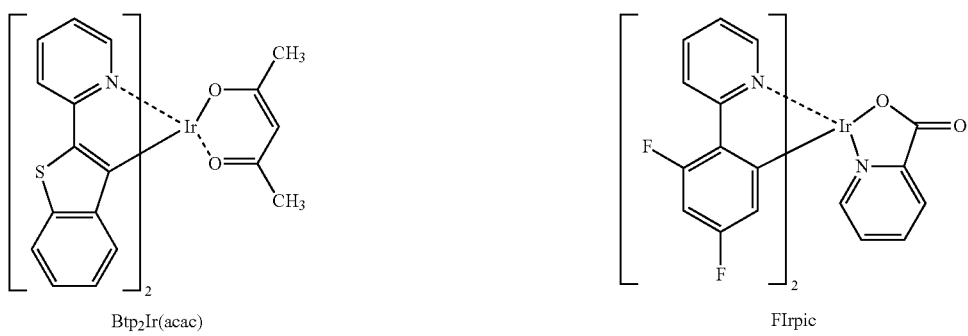
Btp₂Ir(acac)
FIrpic
[Chemical Formula 148]
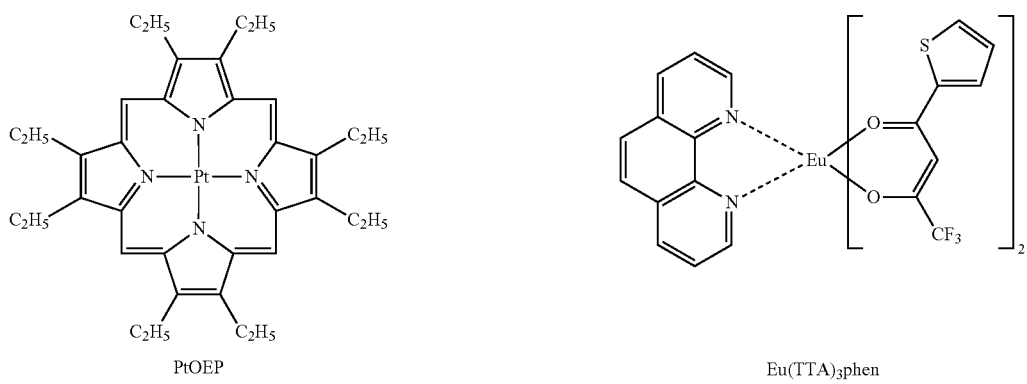
PtOEP
Eu(TTA)₃phen

[Chemical Formula 149]

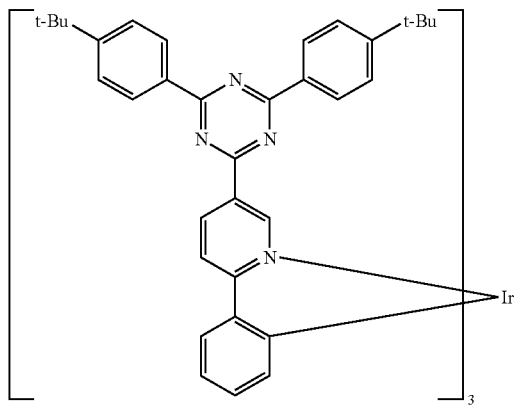

COM-5

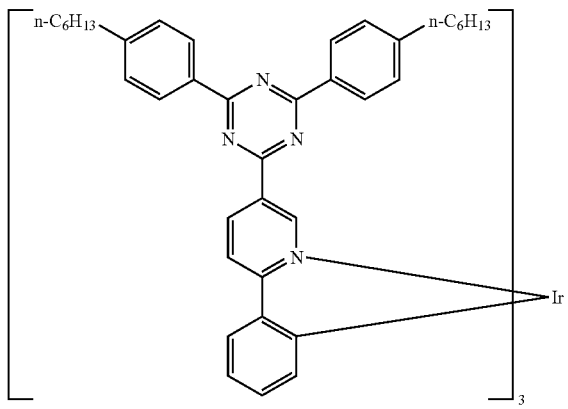

COM-6

The content of a light-emitting material is preferably 1 to 500 parts by weight and more preferably 5 to 200 parts by weight with respect to 100 parts by weight of the polymer compound of the invention in the composition.

(Liquid Composition)

The polymer compound of this embodiment may be in the form of a composition dissolved or dispersed in a solvent, and preferably an organic solvent (hereunder also referred to as "liquid composition", where the liquid composition may be in the form of a solution or dispersion). Such a liquid composition is known as an ink or varnish. When the liquid composition is used to form an organic film to be used in a light emitting device, the liquid composition is preferably a solution.

A liquid composition may comprise at least one material selected from the group consisting of hole transport materials, electron transport materials and light-emitting materials, in addition to the polymer compound of this embodiment. Also, other substances may be added to the liquid composition so long as the effect of the invention is not impeded. Other substances include antioxidants, viscosity modifiers and surfactants.

The organic solvent referred to here is not particularly restricted so long as it forms a solution or dispersion of the polymer compound of this embodiment, and the following organic solvents may be mentioned.

Aromatic hydrocarbon-based solvents: toluene, xylene (including its isomers and mixtures), 1,2,3-trimethylbenzene, 1,2,4-trimethylbenzene, mesitylene (1,3,5-trimethylbenzene), ethylbenzene, propylbenzene, isopropylbenzene, butylbenzene, isobutylbenzene, 2-phenylbutane, tert-butylbenzene, pentylbenzene, neopentylbenzene, isoamylbenzene, hexylbenzene, cyclohexylbenzene, heptylbenzene, octylbenzene, 3-propyltoluene, 4-propyltoluene, 1-methyl-4-propylbenzene, 1,4-diethylbenzene, 1,4-dipropylbenzene, 1,4-di-tert-butylbenzene, indane, tetralin (1,2,3,4-tetrahydronaphthalene) and the like.

Aliphatic hydrocarbon-based solvents: n-pentane, n-hexane, cyclohexane, methylcyclohexane, n-heptane, n-octane, n-nonane, n-decane, decalin and the like.

Aromatic ether-based solvents: anisole, ethoxybenzene, propoxybenzene, butyloxybenzene, pentyloxybenzene, cyclopentyloxybenzene, hexyloxybenzene, cyclohexyloxybenzene, heptyloxybenzene, octyloxybenzene, 2-methylanisole, 3-methylanisole, 4-methylanisole, 4-ethylanisole, 4-propylanisole, 4-butylanisole, 4-pentylanisole, 4-hexylanisole, diphenyl ether, 4-methylphenoxybenzene, 4-ethylphenoxybenzene, 4-propylphenoxybenzene, 4-butylphenoxybenzene, 4-pentylphenoxybenzene, 4-hexylphenoxybenzene, 4-phenoxytoluene, 3-phenoxytoluene, 1,3-dimethoxybenzene, 2,6-dimethylanisole, 2,5-dimethylanisole, 2,3-dimethylanisole, 3,5-dimethylanisole and the like.

Aliphatic ether-based solvents: tetrahydrofuran, dioxane, dioxolane and the like.

Ketone-based solvents: acetone, methyl ethyl ketone, methyl isobutyl ketone, cyclohexanone, acetophenone and the like.

Ester-based solvents: ethyl acetate, butyl acetate, methyl benzoate, ethyl cellosolve acetate and the like.

Chlorinated solvents: methylene chloride, chloroform, 1,2-dichloroethane, 1,1,2-trichloroethane, chlorobenzene, o-dichlorobenzene and the like.

Alcohol-based solvents: methanol, ethanol, propanol, isopropanol, cyclohexanol, phenol and the like.

Polyhydric alcohols and their derivatives: ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin, 1,2-hexanediol and the like.

Aprotic polar solvents: dimethyl sulfoxide, N-methyl-2-pyrrolidone, N,N-dimethylformamide, N,N-dimethylacetamide and the like.

These organic solvents may be used alone, or two or more of them may be used as a mixed solvent. When a mixed solvent is to be used, it is preferably a combination of two or more from among the solvent groups mentioned above, and a plurality of solvents of the same solvent group of any listed above may be combined, or one or more from different solvent groups may be combined. The compositional ratio can be determined in consideration of the physical properties of each of the solvents and the solubility of the polymer compound.

Preferred examples in cases where a plurality of solvents are selected and combined from the same solvent group, are a plurality of aromatic hydrocarbon-based solvents, and a plurality of aromatic ether-based solvents. Preferred examples in cases where one or more solvents are selected and combined from different solvent groups, are combinations of aromatic hydrocarbon-based solvents and aliphatic hydrocarbon-based solvents, aromatic hydrocarbon-based solvents and aromatic ether-based solvents, aromatic hydrocarbon-based solvents and aliphatic ether-based solvents, aromatic hydrocarbon-based solvents and aprotic polar solvents, and aromatic ether-based solvent and aprotic polar solvents.

Also, water can be added to simple solvents or mixed solvents.

Of these organic solvents, from the viewpoint of viscosity and film formability there are preferred simple solvents or mixed solvents comprising one or more organic solvents having a structure containing a benzene ring, a melting point of no higher than 0° C. and a boiling point of 100° C. or higher, and more preferred are simple solvents or mixed solvents comprising one or more aromatic hydrocarbon-based solvents or aromatic ether-based solvents.

An organic solvent used may be a single one alone or a mixed solvent comprising two or more, but from the viewpoint of controlling the film formability it is preferably used as a mixed solvent. Also, if necessary, the organic solvent may be used after purification by a method such as rinsing, distillation or contact with an adsorbent.

Such liquid compositions allow easy production of an organic film comprising a polymer compound of this embodiment. Specifically, the liquid composition can be coated onto a substrate, and heated, blown and subjected to pressure reduction and the like to remove the organic solvent, thereby producing an organic film comprising a polymer compound of this embodiment. Removal of the organic solvent can be accomplished, for example, by a step of heating at a temperature of at least 50° C. and no higher than 250° C., or a step of holding in a reduced pressure atmosphere at about $10^{-3}$ Pa, varying the conditions as appropriate for the organic solvent used.

The coating can be accomplished using a coating method such as spin coating method, casting method, microgravure method, gravure coating method, bar coating method, roll coating method, wire bar coating method, dip coating method, slit coating method, capillary coating method, spray coating method, screen printing method, flexographic printing method, offset printing method, ink jet printing method, nozzle coating method or the like.

The preferred viscosity for the liquid composition will differ depending on the printing method, but it is preferably 0.5 to 1000 mPa·s and more preferably 0.5 to 500 mPa·s, at 25° C. When the liquid composition is to be passed through a discharge device such as in ink jet printing, the viscosity at 25° C. is preferably 0.5 to 50 mPa·s and more preferably 0.5 to 20 mPa·s to prevent clogging or curving trajectory during discharge. The concentration of the polymer compound of this embodiment in the liquid composition is preferably 0.01 to 10 wt % and more preferably 0.1 to 5 wt %.

(Organic Film)

The organic film of this embodiment comprises the aforementioned polymer compound or composition. The organic film of this embodiment can be easily produced from the aforementioned liquid composition, as described above. Also, the second organic film of the invention is an insolubilized organic film that has been insolubilized by crosslinking a polymer compound of this embodiment, and in most cases it is crosslinked and cured by external stimulation such as heating or photoirradiation. An insolubilized organic film is advantageous for layering of a light emitting device because it is poorly soluble in solvents.

The heating temperature for crosslinking of an organic film will generally be in the range of room temperature to 300° C., with the upper limit being preferably 250° C., more preferably 200° C. and even more preferably 180° C. from the viewpoint of luminous efficiency. Also, the lower limit is preferably 50° C., more preferably 70° C. and even more preferably 100° C. from the viewpoint of ease of forming an insolubilized organic film.

Ultraviolet light, near ultraviolet light and visible light are generally used for photoirradiation for crosslinking of an organic film, but ultraviolet light or near ultraviolet light is preferably used.

The organic film and insolubilized organic film of this embodiment can be suitably used as a hole injection layer or hole transport layer for a light emitting device as described below. It can also be suitably used in an organic semiconductor device such as an organic transistor or organic solar cell. Since the organic film and insolubilized organic film of this embodiment is fabricated using the aforementioned polymer compound or composition, its use as a hole injection layer or hole transport layer of a light emitting device will result in more excellent luminous efficiency for the light emitting device.

(Light Emitting Device)

The light emitting device of this embodiment has the aforementioned organic film or insolubilized organic film.

Specifically, the light emitting device of this embodiment comprises an anode, a cathode, and a layer containing a polymer compound of the invention between the anode and cathode. The layer containing the polymer compound is preferably a layer composed of the aforementioned organic film or insolubilized organic film, and the layer preferably functions as a hole injection layer or hole transport layer. When the layer containing the polymer compound of the invention is to function as a hole injection layer or hole transport layer, the layer is preferably a layer composed of the aforementioned insolubilized organic film.

Examples for the light emitting device of this embodiment include light emitting devices having an electron transport layer formed between a cathode and a luminescent layer, light emitting devices having a hole transport layer formed between an anode and a luminescent layer, and light emitting devices having an electron transport layer formed between a cathode and a luminescent layer and having a hole transport layer formed between an anode and a luminescent layer.

The following structures a) to d) are specific examples as light emitting devices of this embodiment.

a) Anode/luminescent layer/cathode
b) Anode/hole transport layer/luminescent layer/cathode
c) Anode/luminescent layer/electron transport layer/cathode
d) Anode/hole transport layer/luminescent layer/electron transport layer/cathode (Here, the "/" indicates that the layers are laminated adjacent to each other; same hereunder.)

When the light emitting device of this embodiment has a hole transport layer, the polymer compound of this embodiment can be used in the hole transport layer. A hole transport material (including low molecular weight and high-molecular-weight compounds) can also be used in the hole transport layer. Such a hole transport material may be any of the hole transport materials given as examples that may be contained in the composition of the invention.

Specific examples of such hole transport materials include those mentioned in Japanese Unexamined Patent Application Publication SHO No. 63-70257, Japanese Unexamined Patent Application Publication SHO No. 63-175860, Japanese Unexamined Patent Application Publication HEI No. 2-135359, Japanese Unexamined Patent Application Publication HEI No. 2-135361, Japanese Unexamined Patent Application Publication HEI No. 2-209988, Japanese Unexamined Patent Application Publication HEI No. 3-37992 and Japanese Unexamined Patent Application Publication HEI No. 3-152184.

Preferred among these as hole transport materials to be used in the hole transport layer are high-molecular-weight hole transport materials such as polyvinylcarbazole and its derivatives, polysilane and its derivatives, polysiloxane derivatives having an aromatic amine compound group on a side chain or the main chain, polyaniline and its derivatives, polythiophene and its derivatives, poly(p-phenylenevinylene) and its derivatives and poly(2,5-thienylenevinylene) and its derivatives, and more preferably are polyvinylcarbazole and its derivatives, polysilane and its derivatives and polysiloxane derivatives having an aromatic amine on a side chain or the main chain.

Also, examples of low-molecular-weight hole transport materials include pyrazoline derivatives, arylamine derivatives, stilbene derivatives and triphenyldiamine derivatives. A low-molecular-weight hole transport material is preferably used after dispersion in a high molecular binder.

As macromolecular binders there may be suitably used ones that cause minimal interference with charge transport, or ones that do not have strong absorption for visible light. Examples of high molecular binders include poly(N-vinylcarbazole), polyaniline and its derivatives, polythiophene and its derivatives, poly(p-phenylenevinylene) and its derivatives, poly(2,5-thienylenevinylene) and its derivatives, polycarbonate, polyacrylate, polymethyl acrylate, polymethyl methacrylate, polystyrene, polyvinyl chloride, polysiloxane and the like.

Polyvinylcarbazole and its derivatives may be obtained, for example, by cationic polymerization or radical polymerization from vinyl monomers.

Examples of polysilane and its derivatives include the compounds mentioned in Chem. Rev. Vol. 89, p. 1359 (1989) and GB2300196. The synthesis methods described in this literature can be used, although the Kipping method is preferred.

Because the skeletal structure of siloxane has essentially no hole transport property, polysiloxane and its derivatives are preferably compounds having a structure with the aforementioned low-molecular-weight hole transport material on a side chain or the main chain. Notable examples are those having a hole transporting aromatic amine on a side chain or the main chain.

The method of forming the hole transport layer may be film formation from a mixed solution with a high molecular binder, for a low-molecular-weight hole transport material. For a high-molecular-weight hole transport material, there may be mentioned a method of forming a film from a solution (that is, a mixture of the hole transport material with a solvent).

The solvent used for film formation from a solution is preferably one that can dissolve or evenly disperse the hole transport material. The solvent may be a chlorine-based solvent such as chloroform, methylene chloride, 1,2-dichloroethane, 1,1,2-trichloroethane, chlorobenzene or o-dichlorobenzene, an ether-based solvent such as tetrahydrofuran or dioxane, an aromatic hydrocarbon-based solvent such as toluene or xylene, an aliphatic hydrocarbon-based solvent such as cyclohexane, methylcyclohexane, n-pentane, n-hexane, n-heptane, n-octane, n-nonane or n-decane, a ketone-based solvent such as acetone, methyl ethyl ketone or cyclohexanone, an ester-based solvent such as ethyl acetate, butyl acetate or ethyl cellosolve acetate, a polyhydric alcohol such as ethylene glycol, ethyleneglycol monobutyl ether, ethyleneglycol monoethyl ether, ethyleneglycol monomethyl ether, dimethoxyethane, propylene glycol, diethoxymethane, triethyleneglycol monoethyl ether, glycerin or 1,2-hexanediol, or a derivative thereof, an alcohol-based solvent such as methanol, ethanol, propanol, isopropanol or cyclohexanol, a sulfoxide-based solvent such as dimethyl sulfoxide, or an amide-based solvent such as N-methyl-2-pyrrolidone or N,N-dimethylformamide. These organic solvents may be used alone or in combinations of two or more.

Examples of film formation from a solution include methods of coating from a solution, such as spin coating method, casting method, microgravure coating method, gravure coating method, bar coating method, roll coating method, wire bar coating method, dip coating method, spray coating method, screen printing method, flexographic printing method, offset printing method, ink jet printing method and the like.

The optimum value for the thickness of the hole transport layer will differ depending on the material used, and it may be selected so that the driving voltage and luminous efficiency are suitable values, but the thickness must be at least sufficient to avoid generation of pinholes, while an excessive thickness is not preferred as it may increase the driving voltage of the device. The thickness of the hole transport layer is therefore usually 1 nm to 1 μm, preferably 2 nm to 500 nm and more preferably 5 nm to 200 nm.

When the light emitting device of this embodiment has an electron transport layer, an electron transport material (including low molecular weight and high-molecular-weight compounds) can be used in the electron transport layer. Such an electron transport material may be any of the electron transport materials given as examples that may be contained in the composition of the invention.

Specific examples of such electron transport materials include those mentioned in Japanese Unexamined Patent Application Publication SHO No. 63-70257, Japanese Unexamined Patent Application Publication SHO No. 63-175860, Japanese Unexamined Patent Application Publication HEI No. 2-135359, Japanese Unexamined Patent Application Publication HEI No. 2-135361, Japanese Unexamined Patent Application Publication HEI No. 2-209988, Japanese Unexamined Patent Application Publication HEI No. 3-37992 and Japanese Unexamined Patent Application Publication HEI No. 3-152184.

Preferred among these are oxadiazole derivatives, benzoquinone and its derivatives, anthraquinone and its derivatives, metal complexes of 8-hydroxyquinoline and its derivatives, polyquinoline and its derivatives, polyquinoxaline and its derivatives and polyfluorene and its derivatives, with 2-(4-biphenylyl)-5-(4-tert-butylphenyl)-1,3,4-oxadiazole, benzoquinone, anthraquinone, tris(8-quinolinol)aluminum and polyquinoline being even more preferred.

The method of forming a film of an electron transport layer may be vacuum vapor deposition from a powder or film formation from a solution or molten state, in the case of a low-molecular-weight electron transport material, or film formation from a solution or molten state, in the case of a high-molecular-weight electron transport material. The aforementioned high molecular binder may also be used in combination therewith during film formation from a solution or molten state.

The solvent used for film formation from a solution is preferably one that can dissolve or evenly disperse the electron transport material and/or high molecular binder. Specific examples include those mentioned above as solvents to be used for film formation from a solution of the hole transport layer, in the description of the hole transport layer. The solvents may be used alone or in combinations of two or more.

Film-forming methods from a solution or molten state include the methods of forming a film from a solution of the hole transport layer mentioned in the description of the hole transport layer.

The optimum value for the thickness of the electron transport layer will differ depending on the material used, and it may be selected so that the driving voltage and luminous efficiency are suitable values, but the thickness must be at least sufficient to avoid generation of pinholes, while an excessive thickness is not preferred as it increases the driving voltage of the device. The thickness of the electron transport layer is therefore usually 1 nm to 1 μm, preferably 2 nm to 500 nm and more preferably 5 nm to 200 nm.

Of hole transport layers and electron transport layers formed adjacent to the electrodes, those having the function of improving the charge injection efficiency from the electrodes and having an effect of lowering the driving voltage of the light emitting device, are often generally referred to particularly as hole injection layers and electron injection layers, respectively (these will hereunder be collectively referred to as "charge injection layer").

Also, in order to increase adhesiveness with the electrodes and improve charge injection from the electrodes, there may be provided adjacent to the electrodes a charge injection layer or insulating layer, while a thin buffer layer may be inserted at the interface with the charge transport layer or luminescent layer to improve the interfacial adhesiveness and prevent intermixture.

The order and number of layers to be laminated and the thickness of each layer can be appropriately determined in consideration of the desired luminous efficiency and device lifespan.

For this embodiment, examples of light emitting devices provided with charge injection layers include light emitting devices provided with a charge injection layer adjacent to the cathode and light emitting devices provided with a charge injection layer adjacent to the anode. Specifically, the following structures e) to p) may be mentioned.

e) Anode/hole injection layer/luminescent layer/cathode
f) Anode/luminescent layer/electron injection layer/cathode
g) Anode/hole injection layer/luminescent layer/electron injection layer/cathode
h) Anode/hole injection layer/hole transport layer/luminescent layer/cathode
i) Anode/hole transport layer/luminescent layer/electron injection layer/cathode
j) Anode/hole injection layer/hole transport layer/luminescent layer/electron injection layer/cathode
k) Anode/hole injection layer/luminescent layer/electron transport layer/cathode
l) Anode/luminescent layer/electron transport layer/electron injection layer/cathode
m) Anode/hole injection layer/luminescent layer/electron transport layer/electron injection layer/cathode
n) Anode/hole injection layer/hole transport layer/luminescent layer/electron transport layer/cathode
o) Anode/hole transport layer/luminescent layer/electron transport layer/electron injection layer/cathode
p) Anode/hole injection layer/hole transport layer/luminescent layer/electron transport layer/electron injection layer/cathode As mentioned above, the light emitting device of this embodiment includes types wherein the polymer compound of this embodiment is present in the hole transport layer and/or the electron transport layer. The light emitting device of this embodiment also includes types wherein the polymer compound of this embodiment is present in the hole injection layer and/or the electron injection layer.

When the polymer compound or composition of this embodiment is to be used in a hole injection layer, it is preferably used simultaneously with an electron-accepting compound. When the polymer compound or composition of this embodiment is to be used in an electron injection layer, it is preferably used simultaneously with an electron donor compound. Methods for simultaneous use include mixing, copolymerization, and introduction as side chains.

Specific examples for the charge injection layer include a layer comprising a conductive polymer, a layer provided between the anode and hole transport layer which comprises a material having an ionization potential between that of the anode material and the hole transport material in the hole transport layer, or a layer provided between the cathode and electron transport layer which comprises a material having electron affinity between that of the cathode material and the electron transport material in the electron transport layer.

When the charge injection layer is a layer comprising a conductive polymer, the electric conductivity of the conductive polymer is preferably $10^{-5}$ S/cm to $10^3$ S/cm, and for reduced leak current between light-emitting picture devices, it is more preferably $10^{-5}$ S/cm to $10^2$ S/cm and more preferably $10^{-5}$ S/cm to $10^1$ S/cm. In order for the electric conductivity of the conductive polymer to be between $10^{-5}$ S/cm and $10^3$ S/cm, the conductive polymer is usually doped with an appropriate ion.

The type of ion used for doping may be an anion for the hole injection layer or a cation for the electron injection layer. Examples of anions include polystyrenesulfonate ion, alkylbenzenesulfonate ions and camphorsulfonate ion. Examples of cations include lithium ion, sodium ion, potassium ion and tetrabutylammonium ion.

The thickness of the charge injection layer will usually be 1 nm to 100 nm and is preferably 2 nm to 50 nm The material used for the charge injection layer may be appropriately selected in consideration of the relationship between the materials of the electrode and the adjacent layer, and examples include conductive polymers, such as polyaniline and its derivatives, polythiophene and its derivatives, polypyrrole and its derivatives, polyphenylenevinylene and its derivatives, polythienylenevinylene and its derivatives, polyquinoline and its derivatives and polyquinoxaline and its derivatives, polymers comprising an aromatic amine structure on the main chain or a side chain, or metal phthalocyanines (copper phthalocyanine or the like), and carbon.

The thickness of the insulating layer will usually be 0.5 to 7.0 nm, and it has the function of facilitating charge injection. The material of the insulating layer may be a metal fluoride, metal oxide, organic insulating material, or the like.

A light emitting device provided with the insulating layer may be a light emitting device with the insulating layer adjacent to the cathode or a light emitting device with the insulating layer adjacent to the anode. Specifically, the following structures q) to ab) may be mentioned as examples.

q) Anode/insulating layer/luminescent layer/cathode
r) Anode/luminescent layer/insulating layer/cathode
s) Anode/insulating layer/luminescent layer/insulating layer/cathode
t) Anode/insulating layer/hole transport layer/luminescent layer/cathode u) Anode/hole transport layer/luminescent layer/insulating layer/cathode
v) Anode/insulating layer/hole transport layer/luminescent layer/insulating layer/cathode
w) Anode/insulating layer/luminescent layer/electron transport layer/cathode
x) Anode/luminescent layer/electron transport layer/insulating layer/cathode
y) Anode/insulating layer/luminescent layer/electron transport layer/insulating layer/cathode
z) Anode/insulating layer/hole transport layer/luminescent layer/electron transport layer/cathode
aa) Anode/hole transport layer/luminescent layer/electron transport layer/insulating layer/cathode
ab) Anode/insulating layer/hole transport layer/luminescent layer/electron transport layer/insulating layer/cathode The light emitting device of this embodiment comprises a polymer compound or composition of this embodiment in any of the layers among the hole injection layer, hole transport layer, luminescent layer, electron transport layer and electron injection layer, in the device structures of a) to ab) listed above. Preferably, the hole injection layer and/or hole transport layer comprises a polymer compound or composition of this embodiment.

The light emitting device of this embodiment is usually formed on a substrate. The substrate may be one that is not altered during formation of electrodes or formation of organic material layers. Examples of substrate materials include glass, plastic, polymer films, silicon and the like. In the case of an opaque substrate, the opposite electrode (that is, the electrode at the far end from the substrate) is preferably transparent or semi-transparent. Either or both the anode and cathode in a light emitting device of this embodiment will usually be transparent or semi-transparent. The anode side is preferably transparent or semi-transparent.

The material of the anode may be a conductive metal oxide film or a semi-transparent metal film. Specifically, there are preferred films (NESA and the like) made using conducting glass composed of indium oxide, zinc oxide, tin oxide or a complex thereof such as indium tin oxide (ITO) or indium/zinc/oxide, or gold, platinum, silver, copper or the like, with ITO, indium/zinc/oxide and tin oxide being preferred. The method of forming the anode may be vacuum vapor deposition, sputtering, ion plating, plating or the like. The anode used may be an organic transparent conductive film made of polyaniline or its derivative or polythiophene or its derivative.

The thickness of the anode can be appropriately adjusted in consideration of light permeability and electric conductivity, and it will usually be 10 nm to 10 µm, preferably 20 nm to 1 µm and more preferably 40 nm to 500 nm.

In order to facilitate charge injection, there may be provided on the anode a layer composed of a phthalocyanine derivative, conductive polymer, carbon or the like, or a layer composed of a metal oxide, metal fluoride, organic insulating material or the like.

The material of the cathode is preferably a material with a low work function. For example, there may be used metals such as lithium, sodium, potassium, rubidium, cesium, beryllium, magnesium, calcium, strontium, barium, aluminum, scandium, vanadium, zinc, yttrium, indium, cerium, samarium, europium, terbium and ytterbium, or alloys of two or more of these metals, or alloys of one or more of these metals with one or more from among gold, silver, platinum, copper, manganese, titanium, cobalt, nickel, tungsten and tin, or graphite or graphite interlaminar compounds or the like. Examples of alloys include magnesium-silver alloys, magnesium-indium alloys, magnesium-aluminum alloys, indium-silver alloys, lithium-aluminum alloys, lithium-magnesium alloys, lithium-indium alloys and calcium-aluminum alloys. The cathode may also consist of a multilayer structure of two or more layers.

The thickness of the cathode can be appropriately adjusted in consideration of electric conductivity and durability, and for example, it will usually be 10 nm to 10 µm, preferably 20 nm to 1 µm and more preferably 50 nm to 500 nm The method used to form the cathode may be vacuum vapor deposition method, sputtering method, or laminating method that employs thermocompression bonding of a metal film. Also, between the cathode and the organic layer there may be provided a layer composed of a conductive polymer, or a layer composed of a metal oxide, metal fluoride or organic insulating material, and a protective layer for protection of the light emitting device may also be formed after formation of the cathode. For prolonged stable use of the light emitting device, a protective layer and/or protective cover is preferably provided to protect the device from the external environment.

A protective layer can be used a polymer compound, metal oxide, metal fluoride, metal boride, metal nitride, organic inorganic hybrid material or the like. The protective cover may be a glass plate, or a plastic sheet that has been subjected to low-permeability treatment on the surface, and there may be employed a method of hermetically attaching the cover to the device board with a thermosetting resin or photocuring resin. A spacer may be used to maintain spacing, thus helping to prevent damage to the device. By filling an inert gas such as nitrogen or argon into the spacing, it is possible to prevent oxidation of the cathode, and setting a desiccant such as barium oxide in the space will help to prevent damage to the device by moisture adsorbed during the production steps. It is preferred to employ any one or more of these strategies.

The light emitting device of this embodiment can be used, for example, for a planar light source such as a curved light source or flat light source (for example, illumination); or for display devices such as segment display devices (for example, segment-type display devices), dot matrix display devices (for example, dot matrix flat displays), and liquid crystal display devices (for example, liquid crystal display devices, liquid crystal display backlights and the like).

A planar anode and cathode may be stacked together in order to obtain planar luminescence using the light emitting device of this embodiment. Luminescence in a pattern form can be obtained by a method in which a mask with a patterned window is set on the front side of the planar light emitting device, a method in which the organic material layer is formed extremely thin at the non-luminous sections to render it essentially non-luminous, and a method in which either of the anode or cathode, or both electrodes, are formed in a pattern shape. By forming a pattern by any of these methods, and configuring some electrodes to be independently ON/OFF switchable, it is possible to obtain a segment type display device allowing display of numerals, letters or simple symbols. Furthermore, for a dot matrix device, the anode and cathode may both be formed as stripes and configured in a crossing manner. A partial color display or multicolor display can also be formed by a method in which different types of polymer fluorescent materials with different luminescent colors are coated or a method using a color filter or fluorescence conversion filter. The dot matrix device may be passively driven or actively driven in combination with a TFT or the like. These display devices can be used as display devices for computers, televisions, portable terminals, cellular phones, car navigation systems, video camera viewfinders, and the like.

A planar light emitting device is a self-luminous thin type, and can therefore also be suitably used as a backlight planar light source for a liquid crystal display device, or a planar illumination light source. Using a flexible substrate will allow its use as a curved light source or display device.

EXAMPLES

Examples will now be explained for more detailed explanation of the invention, with the understanding that the invention is not limited by the examples.
[Measuring Methods]
In the following synthesis examples and examples, measurement of the number-average molecular weight and weight-average molecular weight, and the high-performance liquid chromatography (HPLC), NMR, LC-MS, TLC-MS measurements and measurement of the polymer compound energy gaps, were conducted by the following methods.

For the number-average molecular weight (Mn) and weight-average molecular weight (Mw), analysis was performed by gel permeation chromatography (GPC), and the number-average molecular weight (Mn) and weight-average molecular weight (Mw) were calculated from the analysis results based on polystyrene.
<Analysis Conditions>
Measuring apparatus: HLC-8320GPC (product of Tosoh Corp.)
Column: PLgel MIXED-B (product of Polymer Laboratories, Ltd.).
Column temperature: 40° C.
Moving bed: Tetrahydrofuran
Flow rate: 2.0 mL/min
Detection wavelength: 228 nm
(High-Performance Liquid Chromatography (HPLC))
The HPLC-area percent value was used as an index of compound purity.

The compound to be measured was dissolved in tetrahydrofuran or chloroform to a concentration of 0.01 to 0.2 wt %, and 1 to 10 μL, depending on the concentration, was injected for HPLC.
<Analysis Conditions 1>
Measuring apparatus: LC-20A (product of Shimadzu Corp.)
Column: Kaseisorb LC ODS 2000 (product of Tokyo Kasei Kogyo Co., Ltd.), or a column with equivalent performance
Detector: SPD-M20A (product of Shimadzu Corp.)
Detection wavelength: 254 nm
Using acetonitrile and tetrahydrofuran as the mobile phase for HPLC, gradient analysis was performed with acetonitrile/tetrahydrofuran=100/0 to 0/100 (volume ratio), at a flow rate of 1 mL/min.
<Analysis Conditions 2>
Measuring apparatus: Apparatus having equivalent performance as for analysis conditions 1
Column: Ascentis Express C18, or a column having equivalent performance
Detector: Apparatus having equivalent performance as for analysis conditions 1
Detection wavelength: Wavelength allowing measurement of target compound and impurities
Using water and tetrahydrofuran as the mobile phase for HPLC, gradient analysis was performed with water/tetrahydrofuran=100/0 to 0/100 (volume ratio), at a flow rate of 1 mL/min NMR measurement was conducted with a sample comprising 5 to 20 mg of measuring sample dissolved in approximately 0.5 mL of organic solvent. The measuring frequencies are listed in the measurement data. For 300 MHz, measurement was carried out using NMR (trade name: INOVA300, product of Varian, Inc.).

The LC-MS measurement was conducted by the following method. The measuring sample was dissolved in an appropriate organic solvent (chloroform, tetrahydrofuran, ethyl acetate, toluene or the like) to a concentration of 1 to 10 mg/mL, and measurement and analysis were performed by LC-MS. The mobile phase used for LC-MS was ion-exchanged water, acetonitrile, tetrahydrofuran or a liquid mixture thereof, with addition of acetic acid when necessary.
<Analysis Conditions 1>
Measuring apparatus: 1100LCMSD (product of Agilent Technologies)
Column: L-column 2 ODS (3 μm) (product of Chemicals Evaluation and Research Institute, Japan, inner diameter: 4.6 mm, length: 250 mm, particle diameter: 3 μm)<
Analysis Conditions 2>
Measuring apparatus: Apparatus having equivalent performance as for analysis conditions 1
Column: Zorbax Extend C18 (inner diameter: 4.6 mm, length: 50 mm, particle diameter: 5 μm)

TLC-MS measurement was conducted by the following method. The measuring sample was dissolved in an appropriate organic solvent (chloroform, tetrahydrofuran, ethyl acetate, toluene or the like) to a concentration of 1 to 10 mg/mL, the sample solution was set on a glass plate, and measurement and analysis were performed by TLC-MS.
Measuring apparatus: Accu TOF TLC (product of JEOL Corp.)
(Polymer Compound Energy Gap Measuring Method and Calculation Method)

An organic film comprising a polymer compound was fabricated by spin coating a 0.8 wt % xylene solution of the polymer compound on a quartz plate. The organic film was used as the measuring sample, and the absorption spectrum of the polymer compound was measured with an ultraviolet/visible spectrophotometer (product name: Cary5E by Varian Co.).

The obtained absorption edge wavelength and the following calculation formula (E) were used to calculate the energy gap of the polymer compound.

$$\text{Energy gap(eV)}=1239/\text{absorption edge wavelength(nm)} \quad \text{Calculation formula (E)}$$

Synthesis Example 1: Synthesis of Monomer CM1, Monomers CM3 to CM17 and Monomers CM22 to CM24

CM1 was synthesized by the synthesis method described in Japanese Unexamined Patent Application Publication No. 2010-189630.
CM2 was synthesized by the method described below.
CM3 was synthesized by the synthesis method described in Japanese Unexamined Patent Application Publication No. 2010-189630.
CM4 was synthesized by the synthesis method described in Japanese Unexamined Patent Application Publication No. 2010-189630.
CM5 was synthesized by the synthesis method described in Japanese Unexamined Patent Application Publication No. 2011-174061.

CM6 was synthesized by the synthesis method described in WO2002/045184.
CM7 was synthesized by the synthesis method described in WO2009/131255.
CM8 was synthesized by the synthesis method described in WO2002/045184.
CM9 was synthesized by the synthesis method described in WO2009/131255.
CM10 was synthesized by the synthesis method described in WO2005/049546.
CM11 was synthesized by the synthesis method described in WO2011/049241.
CM12 was synthesized by the synthesis method described in Japanese Unexamined Patent Application Publication No. 2009-052032.
CM13 was synthesized by the synthesis method described in WO2009/110642.
CM14 was synthesized by the synthesis method described in WO2002/045184.
CM15 was synthesized by the synthesis method described in Japanese Unexamined Patent Application Publication No. 2006-169265.
CM16 was synthesized by the synthesis method described in Japanese Unexamined Patent Application Publication No. 2006-169265.
CM17 was synthesized by the synthesis method described in Japanese Unexamined Patent Application Publication No. 2010-189630.
CM18 was synthesized by the method described below.
CM19 was synthesized by the method described below.
CM20 was synthesized by the method described below.
CM21 was synthesized by the method described below.
CM22 was synthesized by the synthesis method described in Japanese Unexamined Patent Application Publication No. 2008-106241.
CM23 was synthesized by the synthesis method described in Japanese Unexamined Patent Application Publication No. 2010-215886.
CM24 was synthesized by the synthesis method described in Japanese Unexamined Patent Application Publication No. 2010-215886.
CM25 was synthesized by the method described below.
CM26 was synthesized by the method described below.
CM27 was synthesized by the method described below.
CM28 was synthesized by the method described below.

[Chemical Formula 150]

CM1
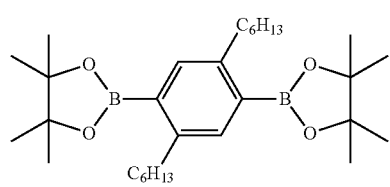

CM2
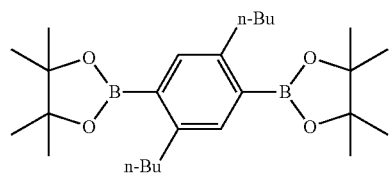

CM3
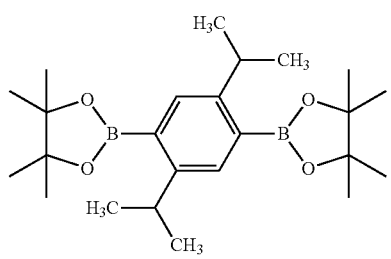

CM4
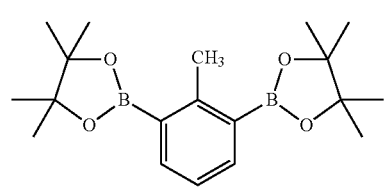

CM5
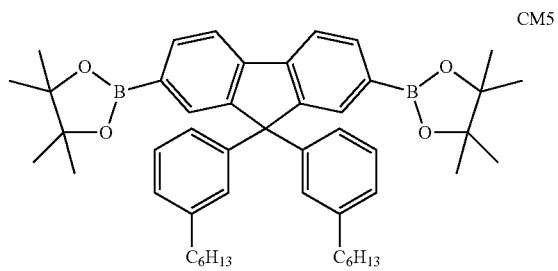

CM6
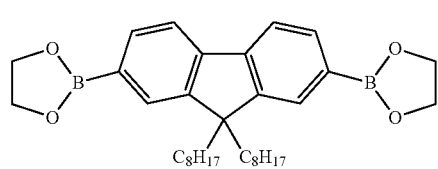

CM7
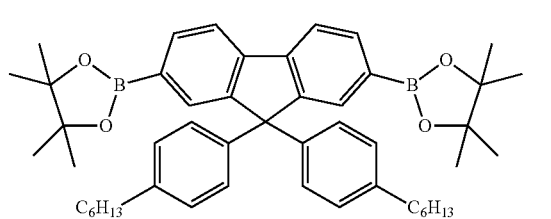

CM8
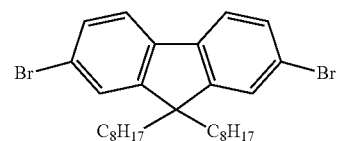

CM9
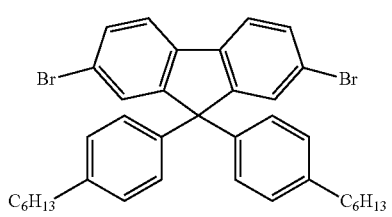

[Chemical Formula 151]
CM10
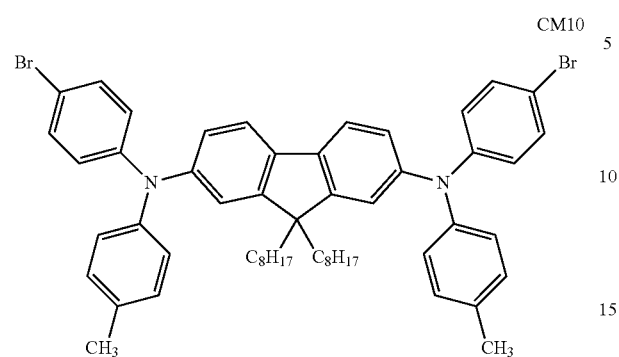
CM11
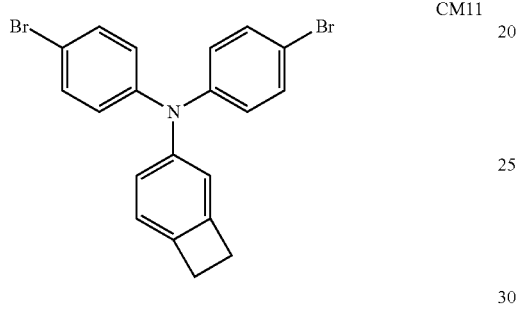
CM12
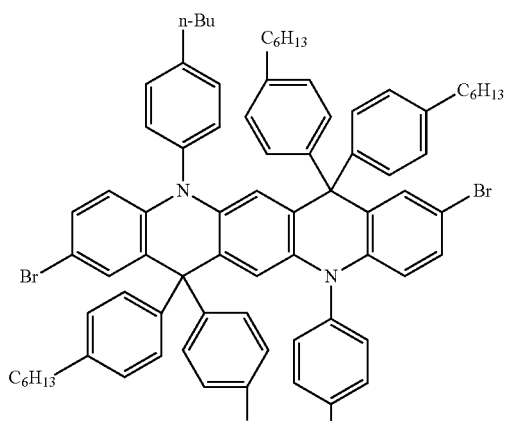
CM13
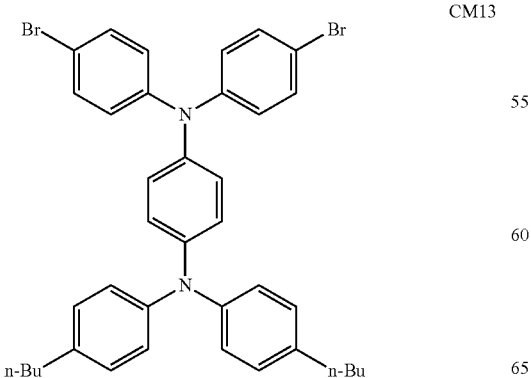
CM14
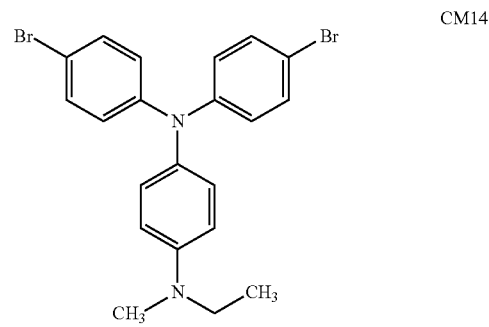
CM15
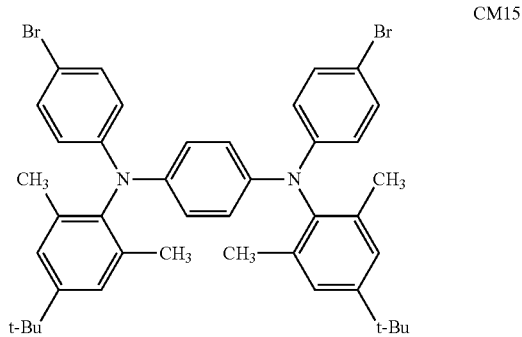
CM16
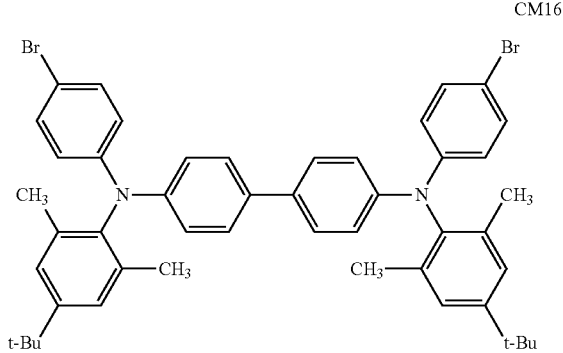
CM17
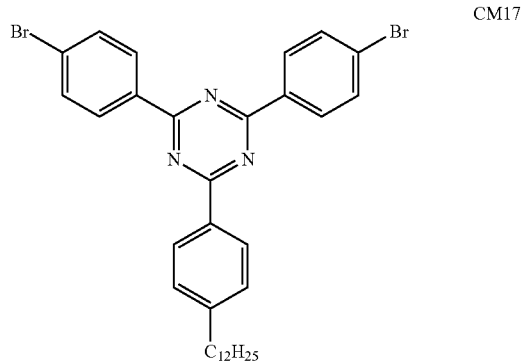

-continued
[Chemical Formula 152]
CM18
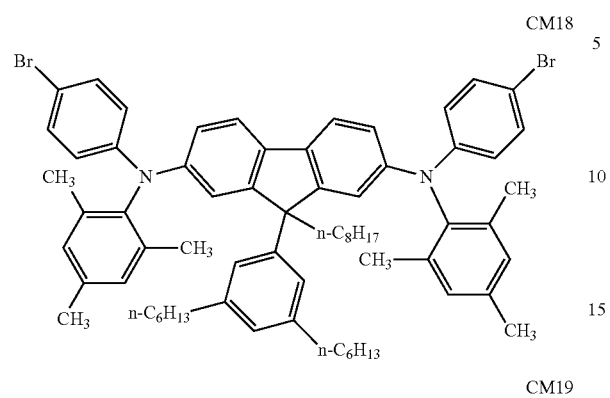
CM19
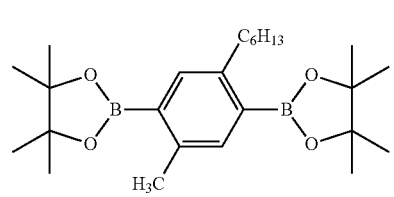
CM20
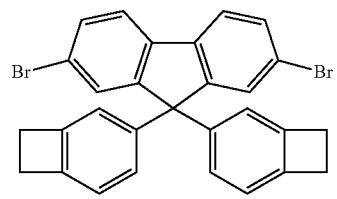
CM21
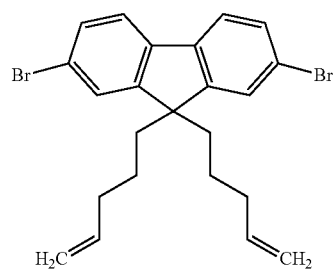
CM22
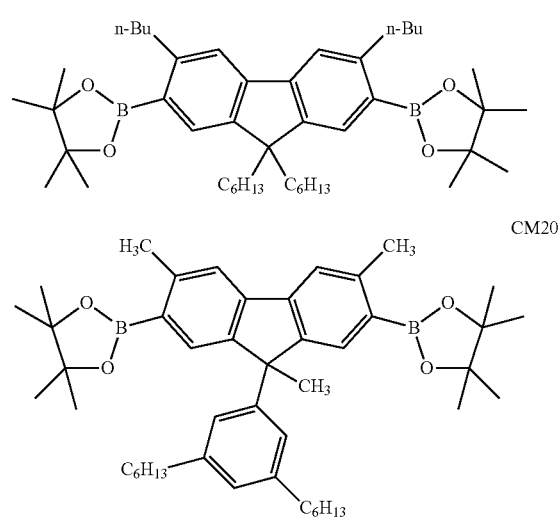
CM23
-continued
CM24
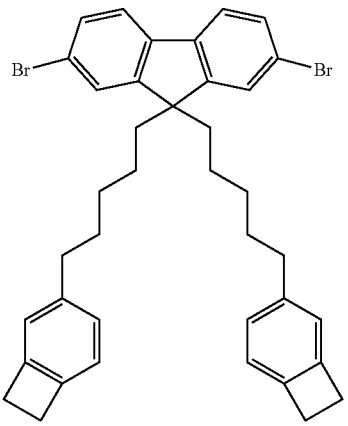
[Chemical Formula 153]
CM25
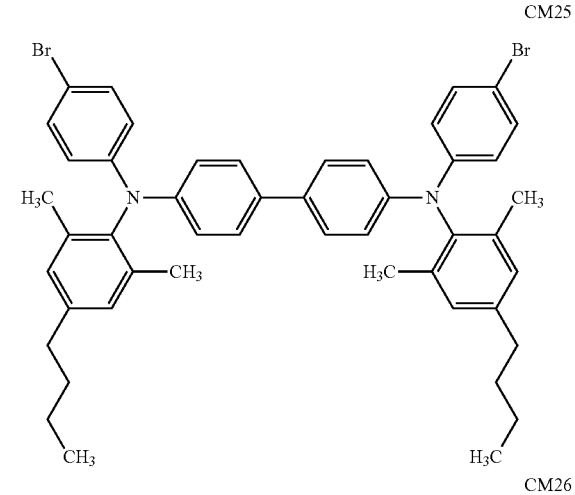
CM26
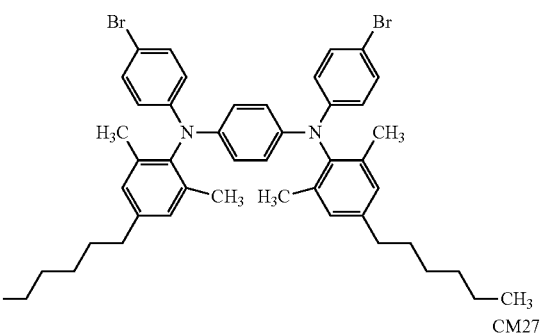
CM27
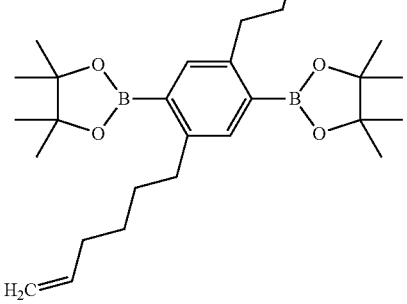

CM28

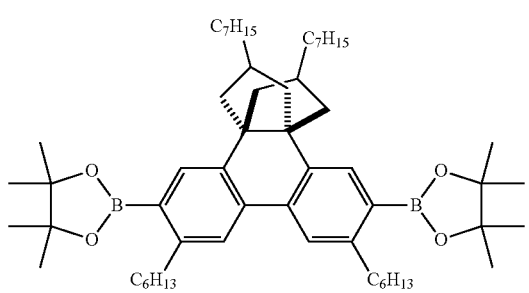

Synthesis Example 2: Synthesis of Monomer CM2

After shielding a four-necked flask equipped with a dropping funnel and exchanging the flask interior with argon gas, 1,4-dibutylbenzene (100 g, 0.53 mol), iron powder (2.9 g, 0.053 mol), CHCl$_3$ (140 mL) and trifluoroacetic acid (hereunder also referred to as "TFA") (4 mL) were added. Next, a solution of bromine (185 g, 1.16 mol) dissolved in CHCl$_3$ (330 mL) was added dropwise through the dropping funnel while cooling the flask in an ice bath. Upon completion of the dropwise addition, the mixture was stirred for 4 hours under conditions of shielding in an ice bath. The reaction solution was then rinsed with a 2M potassium hydroxide aqueous solution (250 mL), and repeatedly rinsed with ion-exchanged water (250 mL) until the aqueous layer reached colorless transparency. After drying the organic layer over Na$_2$SO$_4$, the solvent was distilled off under reduced pressure to obtain an orange liquid. The liquid was dissolved in hexane (500 mL), and after adding active carbon (15 g) and stirring, it was subjected to diatomaceous earth filtration and the solvent was distilled off under reduced pressure. The obtained residue was recrystallized 3 times with ethanol (100 mL) to obtain 120 g of a slightly yellow-tinged white powder CM2a (yield: 94%).

$^1$HNMR (300 MHz, CDCl$_3$): δ (ppm)=7.35 (s, 2H), 2.64 (t, J=8.0 Hz, 4H), 1.61-1.51 (m, 4H), 1.42-1.35 (m, 4H), 0.94 (t, J=7.4 Hz, 6H).

$^{13}$CNMR (75.5 MHz, CDCl$_3$): δ (ppm)=141.56, 134.05, 123.35, 35.52, 32.24, 22.73, 14.21.

LC-MS measured under analysis conditions 1 (APPI, positive): m/z$^+$=346 ([M]$^+$).

[Chemical Formula 154]

CM2a

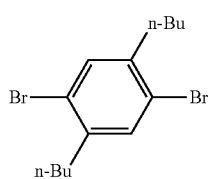

In a separable flask there were added CM2a (100 g, 288 mmol), bispinacolatodiboron (168 g, 660 mmol), potassium acetate (170 g, 1724 mmol) and dehydrated dioxane (1340 mL), and the mixture was bubbled with argon gas for 30 minutes. Next, PdCl$_2$(dppf)$_2$·CH$_2$Cl$_2$ (14.12 g, 17.28 mmol) was added, the mixture was heated and stirred at 110° C. for 12 hours, and the solvent was distilled off under reduced pressure. The residue was dispersed in toluene (1.5 L) and Celite was used for filtration. The filtrate was repeatedly rinsed with ion-exchanged water (1.5 L). The organic layer was dehydrated with Na$_2$SO$_4$ and the solvent was distilled off under reduced pressure to obtain 185 g of a dark red tar-like product. The product was dissolved in toluene (2 L), 200 g of active carbon was added and the mixture was heated and stirred at 80° C. for 2 hours, and then Celite was used for hot filtration and the solvent was distilled off under reduced pressure. The residue was subjected to repeated recrystallization in the order: hexane (150 mL), ethanol (800 mL), ethanol (550 mL), and the obtained white crystals were dried under reduced pressure to obtain 80 g of the target monomer CM2 (yield: 63%).

$^1$HNMR (300 MHz, CDCl$_3$): δ (ppm)=7.53 (s, 2H), 2.82 (t, J=7.9 Hz, 4H), 1.59-1.33 (m, 32H (4H+4H+24H)), 0.92 (t, J=7.2 Hz, 6H).

$^{13}$CNMR (75.5 MHz, CDCl$_3$): δ (ppm)=146.09, 136.47, 83.26, 35.97, 35.19, 24.83, 23.00, 14.02.

TLC-MS (DART, positive): m/z$^+$=440 ([M]$^+$), 441 ([M+H]$^+$).

Synthesis Example 3: Synthesis of Monomer CM18

Monomer CM18 was synthesized by the following step 1 to step 6.

[Chemical Formula 155]

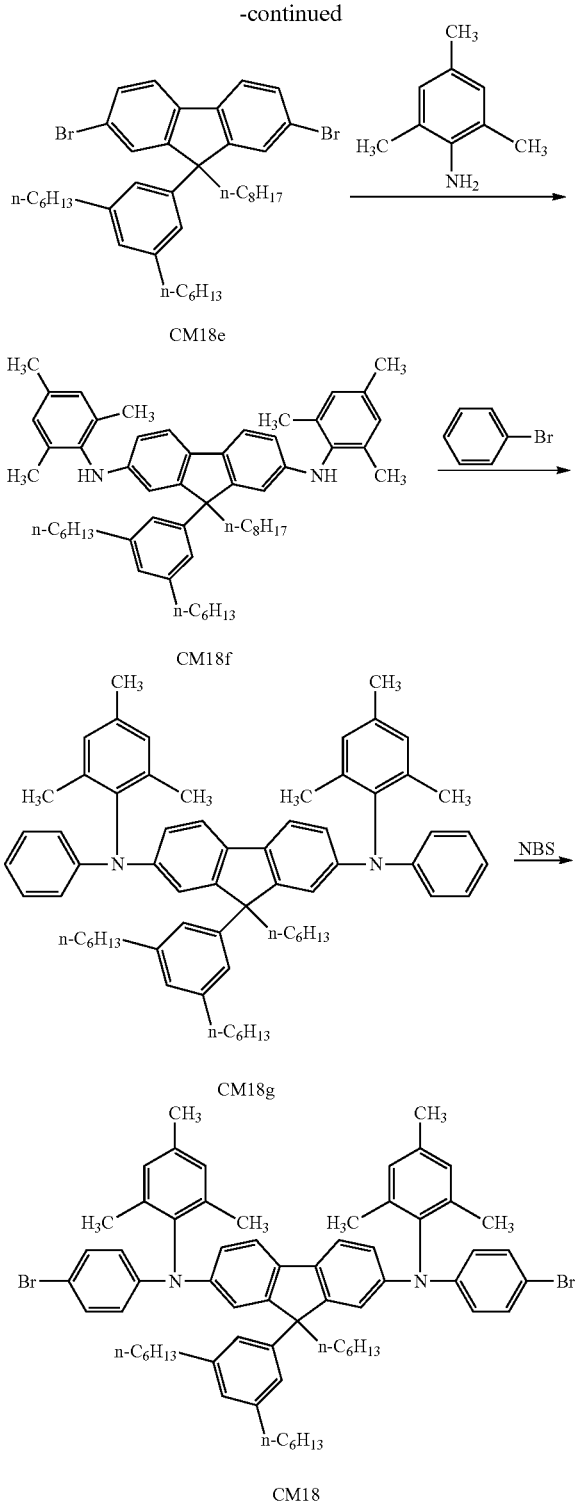

<Step 1: Synthesis of Compound CM18c>

To a solution comprising 1-bromo-3,5-di-n-hexylbenzene (compound CM18a, 650 g) and tetrahydrofuran (6.5 L) there was added dropwise over a period of 1 hour n-butyllithium (1.6 M hexane solution, 1237 mL) at −75 to −70° C. under a nitrogen gas atmosphere, and the mixture was further stirred for 4 hours at the same temperature. Next, 2,7-dibromofluorenone (compound CM18b, 613 g) was added over a period of 1 hour at −75 to −70° C., and the temperature of the reaction mixture temperature was raised to room temperature while stirring. Next, 2M hydrochloric acid (982 mL) was added to adjust the pH of the reaction mixture to 7. The tetrahydrofuran was removed under reduced pressure, n-hexane was added to the remaining mixture and the oil layer obtained upon stirring and liquid separation was rinsed with water. Anhydrous sodium sulfate was added to the oil layer, the mixture was stirred and filtered, and then the filtrate was concentrated under reduced pressure to remove the solvent and obtain an oil. The oil was recrystallized from n-hexane to obtain the target compound CM18c (674 g).

<Step 2: Synthesis of Compound CM18d>

To compound CM18c (674 g) there was added n-hexane (1215 mL) under a nitrogen gas atmosphere, trifluoroacetic acid (877 mL) was added while stirring at 10° C., and then a solution comprising triethylsilane (147 g) and n-hexane (300 mL) was added dropwise at 10° C. to 15° C. The reaction mixture was then stirred overnight at room temperature. Next, water (1200 mL) was slowly added to the obtained reaction mixture at 10° C., and the solvent was removed by concentration under reduced pressure. After adding n-hexane to the obtained mixture and stirring, the aqueous layer formed after standing was separated from the oil layer. To the obtained oil layer there was added a 10% potassium phosphate aqueous solution (5 L), the mixture was stirred for 2 hours, and the aqueous layer formed after standing was separated from the oil layer. After rinsing the oil layer with water, anhydrous sodium sulfate was added, the mixture was stirred and filtered and the filtrate was concentrated under reduced pressure to remove the solvent and obtain an oil. The oil was dissolved in dichloromethane (610 mL) to prepare a solution which was then added to stirred methanol (8.5 L) over a period of 1 hour, and the mixture was stirred for 3 hours and the deposited crystals were filtered out and dried under reduced pressure to obtain 538 g of the target compound CM18d.

<Step 3: Synthesis of Compound CM18e>

To a mixture of compound CM18d (25 g), 1-bromooctane (12.9 g) and tetraethylammonium chloride (Aliquat336™ by Aldrich) there was slowly added a 26.7 wt % potassium hydroxide aqueous solution at 85° C. while stirring under a nitrogen gas atmosphere, and stirring was continued for 20 hours at the same temperature. To the obtained reaction mixture there were added water (120 mL) and dichloromethane (250 mL) at room temperature, the mixture was stirred, and the aqueous layer formed after standing was removed from the oil layer. Anhydrous sodium sulfate was added to the oil layer, and the filtrate obtained by stirring and filtering the mixture was concentrated under reduced pressure to remove the solvent and obtain an oil. Dichloromethane and methanol were added to the oil, and recrystallization was performed to obtain a white solid. The solid was recrystallized from isopropyl alcohol to obtain 22 g of the target compound CM18e.

<Step 4: Synthesis of Compound CM18f>

Compound CM18e (125 g), 2,4,6-trimethylaniline (54.63 g), toluene (1.7 L), [tris(dibenzylideneacetone)]dipalladium (0.84 g), tri-tert-butylphosphine tetrafluoroborate (t-Bu₃P.BF₄H, 0.400 g) and sodium tert-butoxide (53 g) were stirred for 16 hours under a nitrogen gas atmosphere. Next, water (400 mL) was added at room temperature, the mixture was stirred, and the aqueous layer formed after standing was removed from the oil layer. The oil layer was concentrated under reduced pressure to remove the solvent and obtain an oil. The oil was dissolved in toluene (500 mL) to prepare a solution, and the solution was passed through a filter packed with Celite and a filter packed with silica gel, in that order. The obtained filtrate was concentrated under reduced pressure to remove the solvent and obtain an oil. Isopropyl alcohol and dichloromethane were added to the oil and the mixture was allowed to stand, and the deposited crystals were filtered to obtain a yellow solid. The solid was recrystallized with isopropyl alcohol and toluene to obtain 94 g of the target compound CM18f.

<Step 5: Synthesis of Compound CM18g>

Compound CM18f (94.2 g), bromobenzene (32 mL), toluene (1.4 L), [tris(dibenzylideneacetone)]dipalladium (1.09 g), tri-tert-butylphosphine tetrafluoroborate (t-Bu₃P.BF₄H, 0.69 g) and sodium tert-butoxide (34.4 g) were stirred overnight under reflux under a nitrogen gas atmosphere. Next, water (300 mL) was added at room temperature, the mixture was stirred, and the aqueous layer formed after standing was removed from the oil layer. The oil layer was concentrated under reduced pressure to remove the solvent and obtain an oil. The oil was dissolved in toluene (200 mL) to prepare a solution, and the solution was passed through a filter packed with Celite and a filter packed with silica gel, in that order. The obtained filtrate was concentrated under reduced pressure to remove the solvent and obtain an oil. Isopropyl alcohol and methanol were added to the oil, the mixture was stirred and allowed to stand, the separated supernatant was removed, and the solvent was removed from the obtained oil under reduced pressure to obtain 82 g of the target compound CM18g.

<Step 6: Synthesis of Monomer CM18>

A solution comprising N-bromosuccinimide (NBS, 21.2 g) and N,N-dimethylformamide (550 mL) was added dropwise to a solution comprising compound CM18g (55.8 g) and chloroform (550 mL) while stirring at −15° C., and stirring was continued for 3 hours at the same temperature. Next, methanol (400 mL) was added at room temperature and stirred therewith, water (400 mL) was added and stirred therewith, and the mixture was concentrated under reduced pressure to remove the solvents. The obtained mixture was allowed to stand, and then the supernatant was removed to obtain a brown solid. Dichloromethane (500 mL) was added to the solid to dissolution, water was added and stirred therewith, and the aqueous layer formed after standing was removed from the oil layer. Next, 10% aqueous sodium carbonate was added and stirred therewith, and the aqueous layer formed after standing was removed from the oil layer. Next, water was added and stirred therewith, and the aqueous layer formed after standing was removed from the oil layer. The solvent was removed from the obtained oil layer under reduced pressure and a brown oil was obtained. The brown oil was subjected to column chromatography using Celite and silica gel, and the solvent was removed to obtain a transparent oil. Isopropyl alcohol and toluene were added to the transparent oil and stirred therewith, and after allowing the mixture to stand, the supernatant was removed to obtain a highly viscous solid. Next, methanol was added to the solid and vigorously stirred therewith, and the obtained solid was filtered. Methanol and n-butyl acetate were then used for recrystallization to obtain 40.6 g of the target monomer CM18.

Synthesis Example 4: Synthesis of Monomer CM19

Monomer CM19 was synthesized by the following step 1 to step 7.

[Chemical Formula 156]

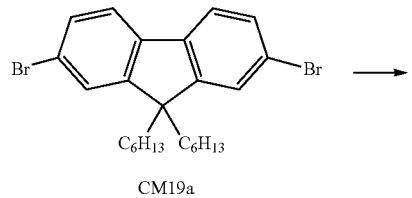

CM19a

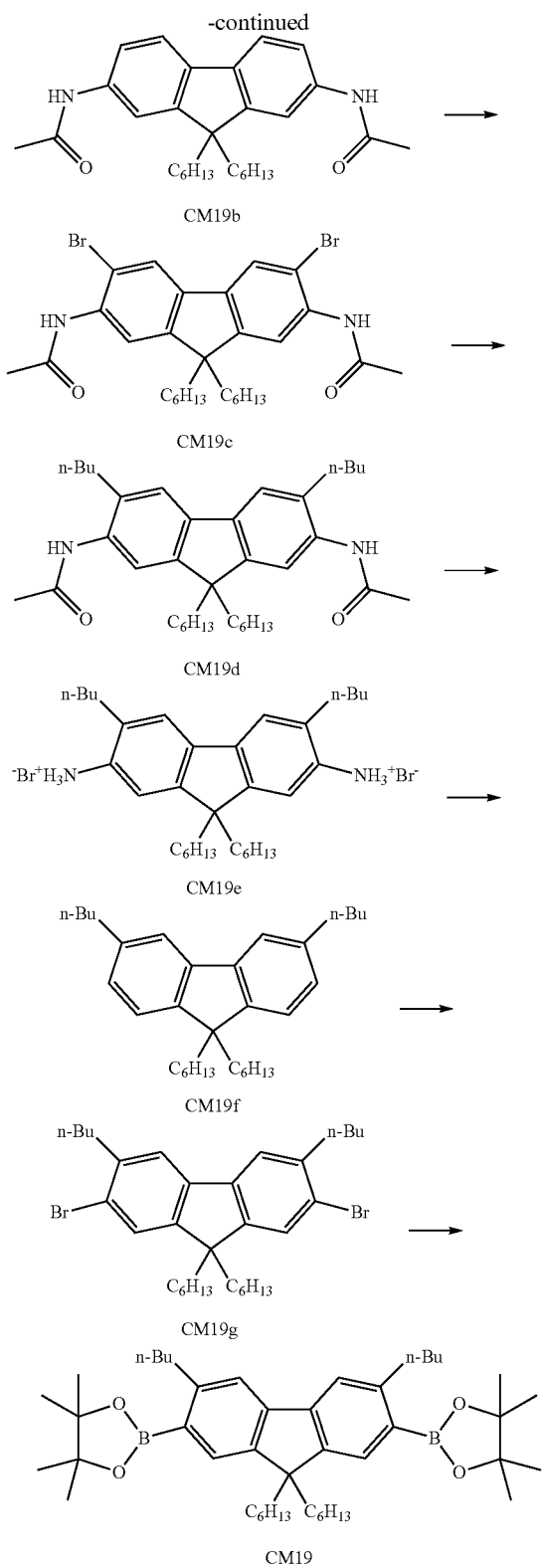

<Step 1>

To a reactor there were added acetamide (59.1 g, 1.00 mol), tris(dibenzylideneacetone)dipalladium(0) (3.66 g, 4 mmol), 4,5-bis(diphenylphosphino)-9,9-dimethylxanthene (common name: Xantphos, 6.94 g, 12 mmol), cesium carbonate (391 g, 1.20 mol), 1,4-dioxane (800 ml) and ion-exchanged water (7.2 ml), and the mixture was bubbled with argon gas to replace the reactor interior with an argon gas atmosphere. After heating to 100° C., a solution of 9,9-dihexyl-2,7-dibromofluorene (compound CM19a above, 98.5 g, 200 mmol) in 1,4-dioxane (300 ml) was slowly added over a period of about 0.5 hour, and the mixture was then stirred for 4 hours at the same temperature. The obtained reaction mixture was passed through a silica gel pad, and after concentrating the obtained filtrate it was slowly added to ion-exchanged water and stirred therewith, and the solid precipitated by stirring was filtered out, rinsed with ion-exchanged water and dried under reduced pressure to obtain 94.5 g of solid. The obtained solid was recrystallized using ethanol/ion-exchanged water and then further recrystallized twice with chloroform-hexane, active carbon was added while dissolved in ethanol, the mixture was heated to reflux, and then the active carbon was filtered out by Celite filtration. Next, a procedure of concentrating the filtrate and adding hexane to precipitate a solid was carried out for purification. The obtained solid was filtered and dried under reduced pressure to obtain the target compound CM19b (52.8 g) as a flesh-colored solid. Yield: 58.9%. The HPLC-area percent value of the obtained compound CM19b measured under analysis conditions 1 was 97.6%.

$^1$H-NMR (300 MHz, THF-$d_8$) δ (ppm)=9.05 (s, 2H), 7.69 (s, 2H), 7.51 (t, 4H), 2.06 (s, 6H), 1.95 (m, 4H), 1.10 (m, 12H), 0.78 (t, 6H), 0.66 (m, 4H).

$^{13}$C-NMR (75 MHz, THF-$d_8$) δ (ppm)=169.1, 152.9, 140.8, 138.3, 120.9, 119.6, 115.3, 56.9, 42.7, 33.7, 31.9, 25.8, 25.3, 24.6, 15.5.

<Step 2>

Compound CM19b (43.1 g, 96 mmol), calcium carbonate (11.5 g, 115 mmol), chloroform (384 ml) and methanol (384 ml) were mixed and the mixture was bubbled with nitrogen gas to replace the system interior with a nitrogen gas atmosphere. Benzyltrimethylammonium tribromide (89.84 g, 230 mmol) was slowly added in small portions at a time over a period of 1 hour while stirring the mixture while it was shielded from light. It was then stirred at room temperature for 17 hours, and subsequently stirred for 2 hours while heating to 50° C., again stirred at room temperature for 23 hours, and subsequently stirred at 50° C. for 9 hours. After cooling to room temperature, the impurities were removed by filtration, and then a 10 wt % sodium sulfite aqueous solution (384 ml) was added and the mixture was stirred for 1 hour, the aqueous layer was removed by liquid separation, and the obtained oil layer was rinsed with a 5 wt % sodium hydrogencarbonate aqueous solution (384 ml), ion-exchanged water (384 ml) and 15 wt % brine (384 ml) in that order, and concentrated under reduced pressure to obtain approximately 80 g of a solid. The obtained solid was dissolved in ethyl acetate (400 ml) at room temperature, and then silica gel (40 g) was added and the mixture was stirred for 30 minutes, after which the silica gel was removed by filtration and the obtained filtrate was concentrated. After heating and dissolution in ethyl acetate (80 ml) and dropwise addition of hexane (320 ml), the mixture was cooled to room temperature and the precipitated solid was filtered out. After further heating and dissolution of the obtained solid in ethyl acetate (68 ml) and dropwise addition of hexane (280 ml), the mixture was cooled to room temperature and the precipitated solid was filtered out. The obtained solid was dried under reduced pressure to obtain the target compound CM19c (39.0 g) as a faint yellow solid. Yield: 67.0%. The HPLC-area percent value of the obtained compound measured under analysis conditions 1 was 98.5%. After combining the recrystallization filtrates and concentrating, purification was carried out by recrystallization under the same conditions, and the obtained crystals were filtered and dried under reduced pressure to recover compound CM19c (7.56 g). Yield: 13.0%. The HPLC-area percent value of the obtained compound CM19c measured under analysis conditions 1 was 96.6%. The total yield was 80.0%.

$^1$H-NMR (300 MHz, THF-$d_8$) δ (ppm)=8.36 (s, 2H), 8.26 (s, 2H), 7.96 (s, 2H), 2.16 (s, 6H), 1.98 (m, 4H), 1.11 (m, 12H), 0.79 (t, 6H), 0.68 (m, 4H).

$^{13}$C-NMR (75 MHz, THF-$d_8$) δ (ppm)=169.5, 152.8, 139.1, 137.8, 125.5, 120.0, 114.8, 57.3, 41.9, 33.5, 31.7, 25.8, 25.2, 24.6, 15.5.

<Step 3>

After mixing compound CM19c (42.5 g, 70 mmol), butylboronic acid (28.5 g, 280 mmol), palladium acetate (157 mg, 0.70 mmol), tri-tert-butylphosphine tetrafluoroborate salt (204 mg, 0.70 mmol), anhydrous potassium carbonate (58.1 g, 420 mmol) and commercially available dehydrated toluene (700 ml), the mixture was bubbled with argon gas to exchange the system with an inert gas. It was then heated in an oil bath and stirred for 19 hours under reflux. Upon confirming progress of the reaction by HPLC, dilution was performed with toluene (350 ml) and ethyl acetate (350 ml) and the dilution was cooled to room temperature, after which it was passed through Celite filtration and a silica gel pad, to remove the insolubles and highly polar impurities. After concentrating the obtained solution, ethyl acetate was used for recrystallizing purification and the obtained crystals were filtered and dried under reduced pressure to obtain the target compound CM19d (19.3 g) as a white solid. The HPLC-area percent value of the obtained compound was 99.2% (UV254 nm) Yield: 49.1%. The target component was extracted with chloroform from the residues of the Celite and silica gel that were used, and was purified by the same procedure as above to recover compound CM19d (8.7 g) as a white solid. The HPLC-area percent value of the obtained compound CM19d measured under analysis conditions 1 was 99.3% (UV254 nm) Yield: 22.1%. This produced a total amount of 28.0 g, with a 71.2% yield.

$^1$H-NMR (300 MHz, THF-$d_8$) δ (ppm)=8.30 (s, 2H), 7.66 (s, 2H), 7.49 (s, 2H), 2.66 (t, 4H), 2.07 (s, 6H), 1.93 (m, 4H), 1.67 (m, 4H), 1.44 (m, 4H), 1.15 (m, 12H), 0.99 (t, 6H), 0.79 (t, 6H), 0.73 (m, 4H).

$^{13}$C-NMR (75 MHz, THF-$d_8$) δ (ppm)=169.1, 150.7, 139.9, 137.3, 135.6, 121.5, 121.3, 56.5, 42.3, 34.3, 33.6, 33.2, 31.9, 26.7, 25.9, 24.8, 24.6, 15.6, 15.5.

<Step 4>

After dissolving compound CM19d (28.0 g, 50 mmol) in 2-propanol (500 ml) at room temperature, a 48 wt % concentration HBr aqueous solution (569 ml) and ion-exchanged water (50 ml) were added and the mixture was stirred for 33 hours under heated reflux. The flask contents during this time were in a white slurry form. Upon completion of the reaction, the product was cooled to room temperature and the precipitated solid was filtered out and rinsed twice with ion-exchanged water (250 ml). After then drying under reduced pressure for 5 hours at room temperature, it was further dried under reduced pressure at 50° C. overnight to obtain the target compound CM19e (26.3 g) as a white solid. Yield: 82.2%. The HPLC-area percent value of the obtained compound CM19e measured under analysis conditions 1 was 92.7%.

$^1$H-NMR (300 MHz, Methanol-$d_4$) δ (ppm)=7.93 (s, 2H), 7.44 (s, 2H), 4.91 (s, 6H), 2.85 (t, 4H), 2.09 (m, 4H), 1.80 (m, 4H), 1.56 (m, 4H), 1.07 (m, 18H), 0.77 (t, 6H), 0.59 (m, 4H).

$^{13}$C-NMR (75 MHz, Methanol-d$_4$) δ (ppm)=152.4, 143.0, 137.8, 130.6, 124.1, 119.9, 57.3, 42.0, 34.2, 33.5, 32.2, 31.4, 25.83, 24.7, 24.3, 15.2, 15.1.

<Step 5>

Compound CM19e (12.8 g, 20 mmol), commercially available dehydrated tetrahydrofuran (1000 ml), commercially available dehydrated ethanol (200 ml) and a 48 wt % concentration HBr aqueous solution (60 ml) were added in that order. The solution at this point had a faint yellow transparent appearance. After cooling to an internal temperature of 1° C. with an ice bath, a solution of tert-butyl nitrite (tert-BuONO, 90% content, 4.82 g, 42 mmol) diluted with commercially available dehydrated tetrahydrofuran (252 ml) was added dropwise over a period of 30 minutes. After stirring for an additional 30 minutes while in the ice bath, a 50 wt % diphosphorous acid aqueous solution (H$_3$PO$_2$, 200 ml) was added dropwise over a period of 1 hour. Upon completion of the dropwise addition, the mixture was stirred for 5 hours while in the ice bath and was allowed to stand overnight at room temperature. Ion-exchanged water was added to the obtained reaction solution, extraction was performed 3 times with ethyl acetate and then the obtained organic layers were combined and rinsed with a 5 wt % sodium hydrogencarbonate aqueous solution, ion-exchanged water and 15 wt % brine and dried over anhydrous magnesium sulfate, the impurities were filtered out and the filtrate was concentrated to obtain 10.8 g of a black amber-like substance.

After combining 7.98 g of a black amber-like substance obtained from compound CM19e (9.58 g) by the same procedure as above, it was purified by medium pressure silica gel chromatography (φ6×30 cm, hexane), the fractions containing the target substance were combined, active white clay (31 g) was added and the mixture was stirred for 1 hour at room temperature, after which the solid was filtered out and the filtrate was concentrated to obtain the target compound CM19f (10.72 g) as a yellow oil. Yield: 68.6%. The HPLC-area percent value of the obtained compound CM19f measured under analysis conditions 1 was 95.1%.

$^1$H-NMR (300 MHz, CDCl$_3$) δ (ppm)=7.49 (s, 2H), 7.20 (d, 2H), 7.08 (d, 2H), 2.68 (t, 4H), 1.89 (m, 4H), 1.67 (m, 4H), 1.40 (m, 4H), 1.04 (m, 12H), 0.95 (t, 6H), 0.76 (t, 6H), 0.66 (m, 4H).

$^{13}$C-NMR (75 MHz, CDCl$_3$) δ (ppm)=148.8, 141.56, 141.52, 127.4, 122.9, 119.7, 54.6, 40.7, 36.2, 34.3, 31.9, 30.2, 24.2, 23.0, 22.9, 14.40, 14.36.

<Step 6>

Compound CM19f (10.1 g, 23 mmol) and chloroform (345 ml) were added and the mixture was bubbled with argon gas, and then N-bromosuccinimide (12.31 g, 69 mmol) was added at room temperature under light-shielded conditions and the mixture was stirred for 10 minutes at room temperature. After cooling to 0° C. in an ice bath, trifluoroacetic acid (85 ml) was added dropwise over a period of 30 minutes. Upon completion of the dropwise addition, the ice bath was removed and the mixture was stirred for 1.5 hours at room temperature. It was then transferred to a different container, methanol (1700 ml) was added and the mixture was stirred for 1 hour at room temperature. The precipitated solid was filtered out, rinsed with methanol and dried under reduced pressure to obtain 11.1 g of a white solid. It was then purified by medium pressure silica gel chromatography (φ5×30 cm, hexane), the fractions containing the target substance were combined, concentrated and dissolved in hexane (232 ml), and then active white clay (23 g) was added and the mixture was stirred for 1 hour at room temperature. The solid was then filtered, and the filtrate was concentrated and then recrystallized from ethyl acetate, filtered and dried under reduced pressure to obtain the target compound CM19 g (10.85 g) as faint yellow crystals. Yield: 74.8%. The HPLC-area percent value of the obtained compound CM19g measured under analysis conditions 1 was 99.52%.

$^1$H-NMR (300 MHz, CDCl$_3$) δ (ppm)=7.49 (s, 2H), 7.43 (s, 2H), 2.79 (t, 4H), 1.86 (m, 4H), 1.67 (m, 4H), 1.45 (m, 4H), 1.05 (m, 12H), 0.99 (t, 6H), 0.78 (t, 6H), 0.63 (m, 4H).

$^{13}$C-NMR (75 MHz, CDCl$_3$) δ (ppm)=149.1, 148.2, 130.5, 120.9, 83.5, 54.8, 40.3, 36.3, 36.2, 31.8, 31.0, 25.3, 24.0, 23.3, 22.9, 14.5, 14.4.

TLC-MS: [M]$^+$=602.

<Step 7>

To compound CM19g (10.6 g, 17.5 mmol) there were added bis(pinacolato)diboron (13.3 g, 52.5 mmol) and commercially available dehydrated 1,4-dioxane (140 ml), and the mixture was heated to 45° C. to dissolution and then bubbled with argon gas for 30 minutes. Potassium acetate (10.3 g, 105 mmol) was added and the mixture was again bubbled with argon gas, after which [1,1'-bis(diphenylphosphino)ferrocene]palladium(II) dichloride dichloromethane addition product (PdCl$_2$(dPPf).CH$_2$Cl$_2$, 400 mg, 0.49 mmol) and 1,1'-bis(diphenylphosphino)ferrocene (dppf, 290 mg, 0.53 mmol) were added, and the mixture was stirred for 20 hours under reflux while heating in an oil bath. Dilution was then performed with toluene (100 ml) and the dilution was cooled to room temperature. It was then passed through a Celite-covered filter to remove the insolubles, the Celite was further rinsed with toluene (twice with 100 ml), and the filtrates were combined and then concentrated. Next, hexane (280 ml) and active carbon (21 g) were added, and the mixture was stirred for 1 hour under heated reflux, cooled to room temperature, and passed through a Celite-covered filter to remove the insolubles. After twice more repeating the procedure of rinsing the Celite with toluene (twice with 100 ml), combining the filtrates and concentrating, ethanol (250 ml) was added and the mixture was stirred for 1 hour under heated reflux. It was then cooled to room temperature, the solid was filtered out and rinsed with ethanol (twice with 30 ml) and dried under reduced pressure to obtain 11.3 g of a white solid. By repeating twice a procedure of complete dissolution in hexane (45 ml) while heating, dropwise addition of ethanol (270 g) followed by cooling to room temperature, filtering out the precipitated solid, rinsing it with a small amount of methanol and drying under reduced pressure, the target monomer CM19 (9.88 g) was obtained as white crystals. Yield: 69.8%. The HPLC-area percent value of the obtained monomer CM19 measured under analysis conditions 1 was 99.96%.

$^1$H-NMR (300 MHz, CDCl$_3$) δ (ppm)=7.66 (s, 2H), 7.49 (s, 2H), 2.95 (t, 4H), 1.93 (m, 4H), 1.59 (m, 4H), 1.41 (m, 28H), 1.08 (m, 12H), 0.95 (t, 6H), 0.76 (t, 6H), 0.64 (m, 4H).

$^{13}$C-NMR (75 MHz, CDCl$_3$) δ (ppm)=149.1, 148.2, 130.5, 120.9, 83.5, 54.8, 40.3, 36.3, 36.2, 31.8, 31.0, 25.3, 24.0, 23.3, 22.9, 14.5, 14.4.

TLC-MS: [M]$^+$=698.

Synthesis Example 5: Synthesis of Monomer CM20

Monomer CM20 was synthesized by the following step 1 to step 7.

[Chemical Formula 157]

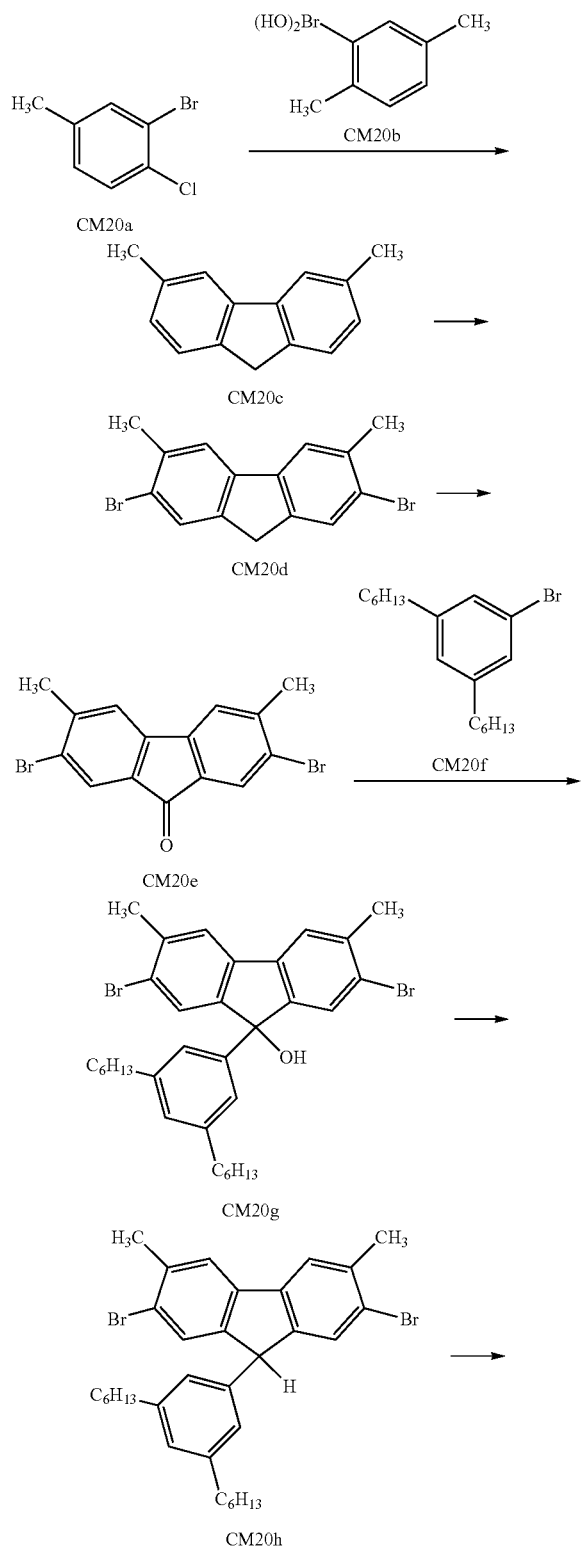

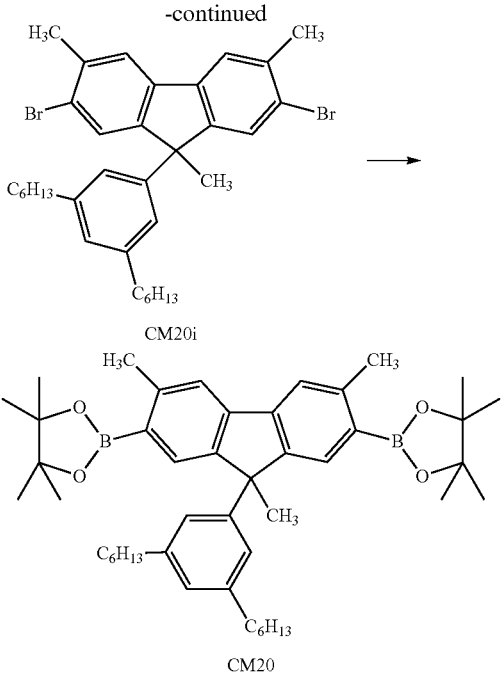

<Step 1>

In a reactor equipped with a reflux condenser, a mixture of 3-bromo-4-chlorotoluene (compound CM20a above, 30.82 g, 150 mmol), 2,5-dimethylphenylboronic acid (compound CM20b above, 24.75 g, 165 mmol), anhydrous potassium carbonate (124.39 g, 900 mmol), palladium(II) acetate (0.67 g, 6 mmol), tricyclohexylphosphine (1.68 g, 12 mmol), dimethylacetamide (commercially available dehydrated product, 600 ml) and pivalic acid (15.32 g and 150 mmol) was stirred for 10 hours under an argon gas atmosphere while heating in an oil bath set to 150° C. After diluting with toluene (500 ml), rinsing and liquid separation were carried out 3 times using ion-exchanged water. Next, there was repeated twice a procedure of adding active white clay (product of Wako Pure Chemical Industries, Ltd., 60 g) to the obtained oil layer, stirring the mixture for 2 hours, and then passing it through Celite and a silica gel pad to remove the insolubles. After removing the solvent from the obtained solution by concentration under reduced pressure, recrystallizing purification was carried out (with a mixed solvent of chloroform and ethanol), and the deposited crystals were filtered out and dried under reduced pressure to obtain the target CM20c (35.5 g) as a solid with a faint yellow-white appearance. Yield: 51%. The HPLC-area percent value of the obtained compound CM20c measured under analysis conditions 1 was 99.3% (UV254 nm)

<Step 2>

To compound CM20c (14.58 g, 75 mmol) there were added trifluoroacetic acid (11.15 mL, 150 mmol) and chloroform (commercially available dehydrated product, 400 mL) under an argon gas atmosphere, and the uniformly blended mixture was cooled to below 5° C. using an ice bath. After slowly adding bromine (8.46 mL, 165 mmol) thereto while taking care so that the temperature of the mixture did not exceed 5° C., the ice bath was removed and the mixture was stirred for 4 hours at room temperature to obtain a reaction solution. To the obtained reaction solution there was added a saturated aqueous solution of sodium dithionite, and after removing the excess bromine, the solvent was removed by concentration under reduced pressure to obtain a solid. Tetrahydrofuran (1 L) was added to the obtained solid and the mixture was stirred at 70° C. for 1 hour, after which it was cooled to room temperature, water was added to dissolve the precipitated inorganic salt, and the solution was again concentrated under reduced pressure to remove the tetrahydrofuran and obtain a solid-liquid mixture. The precipitated solid was filtered out, toluene was added for dissolution, and the solution was then passed through a silica gel short column and the obtained toluene solution was concentrated to obtain a solid. A procedure of recrystallizing purification of the obtained solid using a mixed solvent of toluene and isopropanol was repeated to obtain the target compound CM20d (22.3 g) (yield: 84%). The obtained compound CM20d exhibited an HPLC-area percent value (UV254 nm) of >99.9% as measured under analysis conditions 1.

$^1$H-NMR (300 MHz, CDCl$_3$): δ (ppm)=7.67 (s, 2H), 7.58 (s, 2H), 3.79 (s, 2H), 2.48 (s, 6H).

<Step 3>

After adding pyridine (34.70 mL) to compound CM20d (12.22 g, 34.70 mmol), benzyltrimethylammonium hydroxide (40% pyridine solution) (0.87 mL, prepared according to the procedure described below) was added at room temperature, and the mixture was heated in an oil bath at 40° C. while circulating air through the reactor interior, and stirred for 16 hours. Next, benzyltrimethylammonium hydroxide (40% pyridine solution) (0.87 mL, prepared by the procedure described below) was again added, and the mixture was heated in an oil bath at 60° C. and stirred for 8 hours to obtain a reaction solution.

After adding ion-exchanged water and acetic acid to the obtained reaction solution to create acidic conditions, the mixture was stirred for 1 hour at room temperature and the precipitated yellow solid was filtered out and thoroughly rinsed with water. The obtained solid was dried and then dispersed in a mixed solvent of tetrahydrofuran and methanol (tetrahydrofuran/methanol=4/30 (v/v)), and solid precipitated after stirring the dispersion for 1.5 hours while heating in an oil bath at 80° C. and cooling to room temperature was dried under reduced pressure to obtain the target compound CM20e (11.87 g) as a yellow solid. Yield: 93.5%. The obtained compound CM20e exhibited an HPLC-area percent value (UV254 nm) of 96.7% as measured under analysis conditions 1.

$^1$H-NMR (300 MHz, CDCl$_3$): δ (ppm)=7.77 (s, 2H), 7.36 (s, 2H), 2.47 (s, 6H).

LC-MS (APPI (posi)) measured under analysis conditions 1: 364 [M]$^+$.

<Preparation of Benzyltrimethylammonium Hydroxide (40% Pyridine Solution)>

For this preparation, pyridine (50 mL) was added to benzyltrimethylammonium hydroxide (40% methanol solution) (common name: TRITON B, product of Kanto Kagaku Co., Ltd., 50 mL), and then the mixture was concentrated to no greater than 25 mL with an evaporator and pyridine was again added for dilution to 50 mL The solution obtained by this procedure will be referred to as benzyltrimethylammonium hydroxide (40% pyridine solution).

<Step 4>

A solution of 3,5-di-n-hexyl-1-bromobenzene (compound CM20f, 13.82 g, 42.5 mmol) dissolved in tetrahydrofuran (commercially available dehydrated product, 324 mL) was cooled using a dry ice-methanol bath at −78° C. while stirring under an argon gas atmosphere. Next, a hexane solution of n-butyllithium (1.63 mol/L, 25.7 mL) was slowly added dropwise while maintaining a solution temperature of no higher than −75° C., and the mixture was further stirred for 1 hour. Next, compound CM20e (11.87 g, 32.4 mmol) was gradually added while keeping the solution temperature at no higher than −75° C., and after further stirring for 2 hours, methanol (approximately 20 mL) was slowly added dropwise, the dry ice-methanol bath was removed, and the temperature was slowly raised to room temperature. The solvent was distilled off from the obtained reaction solution by concentration under reduced pressure, and then hexane was added and the mixture was rinsed with ion-exchanged water to obtain an oil layer. The obtained oil layer was dried over anhydrous sodium sulfate and the insolubles were filtered out, the solvent was subsequently distilled off by concentration under reduced pressure, and recrystallizing purification (hexane), filtration and drying under reduced pressure were carried out to obtain the target compound CM20g (9.12 g) as a white solid. Yield: 45%. The obtained compound CM20g exhibited an HPLC-area percent value (UV254 nm) of 97.9% as measured under analysis conditions 1.

LC-MS (ESI (posi)) measured under analysis conditions 1: 610 [M]$^+$.

<Step 5>

Compound CM20g (9.12 g, 14.89 mmol), triethylsilane (4.53 mL, 59.6 mmol) and hexane (39 mL) were mixed under an argon gas atmosphere, and after initiating heating in an oil bath at 70° C., trifluoroacetic acid (4.5 mL, 59.6 mmol) was added dropwise and stirring was continued for 3 hours while heating to obtain a reaction solution.

After cooling the obtained reaction solution to room temperature, a 10 wt % concentration potassium phosphate aqueous solution was added, the organic layer was rinsed with brine and dried over anhydrous sodium sulfate and the insolubles were filtered out, after which the solvent was distilled off by concentration under reduced pressure and drying under reduced pressure, to obtain an oil containing compound CM20h (8.9 g). The obtained oil was used in the following steps without further purification.

LC-MS (ESI (posi)) measured under analysis conditions 1: 594 [M]$^+$.

<Step 6>

To the compound CM20h-containing oil (8.9 g) there was added N,N-dimethylformamide (74 mL) under an argon gas atmosphere, and a homogeneous solution was obtained. After 15 minutes of bubbling with argon gas, an ice bath was used for cooling to no higher than 5° C., and then there was added a potassium hydroxide aqueous solution having potassium hydroxide (2.76 g, 49.1 mmol) dissolved in ion-exchanged water (2.4 mL) and the mixture was bubbled with argon gas for exchange to an argon gas atmosphere. Next, methyl iodide (6.34 g, 44.7 mmol) was added dropwise and the mixture was stirred at 0° C. to 5° C. for 4 hours. The ice bath was removed, ion-exchanged water was added and extraction was performed with hexane to obtain an oil layer. The obtained oil layer was dried using anhydrous sodium sulfate, the insolubles were filtered out and the solvent was distilled off, and then purification was performed by medium pressure silica gel column chromatography (hexane). The fractions containing the target substance CM20i were combined and concentrated, and then subjected to recrystallizing purification (mixed solvent of hexane and isopropanol), and the obtained crystals were filtered and dried under reduced pressure to obtain the target compound CM20i (7.10 g) as a white solid. Yield: 77%. The obtained compound CM20i exhibited an HPLC-area percent value (UV254 nm) of >99.9% as measured under analysis conditions 1.

$^1$H-NMR (300 MHz, CDCl$_3$): δ (ppm)=7.57 (s, 2H), 7.35 (s, 2H), 6.83 (s, 1H), 6.71 (s, 2H), 2.50-2.44 (m, 10H), 1.79 (s, 3H), 1.54-1.45 (m, 4H), 1.34-1.17 (m, 12H), 0.84 (t, 6H).

LC-MS (ESI (posi)) measured under analysis conditions 1: 608 [M]$^+$.

<Step 7>

To a stirred mixture of bispinacolatodiboron (9.10 g, 35.9 mmol), potassium acetate (7.04 g, 71.7 mmol), 1,4-dioxane (36 mL) and [1,1% bis(diphenylphosphino)ferrocene]dichloropalladium(II) dichloromethane complex (1:1) (Pd(dppf)Cl$_2$CH$_2$Cl$_2$, CAS No. 95464-05-4, product of Sigma-Aldrich Co. LLC, 0.293 g, 0.36 mmol), being heated in an oil bath at 115° C. under an argon gas atmosphere, there was added dropwise a separately prepared solution of compound CM20i (7.13 g, 11.9 mmol) dissolved in 1,4-dioxane (36 mL), over a period of 2 hours, and the mixture was stirred at the same temperature for approximately 18 hours to obtain a reaction solution. After cooling the obtained reaction solution to room temperature, toluene was added for dilution, and the dilution was then passed through Celite and a silica gel pad to remove the insolubles and polar components. The obtained solution was dried over anhydrous sodium sulfate and the insolubles were filtered out, and then the solvent was distilled off by concentration under reduced pressure and toluene was added to obtain a homogeneous solution. Active carbon was added to the obtained solution, and the mixture was stirred for 30 minutes while heating in an oil bath at 70° C. and cooled to room temperature, after which the insolubles were removed by Celite filtration and the obtained solution was concentrated and then subjected to recrystallizing purification (toluene and acetonitrile mixed solvent). The obtained crystals were filtered and dried under reduced pressure to obtain the target monomer CM20 (6.94 g) as a white solid. Yield: 82%. The obtained monomer CM20 exhibited an HPLC-area percent value (UV254 nm) of >99.9% as measured under analysis conditions 1.

$^1$H-NMR (300 MHz, CDCl$_3$): δ (ppm)=7.64 (s, 2H), 7.55 (s, 2H), 6.81 (s, 2H), 6.77 (s, 1H), 2.62 (s, 6H), 2.48-2.42 (m, 4H), 1.85 (s, 3H), 1.55-1.45 (m, 4H), 1.31 (s, 24H), 1.31-1.17 (m, 12H), 0.83 (t, 6H).

LC-MS (ESI (p i)) measured under analysis conditions 1: 704 [M]$^+$.

Synthesis Example 6: Synthesis of Monomer CM21

Monomer CM21 was synthesized by the following step 1 to step 3.

[Chemical Formula 158]

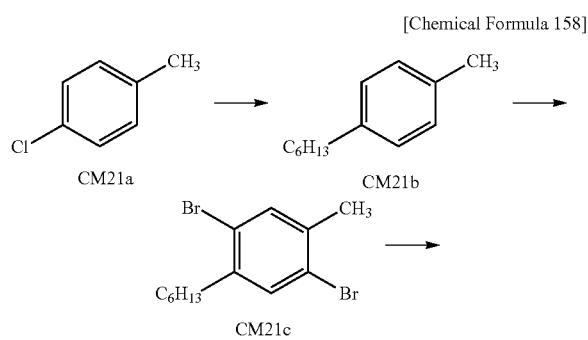

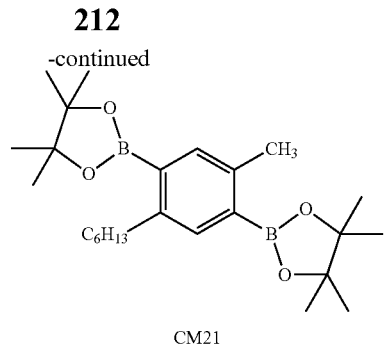

CM21

<Step 1>

A mixture of tetrahydrofuran (commercially available dehydrated product, 600 mL), magnesium (168.2 g, 6.92 mol) and iodine (0.7 g, 2.7 mmol) was heated to 45° C. under a nitrogen gas atmosphere, and then n-hexyl bromide (224 g, 1.36 mol) was added dropwise, tetrahydrofuran (commercially available dehydrated product, 880 mL) was added and a solution of n-hexyl bromide (895 g, 5.42 mol) diluted with tetrahydrofuran (commercially available dehydrated product, 1.82 L) was added dropwise over a period of 3 hours, after which the mixture was stirred at 50° C. for 2 hours. The compound [1,3-bis(diphenylphosphino)propane]nickel(II) dichloride (NiCl$_2$(dppp), 29.4 g, 54.2 mmol) was added, and then 4-chlorotoluene (compound CM21a, 343.5 g, 2.71 mol) was added dropwise at 45° C. The temperature was then raised to 65° C. by heating, and stirring was carried out for 5 hours at the same temperature to obtain a reaction solution. Tetrahydrofuran (commercially available dehydrated product, 5.5 L) was added to the obtained reaction solution. After then cooling to room temperature, the solution was added dropwise to 2 mol/L concentration hydrochloric acid (3.4 L) that had been cooled to 7° C. Next, toluene was used for extraction of the organic layer, and after rinsing the obtained organic layer with water, the solvent was distilled off under reduced pressure to obtain the target compound CM21b (425 g) as a faint yellow oil. Yield: 82%. Compound CM21b was used for the following steps without further purification.

LC-MS measured under analysis conditions 1 (APPI, positive): [M$^+$]176.

<Step 2>

Compound CM21b (424.4 g, purity: 393.3 g, 2.23 mmol), dichloromethane (1.7 L) and iodine (56.6 g, 223 mmol) were charged under a nitrogen gas atmosphere and cooled to 3° C., and then bromine (908.7 g, 5.69 mol) was added dropwise over a period of 2 hours. After stirring at 5° C. for 1 hour, a 10 wt % concentration sodium hydroxide aqueous solution was added dropwise. Ion-exchanged water and dichloromethane were flowed in for extraction, and the obtained organic layer was concentrated under reduced pressure. Toluene and active carbon were added, and after stirring at room temperature for 1 hour, the mixture was filtered. The obtained organic layer was concentrated under reduced pressure to obtain the target compound CM21c (745.7 g) as a yellow oil. Yield: 87%. Compound CM21c was used for the following steps without further purification.

LC-MS (APPI, positive): [M$^+$]332.

<Step 3>

Compound CM21c (744.5 g, purity: 644.9 g, 1.93 mol), 1,2-dimethoxyethane (6.2 L), potassium acetate (1136 g, 11.6 mol) and bis(pinacolato)diboron (alternate name: 4,4,4',4',5,5,5',5'-octamethyl-2,2'-bis-1,3,2-dioxaborolane, 1.12 kg, 4.44 mol) were charged in under an argon gas atmosphere, [1,1'-bis(diphenylphosphino)ferrocene]palladium (II) dichloride dichloromethane addition product (PdCl$_2$(dPPf).CH$_2$Cl$_2$, 47.3 g, 57.9 mmol) was added and the mixture was heated and stirred at 85° C. for 24 hours. Toluene and water were added at room temperature for extraction, and the solvent was distilled off from the obtained organic layer under reduced pressure. After adding toluene and active carbon to the obtained concentrated residue, it was stirred at room temperature for 1 hour and then filtered. The obtained organic layer was rinsed with a sodium chloride aqueous solution and water and then concentrated under reduced pressure, methanol was added, and the precipitated solid was filtered out and dried. After adding isopropanol to the obtained solid and heating to dissolution, it was cooled, and the precipitated solid was filtered out and dried to obtain monomer CM21 (709 g) as a white powdery solid. Yield: 86%. The HPLC-area percent value of the obtained monomer CM21 measured under analysis conditions 1 was >99.5%.

$^1$H-NMR (300 MHz, CDCl$_3$) δ (ppm)=7.53 (s, 2H), 2.81 (t, 2H), 2.48 (s, 3H), 1.55-1.29 (m, 32H), 0.88 (t, 3H).

LC-MS (APPI, positive): [M$^+$]428.

Synthesis Example 7: Synthesis of Monomer CM25

Monomer CM25 was synthesized by the following step 1 to step 2.

[Chemical Formula 159]

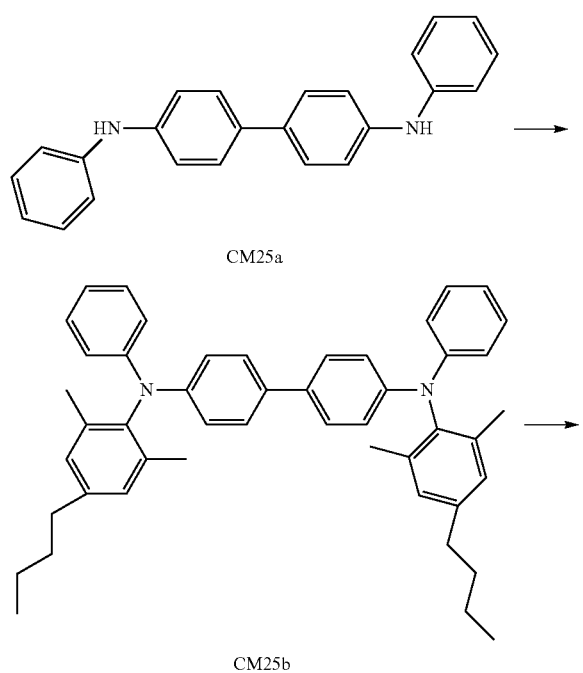

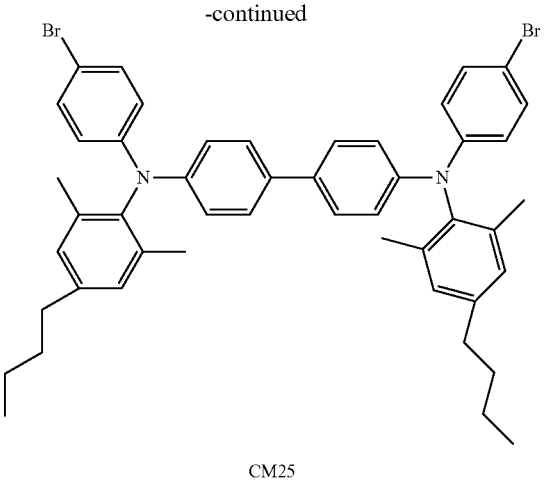

CM25

<Step 1: Synthesis of Compound CM25b>

To N,N'-diphenylbenzidine (CM25a, 65.16 g, 194 mmol), 1-bromo-4-n-butyl-2,5-dimethylbenzene (140.13 g, 582 mmol) and toluene (750 mL) there were added [tris(dibenzylideneacetone)]dipalladium (6.99 g, 4.3 mmol), tri-tert-butylphosphine tetrafluoroborate (t-Bu$_3$P.BF$_4$H, 2.53 g, 8.7 mmol) and sodium-tert-butoxide (74.44 g, 775 mmol) under a nitrogen gas atmosphere, and reaction was conducted at 130° C. for 24 hours. Next, water (500 mL) was added at 0° C., and the oil layer obtained by liquid separation after standing was separated from the aqueous layer and combined with the toluene-extracted portion of the aqueous layer. Magnesium sulfate was added to the oil layer, filtration was performed and the filtrate was concentrated under reduced pressure to remove the solvent and obtain an oil. The oil was dissolved in toluene and passed through a silica gel-packed filter with a hexane/toluene mixed solvent, and the obtained filtrate was concentrated under reduced pressure to obtain an oil. The oil was dissolved in a hexane/toluene mixed solvent and passed through a Fluorisil-packed filter with a hexane/toluene mixed solvent, and the obtained filtrate was concentrated under reduced pressure to obtain an oil. The oil was dissolved in hexane and passed through a Fluorisil-packed filter with hexane, and the obtained filtrate was dried under reduced pressure to obtain an oil. Isopropanol was added to the oil, methanol was added to the resulting oil, and the solid was filtered out. The solid was recrystallized with methanol/toluene, and dichloromethane/methanol was added to obtain 95.79 g of the target compound CM25b. The HPLC-area percent value of the obtained compound CM25b measured under analysis conditions 2 was 99.21%.

<Step 2: Synthesis of Monomer CM25>

To a solution of compound CM25b (95.79 g, 146 mmol) in dichloromethane (1420 mL) there was added N-bromosuccinimide (52.16 g, 293 mmol) at 0° C. under a nitrogen gas atmosphere, and the mixture was raised to room temperature and stirred overnight.

The reaction solution was diluted with dichloromethane (650 mL) and separated with 10 wt % aqueous sodium carbonate and water, magnesium sulfate was added to the oil layer for filtration, and the filtrate was concentrated under reduced pressure to remove the solvent and obtain an oil. The oil was dissolved in dichloromethane and passed through a silica gel-packed filter, and the obtained filtrate was dried under reduced pressure to obtain an oil. Isopropanol was added to the oil and the obtained solid was filtered out. The solid was recrystallized from toluene/isopropanol, toluene/butyl acetate and toluene/acetonitrile. The obtained solid was dissolved in dichloromethane and filtered with filter paper, and isopropanol was added to obtain a solid.

The solid was heated to reflux for 1 hour with acetonitrile and cooled to room temperature, after which the obtained solid was filtered to obtain 83.77 g of the target monomer CM25. The HPLC-area percent value of the obtained monomer CM25 measured under analysis conditions 2 was 99.69%.

$^1$H-NMR (600 MHz, CDCl$_3$) δ (ppm)=7.39 (d, J=8.4 Hz, 4H), 7.27 (d, J=8.8 Hz, 4H), 6.99 (d, J=8.1 Hz, 4H), 6.93 (s, 4H), 6.86 (d, J=8.7 Hz, 4H), 2.58 (t, J=7.74 Hz, 4H), 2.00 (s, 12H), 1.62 (m, 4H), 1.39 (m, 4H), 0.96 (t, J=7.38 Hz, 6H).

Synthesis Example 8: Synthesis of Monomer CM26

Monomer CM26 was synthesized by the following step 1 to step 2.

[Chemical Formula 160]

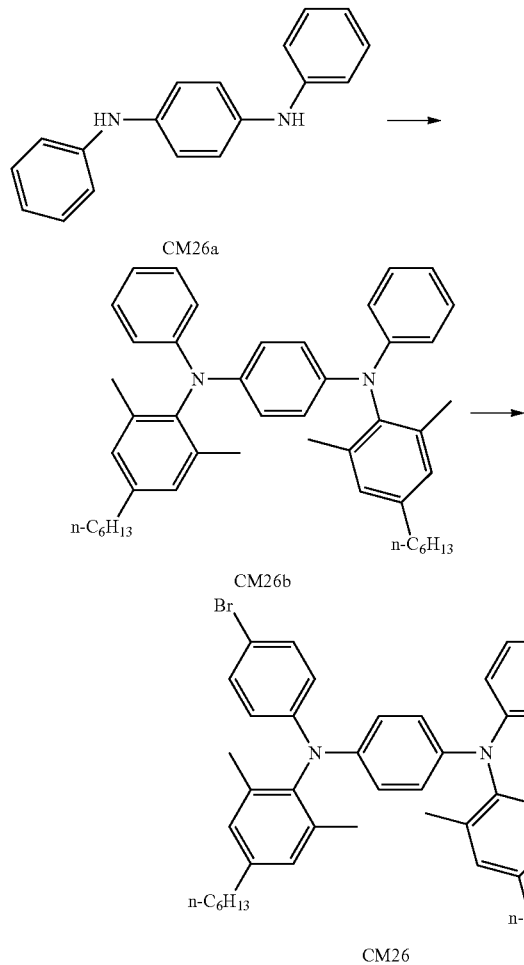

<Step 1: Synthesis of Compound CM26b>
To N,N'-diphenylbenzidine (CM26a, 59.51 g, 228.6 mmol), 2,6-dimethyl-4-hexylbromobenzene (129.24 g, 480 mmol) and toluene (1500 mL) there were added [tris(dibenzylideneacetone)]dipalladium, tri-tert-butylphosphine tetrafluoroborate (t-Bu$_3$P.BF$_4$H) and sodium-tert-butoxide under a nitrogen gas atmosphere, and the mixture was heated to reflux for 16 hours. It was then stirred at 0° C. for 1 hour and allowed to stand, and the separated oil layer was separated out from the aqueous layer and combined with the toluene-extracted portion of the aqueous layer, after which the oil layer was concentrated under reduced pressure to remove the solvent and obtain an oil. The oil was dissolved in toluene and passed through a silica gel-packed filter with a Fluorisil/silica gel/alumina, with a hexane/toluene mixed solvent, and the obtained filtrate was concentrated under reduced pressure to obtain an oil. Hexane was added to the oil, the mixture was stirred and the solid was filtered out to obtain the target compound CM26b. The HPLC-area percent value of the obtained compound CM26b measured under analysis conditions 2 was 99.3%.

<Step 2: Synthesis of Monomer CM26>
To a solution of compound CM26b (50 g, 78.5 mmol) in dichloromethane (1000 mL) there was added N-bromosuccinimide (28.65 g, 161.0 mmol) at −30° C. under a nitrogen gas atmosphere, and the mixture was raised to room temperature and stirred overnight.

The reaction solution was rinsed with water, magnesium sulfate was added to the oil layer, filtration was performed and the filtrate was concentrated under reduced pressure to remove the solvent and obtain a solid. The solid was rinsed with hexane and recrystallized 6 times with heated toluene/isopropanol, to obtain the target monomer CM26 as a white solid. The HPLC-area percent value of the obtained monomer CM26 measured under analysis conditions 2 was 99.62%.

$^1$H-NMR (400 MHz, CDCl$_3$) δ (ppm)=7.22 (d, J=9 Hz, 4H), 6.90 (s, 4H), 6.84 (s, 4H), 6.75 (d, J=9 Hz, 4H), 2.54 (m, 4H), 1.99 (s, 12H), 1.33 (m, 12H), 0.99 (t, 6H).

Synthesis Example 9: Synthesis of Monomer CM27

Monomer CM27 was synthesized by the following step 1 and step 2.

[Chemical Formula 161]

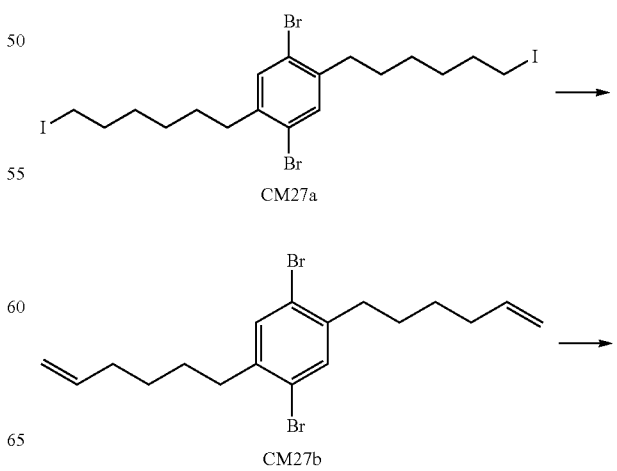

-continued

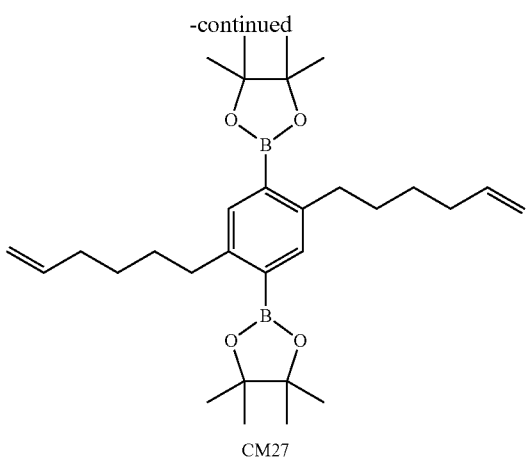

CM27

<Step 1: Synthesis of Compound CM27b>

CM27a (26 g, 39.6 mmol) was dissolved in tetrahydrofuran (500 mL) under a nitrogen gas atmosphere and the solution was cooled to between 0° C. and 5° C. After slowly adding potassium tert-butoxide (17.75 g, 158.5 mmol) in a range of 0° C. to 5° C., the reaction solution was raised to room temperature and stirred for 24 hours. Next, ice water (500 mL) was added to the reaction solution, and the oil layer obtained by liquid separation after standing was separated from the aqueous layer and combined with the ethyl acetate-extracted portion of the aqueous layer. The oil layer was concentrated under reduced pressure to remove the solvent and obtain an oil. The oil was subjected to separating purification by silica gel column chromatography using hexane to obtain 14.5 g of the target compound CM27b. The HPLC-area percent value of the obtained compound CM27b measured under analysis conditions 2 (detection wavelength: 240 nm) was 99.68%.

$^1$H-NMR (400 MHz, CDCl$_3$) δ (ppm)=7.37 (s, 2H), 5.81-5.87 (m, 2H), 4.96-5.07 (m, 4H), 2.67 (t, J=7.64 Hz, 4H), 2.09-2.15 (m, 4H), 1.57-1.64 (m, 4H), 1.47-1.53 (m, 4H).

$^{13}$C-NMR (100 MHz, CDCl$_3$) δ (ppm)=141.19, 138.67, 133.79, 123.08, 114.60, 35.36, 33.54, 29.28, 28.56.

<Step 2: Synthesis of Monomer CM27>

Compound CM27b (11.66 g, 29.1 mmol) was dissolved in tetrahydrofuran (220 mL) under a nitrogen gas atmosphere and cooled to −75° C., and then sec-butyllithium (94 mL, 131.1 mmol) was added dropwise over a period of 2 hours at an internal temperature of no higher than −65° C., and the mixture was stirred for 5.5 hours at an internal temperature of no higher than −65° C. To this reaction solution there was added bis(pinacolato)diboron (30 mL, 145.7 mmol) dropwise over a period of 30 minutes at −70° C. The reaction solution was raised to room temperature and stirred overnight. The reaction solution was then cooled to 0° C., and a 2 mol/L diethyl ether solution of hydrochloric acid was added dropwise until the reaction solution reached transparency. The product was extracted with diethyl ether and concentrated under reduced pressure to remove the solvent and obtain a solid. Acetonitrile (150 mL) was added to the solid, the mixture was stirred at room temperature for 2 hours, and the obtained solid was filtered. Acetonitrile (100 mL) was again added to the solid and the mixture was stirred at room temperature for 2 hours and recrystallized twice from acetonitrile to obtain 3.60 g of the target monomer CM27. The HPLC-area percent value of the obtained monomer CM27 measured under analysis conditions 2 was 99.90%.

The acetonitrile filtrates from recrystallization were combined and recrystallized twice from acetonitrile, to obtain 1.4 g of CM27 (HPLC-area percent value measured under analysis conditions 2: 99.76%).

$^1$H-NMR (500 MHz, THF) δ (ppm)=7.53 (s, 2H), 5.83 (m, 2H), 4.99 (d, 2H), 4.90 (d, 2H), 2.82 (t, 4H), 2.07 (m, 4H), 1.56 (m, 4H), 1.45 (m, 4H), 1.33 (s, 24H).

Synthesis Example 10: Synthesis of Monomer CM28

Monomer CM28 was synthesized by the following step 1 to step 5.

[Chemical Formula 162]

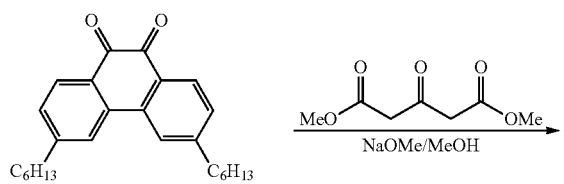

CM28a

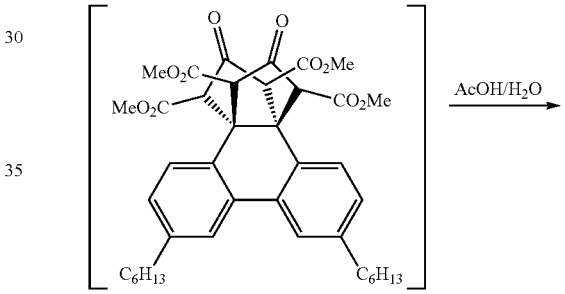

CM28b

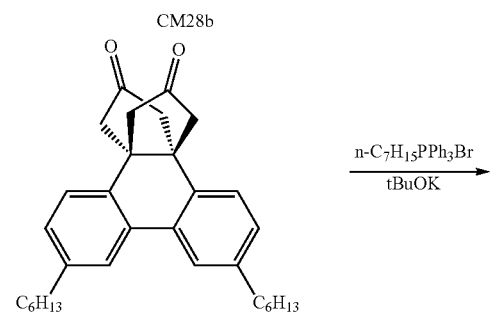

CM28c

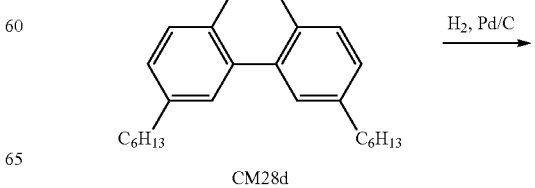

CM28d

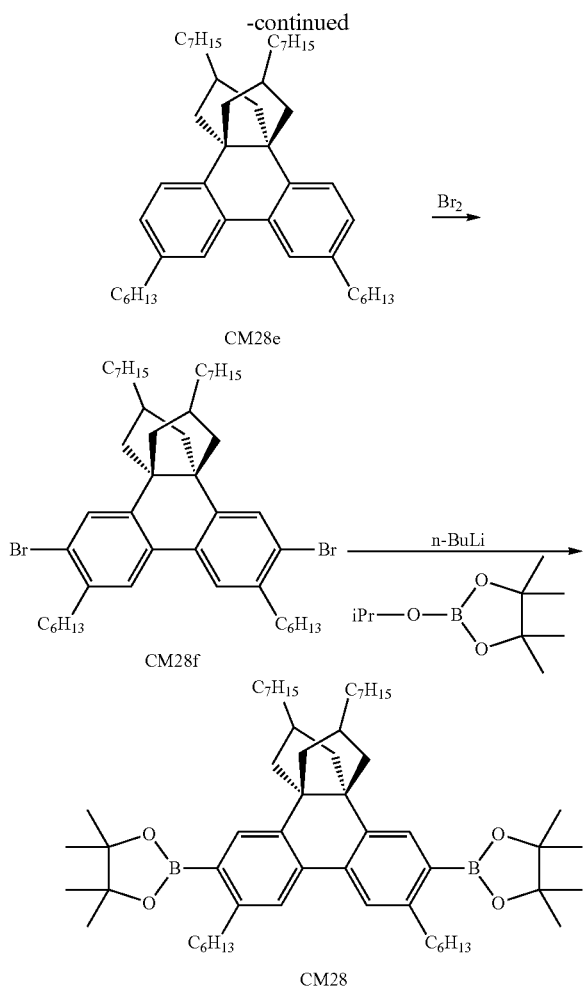

[In the formulas, the wave lines indicate that the compound with wave lines is a mixture of geometric isomers.]

<Step 1>

In a 2000 mL four-necked flask equipped with a stirrer there were placed CM28a (35.31 g) and methanol (1100 mL), and the gas in the flask was exchanged with argon. After then adding dimethyl 1,3-acetonedicarboxylate (34.65 g) thereto, sodium methoxide (5 mol/L methanol solution) (67.62 g) was slowly added dropwise. The mixture was then kept thermally insulated for 2 hours at room temperature, and the mixture was raised to reflux temperature and stirred while thermally insulating for 6 hours. The reaction solution was cooled to room temperature and 35% hydrochloric acid (37.41 g) was added. Water and toluene were added and the mixture was stirred at room temperature, the aqueous layer was separated off, and the organic layer was rinsed with a saturated sodium chloride aqueous solution. Sodium sulfate was added to the obtained organic layer, and after filtering, it was concentrated to obtain 60.1 g of CM28b.

Next, CM28b (60.10 g), acetic acid (450 mL) and ion-exchanged water (60 mL) were placed in a 1000 mL four-necked flask equipped with a stirrer, and the gas in the flask was exchanged with argon. The temperature was then raised to reflux temperature and stirring was carried out while thermally insulating for 5 hours. The reaction solution was cooled to room temperature, water and toluene were added, the aqueous layer was separated off, and the organic layer was rinsed with a saturated sodium chloride aqueous solution. Sodium sulfate was added to the obtained organic layer, and after filtering, it was concentrated to obtain a crude product. The crude product was purified using a silica gel column (developing solvent: hexane/ethyl acetate liquid mixture) to obtain 19.5 g of CM28c as a white solid.

LC-MS (APCI, positive): [M+H]$^+$457.

<Step 2>

After placing heptyltriphenylphosphonium bromide (82.29 g) in a 1 L four-necked flask equipped with a stirrer, the gas in the flask was exchanged with argon. Toluene (520 mL) was placed in the flask and the mixture was cooled to no higher than 5° C. Potassium tert-butoxide (20.92 g) was added and the temperature was raised to room temperature, after which the mixture was stirred at room temperature while thermally insulating for 3 hours. The CM28c (18.0 g) was added to the red slurry produced in the reaction solution, and the mixture was stirred at room temperature while thermally insulating for 6 hours and 30 minutes. Acetic acid (7.2 g) was placed in the reaction solution and stirred therewith for 15 minutes, water and hexane was added and the mixture was stirred at room temperature, after which the aqueous layer was separated off and the organic layer was rinsed with a saturated sodium chloride aqueous solution. Sodium sulfate was added to the obtained organic layer, and after filtering, it was concentrated to obtain a crude product. The crude product was purified with a silica gel column (developing solvent: hexane), active carbon was added to the obtained hexane solution, and the mixture was stirred at 50° C. for 1 hour while thermally insulating. The mixture was then cooled to room temperature and filtered with a filter precoated with Celite, the residue was rinsed several times with hexane, and the filtrates from several rinsings were combined and concentrated to obtain 18.8 g of CM28d as a colorless transparent liquid.

LC-MS (APCI, positive): [M+H]$^+$621.

<Step 3>

After placing CM28d (18.6 g) in a 1 L four-necked flask equipped with a stirrer, ethyl acetate (165 mL) and ethanol (150 mL) were added and the gas in the flask was exchanged with nitrogen. After adding 5 wt % Pd/C (approximately 50 wt % water content) (3.7 g), the gas in the flask was exchanged with hydrogen and the mixture was stirred under a hydrogen atmosphere at 50° C. for 49 hours while thermally insulating. The mixture was then cooled to room temperature and filtered with a filter precoated with Celite, the residue was rinsed several times with ethyl acetate, and the filtrates from several rinsings were combined and concentrated to obtain a crude product. The crude product was purified with a silica gel column (developing solvent: hexane), active carbon was added to the obtained hexane solution, and the mixture was stirred at 50° C. for 1 hour while thermally insulating. The mixture was then cooled to room temperature and filtered with a filter precoated with Celite, the residue was rinsed several times with hexane, and the filtrates from several rinsings were combined and concentrated to obtain 17.6 g of CM28e as a colorless transparent liquid.

LC-MS (APCI, positive): [M+H]$^+$625.

<Step 4>

In a 500 mL four-necked flask equipped with a stirrer there was placed CM28e (17.0 g), and the gas in the flask was exchanged with argon. Chloroform (230 mL) and trifluoroacetic acid (22 mL) were added into the flask and the mixture was cooled to no higher than 5° C. The entire four-necked flask was shielded from light, a mixture of bromine (8.9 g) and chloroform (45 mL) was added dropwise to the flask over a period of 15 minutes, and stirring was carried out for 3 hours while thermally insulating. A 10 wt % water-soluble sodium sulfite solution was added to the reaction solution and the temperature was raised to room temperature. The aqueous layer was separated from the reaction solution, and the oil layer was rinsed with water, a 5 wt % sodium hydrogencarbonate aqueous solution and water in that order. The obtained oil layer was dried over magnesium sulfate and filtered, and the filtrate was concentrated to obtain a crude product. The crude product was purified with a silica gel column (developing solvent: hexane), active carbon was added to the obtained hexane solution, and the mixture was stirred at 50° C. for 1 hour while thermally insulating. The mixture was then cooled to room temperature and filtered with a filter precoated with Celite, the residue was rinsed several times with hexane, and the filtrates from several rinsings were combined and concentrated. This procedure was repeated twice to obtain 19.3 g of CM28f as a colorless transparent liquid.

LC-MS (APCI, positive): [M+H]$^+$781.

$^1$H-NMR (CDCl$_3$, 300 MHz) δ (ppm): 0.91 (12H, m), 1.18-1.43 (36H, m), 1.56-1.77 (8H, m), 2.15-2.33 (4H, m), 2.70-2.75 (4H, m), 7.39-7.53 (2H, m), 7.61-7.66 (2H, m).

<Step 5>

Dehydrated tetrahydrofuran (210 mL) was placed in a 1000 mL four-necked flask equipped with a stirrer and cooled to no higher than −70° C. After slowly adding n-butyllithium (1.6 M hexane solution) (70 mL) dropwise over a period of 30 minutes, the mixture was stirred for 30 minutes while thermally insulating. A mixture of CM28f (18.2 g) and dehydrated tetrahydrofuran (210 mL) was slowly added dropwise over a period of 30 minutes or longer, and the mixture was stirred for 1 hour while thermally insulating. After adding 2-isopropoxy-4,4,5,5-tetramethyl-1,3,2-dioxaborolane (32 mL) dropwise over a period of 10 minutes or longer, the temperature was raised to room temperature and the mixture was stirred for 4 hours at room temperature while thermally insulating. Toluene was added and the reaction solution was diluted, and then water was added, the mixture was stirred at room temperature, the aqueous layer was separated off, and the organic layer was rinsed with a saturated sodium chloride aqueous solution. Sodium sulfate was added to the obtained organic layer, and after filtering, it was concentrated to obtain a crude product. The crude product was treated with a silica gel column (developing solvent: hexane/ethyl acetate liquid mixture), and then recrystallized with a liquid mixture of toluene and acetonitrile to obtain 14.6 g of monomer CM28 as a white solid.

LC-MS (APCI, positive): [M+H]$^+$877.

$^1$H-NMR (CD$_2$Cl$_2$, 300 MHz) δ (ppm): 0.94 (12H, m), 1.27-1.44 (60H, m), 1.64-1.74 (8H, m), 2.25-2.45 (4H, m), 2.94 (4H, m), 7.67-7.82 (4H, m).

Synthesis Example 11: Synthesis of Phospholuminescent Material 1

Phospholuminescent material 1 was synthesized according to the synthesis method described in WO2002/066552.

[Chemical Formula 163]

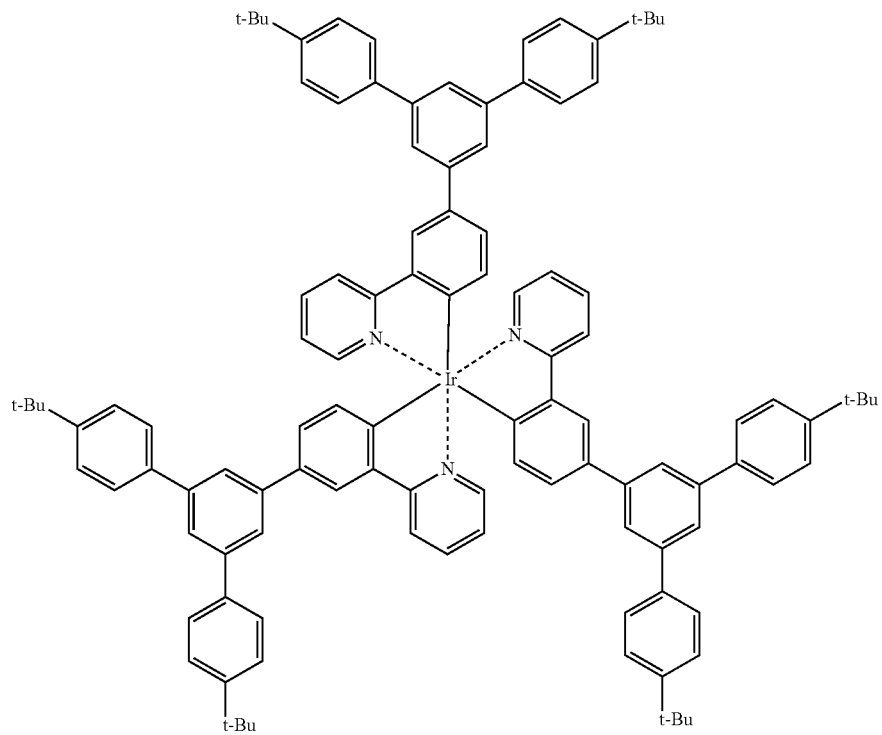

Phospholuminescent Material 1

Synthesis Example 12: Synthesis of Phospholuminescent Material 2

Phospholuminescent material 2 was synthesized according to the synthesis method described in WO2006/062226.

[Chemical Formula 164]

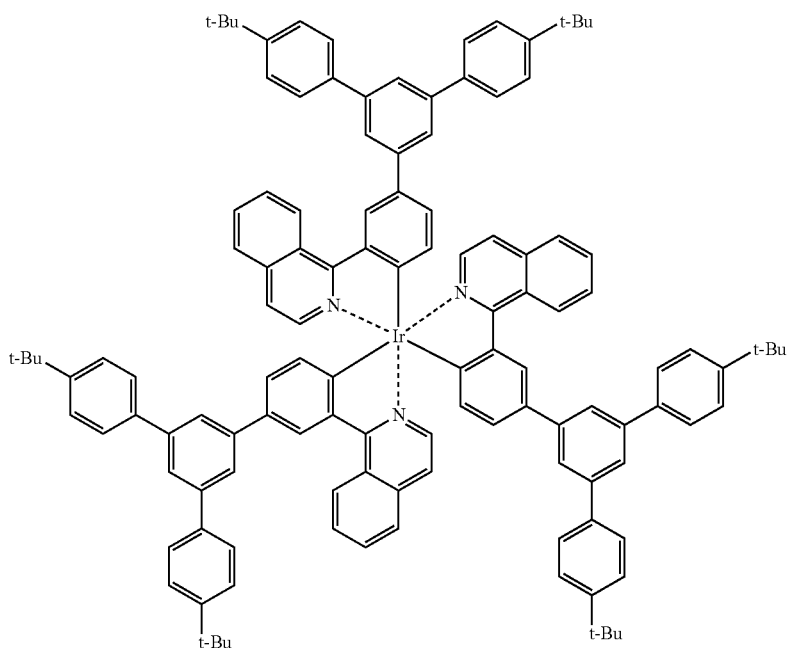

Phospholuminescent Material 2

Example M1: Synthesis of Monomer MM1

Monomer MM 1 was synthesized by the following step 1 to step 3.

[Chemical Formula 165]

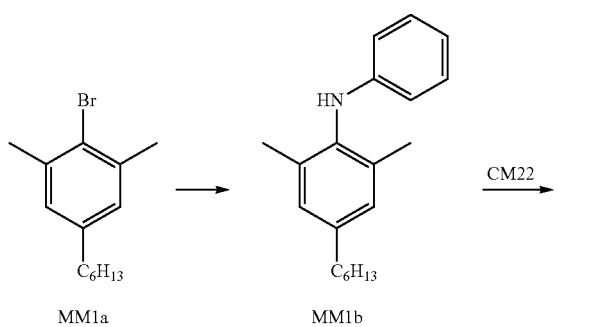

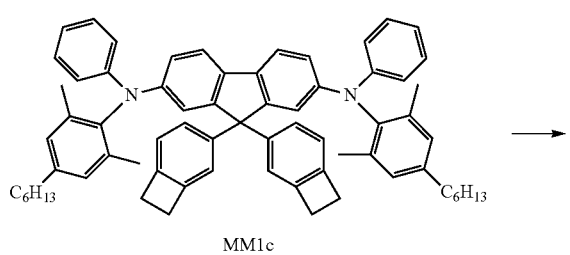

-continued

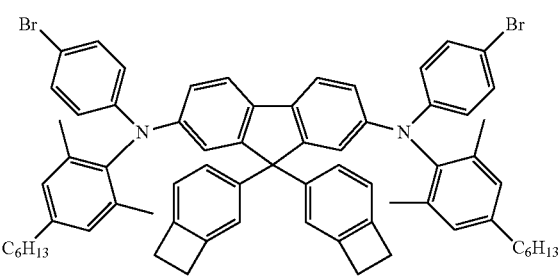

<Step 1: Synthesis of Compound MM1b>

To a solution comprising compound MM1a (100 g, 370 mmol) and toluene (2 L) there was added sodium tert-butoxide (92 g, 960 mmol) under a nitrogen gas atmosphere, and after bubbling nitrogen gas, [tris(dibenzylideneacetone)]dipalladium (10 g, 11 mmol) and tri-tert-butylphosphine tetrafluoroborate (t-Bu₃P.BF₄H, 6.4 g, 22 mmol) were added and the mixture was bubbled with nitrogen gas. Aniline (38 g, 410 mmol) was added thereto and the mixture was stirred at 110° C. for 16 hours under reflux. The reaction solution was then diluted with ethyl acetate (200 mL) at room temperature and the solution was passed through a filter packed with Celite. The obtained filtrate was rinsed and the aqueous layer formed after standing was removed from the oil layer. The oil layer was concentrated under reduced pressure to remove the solvent and obtain an oil. The oil was purified by silica gel column chromatography to obtain 90 g of the target compound MM1b. The HPLC-area percent value of the obtained compound MM1b measured under analysis conditions 2 (detection wavelength: 272 nm) was 99.27%.

$^1$H-NMR (400 MHz, DMSO-d$_6$) δ (ppm)=7.16 (s, 1H), 7.01-7.05 (m, 2H), 6.91 (s, 2H), 6.52-6.55 (m, 1H), 6.35 (d, J=7.7 Hz, 2H), 2.48-2.50 (m, 2H), 2.08 (s, 6H), 1.52-1.59 (m, 2H), 1.23-1.31 (m, 6H), 0.85 (t, J=6.7 Hz, 3H).

$^{13}$C-NMR (100 MHz, DMSO-d$_6$) δ (ppm)=147.32, 139.33, 136.10, 135.56, 128.96, 128.16, 116.28, 112.25, 34.81, 31.18, 31.06, 28.51, 22.11, 18.10, 13.99.

LC-MS measured under analysis conditions 2: [M]$^+$=281.

<Step 2: Synthesis of Compound MM1c>

To a solution comprising compound CM22 (84.5 g, 160 mmol) and toluene (1.7 L) there were added compound MM1b (94.5 g, 336 mmol) and sodium tert-butoxide (76.8 g, 800 mmol) under a nitrogen gas atmosphere, and after bubbling with nitrogen gas, 2-(2'-di-tert-butylphosphine)-biphenylpalladium(II) acetate (2.22 g, 4.8 mmol) was added and the mixture was stirred at 120° C. for 16 hours under reflux. The reaction solution was then diluted with ethyl acetate (50 mL) at room temperature and the solution was passed through a filter packed with Celite. The obtained filtrate was rinsed and the aqueous layer formed after standing was removed from the oil layer. The oil layer was concentrated under reduced pressure to remove the solvent and obtain an oil. The oil was purified by silica gel column chromatography to obtain 69.5 g of the target compound MM1c. The HPLC-area percent value of the obtained compound MM1c measured under analysis conditions 2 (detection wavelength: 379 nm) was 99.35%.

$^1$H-NMR (300 MHz, CDCl$_3$) δ (ppm)=7.45-7.68 (m, 2H), 7.05-7.19 (m, 6H), 6.87-6.97 (m, 7H), 6.80-6.85 (m, 7H), 6.45-6.66 (m, 4H), 3.06-3.14 (m, 8H), 2.52-2.70 (m, 4H), 1.97 (s, 12H), 1.59-1.66 (m, 4H), 1.30-1.43 (m, 12H), 0.85-0.94 (m, 6H).

LC-MS measured under analysis conditions 2: [M]$^+$=928.

<Step 3: Synthesis of Monomer MM1>

To a solution comprising compound MM1c (29.6 g, 31.9 mmol) and chloroform (300 mL) there was added dropwise a solution of N-bromosuccinimide (11.3 g, 63.8 mmol) in dimethylformamide (100 mL) at −20° C. over a period of 2 hours and 30 minutes under a nitrogen gas atmosphere, and the mixture was stirred for 3 hours. The mixture was then stirred for 16 hours at room temperature, and the reaction solution was slowly added dropwise to ice water (500 mL). The oil layer was rinsed with water, the aqueous layer formed after standing was removed from the oil layer, and the oil layer was concentrated under reduced pressure to remove the solvent and obtain an oil. The oil was repeatedly purified by silica gel column chromatography (7 times) to obtain 26 g of the target monomer MM1. The HPLC-area percent value of the obtained monomer MM1 measured under analysis conditions 2 (detection wavelength: 350 nm) was 99.68%.

$^1$H-NMR (400 MHz, DMSO-d$_6$) δ (ppm)=7.57 (d, J=8.2 Hz, 2H), 7.27-7.30 (m, 4H), 6.97 (s, 4H), 6.81-6.85 (m, 6H), 6.65-6.69 (m, 6H), 6.51 (s, 2H), 3.03-3.05 (m, 4H), 2.96-2.99 (m, 4H), 2.51-2.53 (m, 4H), 1.85 (s, 12H), 1.52-1.63 (m, 4H), 1.18-1.30 (m, 12H), 0.82 (t, J=7.0 Hz, 6H).

LC-MS measured under analysis conditions 2: [M]$^+$=1084.

Example M2: Synthesis of Monomer MM2

(1) Synthesis of compound MM2c was accomplished by step 1 to step 2 below.

[Chemical Formula 166]

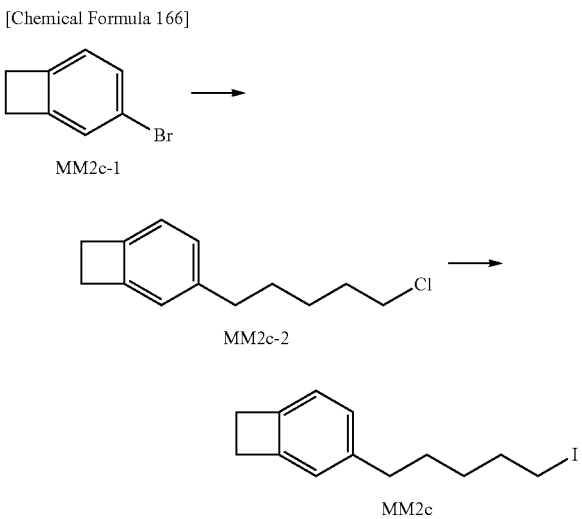

<Step 1: Synthesis of Compound MM2c-2>

To a solution of compound MM2c-1 (40 g, 219 mmol) in tetrahydrofuran (400 mL) there was added dropwise sec-butyllithium (1.4 mol/L, 187 mL, 262 mmol) at −75° C. under a nitrogen gas atmosphere. The obtained solution was stirred for 2 hours and added dropwise to a solution of 1-bromo-5-chloropentene (36.9 g, 198.7 mmol) in tetrahydrofuran (300 mL) at −75° C. The solution was raised to room temperature and stirred overnight, and then quenched with 2 mol/L hydrochloric acid (50 mL) The oil layer separated after standing was separated out from the aqueous layer and combined with the dichloromethane-extracted portion of the aqueous layer. The oil layer was concentrated under reduced pressure to remove the solvent and obtain an oil. The HPLC-area percent value of the obtained oil (MM2c-2, 84 g) measured under analysis conditions 2 was 90%.

<Step 2: Synthesis of Compound MM2c>

To a solution of compound MM2c-2 (77 g, 370 mmol) in acetone (300 mL) there was added dropwise a solution of sodium iodide (166 g, 1100 mmol) in acetone (800 mL) at room temperature under a nitrogen gas atmosphere. The obtained solution was heated to reflux overnight. The reaction solution was concentrated under reduced pressure to remove the solvent, the obtained solid portion was dissolved in dichloromethane and rinsed with water, and the oil layer obtained after liquid separation was concentrated under reduced pressure to remove the solvent and obtain a brown oil (105 g). A 70 g portion of the oil was purified by column chromatography with hexane:dichloromethane=4:1, to obtain a yellow oil (MM2c, 67 g, HPLC-area percent value measured under analysis conditions 2: 84%).

$^1$H-NMR (600 MHz, CDCl$_3$) δ (ppm)=7.01 (d, 1H), 6.97 (d, 1H), 6.89 (s, 1H), 3.19 (t, 2H), 3.15 (m, 4H), 2.59 (t, 2H), 1.87 (q, 2H), 1.63 (q, 2H), 1.45 (q, 2H).

(2) Synthesis of monomer MM2 was accomplished by step 1 to step 4 below.

[Chemical Formula 167]

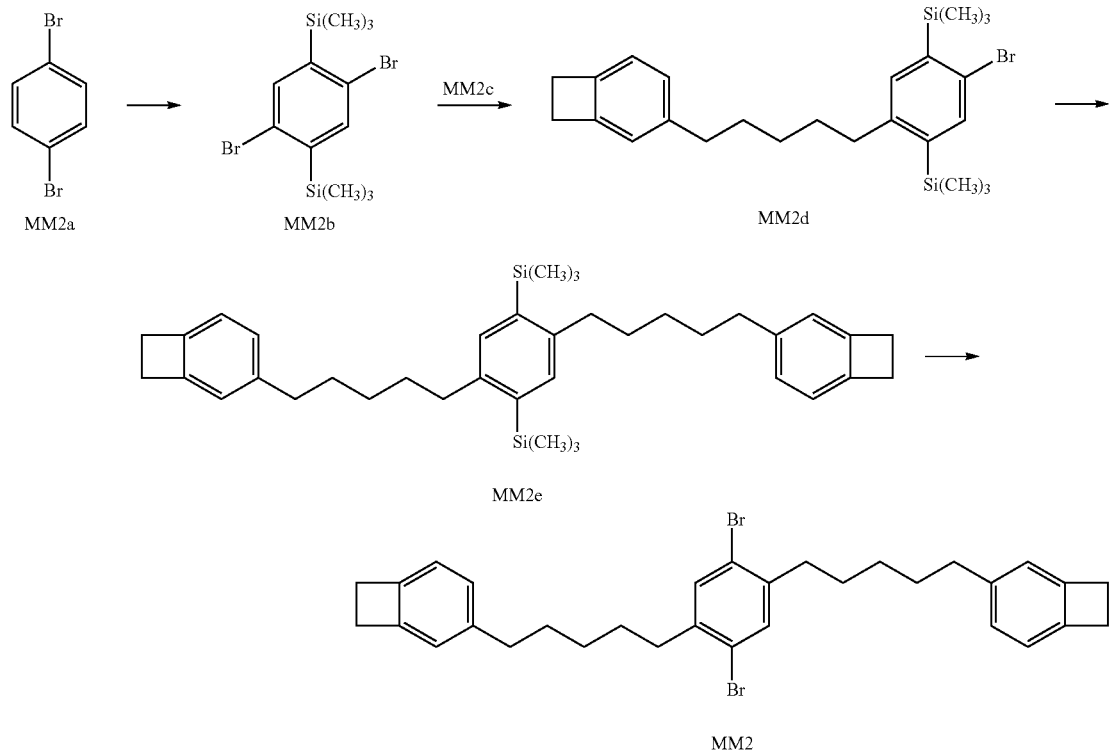

<Step 1: Synthesis of Compound MM2b>

Lithium diisopropylamide (2 mol/L THF solution, 117 mL, 233 mmol) was added dropwise to a solution comprising 1,4-dibromobenzene (MM2a, 25 g, 106 mmol), tetrahydrofuran (250 mL) and trimethylsilyl chloride (25.3 g, 233 mmol) at −75° C. under a nitrogen gas atmosphere. The resulting orange solution was heated to room temperature and stirred overnight. The reaction solution was then cooled to −10° C. and a 15% sulfuric acid aqueous solution (50 mL) was added. After standing, the separated oil layer was separated off from the aqueous layer and combined with the ether-extracted portion of the aqueous layer. The oil layer was concentrated under reduced pressure to remove the solvent and obtain an oil. The oil was rinsed with cooled methanol (500 mL, 3 times), and the solid obtained by filtration was dried. The target compound MM2b was obtained in an amount of 16.5 g. The HPLC-area percent value of the obtained compound MM2b measured under analysis conditions 2 was 100%.

$^1$H-NMR (600 MHz, CDCl$_3$) δ (ppm)=7.51 (s, 2H), 0.38 (s, 18H).

<Step 2: Synthesis of Compound MM2d>

To a solution of compound MM2b (31.5 g, 83 mmol) in tetrahydrofuran (320 mL) there was added dropwise sec-butyllithium (1.4 mol/L, 71 mL, 99.4 mmol) at −75° C. under a nitrogen gas atmosphere. The solution was stirred at −75° C. for 2 hours, and a solution of compound MM2c (26.1 g, 87 mmol) in THF (400 mL) was added dropwise at −75° C. The reaction solution was returned to room temperature and stirred overnight. Hydrochloric acid (2 mol/L, 50 mL) was added while keeping the internal temperature of the reaction solution at −5° C. The oil layer separated after standing was separated out from the aqueous layer and combined with the dichloromethane-extracted portion of the aqueous layer. The oil layer was concentrated under reduced pressure to remove the solvent and obtain an oil. The oil was purified by flash chromatography (hexane: 100%) to obtain 27.5 g of the target compound MM2d. The HPLC-area percent value of the obtained compound MM2d measured under analysis conditions 2 was 92.2%.

$^1$H-NMR (600 MHz, CDCl$_3$) δ (ppm)=7.58 (s, 1H), 7.25 (s, 1H), 7.03 (d, 1H), 6.98 (d, 1H), 6.92 (s, 1H), 3.17 (s, 4H), 2.64 (m, 4H), 1.68 (m, 2H), 1.62 (m, 2H), 1.49 (m, 2H), 0.41 (s, 9H), 0.34 (s, 9H).

<Step 3: Synthesis of Compound MM2e>

Compound MM2d (27.5 g, 58 mmol) was used for reaction under a nitrogen gas atmosphere by the same procedure as for synthesis of compound MM2d. Acetonitrile was added to the reaction mixture at room temperature to obtain 25.2 g of the target compound MM2e as a white solid. The HPLC-area percent value of the obtained compound MM2e measured under analysis conditions 2 was 96.2%.

$^1$H-NMR (600 MHz, CDCl$_3$) δ (ppm)=7.25 (s, 2H), 7.02 (d, 2H), 6.96 (d, 2H), 6.90 (s, 2H), 3.14 (s, 8H), 2.65 (m, 4H), 2.60 (t, 4H), 1.64 (m, 8H), 1.47 (m, 4H), 0.31 (s, 18H).

<Step 4: Synthesis of Monomer MM2>

After dissolving N-bromosuccinimide (15.6 g, 87.6 mmol) in dimethylformamide (50 mL) under a nitrogen gas atmosphere, the solution was bubbled with nitrogen gas and added dropwise to a solution of compound MM2e (24.2 g, 42.7 mmol) in a mixed solvent of acetic acid, chloroform and dimethylformamide [1.8:10:4] (v/wt) at room temperature. The mixture was stirred overnight at room temperature and water (250 mL) was added. The oil layer separated after standing was separated out from the aqueous layer and combined with the dichloromethane-extracted portion of the aqueous layer. The oil layer was concentrated under reduced pressure to remove the solvent and obtain an oil. Acetonitrile was added to the oil at room temperature to obtain 22 g of the target monomer MM2 as a white solid. The HPLC-area percent value of the obtained monomer MM2 measured under analysis conditions 2 was 98.8%.

$^1$H-NMR (600 MHz, CDCl$_3$) δ (ppm)=7.33 (s, 2H), 7.03 (d, 2H), 6.95 (d, 2H), 6.87 (s, 2H), 3.14 (s, 8H), 2.64 (m, 4H), 2.59 (t, 4H), 1.63 (m, 8H), 1.42 (m, 4H).

Example M3: Synthesis of Monomer MM3

Synthesis of monomer MM3 was accomplished as follows.

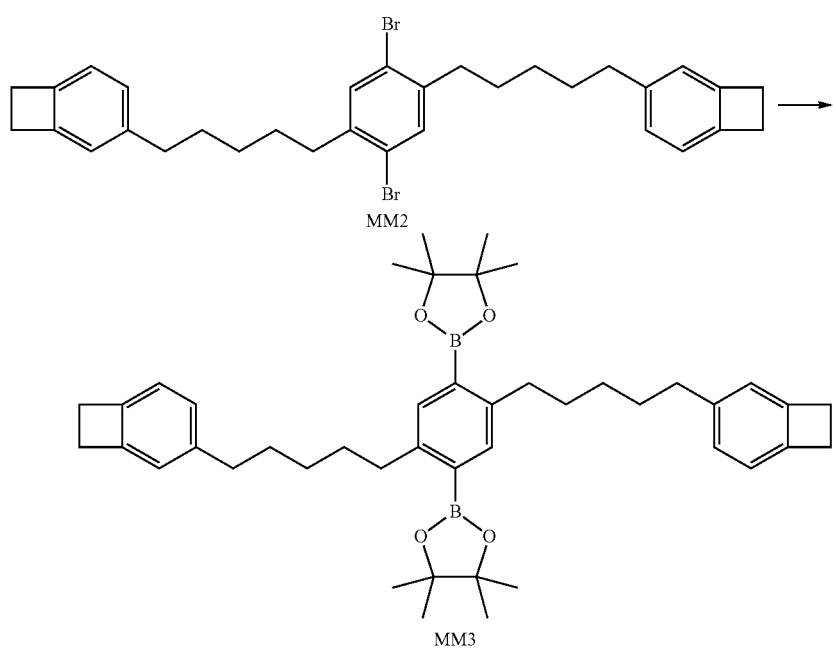

[Chemical Formula 168]

<Synthesis of Monomer MM3>

To a solution of monomer MM2 (17.1 g, 29.4 mmol) and bis(pinacolato)diboron (16.4 g, 64.6 mmol) dissolved in toluene (170 mL) under a nitrogen gas atmosphere and bubbled width nitrogen gas, there were added dichlororneethane 1,1% bis(diphenylphosphino)ferrocene]dichloropalladium(II) (Pd(dppf)Cl$_2$, 0.36 g, 0.44 mmol) and 1,1'-bis(diphenylphosphino)ferrocene (dppf, 0.25 g, 0.44 mmol), and the reaction solution was bubbled with nitrogen gas. Potassium acetate (17.3 g, 176.2 mmol) was added and reaction was conducted overnight at 110° C. The reaction solution was passed through a filter packed with silica gel/Fluorisil/Celite and dissolved in toluene, and a reaction mixture was obtained (22 g, HPLC-area percent value measured under, analysis conditions 2: 97.4%). Acetonitrile was added to the reaction mixture at room temperature and the mixture was stirred and filtered, and recrystallization was carried out with acetonitrile, toluene/acetonitrile and butyl acetate/acetonitrile to obtain 22 g of the target monomer. MM3. The HPLC-area percent value of the obtained monomer MM3 measured under analysis conditions 2 was 98.8%.

$^1$H-NMR (600 MHz, CDCl$_3$) δ (ppm)=7.54 (s, 2H), 7.01 (d, 2H), 6.95 (d, 2H), 6.89 (s, 2H), 3.14 (s, 8H), 2.83 (m, 4H), 2.57 (t, 4H), 1.63 (m, 4H), 1.57 (m, 4H), 1.42 (m, 4H), 1.33 (s, 24H).

Example 1: Synthesis of Polymer Compound 1

A mixture comprising monomer CM1 (1.7273 g), monomer CM10 (2.6836 g), monomer CM11 (0.2231 g) and toluene (73 ml) as a solvent was heated to about 80° C. under a nitrogen atmosphere, and then palladium acetate (0.77 mg), tris(2-methoxyphenyl)phosphine (4.90 mg) and a 20 wt % tetraethylammonium hydroxide aqueous solution (12.3 g) were added and the mixture was stirred for about 4 hours under reflux. Next, phenylboronic acid (85.6 mg), palladium acetate (0.72 mg), tris(2-methoxyphenyl)phosphine (4.89 mg) and a 20 wt % tetraethylammonium hydroxide aqueous solution (12.3 g) were added and the mixture was further stirred for about 19.5 hours under reflux. Next, a solution of sodium N,N-diethyldithiocarbamate trihydrate (0.98 g) dissolved in ion-exchanged water (20 ml) was added and the mixture was stirred for 2 hours while heating at 85° C. The organic layer was then rinsed twice with 3.6 wt % hydrochloric acid, twice with a 2.5 wt % ammonia water solution and 5 times with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 1 (2.907 g). The polystyrene-equivalent number-average molecular weight (Mn) and weight-average molecular weight (Mw) of the polymer compound 1 were Mn=1.9×10$^4$, Mw=9.9×10$^4$.

Polymer compound 1 is presumed to be a polymer compound having the following constitutional units and molar ratios based on the monomer charging ratios, with constitutional unit (PA) and a constitutional unit selected from among (PB) alternately polymerized.

[Chemical Formula 169]

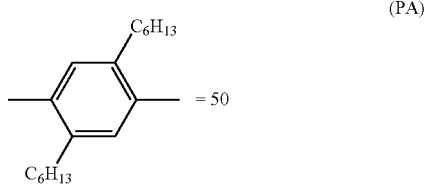
(PA)

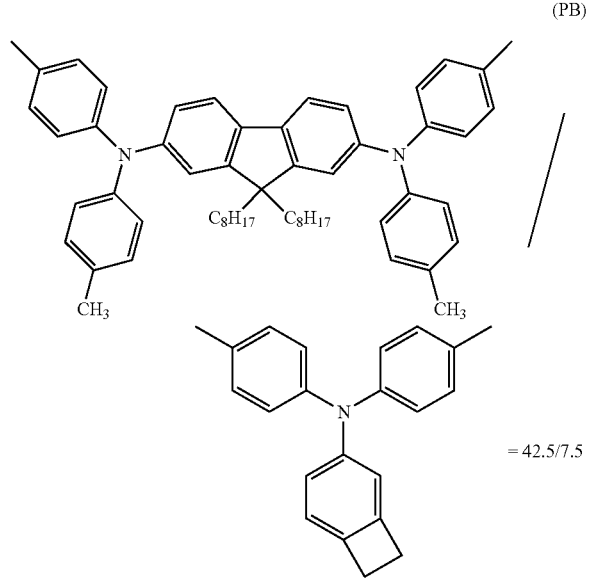
(PB)

= 42.5/7.5

The energy gap of polymer compound 1 was 3.01 eV, as calculated by the method described above.

Example 2: Synthesis of Polymer Compound 2

A mixture comprising monomer CM2 (1.4280 g), monomer CM10 (2.5001 g), monomer CM11 (0.2079 g) and toluene (63 ml) as a solvent was heated to about 80° C. under a nitrogen atmosphere, and then palladium acetate (1.11 mg), tris(2-methoxyphenyl)phosphine (6.91 mg) and a 20 wt % tetraethylammonium hydroxide aqueous solution (11.5 g) were added and the mixture was stirred for about 5.5 hours under reflux. Next, phenylboronic acid (39.7 mg), palladium acetate (1.16 mg), tris(2-methoxyphenyl)phosphine (6.94 mg) and a 20 wt % tetraethylammonium hydroxide aqueous solution (11.5 g) were added and the mixture was further stirred for about 17 hours under reflux. Next, a solution of sodium N,N-diethyldithiocarbamate trihydrate (1.40 g) dissolved in ion-exchanged water (28 ml) was added and the mixture was stirred for 2.5 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 2 (2.601 g). The polystyrene-equivalent number-average molecular weight (Mn) and weight-average molecular weight (Mw) of the polymer compound 2 were Mn=2.7×$10^4$, Mw=2.7×$10^5$, respectively.

Polymer compound 2 is presumed to be a polymer compound having the following constitutional units and molar ratios based on the monomer charging ratios, with constitutional unit (PA) and a constitutional unit selected from among (PB) alternately polymerized.

[Chemical Formula 170]

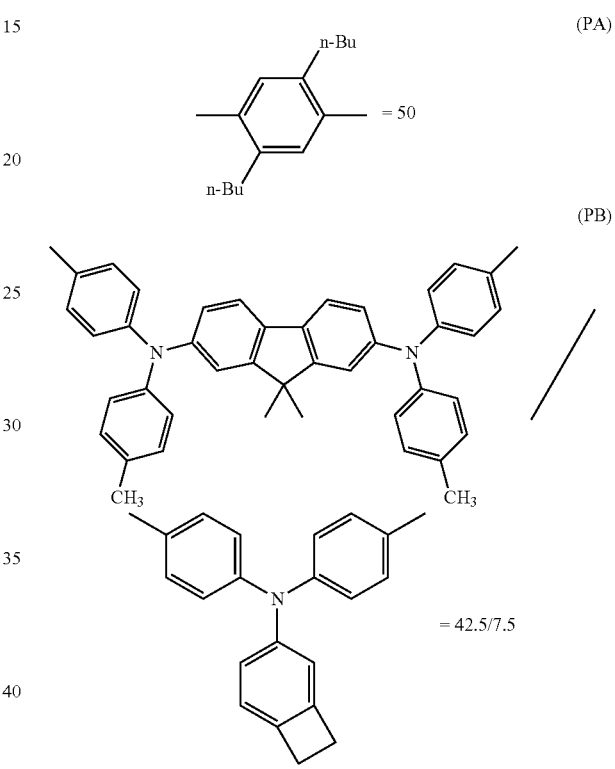

The energy gap of polymer compound 2 was 3.01 eV, as calculated by the method described above.

Example 3: Synthesis of Polymer Compound 3

A mixture comprising monomer CM1 (0.8534 g), monomer CM3 (0.7051 g), monomer CM10 (2.6361 g), monomer CM11 (0.2192 g) and toluene (67 ml) as a solvent was heated to about 80° C. under a nitrogen atmosphere, and then palladium acetate (1.20 mg), tris(2-methoxyphenyl)phosphine (7.21 mg) and a 20 wt % tetraethylammonium hydroxide aqueous solution (12.1 g) were added and the mixture was stirred for about 6 hours under reflux. Next, phenylboronic acid (42.0 mg), palladium acetate (1.17 mg), tris(2-methoxyphenyl)phosphine (7.33 mg) and a 20 wt % tetraethylammonium hydroxide aqueous solution (12.1 g) were added and the mixture was further stirred for about 16 hours under reflux. Next, a solution of sodium N,N-diethyldithiocarbamate trihydrate (1.53 g) dissolved in ion-exchanged water (30 ml) was added and the mixture was stirred for 2 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 3 (2.689 g). The polystyrene-equivalent number-average molecular weight (Mn) and weight-average molecular weight (Mw) of the polymer compound 3 were Mn=$2.3 \times 10^4$, Mw=$2.0 \times 10^5$, respectively.

Polymer compound 3 is presumed to be a polymer compound having the following constitutional units and molar ratios based on the monomer charging ratios, with constitutional unit (PA) and a constitutional unit selected from among (PB) alternately polymerized.

[Chemical Formula 171]

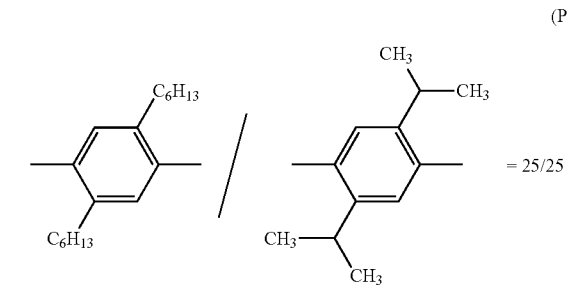

The energy gap of polymer compound 3 was 3.01 eV, as calculated by the method described above.

Example 4: Synthesis of Polymer Compound 4

A mixture comprising monomer CM1 (1.0465 g), monomer CM4 (0.4817 g), monomer CM10 (2.7100 g), monomer CM11 (0.2253 g) and toluene (83 ml) as a solvent was heated to about 80° C. under a nitrogen atmosphere, and then bistriphenylphosphinepalladium dichloride (2.43 mg) and a 20 wt % tetraethylammonium hydroxide aqueous solution (12.1 g) were added and the mixture was stirred for about 30 hours under reflux. Next, phenylboronic acid (42.5 mg) and bistriphenylphosphinepalladium dichloride (2.45 mg) and a 20 wt % tetraethylammonium hydroxide aqueous solution (12.1 g) were added and the mixture was further stirred for about 17.5 hours under reflux. Next, a solution of sodium N,N-diethyldithiocarbamate trihydrate (1.94 g) dissolved in ion-exchanged water (39 ml) was added and the mixture was stirred for 3 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 4 (2.62 g). The polystyrene-equivalent number-average molecular weight (Mn) and weight-average molecular weight (Mw) of the polymer compound 4 were Mn=$1.3 \times 10^4$, Mw=$5.2 \times 10^4$.

Polymer compound 4 is presumed to be a polymer compound having the following constitutional units and molar ratios based on the monomer charging ratios, with constitutional unit (PA) and a constitutional unit selected from among (PB) alternately polymerized.

[Chemical Formula 172]

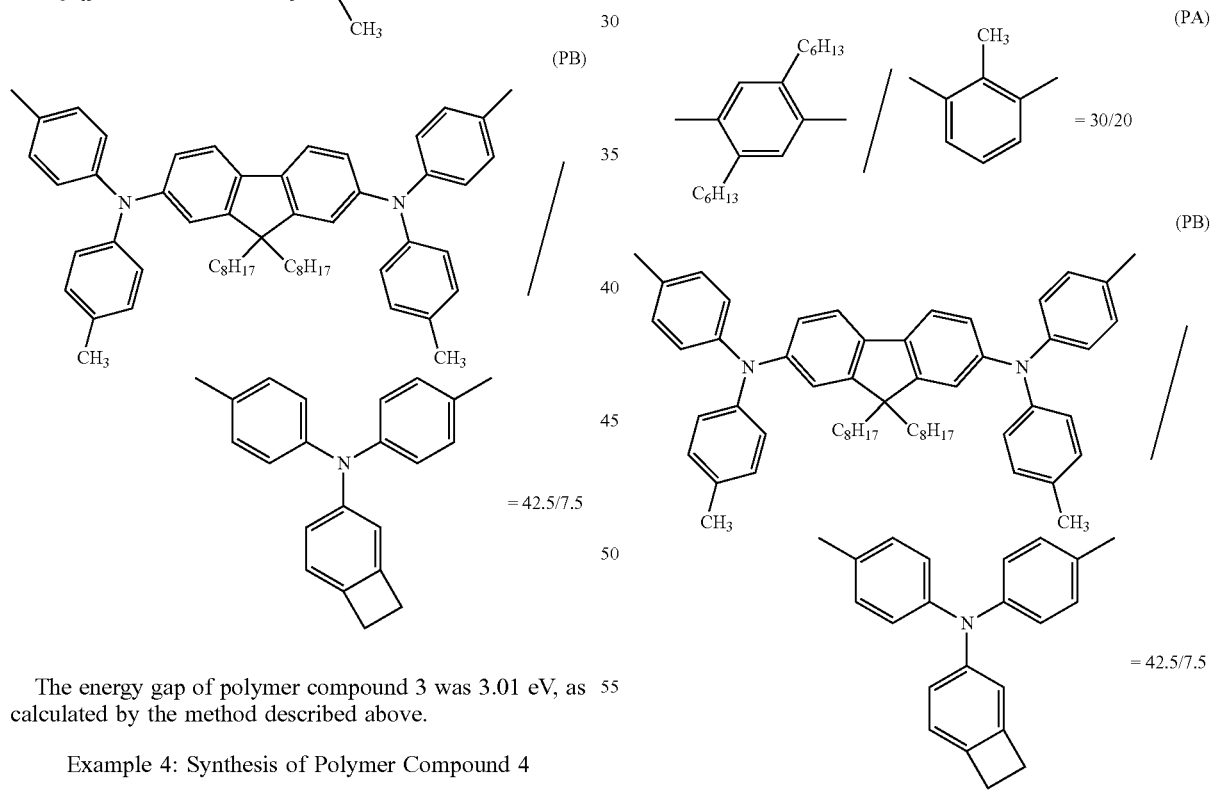

The energy gap of polymer compound 4 was 3.01 eV, as calculated by the method described above.

Example 5: Synthesis of Polymer Compound 5

A mixture comprising monomer CM1 (1.4951 g), monomer CM12 (3.4363 g), monomer CM11 (0.1931 g) and toluene (33 ml) as a solvent was heated to about 80° C. under a nitrogen atmosphere, and then bistriphenylphosphinepalladium dichloride (2.17 mg) and a 20 wt % tetraethylammonium hydroxide aqueous solution (10.4 g) were added and the mixture was stirred for about 48 hours under reflux. Next, phenylboronic acid (0.3671 g), bistriphenylphosphinepalladium dichloride (2.12 mg) and a 20 wt % tetraethylammonium hydroxide aqueous solution (10.4 g) were added and the mixture was further stirred for about 23 hours under reflux. Next, a solution of sodium N,N-diethyldithiocarbamate trihydrate (1.83 g) dissolved in ion-exchanged water (33 ml) was added and the mixture was stirred for 2.5 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 5 (3.349 g). The polystyrene-equivalent number-average molecular weight (Mn) and weight-average molecular weight (Mw) of the polymer compound 5 were $Mn=2.6\times10^4$, $Mw=4.4\times10^4$.

Polymer compound 5 is presumed to be a polymer compound having the following constitutional units and molar ratios based on the monomer charging ratios, with constitutional unit (PA) and a constitutional unit selected from among (PB) alternately polymerized.

[Chemical Formula 173]

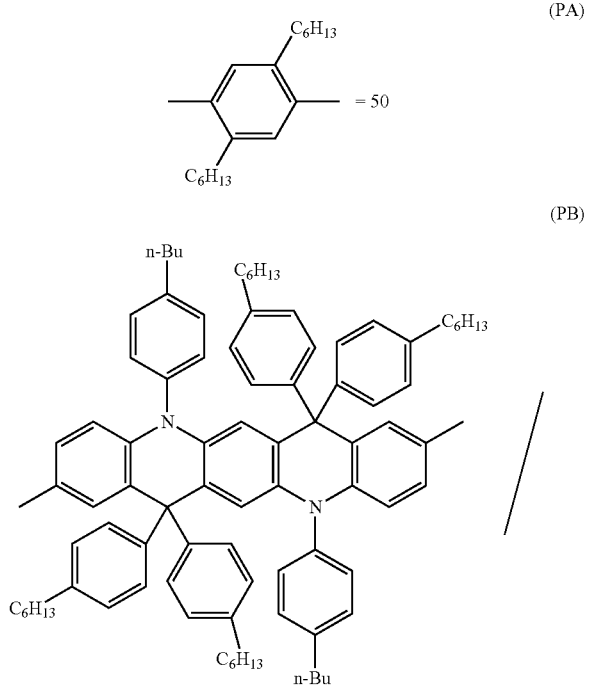

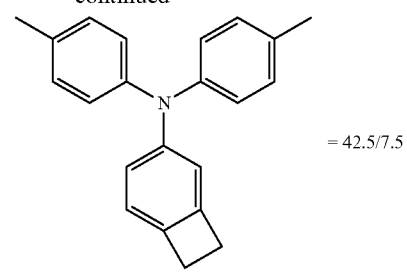

The energy gap of polymer compound 5 was 3.14 eV, as calculated by the method described above.

Example 6: Synthesis of Polymer Compound 9

A mixture of monomer CM1 (3.7376 g), monomer CM10 (5.8070 g), monomer CM22 (0.5943 g) and toluene (182 ml) as a solvent was heated to about 80° C. under a nitrogen atmosphere, and then dichlorobis(tris(2-methoxyphenyl)phosphine)palladium (6.62 mg) and a 20 wt % tetraethylammonium hydroxide aqueous solution (26.0 g) were added and the mixture was stirred for about 7.5 hours under reflux. Next, phenylboronic acid (91.4 mg), dichlorobis(tris(2-methoxyphenyl)phosphine)palladium (6.62 mg) and a 20 wt % tetraethylammonium hydroxide aqueous solution (26.0 g) were added and the mixture was further stirred for about 15 hours under reflux. Next, a solution of sodium N,N-diethyldithiocarbamate trihydrate (4.17 g) dissolved in ion-exchanged water (84 ml) was added and the mixture was stirred for 2 hours while heating at 85° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 9 (6.34 g). The polystyrene-equivalent number-average molecular weight (Mn) and weight-average molecular weight (Mw) of the polymer compound 9 were $Mn=5.5\times10^4$, $Mw=1.4\times10^5$, respectively.

Polymer compound 9 is presumed to be a polymer compound having the following constitutional units and molar ratios based on the monomer charging ratios, with constitutional unit (PA) and a constitutional unit selected from among (PB) alternately polymerized.

[Chemical Formula 174]

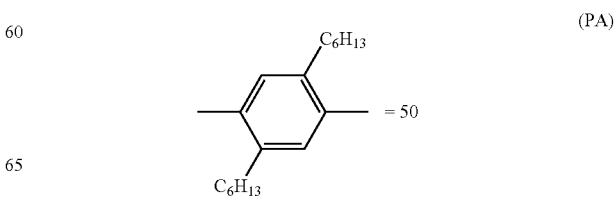

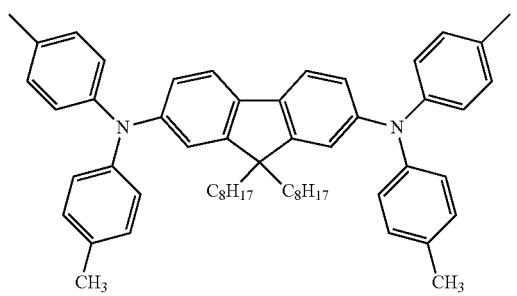

(PB)

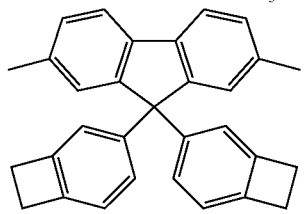

= 42.5/7.5

The energy gap of polymer compound 9 was 3.01 eV, as calculated by the method described above.

Example 7: Synthesis of Polymer Compound 10

A mixture of monomer CM1 (0.9967 g), monomer CM10 (1.4574 g), monomer CM22 (0.1057 g), monomer CM23 (0.0920 g) and toluene (47 ml) as a solvent was heated to about 80° C. under a nitrogen atmosphere, and then dichlorobis(tris(2-methoxyphenyl)phosphine)palladium (1.76 mg) and a 20 wt % tetraethylammonium hydroxide aqueous solution (7.5 g) were added and the mixture was stirred for about 23 hours under reflux. Next, phenylboronic acid (26.6 mg), dichlorobis(tris(2-methoxyphenyl)phosphine)palladium (1.76 mg) and a 20 wt % tetraethylammonium hydroxide aqueous solution (7.5 g) were added and the mixture was further stirred for about 23 hours under reflux. Next, a solution of sodium N,N-diethyldithiocarbamate trihydrate (1.11 g) dissolved in ion-exchanged water (22 ml) was added and the mixture was stirred for 3 hours while heating at 85° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 10 (1.46 g). The polystyrene-equivalent number-average molecular weight (Mn) and weight-average molecular weight (Mw) of the polymer compound 10 were Mn=$1.7 \times 10^4$, Mw=$1.0 \times 10^5$, respectively.

Polymer compound 10 is presumed to be a polymer compound having the following constitutional units and molar ratios based on the monomer charging ratios, with constitutional unit (PA) and a constitutional unit selected from among (PB) alternately polymerized.

[Chemical Formula 175]

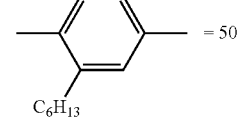

= 50

(PA)

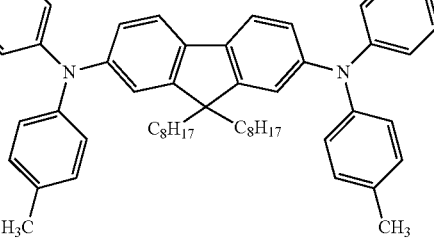

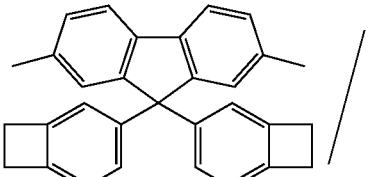

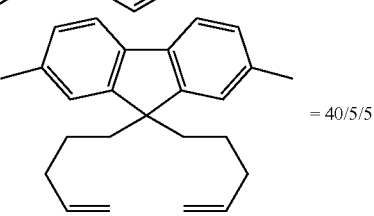

= 40/5/5

(PB)

The energy gap of polymer compound 10 was 3.01 eV, as calculated by the method described above.

Example 8: Synthesis of Polymer Compound 11

A mixture of monomer CM21 (0.8564 g), monomer CM10 (1.5485 g), monomer CM22 (0.1585 g) and toluene (47 ml) as a solvent was heated to about 80° C. under a nitrogen atmosphere, and then dichlorobis(tris(2-methoxyphenyl)phosphine)palladium (1.78 mg) and a 20 wt % tetraethylammonium hydroxide aqueous solution (7.8 g) were added and the mixture was stirred for about 7.5 hours under reflux. Next, phenylboronic acid (26.5 mg), dichlorobis(tris(2-methoxyphenyl)phosphine)palladium (1.77 mg) and a 20 wt % tetraethylammonium hydroxide aqueous solution (7.8 g) were added and the mixture was further stirred for about 15 hours under reflux. Next, a solution of sodium N,N-diethyldithiocarbamate trihydrate (1.11 g) dissolved in ion-exchanged water (22 ml) was added and the mixture was stirred for 1.5 hours while heating at 85° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 11 (1.30 g). The polystyrene-equivalent number-average molecular weight (Mn) and weight-average molecular weight (Mw) of the polymer compound 11 were Mn=$8.4\times10^4$, Mw=$1.6\times10^4$.

Polymer compound 11 is presumed to be a polymer compound having the following constitutional units and molar ratios based on the monomer charging ratios, with constitutional unit (PA) and a constitutional unit selected from among (PB) alternately polymerized.

[Chemical Formula 176]

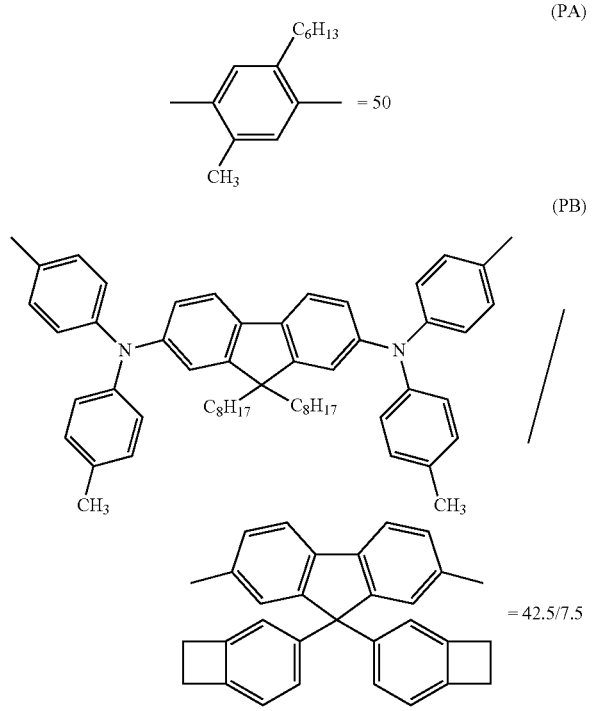

The energy gap of polymer compound 11 was 3.00 eV, as calculated by the method described above.

Example 9: Synthesis of Polymer Compound 12

A mixture comprising monomer CM1 (0.9967 g), monomer CM13 (0.8189 g), monomer CM9 (0.2578 g), monomer CM23 (0.0920 g), monomer CM24 (0.1337 g) and toluene (44 ml) as a solvent was heated to about 80° C. under a nitrogen atmosphere, and then palladium acetate (0.3 mg), tris(2-methoxyphenyl)phosphine (3.0 mg) and a 20 wt % tetraethylammonium hydroxide aqueous solution (8.8 g) were added and the mixture was stirred for about 18 hours under reflux. Next, phenylboronic acid (0.25 g), palladium acetate (0.5 mg) and tris(2-methoxyphenyl)phosphine (3.0 mg) were added and the mixture was stirred for about 4 hours under reflux. Bromobenzene (0.45 g) was further added and the mixture was stirred for about 4 hours under reflux. Next, a solution of sodium N,N-diethyldithiocarbamate trihydrate (1.1 g) dissolved in ion-exchanged water (22 ml) was added and the mixture was stirred for 6 hours while heating at 85° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 12 (1.030 g). The polystyrene-equivalent number-average molecular weight (Mn) and weight-average molecular weight (Mw) of the polymer compound 12 were Mn=$8.8\times10^4$, Mw=$3.0\times10^5$, respectively.

Polymer compound 12 is presumed to be a polymer compound having the following constitutional units and molar ratios based on the monomer charging ratios, with constitutional unit (PA) and a constitutional unit selected from among (PB) alternately polymerized.

[Chemical Formula 177]

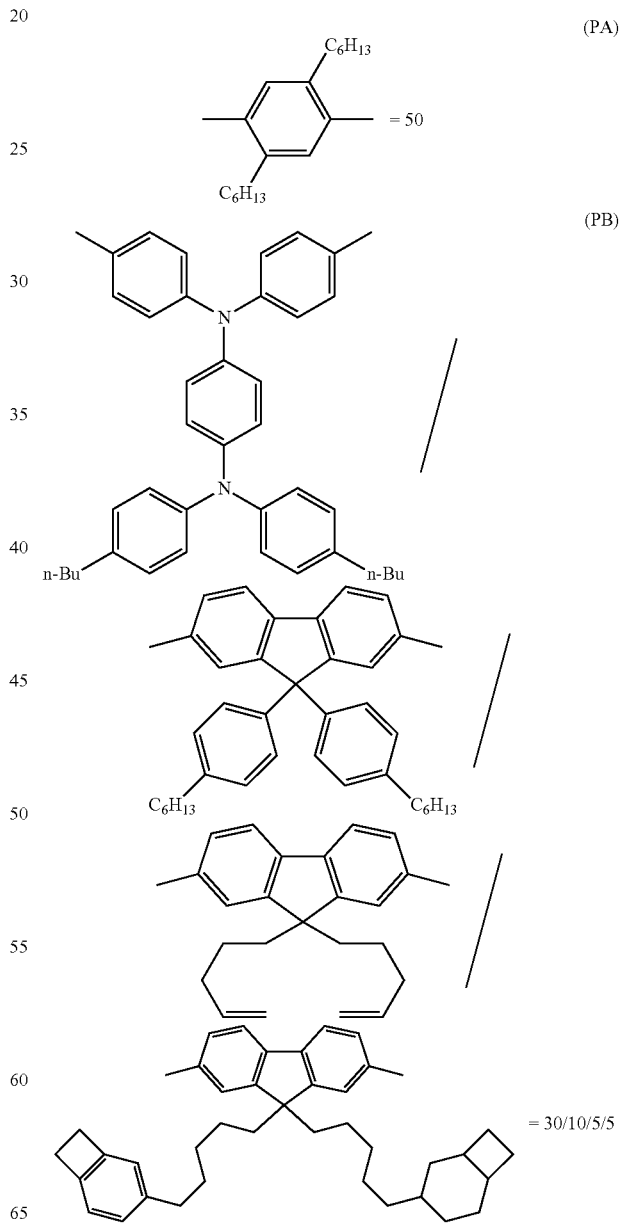

The energy gap of polymer compound 12 was 3.12 eV, as calculated by the method described above.

Example 10: Synthesis of Polymer Compound 13

A mixture comprising monomer CM19 (1.4924 g), monomer CM10 (1.6539 g), monomer CM11 (0.1375 g) and toluene (57 ml) as a solvent was heated to about 80° C. under a nitrogen atmosphere, and then palladium acetate (0.80 mg), tris(2-methoxyphenyl)phosphine (4.57 mg) and a 20 wt % tetraethylammonium hydroxide aqueous solution (7.7 g) were added and the mixture was stirred for about 6 hours under reflux. Next, phenylboronic acid (26.3 mg), palladium acetate (0.82 mg), tris(2-methoxyphenyl)phosphine (4.58 mg) and a 20 wt % tetraethylammonium hydroxide aqueous solution (7.7 g) were added and the mixture was further stirred for about 14.5 hours under reflux. Next, a solution of sodium N,N-diethyldithiocarbamate trihydrate (1.21 g) dissolved in ion-exchanged water (24 ml) was added and the mixture was stirred for 2 hours while heating at 85° C. The organic layer was then rinsed twice with ion-exchanged water, twice with 3 wt % acetic acid and three times with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 13 (2.148 g). The polystyrene-equivalent number-average molecular weight (Mn) and weight-average molecular weight (Mw) of the polymer compound 13 were Mn=4.2×10$^4$, Mw=2.9×10$^5$, respectively.

Polymer compound 13 is presumed to be a polymer compound having the following constitutional units and molar ratios based on the monomer charging ratios, with constitutional unit (PA) and a constitutional unit selected from among (PB) alternately polymerized.

[Chemical Formula 178]

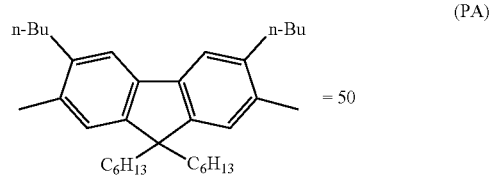
(PA)

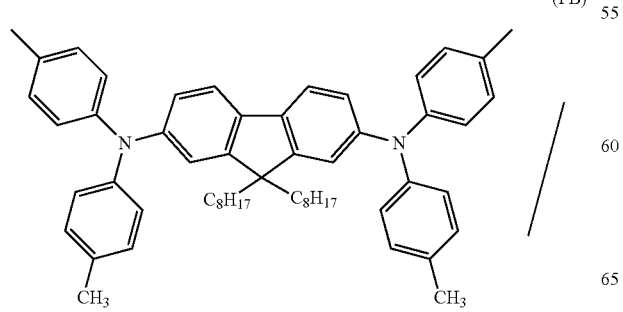
(PB)

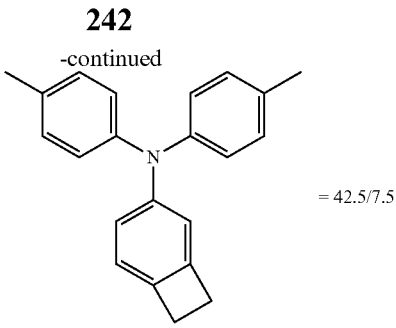
= 42.5/7.5

The energy gap of polymer compound 13 was 2.99 eV, as calculated by the method described above.

Example 11: Synthesis of Polymer Compound 14

A mixture of monomer CM20 (1.4093 g), monomer CM10 (1.4574 g), monomer CM22 (0.1057 g), monomer CM23 (0.0920 g) and toluene (58 ml) as a solvent was heated to about 80° C. under a nitrogen atmosphere, and then dichlorobis(tris(2-methoxyphenyl)phosphine)palladium (3.53 mg) and a 20 wt % tetraethylammonium hydroxide aqueous solution (6.29 g) were added and the mixture was stirred for about 4.5 hours under reflux. Next, phenylboronic acid (24.4 mg), dichlorobis(tris(2-methoxyphenyl)phosphine)palladium (1.76 mg) and a 20 wt % tetraethylammonium hydroxide aqueous solution (6.29 g) were added and the mixture was further stirred for about 18 hours under reflux. Next, a solution of sodium N,N-diethyldithiocarbamate trihydrate (1.11 g) dissolved in ion-exchanged water (27 ml) was added and the mixture was stirred for 2 hours while heating at 85° C.

The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 14 (1.77 g). The polystyrene-equivalent number-average molecular weight (Mn) and weight-average molecular weight (Mw) of the polymer compound 14 were Mn=4.7×10$^4$, Mw=2.8×10$^5$, respectively.

Polymer compound 14 is presumed to be a polymer compound having the following constitutional units and molar ratios based on the monomer charging ratios, with constitutional unit (PA) and a constitutional unit selected from among (PB) alternately polymerized.

[Chemical Formula 179]

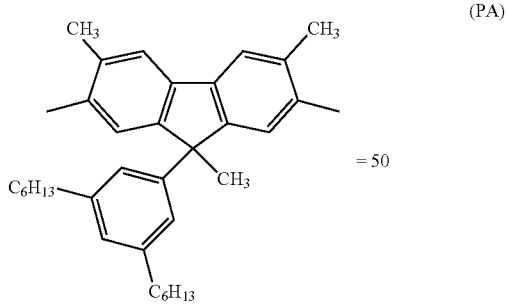
(PA)
= 50

-continued

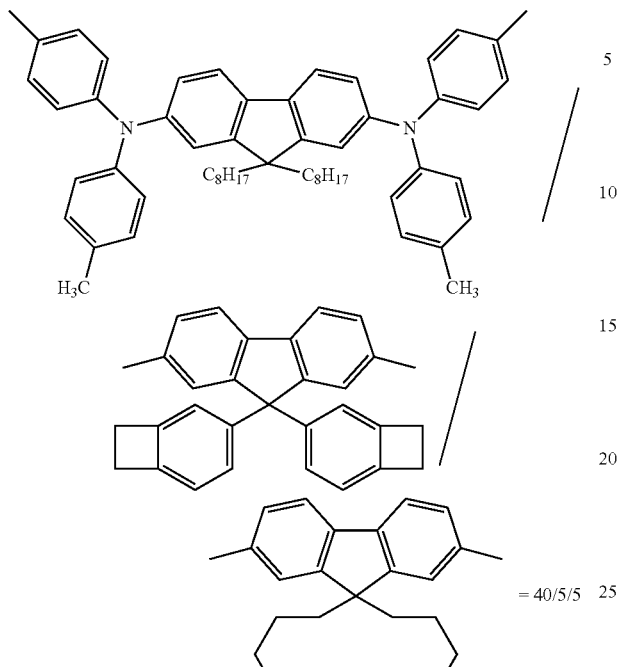
(PB)
= 40/5/5

The energy gap of polymer compound 14 was 2.97 eV, as calculated by the method described above.

Example 12: Synthesis of Polymer Compound 15

A mixture of monomer CM1 (0.9967 g), monomer CM18 (1.7587 g), monomer CM22 (0.1057 g), monomer CM23 (0.0920 g) and toluene (55 ml) as a solvent was heated to about 80° C. under a nitrogen atmosphere, and then dichlorobis(tris(2-methoxyphenyl)phosphine)palladium (1.77 mg) and a 20 wt % tetraethylammonium hydroxide aqueous solution (7.5 g) were added and the mixture was stirred for about 6 hours under reflux.

Next, phenylboronic acid (26.1 mg), dichlorobis(tris(2-methoxyphenyl)phosphine)palladium (1.76 mg) and a 20 wt % tetraethylammonium hydroxide aqueous solution (7.5 g) were added and the mixture was further stirred for about 15 hours under reflux. Next, a solution of sodium N,N-diethyldithiocarbamate trihydrate (1.11 g) dissolved in ion-exchanged water (26 ml) was added and the mixture was stirred for 2 hours while heating at 85° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 15 (1.57 g). The polystyrene-equivalent number-average molecular weight (Mn) and weight-average molecular weight (Mw) of the polymer compound 15 were Mn=3.5×$10^4$, Mw=2.8×$10^5$, respectively.

Polymer compound 15 is presumed to be a polymer compound having the following constitutional units and molar ratios based on the monomer charging ratios, with constitutional unit (PA) and a constitutional unit selected from among (PB) alternately polymerized.

[Chemical Formula 180]

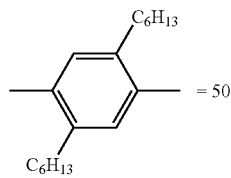
(PA)
= 50

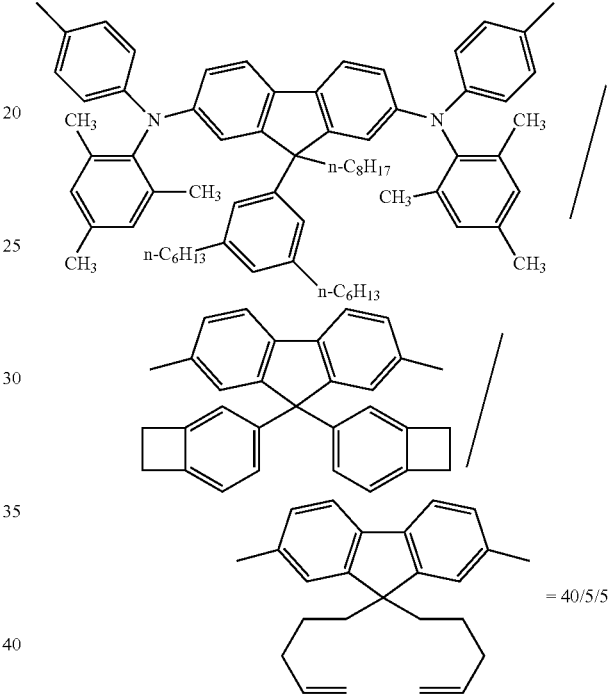
(PB)
= 40/5/5

The energy gap of polymer compound 15 was 3.04 eV, as calculated by the method described above.

Example 13: Synthesis of Polymer Compound 16

A mixture of monomer CM20 (1.4093 g), monomer CM18 (1.7587 g), monomer CM22 (0.1057 g), monomer CM23 (0.0920 g) and toluene (45 ml) as a solvent was heated to about 80° C. under a nitrogen atmosphere, and then dichlorobis(tris(2-methoxyphenyl)phosphine)palladium (1.81 mg) and a 20 wt % tetraethylammonium hydroxide aqueous solution (7.3 g) were added and the mixture was stirred for about 9 hours under reflux. Next, phenylboronic acid (24.6 mg), dichlorobis(tris(2-methoxyphenyl)phosphine)palladium (1.74 mg) and a 20 wt % tetraethylammonium hydroxide aqueous solution (7.4 g) were added and the mixture was further stirred for about 13.5 hours under reflux. Next, a solution of sodium N,N-diethyldithiocarbamate trihydrate (1.11 g) dissolved in ion-exchanged water (31 ml) was added and the mixture was stirred for 2 hours while heating at 85° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 16 (1.92 g). The polystyrene-equivalent number-average molecular weight (Mn) and weight-average molecular weight (Mw) of the polymer compound 16 were Mn=$6.4\times10^4$, Mw=$2.9\times10^5$, respectively.

Polymer compound 16 is presumed to be a polymer compound having the following constitutional units and molar ratios based on the monomer charging ratios, with constitutional unit (PA) and a constitutional unit selected from among (PB) alternately polymerized.

[Chemical Formula 181]

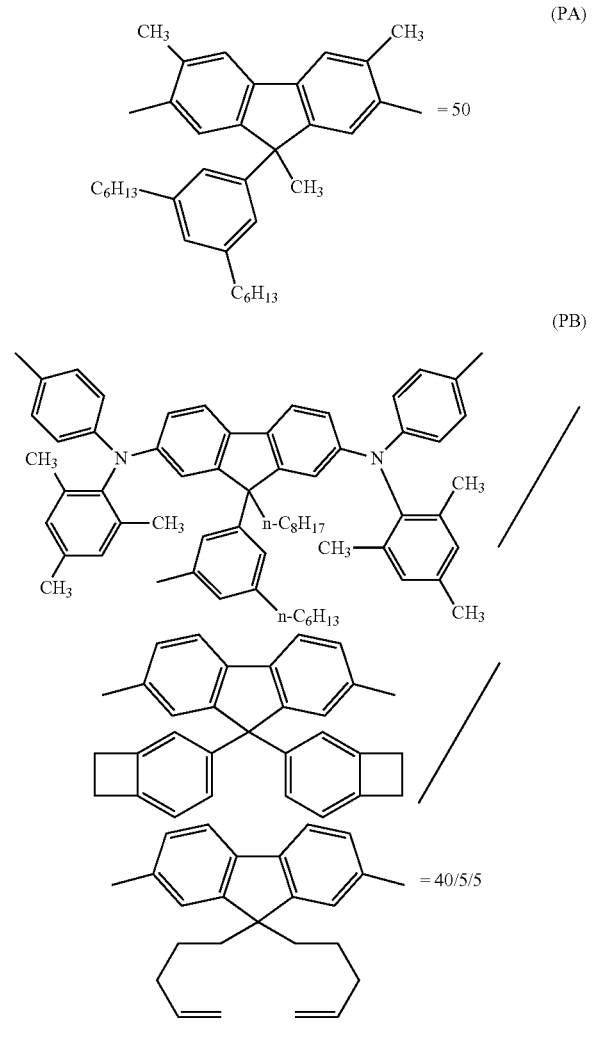

The energy gap of polymer compound 16 was 2.97 eV, as calculated by the method described above.

Example 14: Synthesis of Polymer Compound 17

A mixture of monomer CM1 (1.0148 g), monomer CM18 (1.7588 g), monomer CM22 (0.2114 g) and toluene (55 ml) as a solvent was heated to about 80° C. under a nitrogen atmosphere, and then dichlorobis(tris(2-methoxyphenyl) phosphine)palladium (7.09 mg) and a 20 wt % tetraethylammonium hydroxide aqueous solution (6.9 g) were added and the mixture was stirred for about 9 hours under reflux. Next, phenylboronic acid (24.5 mg), dichlorobis(tris(2-methoxyphenyl)phosphine)palladium (1.76 mg) and a 20 wt % tetraethylammonium hydroxide aqueous solution (6.9 g) were added and the mixture was further stirred for about 12 hours under reflux. Next, a solution of sodium N,N-diethyldithiocarbamate trihydrate (1.11 g) dissolved in ion-exchanged water (26 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 17 (1.64 g). The polystyrene-equivalent number-average molecular weight (Mn) and weight-average molecular weight (Mw) of the polymer compound 17 were Mn=$4.0\times10^4$, Mw=$2.5\times10^5$, respectively.

Polymer compound 17 is presumed to be a polymer compound having the following constitutional units and molar ratios based on the monomer charging ratios, with constitutional unit (PA) and a constitutional unit selected from among (PB) alternately polymerized.

[Chemical Formula 182]

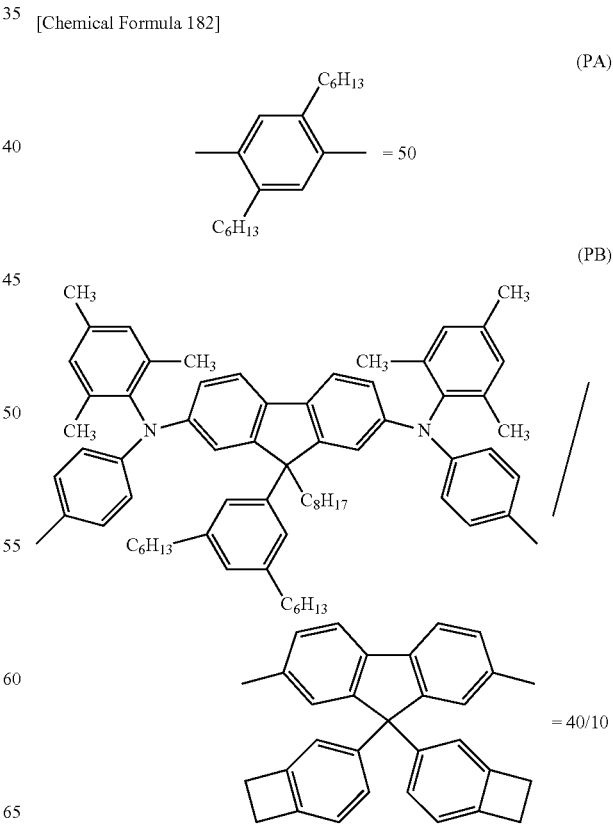

The energy gap of polymer compound 17 was 3.04 eV, as calculated by the method described above.

Example 15: Synthesis of Polymer Compound 18

A mixture of monomer CM20 (1.0661 g), monomer CM10 (1.1614 g), monomer CM22 (0.1189 g) and toluene (50 ml) as a solvent was heated to about 80° C. under a nitrogen atmosphere, and then dichlorobis(tris(2-methoxyphenyl)phosphine)palladium (1.33 mg) and a 20 wt % tetraethylammonium hydroxide aqueous solution (5.4 g) were added and the mixture was stirred for about 7 hours under reflux. Next, phenylboronic acid (18.4 mg), dichlorobis(tris(2-methoxyphenyl)phosphine)palladium (1.32 mg) and a 20 wt % tetraethylammonium hydroxide aqueous solution (5.4 g) were added and the mixture was further stirred for about 12 hours under reflux. Next, a solution of sodium N,N-diethyldithiocarbamate trihydrate (0.90 g) dissolved in ion-exchanged water (22 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 18 (1.16 g). The polystyrene-equivalent number-average molecular weight (Mn) and weight-average molecular weight (Mw) of the polymer compound 18 were Mn=4.4×10$^4$, Mw=3.2×10$^5$, respectively.

Polymer compound 18 is presumed to be a polymer compound having the following constitutional units and molar ratios based on the monomer charging ratios, with constitutional unit (PA) and a constitutional unit selected from among (PB) alternately polymerized.

[Chemical Formula 183]

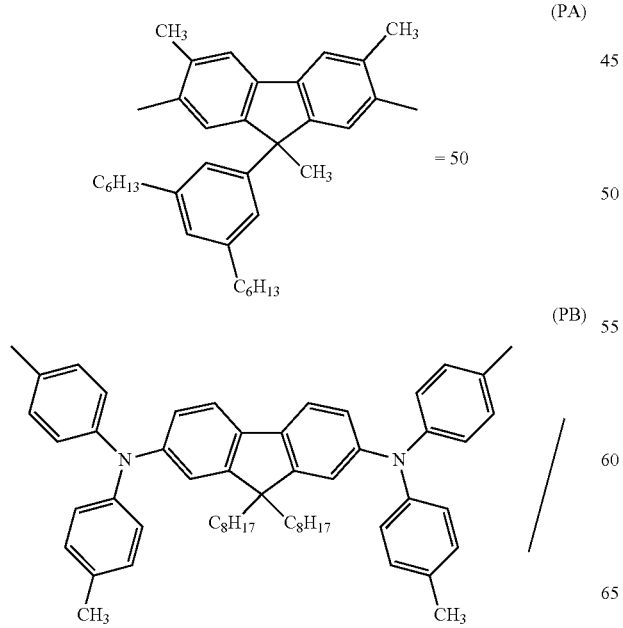

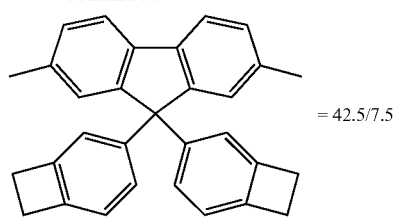

The energy gap of polymer compound 18 was 2.97 eV, as calculated by the method described above.

Example 16: Synthesis of Polymer Compound 19

A mixture of monomer CM1 (1.4953 g), monomer CM25 (1.9554 g), monomer CM22 (0.1585 g), monomer CM23 (0.1381 g) and toluene (73 ml) as a solvent was heated to about 80° C. under a nitrogen atmosphere, and then dichlorobis(tris(2-methoxyphenyl)phosphine)palladium (2.60 mg) and a 20 wt % tetraethylammonium hydroxide aqueous solution (10 g) were added and the mixture was stirred for about 4 hours under reflux. Next, phenylboronic acid (36.6 mg), dichlorobis(tris(2-methoxyphenyl)phosphine)palladium (2.60 mg) and a 20 wt % tetraethylammonium hydroxide aqueous solution (10 g) were added and the mixture was further stirred for about 14 hours under reflux. Next, a solution of sodium N,N-diethyldithiocarbamate trihydrate (1.67 g) dissolved in ion-exchanged water (33 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 19 (1.74 g). The polystyrene-equivalent number-average molecular weight (Mn) and weight-average molecular weight (Mw) of the polymer compound 19 were Mn=5.0×10$^4$, Mw=2.3×10$^5$, respectively.

Polymer compound 19 is presumed to be a polymer compound having the following constitutional units and molar ratios based on the monomer charging ratios, with constitutional unit (PA) and a constitutional unit selected from among (PB) alternately polymerized.

[Chemical Formula 184]

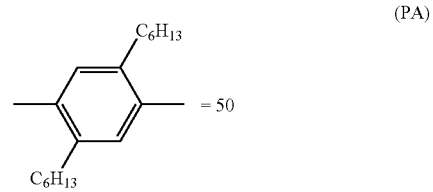

-continued

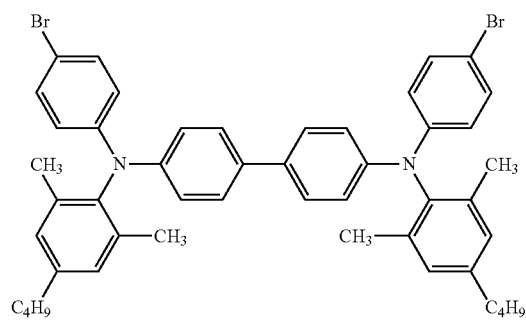

(PB)

= 40/5/5

The energy gap of polymer compound 19 was 3.08 eV, as calculated by the method described above.

Example 17: Synthesis of Polymer Compound 20

A mixture of monomer CM1 (1.4801 g), monomer CM26 (1.9074 g), monomer CM22 (0.1585 g), monomer CM23 (0.1381 g) and toluene (73 ml) as a solvent was heated to about 80° C. under a nitrogen atmosphere, and then dichlorobis(tris(2-methoxyphenyl)phosphine)palladium (2.60 mg) and a 20 wt % tetraethylammonium hydroxide aqueous solution (10 g) were added and the mixture was stirred for about 4 hours under reflux. Next, phenylboronic acid (36.6 mg), dichlorobis(tris(2-methoxyphenyl)phosphine)palladium (2.60 mg) and a 20 wt % tetraethylammonium hydroxide aqueous solution (10 g) were added and the mixture was further stirred for about 14 hours under reflux. Next, a solution of sodium N,N-diethyldithiocarbamate trihydrate (1.67 g) dissolved in ion-exchanged water (33 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 20 (1.92 g). The polystyrene-equivalent number-average molecular weight (Mn) and weight-average molecular weight (Mw) of the polymer compound 20 were Mn=4.9×10$^4$, Mw=7.4×10$^5$, respectively.

Polymer compound 20 is presumed to be a polymer compound having the following constitutional units and molar ratios based on the monomer charging ratios, with constitutional unit (PA) and a constitutional unit selected from among (PB) alternately polymerized.

[Chemical Formula 185]

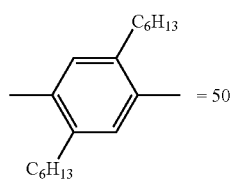

(PA)

= 50

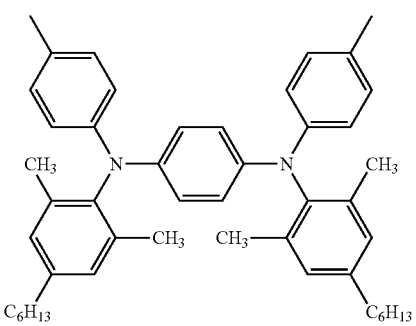

(PB)

= 40/5/5

The energy gap of polymer compound 20 was 3.13 eV, as calculated by the method described above.

Example 18: Synthesis of Polymer Compound 21

A mixture of monomer CM1 (1.7941 g), monomer CM27 (0.2215 g), monomer MM3 (0.3036 g), monomer CM18 (4.9464 g) and toluene (110 ml) as a solvent was heated to about 80° C. under a nitrogen atmosphere, and then dichlorobis(tris(2-methoxyphenyl)phosphine)palladium (4.00 mg) and a 20 wt % tetraethylammonium hydroxide aqueous solution (15 g) were added and the mixture was stirred for about 4 hours under reflux. Next, phenylboronic acid (54.9 mg), dichlorobis(tris(2-methoxyphenyl)phosphine)palladium (4.00 mg) and a 20 wt % tetraethylammonium hydroxide aqueous solution (15 g) were added and the mixture was further stirred for about 14 hours under reflux. Next, a solution of sodium N,N-diethyldithiocarbamate trihydrate (2.50 g) dissolved in ion-exchanged water (50 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 21 (3.32 g). The polystyrene-equivalent number-average molecular weight (Mn) and weight-average molecular weight (Mw) of polymer compound 21 were Mn=$3.3 \times 10^4$, Mw=$2.6 \times 10^5$, respectively.

Polymer compound 21 is presumed to be a polymer compound having the following constitutional units and molar ratios based on the monomer charging ratios, with constitutional unit (PA) and a constitutional unit selected from among (PB) alternately polymerized.

[Chemical Formula 186]

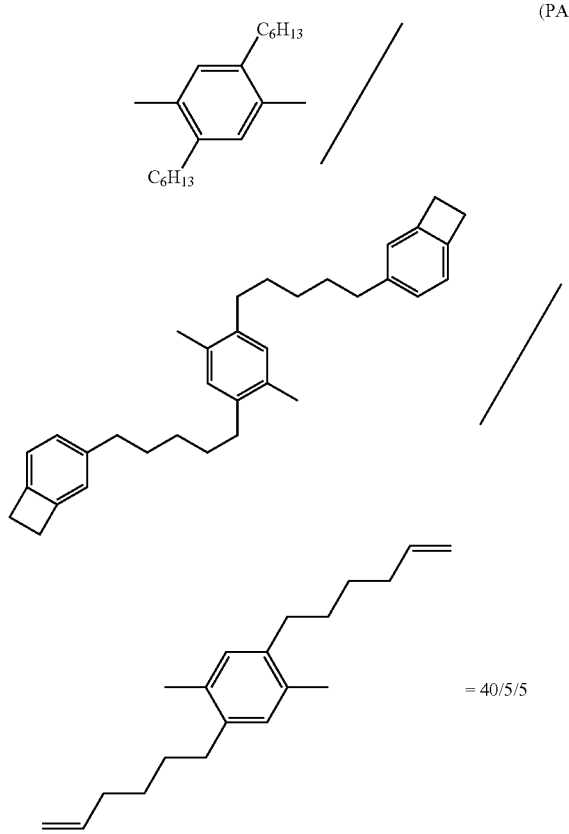

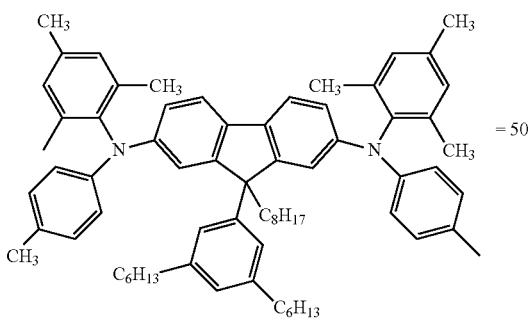

The energy gap of polymer compound 21 was 3.04 eV, as calculated by the method described above.

Example 19: Synthesis of Polymer Compound 22

A mixture of monomer CM1 (1.4951 g), monomer CM18 (2.6381 g), monomer MM1 (0.3261 g), monomer CM23 (0.1381 g) and toluene (73 ml) as a solvent was heated to about 80° C. under a nitrogen atmosphere, and then dichlorobis(tris(2-methoxyphenyl)phosphine)palladium (2.60 mg) and a 20 wt % tetraethylammonium hydroxide aqueous solution (10 g) were added and the mixture was stirred for about 4 hours under reflux. Next, phenylboronic acid (36.6 mg), dichlorobis(tris(2-methoxyphenyl)phosphine)palladium (2.60 mg) and a 20 wt % tetraethylammonium hydroxide aqueous solution (10 g) were added and the mixture was further stirred for about 14 hours under reflux. Next, a solution of sodium N,N-diethyldithiocarbamate trihydrate (1.67 g) dissolved in ion-exchanged water (33 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 22 (2.87 g). The polystyrene-equivalent number-average molecular weight (Mn) and weight-average molecular weight (Mw) of the polymer compound 22 were Mn=$3.8 \times 10^4$, Mw=$3.5 \times 10^5$, respectively.

Polymer compound 22 is presumed to be a polymer compound having the following constitutional units and molar ratios based on the monomer charging ratios, with constitutional unit (PA) and a constitutional unit selected from among (PB) alternately polymerized.

[Chemical Formula 187]

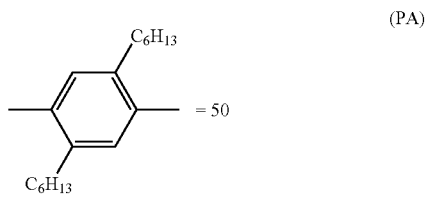

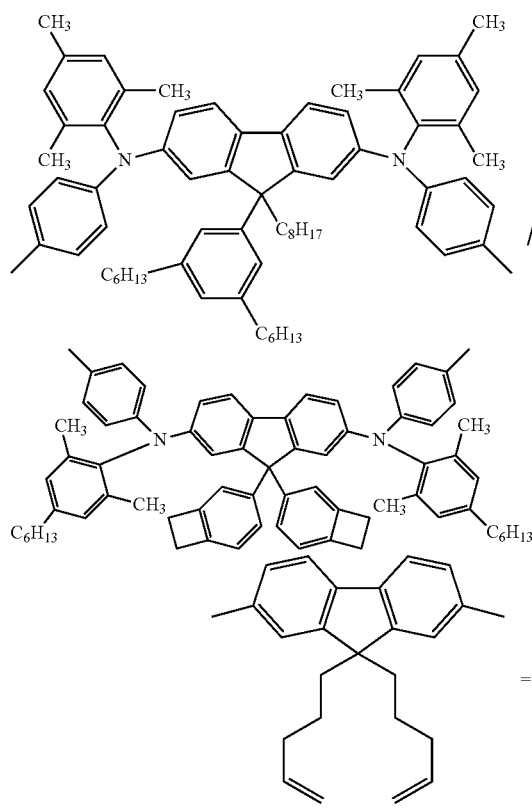

The energy gap of polymer compound 22 was 3.03 eV, as calculated by the method described above.

Example 20: Synthesis of Polymer Compound 23

A mixture of monomer CM28 (1.1061 g), monomer CM18 (1.0992 g), monomer CM22 (0.0660 g), monomer CM23 (0.0575 g) and toluene (47 ml) as a solvent was heated to about 80° C. under a nitrogen atmosphere, and then dichlorobis(tris(2-methoxyphenyl)phosphine)palladium (1.15 mg) and a 20 wt % tetrabutylammonium hydroxide aqueous solution (7.6 g) were added and the mixture was stirred for about 6 hours under reflux. Next, phenylboronic acid (15.3 mg), dichlorobis(tris(2-methoxyphenyl)phosphine)palladium (1.06 mg) and a 20 wt % tetrabutylammonium hydroxide aqueous solution (7.6 g) were added and the mixture was further stirred for about 16 hours under reflux. Next, a solution of sodium N,N-diethyldithiocarbamate trihydrate (0.71 g) dissolved in ion-exchanged water (22 ml) was added and the mixture was stirred for 2 hours while heating at 80° C. The organic layer was then rinsed twice with ion-exchanged water, twice with a 3.0 wt % acetic acid aqueous solution and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 23 (1.58 g). The polystyrene-equivalent number-average molecular weight (Mn) and weight-average molecular weight (Mw) of the polymer compound 23 were Mn=4.8×10$^4$, Mw=2.9×10$^5$, respectively.

Polymer compound 23 is presumed to be a polymer compound having the following constitutional units and molar ratios based on the monomer charging ratios, with constitutional unit (PA) and a constitutional unit selected from among (PB) alternately polymerized.

[Chemical Formula 188]

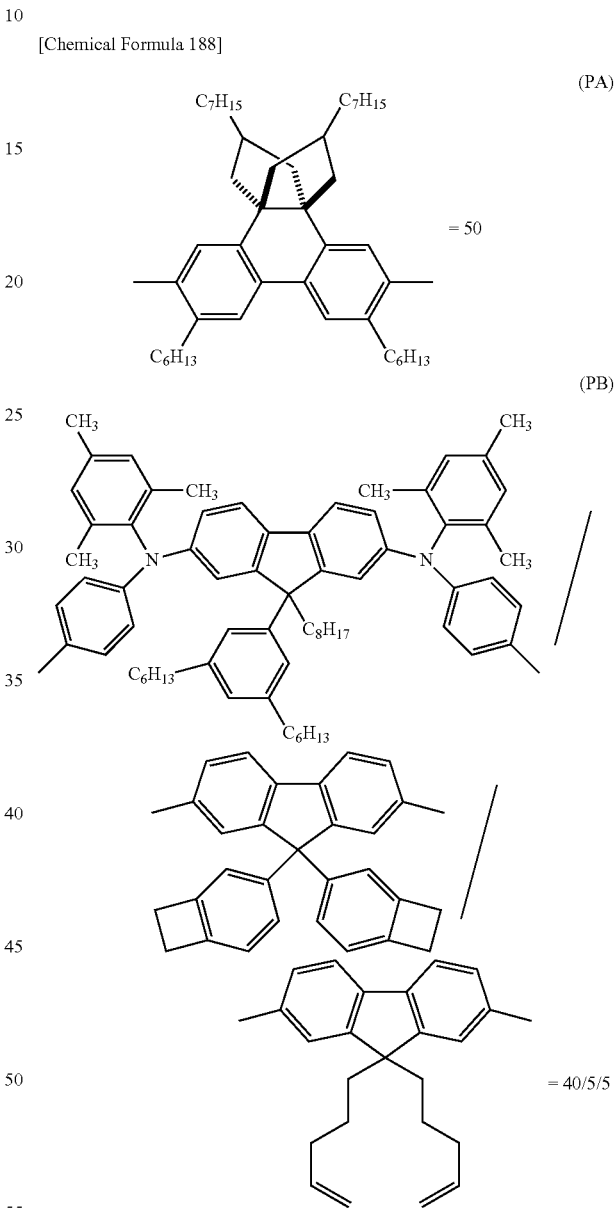

The energy gap of polymer compound 23 was 3.00 eV, as calculated by the method described above.

Comparative Example 1: Synthesis of Polymer Compound 6

A mixture comprising monomer CM5 (3.3249 g), monomer CM10 (3.4842 g), monomer CM11 (0.2897 g) and toluene (100 ml) as a solvent was heated to about 80° C. under a nitrogen atmosphere, and then palladium acetate (1.5 mg), tris(2-methoxyphenyl)phosphine (9.5 mg) and a 20 wt % tetraethylammonium hydroxide aqueous solution (15.2 g) were added and the mixture was stirred for about 22 hours under reflux. Next, pinacol phenylboronate (0.9268 g), palladium acetate (1.4 mg) and tris(2-methoxyphenyl)phosphine (9.4 mg) were added and the mixture was stirred for about 4 hours under reflux. Next, a solution of sodium N,N-diethyldithiocarbamate trihydrate (2.74 g) dissolved in ion-exchanged water (27 ml) was added and the mixture was stirred for 2 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 6 (4.254 g). The polystyrene-equivalent number-average molecular weight (Mn) and weight-average molecular weight (Mw) of the polymer compound 6 were Mn=$4.3\times10^4$, Mw=$1.3\times10^5$, respectively.

Polymer compound 6 is presumed to be a polymer compound having the following constitutional units and molar ratios based on the monomer charging ratios, with constitutional unit (PA) and a constitutional unit selected from among (PB) alternately polymerized.

[Chemical Formula 189]

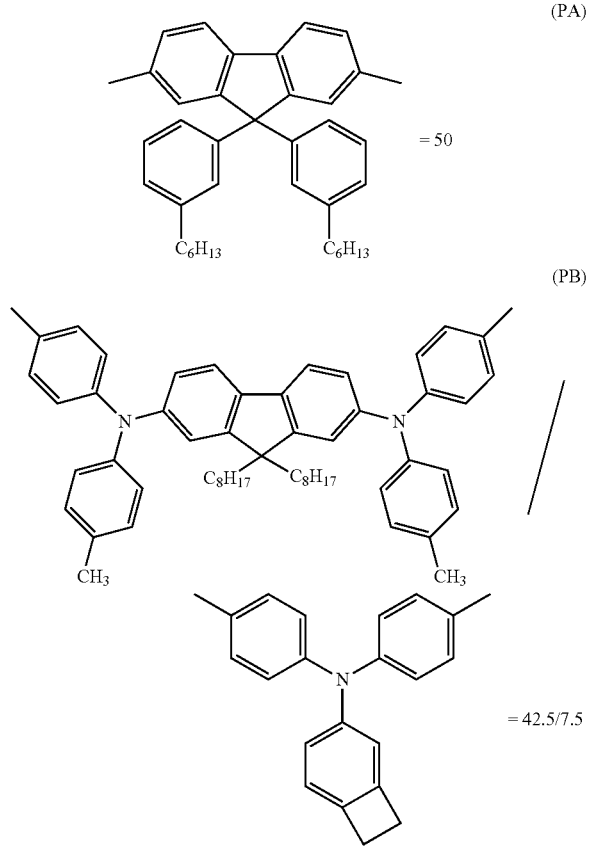

The energy gap of polymer compound 6 was 2.78 eV, as calculated by the method described above.

Comparative Example 2: Synthesis of Polymer Compound 7

A mixture comprising monomer CM5 (1.4773 g), monomer CM12 (2.2909 g), monomer CM11 (0.1287 g), methyltrioctylammonium chloride (trade name: Aliquat® 336 by Aldrich Co.) (0.277 g) and toluene (40 ml) as a solvent was heated to about 80° C. under a nitrogen atmosphere, and then palladium acetate (0.9 mg), tris(2-methoxyphenyl)phosphine (3.5 mg) and 17.5 wt % aqueous sodium carbonate (10.9 g) were added and the mixture was stirred for about 29 hours under reflux. Next, pinacol phenylboronate (0.21 g) was added and the mixture was further stirred for about 18 hours under reflux. Next, a solution of sodium N,N-diethyldithiocarbamate trihydrate (1.22 g) dissolved in ion-exchanged water (12 ml) was added and the mixture was stirred for 2 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 7 (2.32 g). The polystyrene-equivalent number-average molecular weight (Mn) and weight-average molecular weight (Mw) of polymer compound 7 were Mn=$4.5\times10^4$, Mw=$1.1\times10^5$, respectively.

Polymer compound 7 is presumed to be a polymer compound having the following constitutional units and molar ratios based on the monomer charging ratios, with constitutional unit (PA) and a constitutional unit selected from among (PB) alternately polymerized.

[Chemical Formula 190]

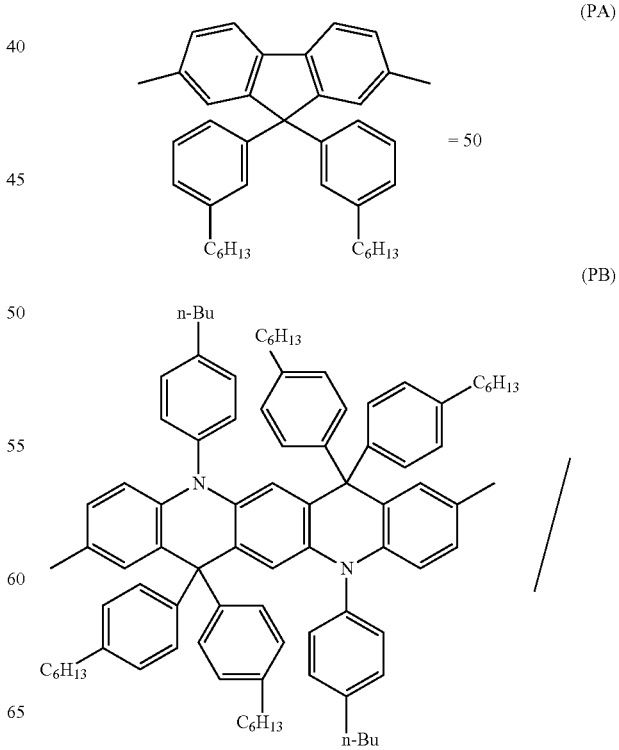

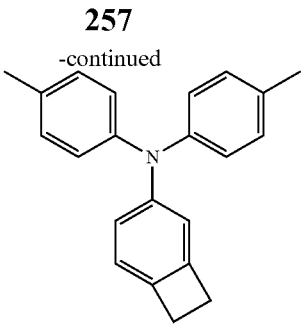

= 42.5/7.5

The energy gap of polymer compound 7 was 2.76 eV, as calculated by the method described above.

Comparative Example 3: Synthesis of Polymer Compound 8

A mixture comprising monomer CM6 (21.218 g), monomer CM8 (5.487 g), monomer CM13 (16.377 g), monomer CM11 (2.575 g), methyltrioctylammonium chloride (trade name: Aliquat® 336 by Aldrich Co.) (5.17 g) and toluene (400 ml) as a solvent was heated to about 80° C. under a nitrogen atmosphere, and then bistriphenylphosphinepalladium dichloride (56.2 mg) and 17.5 wt % aqueous sodium carbonate (109 g) were added and the mixture was stirred for about 6 hours under reflux.

Next, phenylboronic acid (0.49 g) was added and the mixture was further stirred for about 2 hours under reflux. Next, a solution of sodium N,N-diethyldithiocarbamate trihydrate (24.3 g) dissolved in ion-exchanged water (240 ml) was added and the mixture was stirred for 2 hours while heating at 85° C. The organic layer was then rinsed twice with ion-exchanged water, twice with 3 wt % acetic acid and twice with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound 8 (26.23 g). The polystyrene-equivalent number-average molecular weight (Mn) and weight-average molecular weight (Mw) of the polymer compound 8 were Mn=6.4×$10^4$, Mw=1.9×$10^5$, respectively.

Polymer compound 8 is presumed to be a polymer compound having the following constitutional units and molar ratios based on the monomer charging ratios, with constitutional unit (PA) and a constitutional unit selected from among (PB) alternately polymerized.

[Chemical Formula 191]

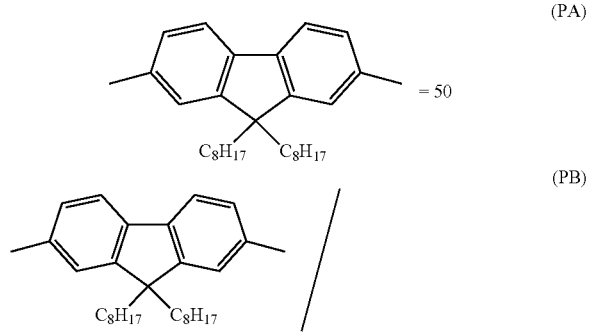

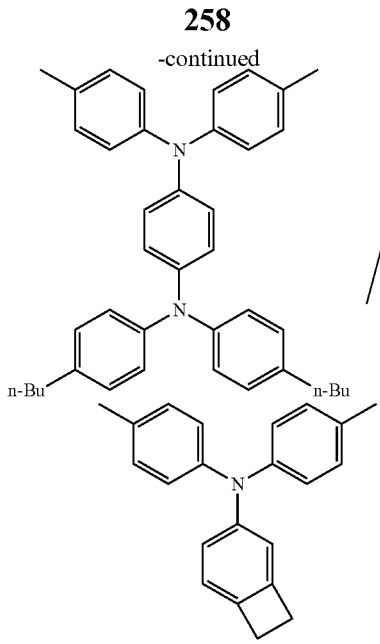

= 12.5/30/7.5

The energy gap of polymer compound 8 was 2.79 eV, as calculated by the method described above.

Synthesis Example 13: Synthesis of Polymer Compound L1

A mixture comprising monomer CM1 (0.8222 g), monomer CM9 (0.8507 g), monomer CM17 (0.2097 g) and toluene (37 ml) as a solvent was heated to about 80° C. under a nitrogen atmosphere, and then palladium acetate (0.41 mg), tris(2-methoxyphenyl)phosphine (2.30 mg) and a 20 wt % tetraethylammonium hydroxide aqueous solution (5.8 g) were added and the mixture was stirred for about 4 hours under reflux. Next, phenylboronic acid (40.6 mg) was added and the mixture was further stirred for about 2 hours under reflux. Next, a solution of sodium N,N-diethyldithiocarbamate trihydrate (0.46 g) dissolved in ion-exchanged water (9 ml) was added and the mixture was stirred for 2 hours while heating at 85° C. The organic layer was then rinsed twice with 3.6 wt % hydrochloric acid, twice with a 2.5 wt % ammonia water solution and 5 times with ion-exchanged water, in that order. The organic layer was added dropwise to methanol, to precipitate a polymer compound which was filtered and dried to obtain a solid. The solid was dissolved in toluene and passed through a silica gel column and alumina column through which toluene had been previously passed. The obtained solution was added dropwise to methanol, to precipitate a polymer compound which was filtered and dried to obtain polymer compound L1 (1.110 g). The polystyrene-equivalent number-average molecular weight (Mn) and weight-average molecular weight (Mw) of the polymer compound L1 were Mn=8.7×$10^4$, Mw=2.3×$10^5$, respectively.

Polymer compound L1 is presumed to be a polymer compound having the following constitutional units and molar ratios based on the monomer charging ratios, with constitutional unit (PA) and a constitutional unit selected from among (PB) alternately polymerized.

[Chemical Formula 192]

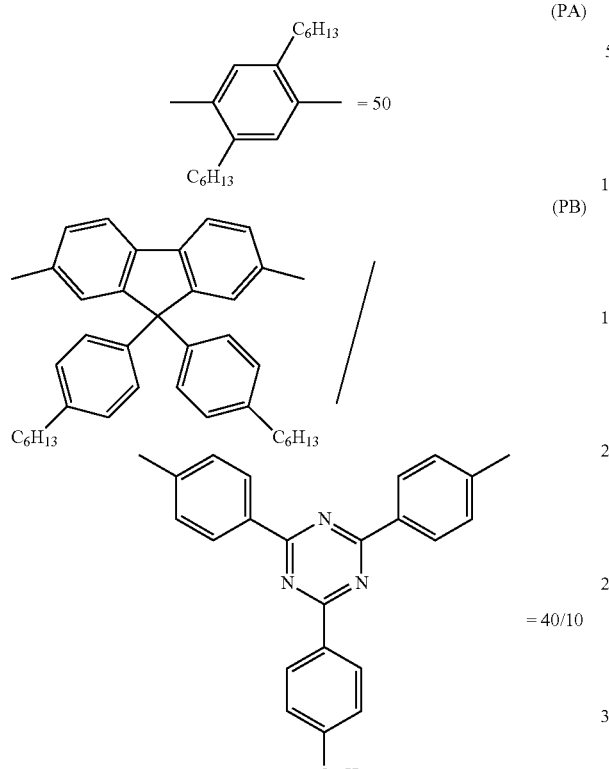

Synthesis Example 14: Synthesis of Polymer Compound L2

A mixture comprising monomer CM8 (9.0 g, 16.4 mmol), monomer CM15 (1.3 g, 1.8 mmol), monomer CM7 (13.4 g, 18.0 mmol), tetraethylammonium hydroxide (43.0 g, 58.3 mmol), palladium acetate (8 mg, 0.04 mmol), tri(2-methoxyphenyl)phosphine (0.05 g, 0.1 mmol) and toluene (200 mL) was heated and stirred at 90° C. for 8 hours under an inert gas atmosphere. Next, phenylboronic acid (0.22 g, 1.8 mmol) was added and the obtained mixture was stirred for 14 hours. After standing to cool, the aqueous layer was removed, a sodium diethyldithiocarbamate aqueous solution was added and the mixture was stirred, after which the aqueous layer was removed and the organic layer was rinsed with water and 3% acetic acid-water. The organic layer was poured into methanol to precipitate a polymer compound, and then the filtered out polymer compound was again dissolved in toluene and passed through a silica gel and alumina column. The eluted toluene solution containing the polymer compound was recovered, and the recovered toluene solution was poured into methanol to precipitate a polymer compound. The precipitated polymer compound was vacuum dried at 50° C. to obtain polymer compound L2 (12.5 g). The polystyrene-equivalent weight-average molecular weight of polymer compound L2 was $3.1 \times 10^5$, and the molecular weight distribution index (Mw/Mn) was 2.9.

Polymer compound L2 is presumed to be a polymer compound having the following constitutional units and molar ratios based on the monomer charging ratios, with constitutional unit (PA) and a constitutional unit selected from among (PB) alternately polymerized.

[Chemical Formula 193]

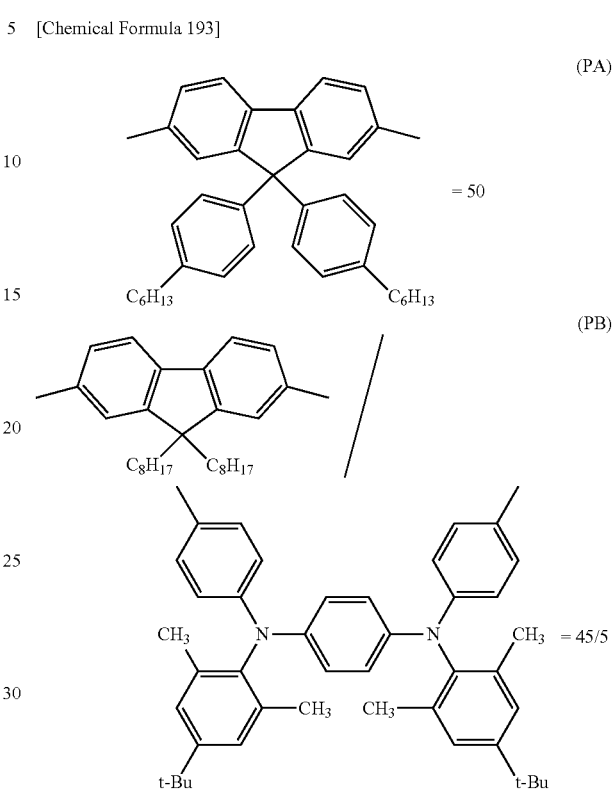

Example D1

Fabrication and Evaluation of Light Emitting Device D1

A glass panel with an ITO film formed to a thickness of 45 nm by sputtering was spin coated using a mixed solution of polythiophenesulfonic acid in ethyleneglycol monobutyl ether/water=3/2 (volume ratio) (trade name: Plexcore OC 1200 by Sigma-Aldrich Japan, KK.) to form a film with a thickness of 65 nm, and it was dried on a hot plate at 170° C. for 15 minutes. Next, polymer compound 1 was dissolved in xylene to prepare a 0.8 wt % xylene solution.

The xylene solution was used for spin coating of the Plexcore OC 1200-formed glass panel to form an organic film of polymer compound 1 to a thickness of 20 nm. This was heated on a hot plate at 180° C. for 60 minutes in a nitrogen gas atmosphere to form an insolubilized organic film.

Next, a composition mixed to polymer compound L2/phospholuminescent material 2=95 wt %/5 wt % was dissolved in xylene to prepare a 1.7 wt % xylene solution. The xylene solution was used to form a 80 nm-thick organic film by spin coating on a glass panel on which the insolubilized organic film of polymer compound 1 had been formed, and this was hot dried for 10 minutes at 130° C. in a nitrogen atmosphere. This was followed by vapor deposition of sodium fluoride to about 4 nm and then aluminum to about 80 nm, as a cathode, to fabricate light emitting device D1. Vapor deposition of the metals was initiated after the degree of vacuum reached no greater than $1 \times 10^{-4}$ Pa.

Upon application of a voltage to the obtained light emitting device D1, EL luminescence with a peak of 625 nm was obtained from the device, with a maximum external quantum efficiency of 13.8%. The results are shown in Table 3.

Example D2: Fabrication and Evaluation of Light Emitting Device D2

Light emitting device D2 was fabricated in the same manner as example D1, except that polymer compound 2 was used instead of polymer compound 1 in example D1, and a 0.7 wt % xylene solution was prepared. Upon application of a voltage to the obtained light emitting device D2, EL luminescence with a peak of 625 nm was obtained from the device, with a maximum external quantum efficiency of 13.7%. The results are shown in Table 3.

Example D3: Fabrication and Evaluation of Light Emitting Device D3

Light emitting device D3 was fabricated in the same manner as example D1, except that polymer compound 3 was used instead of polymer compound 1 in example D1, and a 0.7 wt % xylene solution was prepared. Upon application of a voltage to the obtained light emitting device D3, EL luminescence with a peak of 625 nm was obtained from the device, with a maximum external quantum efficiency of 13.7%. The results are shown in Table 3.

Example D4: Fabrication and Evaluation of Light Emitting Device D4

Light emitting device D4 was fabricated in the same manner as example D1, except that polymer compound 13 was used instead of polymer compound 1 in example D1, and a 0.7 wt % xylene solution was prepared. Upon application of a voltage to the obtained light emitting device D4, EL luminescence with a peak of 625 nm was obtained from the device, with a maximum external quantum efficiency of 13.6%. The results are shown in Table 3.

Comparative Example CD1: Fabrication and Evaluation of Light Emitting Device CD1

Light emitting device CD1 was fabricated in the same manner as example D1, except that polymer compound 7 was used instead of polymer compound 1 in example D1, and a 0.8 wt % xylene solution was prepared. Upon application of a voltage to the obtained light emitting device CD1, EL luminescence with a peak of 625 nm was obtained from the device, with a maximum external quantum efficiency of 9.0%. The results are shown in Table 3.

Example D5: Fabrication and Evaluation of Light Emitting Device D5

A glass panel with an ITO film formed to a thickness of 45 nm by sputtering was spin coated using a mixed solution of polythiophenesulfonic acid in ethyleneglycol monobutyl ether/water=3/2 (volume ratio) (trade name: Plexcore OC 1200 by Sigma-Aldrich Japan, KK.) to form a film with a thickness of 65 nm, and it was dried on a hot plate at 170° C. for 15 minutes. Next, polymer compound 1 was dissolved in xylene to prepare a 0.8 wt % xylene solution. The xylene solution was used for spin coating of the Plexcore OC 1200-formed glass panel to form an organic film of polymer compound 1 to a thickness of 20 nm. This was heated on a hot plate at 180° C. for 60 minutes in a nitrogen gas atmosphere to form an insolubilized organic film.

Next, a composition mixed to polymer compound L1/phospholuminescent material 1=70 wt %/30 wt % was dissolved in xylene to prepare a 2.0 wt % xylene solution. The xylene solution was used to form an 80 nm-thick organic film by spin coating on a glass panel on which the insolubilized film of polymer compound 1 had been formed, and this was hot dried for 10 minutes at 130° C. in a nitrogen atmosphere, after which vapor deposition was carried out with sodium fluoride to about 4 nm and then aluminum to about 80 nm as a cathode, to fabricate light emitting device D5. Vapor deposition of the metals was initiated after the degree of vacuum reached no greater than $1 \times 10^{-4}$ Pa.

Upon application of a voltage to the obtained light emitting device D5, EL luminescence with a peak of 520 nm was obtained from the device, with a maximum external quantum efficiency of 21.3%. Also, the time until the luminance reached an initial luminance of 60% (LT60), during constant current driving with an initial luminance of 12,000 cd/m$^2$, was 116.2 hours. The results are shown in Table 4.

Example D6: Fabrication and Evaluation of Light Emitting Device D6

Light emitting device D6 was fabricated in the same manner as example D5, except that a polymer compound 2 was used instead of polymer compound 1 in example D5, and a 0.7 wt % xylene solution was prepared. Upon application of a voltage to the obtained light emitting device D6, EL luminescence with a peak of 520 nm was obtained from the device, with a maximum external quantum efficiency of 22.8%. The results are shown in Table 4.

Example D7: Fabrication and Evaluation of Light Emitting Device D7

Light emitting device D7 was fabricated in the same manner as example D5, except that polymer compound 3

TABLE 3

| | Hole transport layer | Light-emitting layer | Maximum external quantum efficiency (%) |
|---|---|---|---|
| Example D1 | Polymer compound 1 | Polymer compound L2/Phosphorescent material 2 = 95 wt %/5 wt % | 13.8 |
| Example D2 | Polymer compound 2 | Polymer compound L2/Phosphorescent material 2 = 95 wt %/5 wt % | 13.7 |
| Example D3 | Polymer compound 3 | Polymer compound L2/Phosphorescent material 2 = 95 wt %/5 wt % | 13.7 |
| Example D4 | Polymer compound 13 | Polymer compound L2/Phosphorescent material 2 = 95 wt %/5 wt % | 13.6 |
| Comp. Example CD1 | Polymer compound 7 | Polymer compound L2/Phosphorescent material 2 = 95 wt %/5 wt % | 9.0 | was used instead of polymer compound 1 in example D5, and a 0.7 wt % xylene solution was prepared. Upon application of a voltage to the obtained light emitting device D7, EL luminescence with a peak of 520 nm was obtained from the device, with a maximum external quantum efficiency of 23.6%. The results are shown in Table 4.

Example D8: Fabrication and Evaluation of Light Emitting Device D8

Light emitting device D8 was fabricated in the same manner as example D5, except that polymer compound 4 was used instead of polymer compound 1 in example D5, and a 1.0 wt % xylene solution was prepared. Upon application of a voltage to the obtained light emitting device D8, EL luminescence with a peak of 520 nm was obtained from the device, with a maximum external quantum efficiency of 23.2%. The results are shown in Table 4.

Example D9: Fabrication and Evaluation of Light Emitting Device D9

Light emitting device D9 was fabricated in the same manner as example D5, except that polymer compound 5 was used instead of polymer compound 1 in example D5, and a 0.9 wt % xylene solution was prepared. Upon application of a voltage to the obtained light emitting device D9, EL luminescence with a peak of 515 nm was obtained from the device, with a maximum external quantum efficiency of 23.4%. The results are shown in Table 4.

Example D10: Fabrication and Evaluation of Light Emitting Device D10

Light emitting device D10 was fabricated in the same manner as example D5, except that polymer compound 9 was used instead of polymer compound 1 in example D5, and a 0.7 wt % xylene solution was prepared. Upon application of a voltage to the obtained light emitting device D10, EL luminescence with a peak of 520 nm was obtained from the device, with a maximum external quantum efficiency of 21.9%. The results are shown in Table 4.

Example D11: Fabrication and Evaluation of Light Emitting Device D11

Light emitting device D11 was fabricated in the same manner as example D5, except that polymer compound 10 was used instead of polymer compound 1 in example D5, and a 0.8 wt % xylene solution was prepared. Upon application of a voltage to the obtained light emitting device D11, EL luminescence with a peak of 520 nm was obtained from the device, with a maximum external quantum efficiency of 22.2%. Also, the time until the luminance reached an initial luminance of 60% (LT60), during constant current driving with an initial luminance of 12,000 cd/m$^2$, was 129.6 hours. The results are shown in Table 4.

Example D12: Fabrication and Evaluation of Light Emitting Device D12

Light emitting device D12 was fabricated in the same manner as example D5, except that polymer compound 11 was used instead of polymer compound 1 in example D5, and a 0.7 wt % xylene solution was prepared. Upon application of a voltage to the obtained light emitting device D12, EL luminescence with a peak of 520 nm was obtained from the device, with a maximum external quantum efficiency of 20.9%. The results are shown in Table 4.

Example D13: Fabrication and Evaluation of Light Emitting Device D13

Light emitting device D13 was fabricated in the same manner as example D5, except that polymer compound 12 was used instead of polymer compound 1 in example D5, and a 0.7 wt % xylene solution was prepared. Upon application of a voltage to the obtained light emitting device D13, EL luminescence with a peak of 520 nm was obtained from the device, with a maximum external quantum efficiency of 23.8%. The results are shown in Table 4.

Example D14: Fabrication and Evaluation of Light Emitting Device D14

Light emitting device D14 was fabricated in the same manner as example D5, except that polymer compound 13 was used instead of polymer compound 1 in example D5, and a 0.7 wt % xylene solution was prepared. Upon application of a voltage to the obtained light emitting device D14, EL luminescence with a peak of 520 nm was obtained from the device, with a maximum external quantum efficiency of 22.2%. The results are shown in Table 4.

Example D15: Fabrication and Evaluation of Light Emitting Device D15

Light emitting device D15 was fabricated in the same manner as example D5, except that polymer compound 14 was used instead of polymer compound 1 in example D5, and a 0.7 wt % xylene solution was prepared. Upon application of a voltage to the obtained light emitting device D15, EL luminescence with a peak of 520 nm was obtained from the device, with a maximum external quantum efficiency of 19.2%. Also, the time until the luminance reached an initial luminance of 60% (LT60), during constant current driving with an initial luminance of 12,000 cd/m$^2$, was 154.6 hours. The results are shown in Table 4.

Example D16: Fabrication and Evaluation of Light Emitting Device D16

Light emitting device D16 was fabricated in the same manner as example D5, except that polymer compound 15 was used instead of polymer compound 1 in example D5, and a 0.7 wt % xylene solution was prepared. Upon application of a voltage to the obtained light emitting device D16, EL luminescence with a peak of 520 nm was obtained from the device, with a maximum external quantum efficiency of 21.4%. Also, the time until the luminance reached an initial luminance of 60% (LT60), during constant current driving with an initial luminance of 12,000 cd/m$^2$, was 218.0 hours. The results are shown in Table 4.

Example D17: Fabrication and Evaluation of Light Emitting Device D17

Light emitting device D17 was fabricated in the same manner as example D5, except that polymer compound 16 was used instead of polymer compound 1 in example D5, and a 0.7 wt % xylene solution was prepared. Upon application of a voltage to the obtained light emitting device D17, EL luminescence with a peak of 520 nm was obtained from the device, with a maximum external quantum efficiency of

Example D18: Fabrication and Evaluation of Light Emitting Device D18

Light emitting device D18 was fabricated in the same manner as example D5, except that polymer compound 17 was used instead of polymer compound 1 in example D5, and a 0.7 wt % xylene solution was prepared. Upon application of a voltage to the obtained light emitting device D18, EL luminescence with a peak of 520 nm was obtained from the device, with a maximum external quantum efficiency of 21.4%. Also, the time until the luminance reached an initial luminance of 60% (LT60), during constant current driving with an initial luminance of 12,000 cd/m$^2$, was 167.0 hours. The results are shown in Table 4.

Example D19: Fabrication and Evaluation of Light Emitting Device D19

Light emitting device D19 was fabricated in the same manner as example D5, except that polymer compound 18 was used instead of polymer compound 1 in example D5, and a 0.7 wt % xylene solution was prepared. Upon application of a voltage to the obtained light emitting device D19, EL luminescence with a peak of 520 nm was obtained from the device, with a maximum external quantum efficiency of 18.7%. Also, the time until the luminance reached an initial luminance of 60% (LT60), during constant current driving with an initial luminance of 12,000 cd/m$^2$, was 112.0 hours. The results are shown in Table 4.

Example D20: Fabrication and Evaluation of Light Emitting Device D20

Light emitting device D20 was fabricated in the same manner as example D5, except that polymer compound 19 was used instead of polymer compound 1 in example D5, and a 0.7 wt % xylene solution was prepared. Upon application of a voltage to the obtained light emitting device D20, EL luminescence with a peak of 520 nm was obtained from the device, with a maximum external quantum efficiency of 22.3%. The results are shown in Table 4.

Example D21: Fabrication and Evaluation of Light Emitting Device D21

Light emitting device D21 was fabricated in the same manner as example D5, except that polymer compound 20 was used instead of polymer compound 1 in example D5, and a 0.7 wt % xylene solution was prepared. Upon application of a voltage to the obtained light emitting device D21, EL luminescence with a peak of 520 nm was obtained from the device, with a maximum external quantum efficiency of 23.4%. The results are shown in Table 4.

Example D22: Fabrication and Evaluation of Light Emitting Device D22

Light emitting device D22 was fabricated in the same manner as example D5, except that polymer compound 21 was used instead of polymer compound 1 in example D5, and a 0.7 wt % xylene solution was prepared. Upon application of a voltage to the obtained light emitting device D22, EL luminescence with a peak of 520 nm was obtained from the device, with a maximum external quantum efficiency of 19.9%. The results are shown in Table 4.

Example D23: Fabrication and Evaluation of Light Emitting Device D23

Light emitting device D23 was fabricated in the same manner as example D5, except that polymer compound 22 was used instead of polymer compound 1 in example D5, and a 0.7 wt % xylene solution was prepared. Upon application of a voltage to the obtained light emitting device D23, EL luminescence with a peak of 520 nm was obtained from the device, with a maximum external quantum efficiency of 19.6%. The results are shown in Table 4.

Example D24: Fabrication and Evaluation of Light Emitting Device D24

Light emitting device D24 was fabricated in the same manner as example D5, except that polymer compound 23 was used instead of polymer compound 1 in example D5, and a 0.7 wt % xylene solution was prepared. Upon application of a voltage to the obtained light emitting device D24, EL luminescence with a peak of 520 nm was obtained from the device, with a maximum external quantum efficiency of 20.2%. The results are shown in Table 4.

Comparative Example CD2: Fabrication and Evaluation of Light Emitting Device CD2

Light emitting device CD2 was fabricated in the same manner as example D5, except that polymer compound 6 was used instead of polymer compound 1 in example D5, and a 0.8 wt % xylene solution was prepared. Upon application of a voltage to the obtained light emitting device CD2, EL luminescence with a peak of 520 nm was obtained from the device, with a maximum external quantum efficiency of 13.1%. The results are shown in Table 4.

Comparative Example CD3: Fabrication and Evaluation of Light Emitting Device CD3

Light emitting device CD3 was fabricated in the same manner as example D5, except that polymer compound 1 was used instead of polymer compound 7 in example D5, and a 0.8 wt % xylene solution was prepared. Upon application of a voltage to the obtained light emitting device CD3, EL luminescence with a peak of 520 nm was obtained from the device, with a maximum external quantum efficiency of 9.3%. The results are shown in Table 4.

Comparative Example CD4: Fabrication and Evaluation of Light Emitting Device CD4

Light emitting device CD4 was fabricated in the same manner as example D5, except that polymer compound 8 was used instead of polymer compound 1 in example D5, and a 0.7 wt % xylene solution was prepared. Upon application of a voltage to the obtained light emitting device CD4, EL luminescence with a peak of 520 nm was obtained from the device, with a maximum external quantum efficiency of 11.0%. The results are shown in Table 4.

TABLE 4

| | Positive hole transport layer | Light-emitting layer | Maximum external quantum efficiency (%) | LT60 (hour) (Initial luminance: 12,000 cd/m$^2$) |
|---|---|---|---|---|
| Example D5 | Polymer compound 1 | Polymer compound L1/phosphorescent material 1 =70 wt %/30 wt % | 21.3 | 116.2 |
| Example D6 | Polymer compound 2 | Polymer compound Ll/phosphorescent material 1 =70 wt %/30 wt % | 22.8 | — |
| Example D7 | Polymer compound 3 | Polymer compound Ll/phosphorescent material 1 =70 wt %/30 wt % | 23.6 | — |
| Example D8 | Polymer compound 4 | Polymer compound Ll/phosphorescent material 1 =70 wt %/30 wt % | 23.2 | — |
| Example D9 | Polymer compound 5 | Polymer compound Ll/phosphorescent material 1 =70 wt %/30 wt % | 23.4 | — |
| Example D10 | Polymer compound 9 | Polymer compound Ll/phosphorescent material 1 =70 wt %/30 wt % | 21.9 | — |
| Example D11 | Polymer compound 10 | Polymer compound Ll/phosphorescent material 1 =70 wt %/30 wt % | 22.2 | 129.6 |
| Example D12 | Polymer compound 11 | Polymer compound Ll/phosphorescent material 1 =70 wt %/30 wt % | 20.9 | — |
| Example D13 | Polymer compound 12 | Polymer compound Ll/phosphorescent material 1 =70 wt %/30 wt % | 23.8 | — |
| Example D14 | Polymer compound 13 | Polymer compound Ll/phosphorescent material 1 =70 wt %/30 wt % | 22.2 | — |
| Example D15 | Polymer compound 14 | Polymer compound Ll/phosphorescent material 1 =70 wt %/30 wt % | 19.2 | 154.6 |
| Example D16 | Polymer compound 15 | Polymer compound Ll/phosphorescent material 1 =70 wt %/30 wt % | 21.4 | 218.0 |
| Example D17 | Polymer compound 16 | Polymer compound Ll/phosphorescent material 1 =70 wt %/30 wt % | 18.7 | 192.9 |
| Example D18 | Polymer compound 17 | Polymer compound Ll/phosphorescent material 1 =70 wt %/30 wt % | 21.4 | 167.0 |
| Example D19 | Polymer compound 18 | Polymer compound Ll/phosphorescent material 1 =70 wt %/30 wt % | 18.7 | 112.0 |
| Example D20 | Polymer compound 19 | Polymer compound Ll/phosphorescent material 1 =70 wt %/30 wt % | 22.3 | — |
| Example D21 | Polymer compound 20 | Polymer compound Ll/phosphorescent material 1 =70 wt %/30 wt % | 23.4 | — |
| Example D22 | Polymer compound 21 | Polymer compound Ll/phosphorescent material 1 =70 wt %/30 wt % | 19.9 | — |
| Example D23 | Polymer compound 22 | Polymer compound Ll/phosphorescent material 1 =70 wt %/30 wt % | 19.6 | — |
| Example D24 | Polymer compound 23 | Polymer compound Ll/phosphorescent material 1 =70 wt %/30 wt % | 20.2 | — |
| Comp. Ex. CD2 | Polymer compound 6 | Polymer compound Ll/phosphorescent material 1 =70 wt %/30 wt % | 13.1 | — |
| Comp. Ex. CD3 | Polymer compound 7 | Polymer compound Ll/phosphorescent material 1 =70 wt %/30 wt % | 9.3 | — |
| Comp. Ex. CD4 | Polymer compound 8 | Polymer compound Ll/phosphorescent material 1 =70 wt %/30 wt % | 11.0 | — |

Example D25: Fabrication and Evaluation of Light Emitting Device D25

A glass panel with an ITO film formed to a thickness of 45 nm by sputtering was spin coated using a mixed solution of polythiophenesulfonic acid in ethyleneglycol monobutyl ether/water=3/2 (volume ratio) (trade name: Plexcore OC 1200 by Sigma-Aldrich Japan, KK.) to form a film with a thickness of 65 nm, and it was dried on a hot plate at 170° C. for 15 minutes. Next, polymer compound 1 was dissolved in xylene to prepare a 0.8 wt % xylene solution.

The xylene solution was used for spin coating of the Plexcore OC 1200-formed glass panel to form an organic film of polymer compound 1 to a thickness of 20 nm. This was heated on a hot plate at 180° C. for 60 minutes in a nitrogen gas atmosphere to form an insolubilized organic film.

Next, polymer compound L2 was dissolved in xylene to prepare a 1.3 wt % xylene solution. The xylene solution was used to form an 60 nm-thick organic film by spin coating on a glass panel on which the insolubilized film of polymer compound 1 had been formed, and this was hot dried for 10 minutes at 130° C. in a nitrogen atmosphere, after which vapor deposition was carried out with sodium fluoride to about 4 nm and then aluminum to about 80 nm as a cathode, to fabricate light emitting device D25. Vapor deposition of the metals was initiated after the degree of vacuum reached no greater than 1×10$^{-4}$ Pa.

Upon application of a voltage to the obtained light emitting device D25, EL luminescence with a peak of 460 nm was obtained from the device, with a maximum external quantum efficiency of 6.1%. Also, the time until the luminance reached an initial luminance of 50% (LT50), during constant current driving with an initial luminance of 4,000 cd/m$^2$, was 37.9 hours. The results are shown in Table 5.

Example D26: Fabrication and Evaluation of Light Emitting Device D26

Light emitting device D26 was fabricated in the same manner as example D25, except that polymer compound 2 was used instead of polymer compound 1 in example D25, and a 0.7 wt % xylene solution was prepared. Upon application of a voltage to the obtained light emitting device D26, EL luminescence with a peak of 460 nm was obtained from the device, with a maximum external quantum efficiency of 6.6%. The results are shown in Table 5.

Example D27: Fabrication and Evaluation of Light Emitting Device D27

Light emitting device D27 was fabricated in the same manner as example D25, except that polymer compound 3 was used instead of polymer compound 1 in example D25, and a 0.7 wt % xylene solution was prepared. Upon application of a voltage to the obtained light emitting device D27, EL luminescence with a peak of 460 nm was obtained from the device, with a maximum external quantum efficiency of 6.6%. The results are shown in Table 5.

Example D28: Fabrication and Evaluation of Light Emitting Device D28

Light emitting device D28 was fabricated in the same manner as example D25, except that polymer compound 4 was used instead of polymer compound 1 in example D25, and a 1.0 wt % xylene solution was prepared. Upon application of a voltage to the obtained light emitting device D28, EL luminescence with a peak of 460 nm was obtained from the device, with a maximum external quantum efficiency of 6.8%. The results are shown in Table 5.

Example D29: Fabrication and Evaluation of Light Emitting Device D29

Light emitting device D29 was fabricated in the same manner as example D25, except that polymer compound 9 was used instead of polymer compound 1 in example D25, and a 0.7 wt % xylene solution was prepared. Upon application of a voltage to the obtained light emitting device D29, EL luminescence with a peak of 460 nm was obtained from the device, with a maximum external quantum efficiency of 6.0%. The results are shown in Table 5.

Example D30: Fabrication and Evaluation of Light Emitting Device D30

Light emitting device D30 was fabricated in the same manner as example D25, except that polymer compound 10 was used instead of polymer compound 1 in example D25, and a 0.8 wt % xylene solution was prepared. Upon application of a voltage to the obtained light emitting device D30, EL luminescence with a peak of 460 nm was obtained from the device, with a maximum external quantum efficiency of 6.0%. Also, the time until the luminance reached an initial luminance of 50% (LT50), during constant current driving with an initial luminance of 4,000 cd/m$^2$, was 78.0 hours. The results are shown in Table 5.

Example D31: Fabrication and Evaluation of Light Emitting Device D31

Light emitting device D31 was fabricated in the same manner as example D25, except that polymer compound 11 was used instead of polymer compound 1 in example D25, and a 0.7 wt % xylene solution was prepared. Upon application of a voltage to the obtained light emitting device D31, EL luminescence with a peak of 460 nm was obtained from the device, with a maximum external quantum efficiency of 6.0%. The results are shown in Table 5.

Example D32: Fabrication and Evaluation of Light Emitting Device D32

Light emitting device D32 was fabricated in the same manner as example D25, except that polymer compound 12 was used instead of polymer compound 1 in example D25, and a 0.7 wt % xylene solution was prepared. Upon application of a voltage to the obtained light emitting device D32, EL luminescence with a peak of 460 nm was obtained from the device, with a maximum external quantum efficiency of 6.0%. The results are shown in Table 5.

Example D33: Fabrication and Evaluation of Light Emitting Device D33

Light emitting device D33 was fabricated in the same manner as example D25, except that polymer compound 13 was used instead of polymer compound 1 in example D25, and a 0.7 wt % xylene solution was prepared. Upon application of a voltage to the obtained light emitting device D33, EL luminescence with a peak of 460 nm was obtained from the device, with a maximum external quantum efficiency of 6.8%. The results are shown in Table 5.

Example D34: Fabrication and Evaluation of Light Emitting Device D34

Light emitting device D34 was fabricated in the same manner as example D25, except that polymer compound 14 was used instead of polymer compound 1 in example D25, and a 0.7 wt % xylene solution was prepared. Upon application of a voltage to the obtained light emitting device D34, EL luminescence with a peak of 460 nm was obtained from the device, with a maximum external quantum efficiency of 6.8%. Also, the time until the luminance reached an initial luminance of 50% (LT50), during constant current driving with an initial luminance of 4,000 cd/m$^2$, was 82.5 hours. The results are shown in Table 5.

Example D35: Fabrication and Evaluation of Light Emitting Device D35

Light emitting device D35 was fabricated in the same manner as example D25, except that polymer compound 15 was used instead of polymer compound 1 in example D25, and a 0.7 wt % xylene solution was prepared. Upon application of a voltage to the obtained light emitting device D35, EL luminescence with a peak of 460 nm was obtained from the device, with a maximum external quantum efficiency of 6.9%. Also, the time until the luminance reached an initial luminance of 50% (LT50), during constant current driving with an initial luminance of 4,000 cd/m$^2$, was 80.5 hours. The results are shown in Table 5.

Example D36: Fabrication and Evaluation of Light Emitting Device D36

Light emitting device D36 was fabricated in the same manner as example D25, except that polymer compound 16 was used instead of polymer compound 1 in example D25, and a 0.7 wt % xylene solution was prepared. Upon application of a voltage to the obtained light emitting device D36, EL luminescence with a peak of 460 nm was obtained from the device, with a maximum external quantum efficiency of 5.7%. Also, the time until the luminance reached an initial luminance of 50% (LT50), during constant current driving

Example D37: Fabrication and Evaluation of Light Emitting Device D37

Light emitting device D37 was fabricated in the same manner as example D25, except that polymer compound 17 was used instead of polymer compound 1 in example D25, and a 0.7 wt % xylene solution was prepared. Upon application of a voltage to the obtained light emitting device D37, EL luminescence with a peak of 460 nm was obtained from the device, with a maximum external quantum efficiency of 6.8%. Also, the time until the luminance reached an initial luminance of 50% (LT50), during constant current driving with an initial luminance of 4,000 cd/m², was 53.9 hours. The results are shown in Table 5.

Example D38: Fabrication and Evaluation of Light Emitting Device D38

Light emitting device D38 was fabricated in the same manner as example D25, except that polymer compound 18 was used instead of polymer compound 1 in example D25, and a 0.7 wt % xylene solution was prepared. Upon application of a voltage to the obtained light emitting device D38, EL luminescence with a peak of 460 nm was obtained from the device, with a maximum external quantum efficiency of 6.5%. Also, the time until the luminance reached an initial luminance of 50% (LT50), during constant current driving with an initial luminance of 4,000 cd/m², was 56.0 hours. The results are shown in Table 5.

Example D39: Fabrication and Evaluation of Light Emitting Device D39

Light emitting device D39 was fabricated in the same manner as example D25, except that polymer compound 19 was used instead of polymer compound 1 in example D25, and a 0.7 wt % xylene solution was prepared. Upon application of a voltage to the obtained light emitting device D39, EL luminescence with a peak of 460 nm was obtained from the device, with a maximum external quantum efficiency of 6.9%. The results are shown in Table 5.

Example D40: Fabrication and Evaluation of Light Emitting Device D40

Light emitting device D40 was fabricated in the same manner as example D25, except that polymer compound 20 was used instead of polymer compound 1 in example D25, and a 0.7 wt % xylene solution was prepared. Upon application of a voltage to the obtained light emitting device D40, EL luminescence with a peak of 460 nm was obtained from the device, with a maximum external quantum efficiency of 7.1%. The results are shown in Table 5.

Example D41: Fabrication and Evaluation of Light Emitting Device D41

Light emitting device D41 was fabricated in the same manner as example D25, except that polymer compound 21 was used instead of polymer compound 1 in example D25, and a 0.7 wt % xylene solution was prepared. Upon application of a voltage to the obtained light emitting device D41, EL luminescence with a peak of 460 nm was obtained from the device, with a maximum external quantum efficiency of 6.1%. The results are shown in Table 5.

Example D42: Fabrication and Evaluation of Light Emitting Device D42

Light emitting device D42 was fabricated in the same manner as example D25, except that polymer compound 22 was used instead of polymer compound 1 in example D25, and a 0.7 wt % xylene solution was prepared. Upon application of a voltage to the obtained light emitting device D42, EL luminescence with a peak of 460 nm was obtained from the device, with a maximum external quantum efficiency of 5.9%. The results are shown in Table 5.

Example D43: Fabrication and Evaluation of Light Emitting Device D43

Light emitting device D43 was fabricated in the same manner as example D25, except that polymer compound 23 was used instead of polymer compound 1 in example D25, and a 0.7 wt % xylene solution was prepared. Upon application of a voltage to the obtained light emitting device D43, EL luminescence with a peak of 460 nm was obtained from the device, with a maximum external quantum efficiency of 6.4%. The results are shown in Table 5.

Comparative Example CD5: Fabrication and Evaluation of Light Emitting Device CD5

Light emitting device CD5 was fabricated in the same manner as example D25, except that polymer compound 6 was used instead of polymer compound 1 in example D25, and a 0.8 wt % xylene solution was prepared. Upon application of a voltage to the obtained light emitting device CD5, EL luminescence with a peak of 470 nm was obtained from the device, with a maximum external quantum efficiency of 5.3%. The results are shown in Table 5.

Comparative Example CD6: Fabrication and Evaluation of Light Emitting Device CD6

Light emitting device CD6 was fabricated in the same manner as example D25, except that polymer compound 7 was used instead of polymer compound 1 in example D25, and a 0.8 wt % xylene solution was prepared. Upon application of a voltage to the obtained light emitting device CD6, EL luminescence with a peak of 460 nm was obtained from the device, with a maximum external quantum efficiency of 5.2%. The results are shown in Table 5.

Comparative Example CD7: Fabrication and Evaluation of Light Emitting Device CD7

Light emitting device CD7 was fabricated in the same manner as example D25, except that polymer compound 8 was used instead of polymer compound 1 in example D25, and a 0.7 wt % xylene solution was prepared. Upon application of a voltage to the obtained light emitting device CD7, EL luminescence with a peak of 475 nm was obtained from the device, with a maximum external quantum efficiency of 5.2%. The results are shown in Table 5.

TABLE 5

| | Hole transport layer | Light-emitting layer | Maximum external quantum efficiency (%) | LT50 (hour) (Initial luminance: 4,000 cd/m$^2$) |
|---|---|---|---|---|
| Example D25 | Polymer compound 1 | Polymer compound L2 | 6.1 | 37.9 |
| Example D26 | Polymer compound 2 | Polymer compound L2 | 6.6 | — |
| Example D27 | Polymer compound 3 | Polymer compound L2 | 6.6 | — |
| Example D28 | Polymer compound 4 | Polymer compound L2 | 6.8 | — |
| Example D29 | Polymer compound 9 | Polymer compound L2 | 6.0 | — |
| Example D30 | Polymer compound 10 | Polymer compound L2 | 6.0 | 78.0 |
| Example D31 | Polymer compound 11 | Polymer compound L2 | 6.0 | — |
| Example D32 | Polymer compound 12 | Polymer compound L2 | 6.0 | — |
| Example D33 | Polymer compound 13 | Polymer compound L2 | 6.8 | — |
| Example D34 | Polymer compound 14 | Polymer compound L2 | 6.9 | 82.5 |
| Example D35 | Polymer compound 15 | Polymer compound L2 | 6.9 | 80.5 |
| Example D36 | Polymer compound 16 | Polymer compound L2 | 5.7 | 104.1 |
| Example D37 | Polymer compound 17 | Polymer compound L2 | 6.8 | 53.9 |
| Example D38 | Polymer compound 18 | Polymer compound L2 | 6.5 | 56.0 |
| Example D39 | Polymer compound 19 | Polymer compound L2 | 6.9 | — |
| Example D40 | Polymer compound 20 | Polymer compound L2 | 7.1 | — |
| Example D41 | Polymer compound 21 | Polymer compound L2 | 6.1 | — |
| Example D42 | Polymer compound 22 | Polymer compound L2 | 5.9 | — |
| Example D43 | Polymer compound 23 | Polymer compound L2 | 6.4 | — |
| Comp. Ex. CD5 | Polymer compound 6 | Polymer compound L2 | 5.3 | — |
| Comp. Ex. CD6 | Polymer compound 7 | Polymer compound L2 | 5.2 | — |
| Comp. Ex. CD7 | Polymer compound 8 | Polymer compound L2 | 5.2 | — |

Example D42: Fabrication and Evaluation of Light Emitting Device D42

A glass panel with an ITO film formed to a thickness of 45 nm by sputtering was spin coated using a mixed solution of polythiophenesulfonic acid in ethyleneglycol monobutyl ether/water=3/2 (volume ratio) (trade name: Plexcore OC 1200 by Sigma-Aldrich Japan, KK.) to form a film with a thickness of 65 nm, and it was dried on a hot plate at 170° C. for 15 minutes. A composition mixed to polymer compound 14/phospholuminescent material 1=70 wt %/30 wt % was dissolved in xylene to prepare a 2.0 wt % xylene solution. The xylene solution was used for spin coating of the Plexcore OC 1200-formed glass panel to form an organic film to a thickness of 80 nm. This was heated on a hot plate at 180° C. for 60 minutes in a nitrogen gas atmosphere to form an insolubilized organic film. This was followed by vapor deposition of sodium fluoride to about 4 nm and then aluminum to about 80 nm, as a cathode, to fabricate light emitting device D42. Vapor deposition of the metals was initiated after the degree of vacuum reached no greater than $1\times10^{-4}$ Pa.

Upon application of a voltage to the obtained light emitting device D42, EL luminescence with a peak of 520 nm was obtained from the device with a maximum external quantum efficiency of 2.7%.

Comparative Example CD8: Fabrication and Evaluation of Light Emitting Device CD8

Light emitting device CD8 was fabricated in the same manner as example D42, except that polymer compound 6 was used instead of polymer compound 14 in example D42, and a 2.0 wt % xylene solution was prepared as a mixture to polymer compound 6/phospholuminescent material 1=70 wt %/30 wt %. Upon application of a voltage to the obtained light emitting device CD8, EL luminescence with a peak of 520 nm was obtained from the device, with a maximum external quantum efficiency of 0.1 cd/A.

The invention claimed is:
1. A polymer compound comprising:
a constitutional unit represented by the following formula (1),
a constitutional unit represented by the following formula (2), and at least one of a constitutional unit represented by the following formula (3) and a constitutional unit represented by the following formula (4');

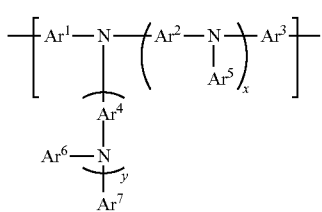

wherein $Ar^1$ and $Ar^3$ each independently represent an unsubstituted or substituted arylene group or an unsubstituted or substituted divalent heterocyclic group;
$Ar^2$ and $Ar^4$ each independently represent an unsubstituted or substituted arylene group, an unsubstituted or substituted divalent heterocyclic group, or a divalent group having two or more identical or different linked groups selected from arylene groups and divalent heterocyclic groups, wherein the divalent group can be substituted;
$Ar^5$, $Ar^6$ and $Ar^7$ each independently represent a hydrogen atom, an unsubstituted or substituted alkyl group, an unsubstituted or substituted aryl group or an unsubstituted or substituted monovalent heterocyclic group;
$Ar^1$, $Ar^2$, $Ar^3$, $Ar^4$, $Ar^5$, $Ar^6$ and $Ar^7$ can each be directly bonded to a group other than a group bonded to the nitrogen atom to which the group is bonded, and can be bonded via —O—, —S—, —C(=O)—, —C(=O)—O—, —N($R_a$)—, —C(=O)—N($R_a$)— or —C($R_a$)$_2$—;
$R_a$ represents a hydrogen atom, an unsubstituted or substituted alkyl group, an unsubstituted or substituted alkoxy group, an unsubstituted or substituted aryl group, a halogen atom, or an unsubstituted or substituted monovalent heterocyclic group;
when two $R_a$ are present, they can be the same or different;
x and y each independently represent 0 or 1, and x+y=1;

wherein $Ar^8$ represents a (2+p)-valent aromatic hydrocarbon group;
$R^1$ represents an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxyl group, a nitro group or a cyano group;
when a plurality of $R^1$ are present, they can be the same or different;
at least one $R^1$ substitutes a hydrogen atom that is directly bonded to a carbon atom adjacent to the carbon atom forming a bond with another constitutional unit of the aromatic hydrocarbon group;
p represents an integer of 1 or greater;

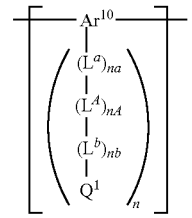

wherein na represents an integer of 0 to 3, nb represents an integer of 0 to 12, nA represents 0 or 1 and n represents an integer of 1 to 4;
$Ar^{10}$ represents an unsubstituted or substituted (2+n)-valent aromatic hydrocarbon group or an unsubstituted or substituted (2+n)-valent heterocyclic group;
$L^a$ and $L^b$ each independently represent an unsubstituted or substituted alkylene group or an unsubstituted or substituted phenylene group;
when a plurality of $L^a$ are present they can be the same or different;
when a plurality of $L^b$ are present they can be the same or different;
$L^A$ represents an oxygen atom or a sulfur atom;
when a plurality of $L^A$ are present, they can be the same or different;
$Q^1$ represents a monovalent crosslinkable group selected from the group consisting of formula (Q-1), (Q-2), and (Q-01) to (Q-19);

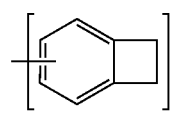

wherein the benzocyclobutene ring in formula (Q-1) is optionally substituted;

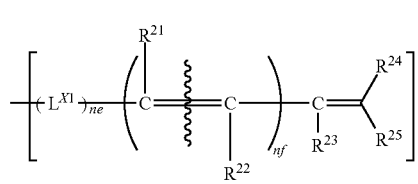

wherein ne is 0 or 1;
nf is 0;
$L^{X1}$ is an oxygen atom, a sulfur atom, a carbonyl group or —O—CO—;
$R^{21}$, $R^{22}$, $R^{23}$, $R^{24}$ and $R^{25}$ each independently represent a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted monovalent heterocyclic group, an unsubstituted or substituted amino group, an unsubstituted or substituted silyl group, an unsubstituted or substituted acyl group, an unsubstituted or substituted acyloxy group, a halogen atom, a cyano group or a nitro group;
(Q-01)
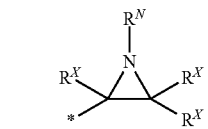
(Q-02)
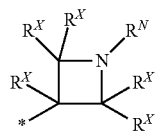
(Q-03)
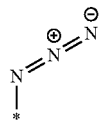
(Q-04)
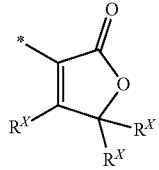
(Q-05)
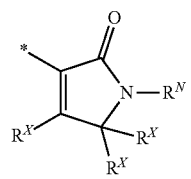
(Q-06)
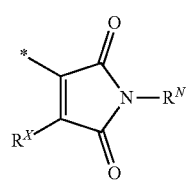
(Q-07)
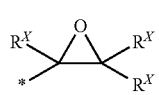
(Q-08)
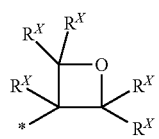
(Q-09)
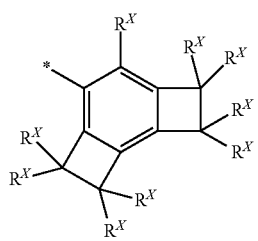
(Q-10)
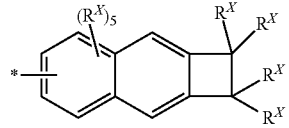
(Q-11)
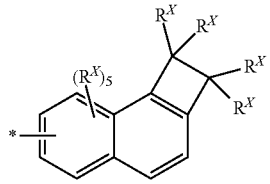
(Q-12)
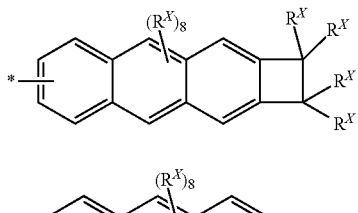
(Q-13)
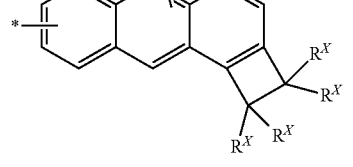
(Q-14)
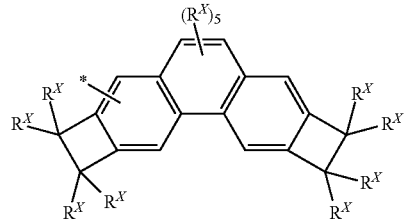
(Q-15)
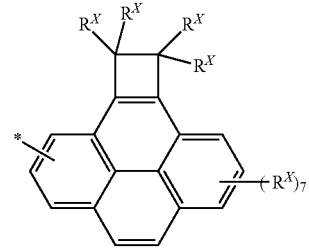
(Q-16)
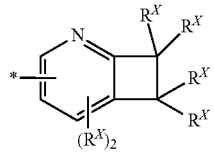
(Q-17)
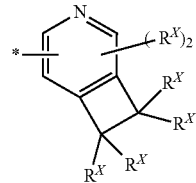

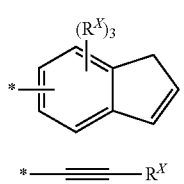

(Q-18)

(Q-19)

wherein $R^X$ is a hydrogen atom, an unsubstituted or substituted alkyl group, an unsubstituted or substituted alkoxy group, an unsubstituted or substituted alkylthio group, an unsubstituted or substituted aryl group, an unsubstituted or substituted aryloxy group, an unsubstituted or substituted arylthio group, an unsubstituted or substituted amino group, an unsubstituted or substituted silyl group, a halogen atom, an acyl group, an acyloxy group, an imine group, a carbamoyl group, an acid imide group, an unsubstituted or substituted monovalent heterocyclic group, an unsubstituted or substituted carboxyl group, a cyano group or a nitro group;

when a plurality of $R^X$ are present, each $R^X$ can be the same or different;

$R^N$ is a hydrogen atom, an unsubstituted or substituted alkyl group, an unsubstituted or substituted acyl group, an unsubstituted or substituted aryl group, or an unsubstituted or substituted monovalent heterocyclic group;

* indicates a bonding site;

when a plurality of $Q^1$ are present, they can be the same or different;

the constitutional unit represented by formula (3) is different from the constitutional unit represented by formula (2);

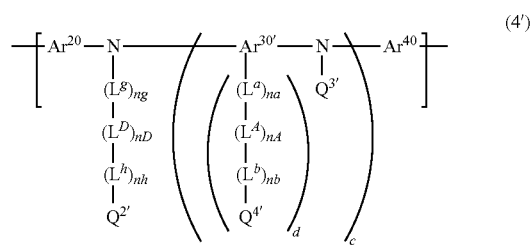

(4')

wherein c represents 0 or 1, and d represents an integer of 0 to 4, $Ar^{20}$ and $Ar^{40}$ each independently represent an unsubstituted or substituted arylene group or an unsubstituted or substituted divalent heterocyclic group, and $Ar^{30'}$ represents an unsubstituted or substituted (2+d)-valent aromatic hydrocarbon group, an unsubstituted or substituted (2+d)-valent heterocyclic group, or a (2+d)-valent group having a structure in which two or more identical or different rings selected from among aromatic rings and heterocyclic rings are linked, where the (2+d)-valent group can be substituted;

$Q^{2'}$, $Q^{3'}$ and $Q^{4'}$ represent a monovalent crosslinkable group, an unsubstituted or substituted alkyl group, an unsubstituted or substituted aryl group, or an unsubstituted or substituted monovalent heterocyclic group, with the proviso that at least one of $Q^{2'}$, $Q^{3'}$ and $Q^{4'}$ is a monovalent crosslinkable group;

when a plurality of $Q^{4'}$ are present, they can be the same or different;

na represents an integer of 0 to 3, nb represents an integer of 0 to 12, and nA represents 0 or 1;

$L^a$ and $L^b$ each independently represent an unsubstituted or substituted alkylene group or an unsubstituted or substituted phenylene group;

when a plurality of $L^a$ are present, they can be the same or different;

when a plurality of $L^b$ are present, they can be the same or different;

$L^A$ represents an oxygen atom or a sulfur atom;

when a plurality of $L^A$ are present, they can be the same or different;

ng represents an integer of 0 to 3, nh represents an integer of 0 to 12, and nD represents 0 or 1;

$L^g$ and $L^h$ each independently represent an unsubstituted or substituted alkylene group or an unsubstituted or substituted phenylene group;

when a plurality of $L^g$ are present, they can be the same or different;

when a plurality of $L^h$ are present, they can be the same or different;

$L^D$ represents an oxygen atom or a sulfur atom;

when a plurality of $L^D$ are present, they can be the same or different;

the constitutional unit represented by formula (4') differs from the constitutional unit represented by formula (1).

2. The polymer compound according to claim 1, wherein the constitutional unit represented by formula (4') is a constitutional unit represented by the following formula (4);

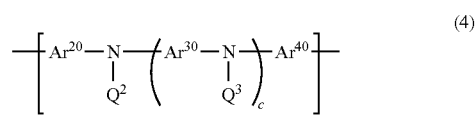

(4)

wherein c represents 0 or 1, $Ar^{20}$ and $Ar^{40}$ each independently represent an unsubstituted or substituted arylene group or an unsubstituted or substituted divalent heterocyclic group, $Ar^{30}$ represents an unsubstituted or substituted arylene group, an unsubstituted or substituted divalent heterocyclic group, or a divalent group having two or more identical or different linked groups selected from arylene groups and divalent heterocyclic groups, wherein the divalent groups can be substituted;

$Q^2$ represents a monovalent crosslinkable group, and $Q^3$ represents a monovalent crosslinkable group, an unsubstituted or substituted alkyl group, an unsubstituted or substituted aryl group, or an unsubstituted or substituted monovalent heterocyclic group.

3. The polymer compound according to claim 1, wherein the constitutional unit represented by formula (1) is a constitutional unit represented by the following formula (1A);

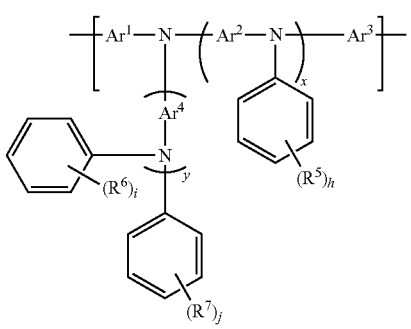

(1A)

wherein $R^5$, $R^6$ and $R^7$ each independently represent an alkyl group, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxy group, a nitro group or a cyano group;

when a plurality of $R^5$ are present, they can be the same or different, when a plurality of $R^6$ are present, they can be the same or different, and when a plurality of $R^7$ are present, they can be the same or different;

h, i and j each independently represent an integer of 0 to 5.

4. The polymer compound according to claim 1, wherein:
Ar$^1$ and Ar$^3$ are unsubstituted or substituted phenylene groups, and
Ar$^2$ or Ar$^4$ is a group selected from the group consisting of an unsubstituted or substituted phenylene group, an unsubstituted or substituted biphenylylene group and an unsubstituted or substituted fluorenediyl group.

5. The polymer compound according to claim 4, wherein Ar$^1$ and Ar$^3$ are unsubstituted or substituted 1,4-phenylene groups.

6. The polymer compound according to claim 4, wherein Ar$^2$ or Ar$^4$ is an unsubstituted or substituted 2,7-fluorenediyl group.

7. The polymer compound according to claim 1, wherein x is 1 and y is 0.

8. The polymer compound according to claim 1, wherein Ar$^8$ is a phenylene group.

9. The polymer compound according to claim 1, wherein Ar$^8$ is a fluorenediyl group.

10. The polymer compound according to claim 1, wherein the constitutional unit represented by formula (3) is a constitutional unit represented by the following formula (3-1);

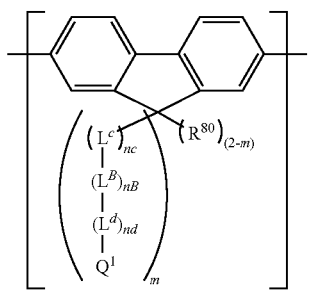

(3-1)

wherein nc represents an integer of 0 to 3, nd represents an integer of 0 to 12, nB represents 0 or 1 and m represents 1 or 2;

$L^c$ and $L^d$ each independently represent an unsubstituted or substituted alkylene group or an unsubstituted or substituted phenylene group;

when a plurality of $L^c$ are present, they can be the same or different;

when a plurality of $L^d$ are present, they can be the same or different;

$L^B$ represents an oxygen atom or a sulfur atom;

when a plurality of $L^B$ are present, they can be the same or different;

$Q^1$ has the same meaning as explained above;

when a plurality of $Q^1$ are present, they can be the same or different;

$R^{80}$ represents a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, or an unsubstituted or substituted heterocyclooxy group.

11. The polymer compound according to claim 1, wherein the constitutional unit represented by formula (3) is a constitutional unit represented by the following formula (3-2);

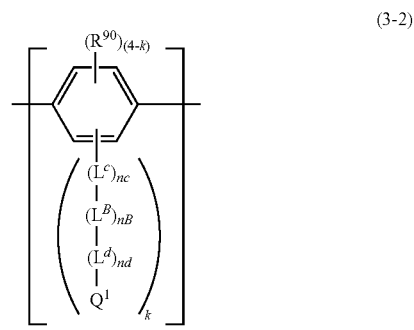

(3-2)

wherein nc represents an integer of 0 to 3, nd represents an integer of 0 to 12, nB represents 0 or 1 and k represents an integer of 1 to 4;

$L^c$ and $L^d$ each independently represent an unsubstituted or substituted alkylene group or an unsubstituted or substituted phenylene group;

when a plurality of $L^c$ are present, they can be the same or different;

when a plurality of $L^d$ are present, they can be the same or different;

$L^B$ represents an oxygen atom or a sulfur atom;

when a plurality of $L^B$ are present, they can be the same or different;

$Q^1$ has the same meaning as explained above;

when a plurality of $Q^1$ are present, they can be the same or different;

$R^{90}$ represents a hydrogen atom, an unsubstituted or substituted alkyl group, an unsubstituted or substituted alkoxy group, an unsubstituted or substituted aryl group, an unsubstituted or substituted aryloxy group, an unsubstituted or substituted monovalent heterocyclic group, or an unsubstituted or substituted heterocyclooxy group;

when a plurality of $R^{90}$ are present, they can be the same or different.

12. The polymer compound according to claim 1, wherein the monovalent crosslinkable groups represented by $Q^1$, $Q^2$, $Q^3$, $Q^{2'}$, $Q^{3'}$, and $Q^{4'}$ are monovalent crosslinkable groups represented by the following formula (Q-1);

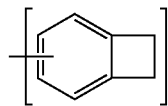

(Q-1)

wherein the benzocyclobutene ring can be substituted;
when a plurality of substituents are present, they can be the same or different.

13. The polymer compound according to claim 1, comprising:
   a constitutional unit represented by formula (1),
   a constitutional unit represented by formula (2) and
   at least two different constitutional units represented by formula (3).

14. A composition comprising the polymer compound according to claim 1, and at least one material selected from the group consisting of hole transport materials, electron transport materials and light-emitting materials.

15. A composition comprising the polymer compound according to claim 1, and a solvent.

16. The composition according to claim 14, further comprising a solvent.

17. An organic film comprising the polymer compound according to claim 1.

18. An insolubilized organic film that has been insolubilized to a solvent by heating the organic film according to claim 17.

19. A light emitting device having the organic film according to claim 17.

20. The light emitting device according to claim 19, wherein the organic film is a hole transport layer.

21. The polymer compound according to claim 1, wherein $R^1$ represents an alkyl group having two or more carbon atoms, an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxyl group, a nitro group or a cyano group.

22. The polymer compound according to claim 1, wherein $R^1$ represents an alkoxy group, an alkylthio group, an aryl group, an aryloxy group, an arylthio group, an alkenyl group, an alkynyl group, an amino group, a silyl group, a halogen atom, an acyl group, an acyloxy group, an oxycarbonyl group, a monovalent heterocyclic group, a heterocyclooxy group, a heterocyclothio group, an imine residue, an amide compound residue, an acid imide residue, a carboxyl group, a hydroxyl group, a nitro group or a cyano group.

* * * * *